US010213826B2

(12) United States Patent
Samuelson et al.

(10) Patent No.: US 10,213,826 B2
(45) Date of Patent: Feb. 26, 2019

(54) SYSTEMS AND METHODS FOR PROVIDING PROSTHETIC COMPONENTS

(71) Applicants: Connor E Samuelson, Salt Lake City, UT (US); Marcus F. Samuelson, Salt Lake City, UT (US); Alec C. Samuelson, Salt Lake City, UT (US); Kent M. Samuelson, Salt Lake City, UT (US)

(72) Inventors: Connor E Samuelson, Salt Lake City, UT (US); Marcus F. Samuelson, Salt Lake City, UT (US); Alec C. Samuelson, Salt Lake City, UT (US); Kent M. Samuelson, Salt Lake City, UT (US)

( * ) Notice: Subject to any disclaimer, the term of this patent is extended or adjusted under 35 U.S.C. 154(b) by 0 days.

(21) Appl. No.: 15/134,342

(22) Filed: Apr. 20, 2016

(65) Prior Publication Data
US 2016/0228255 A1 Aug. 11, 2016

Related U.S. Application Data

(63) Continuation-in-part of application No. 14/975,736, filed on Dec. 19, 2015, now Pat. No. 9,872,774,
(Continued)

(51) Int. Cl.
*A61B 17/17* (2006.01)
*B22C 9/22* (2006.01)
(Continued)

(52) U.S. Cl.
CPC ............ *B22C 9/22* (2013.01); *A61B 17/1764* (2013.01); *A61F 2/389* (2013.01); *A61F 2/3859* (2013.01);
(Continued)

(58) Field of Classification Search
CPC ...... A61B 17/15; A61B 17/154; A61B 17/155
See application file for complete search history.

(56) References Cited

U.S. PATENT DOCUMENTS 4,209,861 A   7/1980  Walker et al.
4,487,203 A  12/1984  Androphy
(Continued)

FOREIGN PATENT DOCUMENTS

CN      1874738 A   12/2006
CN    101123928 A    2/2008
(Continued)

*Primary Examiner* — Anu Ramana
(74) *Attorney, Agent, or Firm* — David B. Tingey; Bryant J. Keller; Kirton McConkie

(57) ABSTRACT

Methods for forming prosthetic implants, including femoral implants, are discussed. While the methods can include any suitable step, in some cases, they include providing a master negative mold defining an internal space shaped to form a femoral component configured to replace a distal portion of a femur, wherein the femoral component comprises at least one of: an anterior flange that is disposed at an anterior proximal end of the femoral component, and a proximal extension disposed at a proximal portion of a posterior condyle of the femoral component, the proximal extension comprising a concave articulation surface that is configured to articulate against at least one of: a tibial prosthetic component and a tibia; filling the master negative mold with a molding material to form a molded femoral component; and removing at least one of: the anterior flange, and the proximal extension from the molded femoral component to form a modified molded femoral component. Other implementations are described.

21 Claims, 88 Drawing Sheets

Related U.S. Application Data which is a continuation-in-part of application No. 14/828,340, filed on Aug. 17, 2015, now Pat. No. 9,427,332, which is a continuation of application No. 13/802,596, filed on Mar. 13, 2013, now Pat. No. 9,107,769, which is a continuation-in-part of application No. 13/758,855, filed on Feb. 4, 2013, now Pat. No. 9,101,478, which is a continuation of application No. 12/797,372, filed on Jun. 9, 2010, now Pat. No. 8,366,783, which is a continuation-in-part of application No. 12/482,280, filed on Jun. 10, 2009, now Pat. No. 8,382,846, which is a continuation-in-part of application No. 12/198,001, filed on Aug. 25, 2008, now Pat. No. 8,273,133.

(60) Provisional application No. 62/150,756, filed on Apr. 21, 2015, provisional application No. 60/972,191, filed on Sep. 13, 2007, provisional application No. 60/968,246, filed on Aug. 27, 2007.

(51) Int. Cl.
*A61F 2/38* (2006.01)
*B22D 23/00* (2006.01)
*B22D 25/02* (2006.01)
*B22D 23/02* (2006.01)
*A61F 2/30* (2006.01)
*B22D 25/00* (2006.01)
*A61B 17/15* (2006.01)

(52) U.S. Cl.
CPC ............ *B22D 23/00* (2013.01); *B22D 23/02* (2013.01); *B22D 25/02* (2013.01); *A61B 17/155* (2013.01); *A61F 2/30965* (2013.01); *A61F 2/3877* (2013.01); *A61F 2002/30018* (2013.01); *A61F 2002/30029* (2013.01); *A61F 2002/30116* (2013.01); *A61F 2002/30245* (2013.01); *A61F 2002/30604* (2013.01); *A61F 2002/30934* (2013.01); *A61F 2002/3863* (2013.01); *A61F 2002/3895* (2013.01); *A61F 2310/00011* (2013.01); *A61F 2310/00179* (2013.01); *A61F 2310/00329* (2013.01); *A61F 2310/00353* (2013.01); *B22D 25/00* (2013.01)

(56) References Cited

U.S. PATENT DOCUMENTS

| | | | |
|---|---|---|---|
| 4,721,104 A | 1/1988 | Kaufman et al. | |
| 4,743,261 A | 5/1988 | Epinette | |
| 4,865,606 A | 9/1989 | Rehder | |
| 5,133,760 A | 7/1992 | Petersen et al. | |
| 5,219,362 A | 6/1993 | Tuke et al. | |
| 5,236,461 A | 8/1993 | Forte | |
| 5,250,050 A | 10/1993 | Poggie et al. | |
| 5,258,032 A * | 11/1993 | Bertin .................. | A61B 17/155 606/88 |
| 5,358,527 A | 10/1994 | Forte | |
| 5,387,240 A | 2/1995 | Pottenger et al. | |
| 5,549,688 A | 8/1996 | Ries et al. | |
| 5,709,689 A * | 1/1998 | Ferrante ............... | A61B 17/155 606/80 |
| 5,728,162 A | 3/1998 | Eckhoff | |
| 5,788,916 A | 8/1998 | Caldarise | |
| 5,800,438 A | 9/1998 | Tuke et al. | |
| 5,824,100 A | 10/1998 | Kester et al. | |
| 5,879,389 A | 3/1999 | Koshino | |
| 5,925,049 A | 7/1999 | Gustilo et al. | |
| 5,964,808 A | 10/1999 | Blaha et al. | |
| 6,013,103 A | 1/2000 | Kaufman et al. | |
| 6,039,764 A | 3/2000 | Pottenger et al. | |
| 6,126,691 A | 10/2000 | Kasra et al. | |
| 6,146,424 A | 11/2000 | Gray, Jr. et al. | |
| 6,149,687 A | 11/2000 | Gray, Jr. et al. | |
| 6,159,217 A | 12/2000 | Robie et al. | |
| 6,190,415 B1 | 2/2001 | Cooke et al. | |
| 6,206,927 B1 | 3/2001 | Fell et al. | |
| 6,319,283 B1 | 11/2001 | Insall et al. | |
| 6,402,786 B1 | 6/2002 | Insall et al. | |
| 6,491,726 B2 | 12/2002 | Pappas | |
| 6,962,593 B2 * | 11/2005 | Sanford ............... | A61B 17/155 606/88 |
| 7,264,635 B2 | 9/2007 | Suguro et al. | |
| 7,297,164 B2 | 11/2007 | Johnson et al. | |
| 7,326,252 B2 | 2/2008 | Otto et al. | |
| 7,615,082 B2 | 11/2009 | Naegerl et al. | |
| 7,766,969 B2 | 8/2010 | Justin et al. | |
| 8,273,133 B2 | 9/2012 | Samuelson | |
| 8,366,783 B2 | 2/2013 | Samuelson et al. | |
| 8,382,846 B2 | 2/2013 | Samuelson et al. | |
| 8,715,357 B2 | 5/2014 | Samuelson et al. | |
| 8,715,360 B2 | 5/2014 | Samuelson et al. | |
| 8,715,361 B2 | 5/2014 | Samuelson et al. | |
| 8,721,731 B2 | 5/2014 | Samuelson et al. | |
| 8,721,732 B2 | 5/2014 | Samuelson et al. | |
| 8,784,497 B2 | 7/2014 | Samuelson et al. | |
| 9,101,478 B2 | 8/2015 | Samuelson et al. | |
| 9,107,769 B2 | 8/2015 | Samuelson et al. | |
| 9,265,624 B2 | 2/2016 | Samuelson et al. | |
| 9,320,616 B2 | 4/2016 | Samuelson et al. | |
| 9,265,615 B2 | 5/2016 | Samuelson et al. | |
| 9,326,867 B2 | 5/2016 | Samuelson et al. | |
| 9,326,868 B2 | 5/2016 | Samuelson et al. | |
| 9,339,391 B2 | 5/2016 | Samuelson et al. | |
| 9,427,332 B2 | 8/2016 | Samuelson et al. | |
| 2002/0115934 A1 | 8/2002 | Tuke | |
| 2003/0100953 A1 | 5/2003 | Rosa et al. | |
| 2003/0139817 A1 | 7/2003 | Tuke et al. | |
| 2004/0006393 A1 | 1/2004 | Burkinshaw | |
| 2004/0078042 A1 | 4/2004 | Masini | |
| 2004/0243244 A1 | 12/2004 | Otto et al. | |
| 2004/0260301 A1 * | 12/2004 | Lionberger .......... | A61B 17/155 606/88 |
| 2005/0021147 A1 | 1/2005 | Tarabichi | |
| 2005/0096747 A1 | 5/2005 | Tuttle et al. | |
| 2005/0143837 A1 | 6/2005 | Ferree | |
| 2005/0197710 A1 | 9/2005 | Naegerl | |
| 2005/0278034 A1 | 12/2005 | Johnson et al. | |
| 2006/0004465 A1 | 1/2006 | Bergin et al. | |
| 2007/0135926 A1 | 6/2007 | Walker | |
| 2008/0009950 A1 | 1/2008 | Richardson | |
| 2008/0058945 A1 | 3/2008 | Hajaj et al. | |
| 2008/0140212 A1 | 6/2008 | Metzger et al. | |
| 2008/0161918 A1 | 7/2008 | Fankhauser et al. | |
| 2008/0243258 A1 | 10/2008 | Sancheti | |
| 2009/0043395 A1 | 2/2009 | Hotokebuchi et al. | |
| 2009/0082873 A1 | 3/2009 | Hazebrouck et al. | |
| 2009/0088861 A1 | 4/2009 | Tuke et al. | |
| 2009/0149963 A1 | 6/2009 | Sekel | |
| 2009/0326667 A1 | 12/2009 | Williams et al. | |
| 2010/0036499 A1 | 2/2010 | Pinskerova | |
| 2011/0266265 A1 | 11/2011 | Lang | |
| 2012/0209394 A1 | 8/2012 | Bojarski et al. | |
| 2013/0024002 A1 | 1/2013 | Samuelson | |
| 2013/0204252 A1 | 8/2013 | Samuelson et al. | |
| 2014/0142713 A1 | 5/2014 | Wright et al. | |
| 2015/0351920 A1 | 12/2015 | Samuelson et al. | |
| 2016/0038292 A1 | 2/2016 | Samuelson et al. | |
| 2016/0235541 A1 | 8/2016 | Samuelson et al. | |
| 2016/0242915 A1 | 8/2016 | Samuelson et al. | |
| 2016/0242916 A1 | 8/2016 | Samuelson et al. | |
| 2016/0242918 A1 | 8/2016 | Samuelson et al. | |
| 2016/0256283 A1 | 9/2016 | Samuelson et al. | |

FOREIGN PATENT DOCUMENTS

| | | |
|---|---|---|
| EP | 0 978 261 A1 | 2/2000 |
| GB | 1360485 | 7/1974 |
| JP | H01068257 | 3/1989 |
| JP | H02203854 | 8/1990 |
| JP | H10155824 | 6/1998 |

(56) References Cited

FOREIGN PATENT DOCUMENTS

| | | |
|---|---|---|
| JP | 2007509709 | 4/2007 |
| JP | 2007152116 | 6/2007 |
| JP | 2009515610 | 4/2009 |
| WO | WO 1994/20047 A1 | 9/1994 |
| WO | WO 1996/024311 A1 | 8/1996 |
| WO | WO 1998/052499 A1 | 5/1998 |
| WO | WO 2003/099106 A2 | 12/2003 |
| WO | WO 2004/058108 A1 | 7/2004 |
| WO | WO 2004/066882 A1 | 8/2004 |
| WO | WO 2006/092167 A1 | 9/2006 |
| WO | WO 2007/007841 A1 | 1/2007 |
| WO | WO 2007/053905 A2 | 10/2007 |
| WO | WO 2007/119173 A2 | 10/2007 |
| WO | WO 2008/028481 A1 | 3/2008 |
| WO | WO 2009/029631 A1 | 3/2009 |
| WO | WO 2010/144736 A1 | 12/2010 |

\* cited by examiner

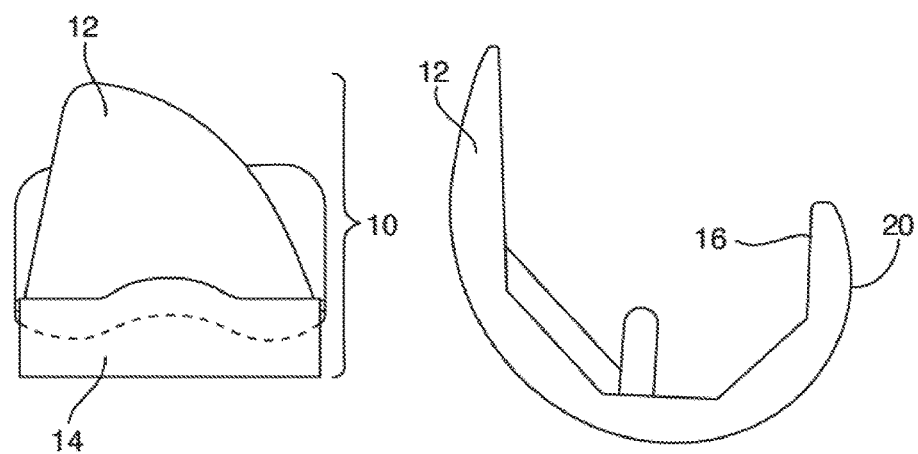
FIG. 3A
(PRIOR ART)
FIG. 3B
(PRIOR ART)
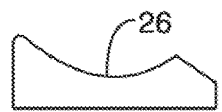
FIG. 3C
(PRIOR ART)

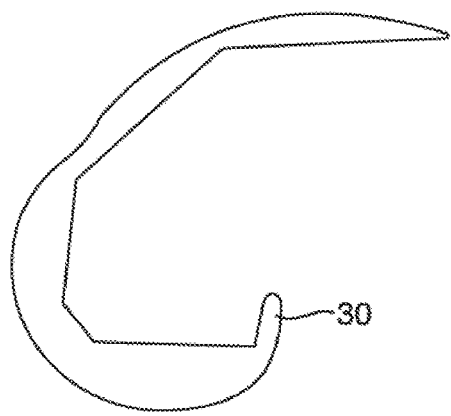
FIG. 4A
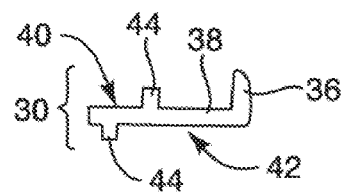
FIG. 4B
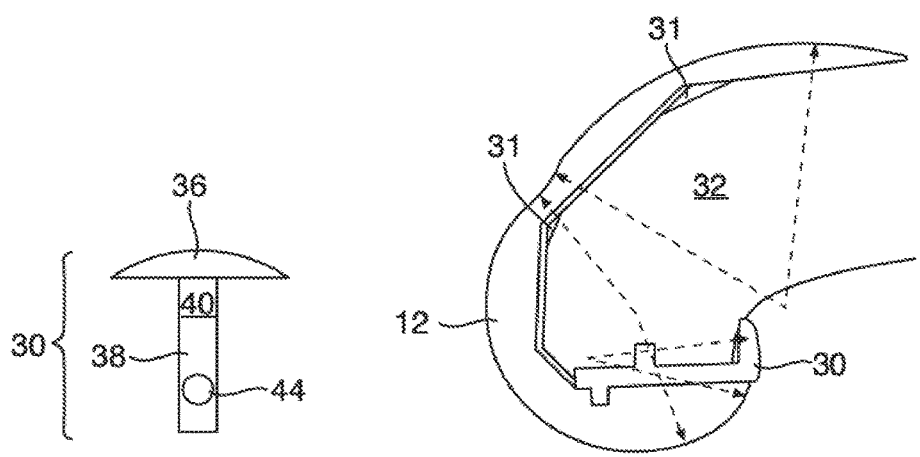
FIG. 4C
FIG. 4D

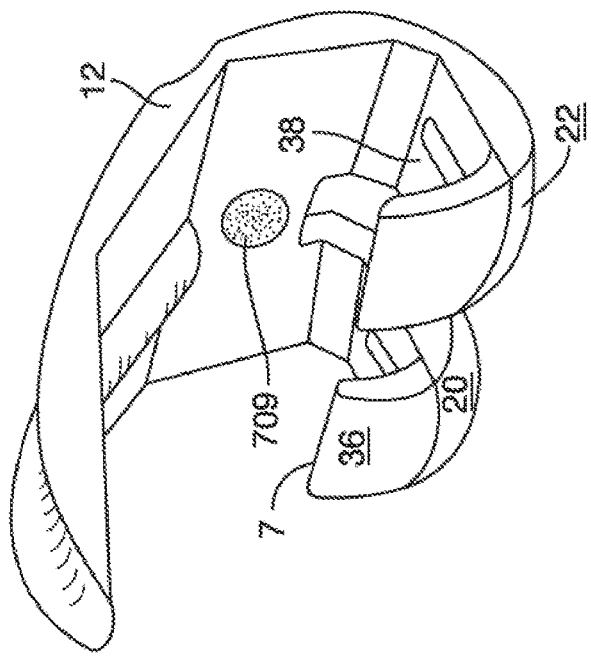
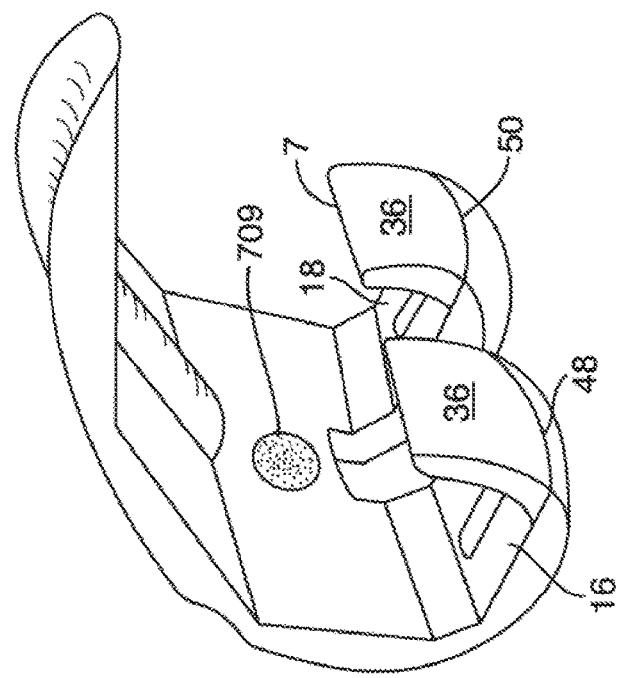
FIG. 5D
FIG. 5C

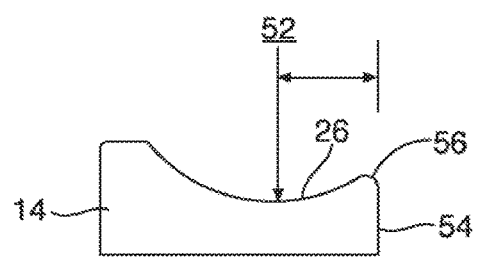
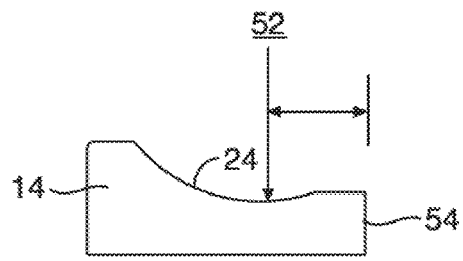
FIG. 6A  FIG. 6B
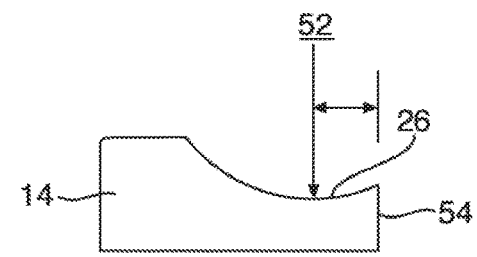
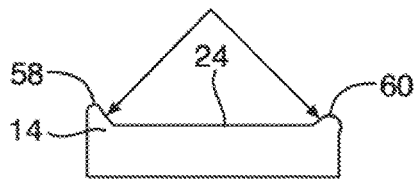
FIG. 6C  FIG. 6D
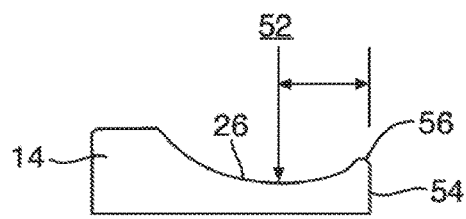
FIG. 6J  FIG. 6K

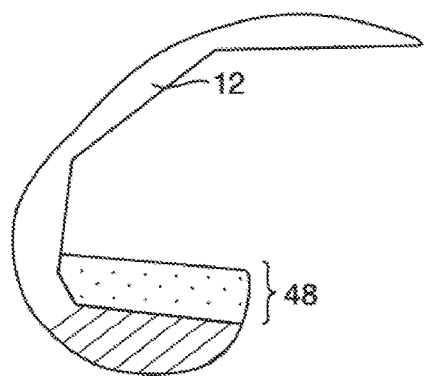
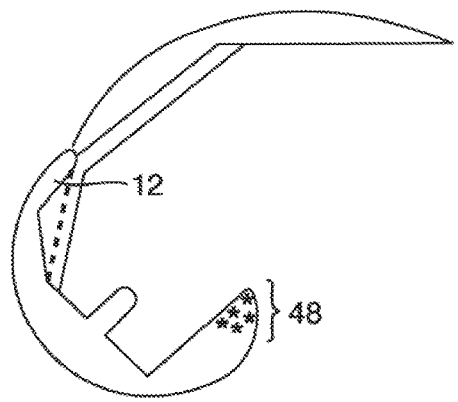
FIG. 15A          FIG. 15B
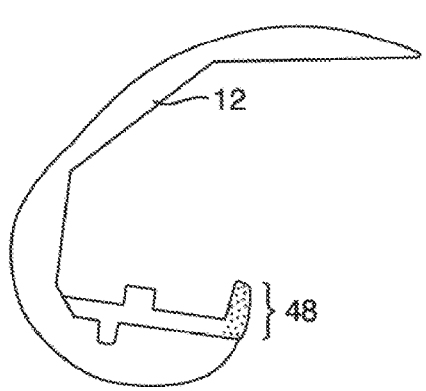
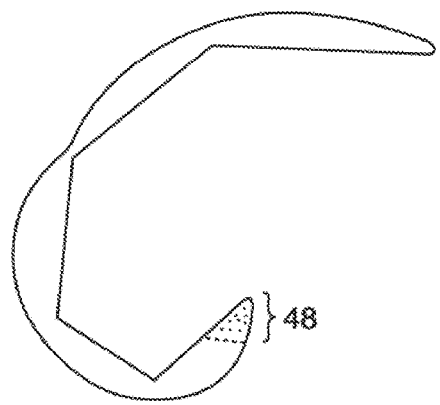
FIG. 15C          FIG. 15D
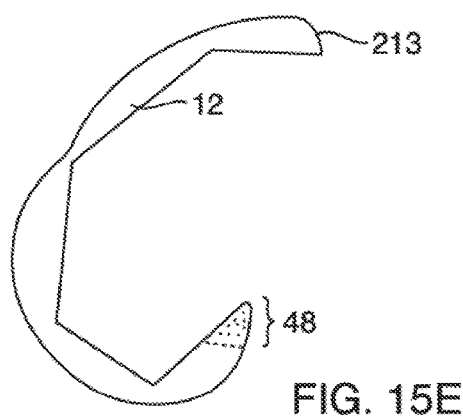
FIG. 15E

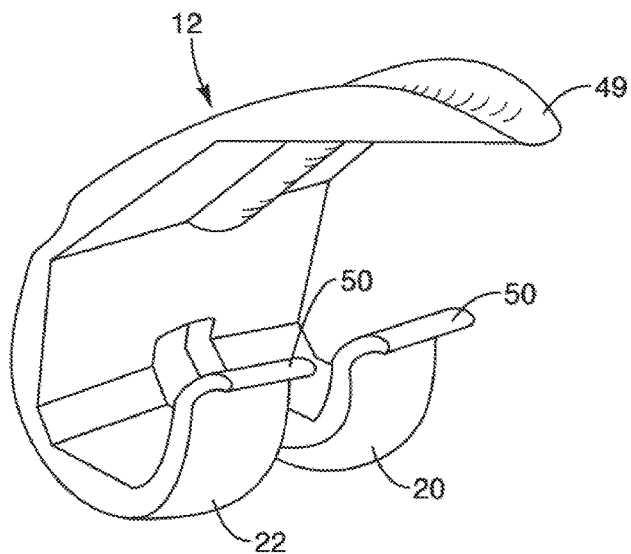
FIG. 15F
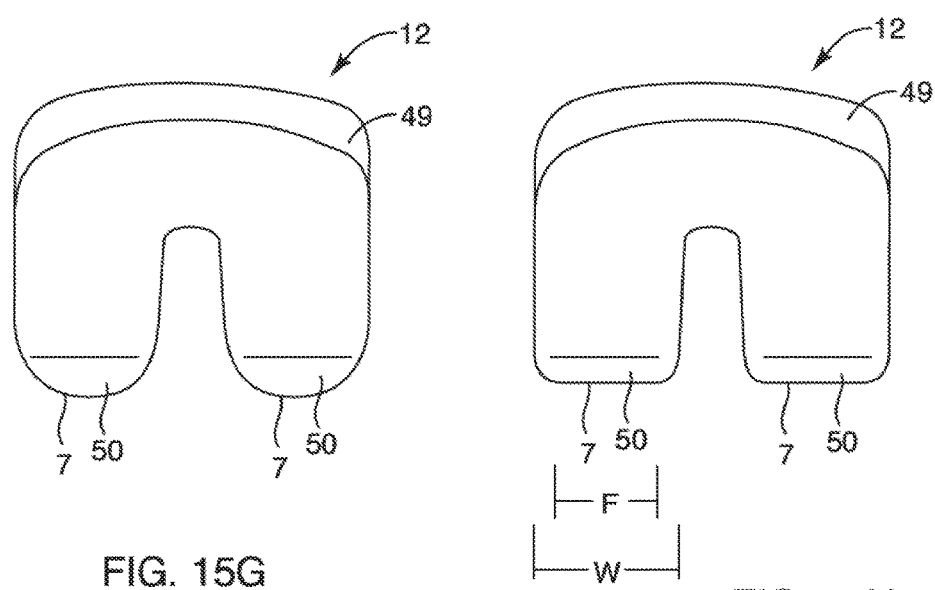
FIG. 15G
FIG. 15H

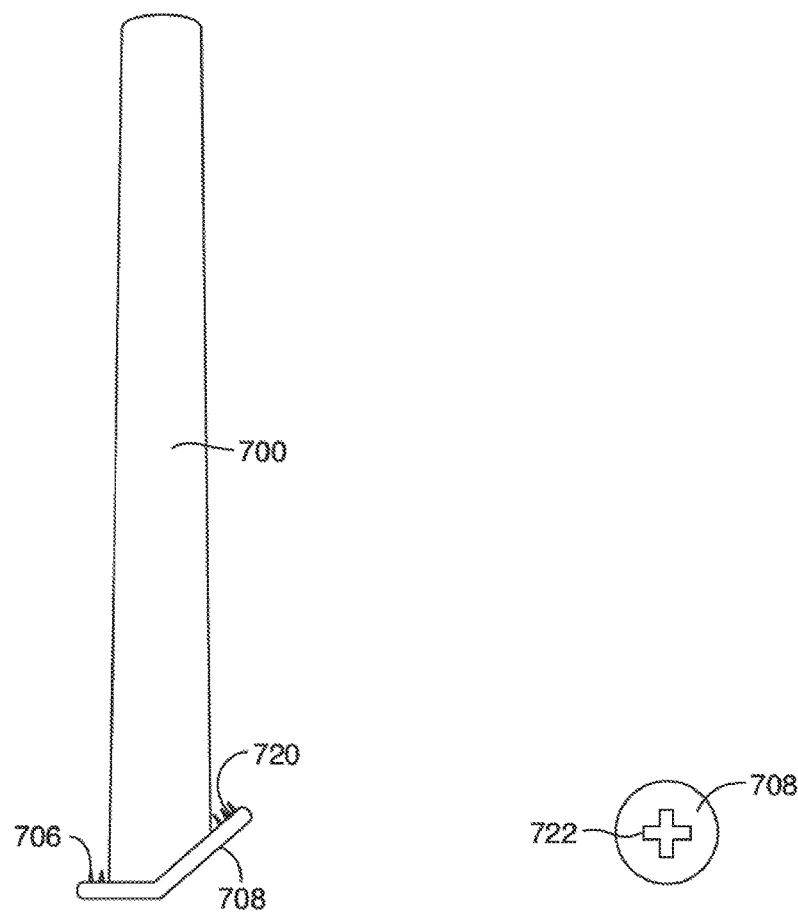

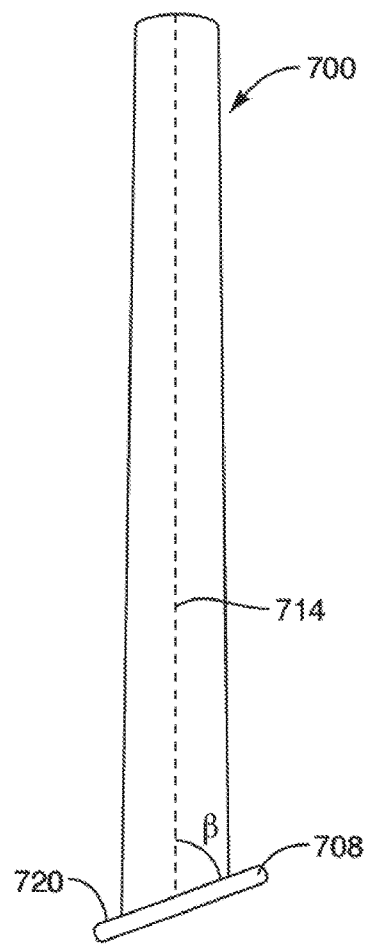
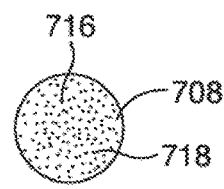 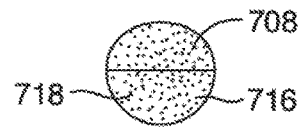
FIG. 31A
FIG. 31B          FIG. 31C

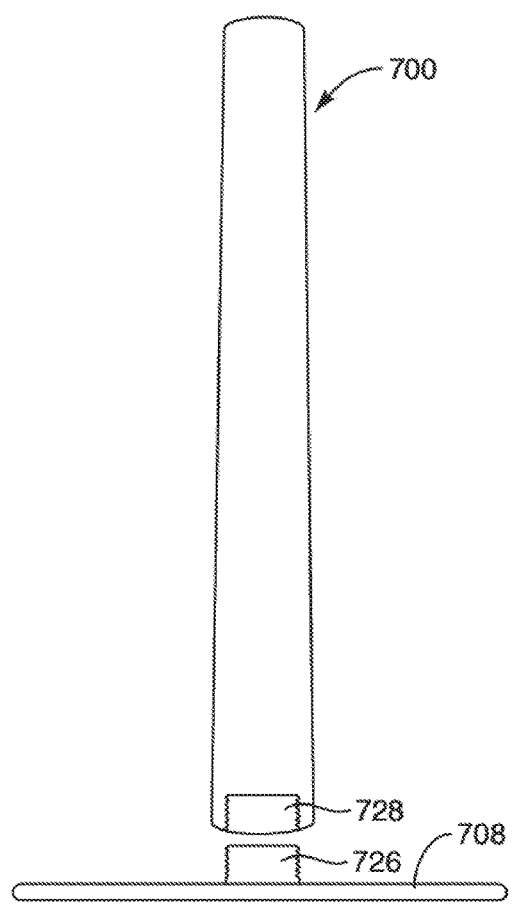
FIG. 36A
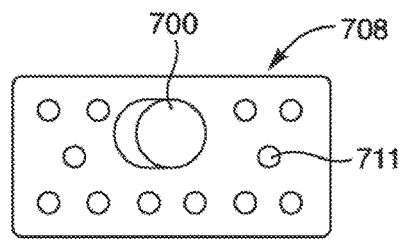 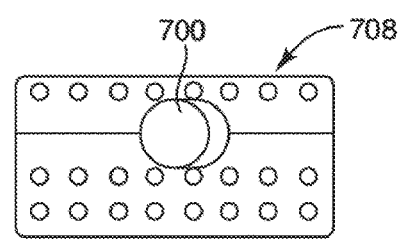
FIG. 36B  FIG. 36C

SYSTEMS AND METHODS FOR PROVIDING PROSTHETIC COMPONENTS

RELATED APPLICATIONS

This is a continuation-in-part application of U.S. patent application Ser. No. 14/975,736, filed Dec. 19, 2015, and entitled SYSTEMS AND METHODS FOR PROVIDING A FEMORAL COMPONENT HAVING A MODULAR STEM, which is a continuation-in-part application of U.S. patent application Ser. No. 14/828,340, filed Aug. 17, 2015, and entitled SYSTEMS AND METHODS FOR PROVIDING A FEMORAL COMPONENT, which is a continuation application of U.S. patent application Ser. No. 13/802,596, filed Mar. 13, 2013, and entitled SYSTEMS AND METHODS FOR PROVIDING A FEMORAL COMPONENT, which is a continuation-in-part application of U.S. patent application Ser. No. 13/758,855 (now U.S. Pat. No. 9,101,478), filed Feb. 4, 2013, and entitled SYSTEMS AND METHODS FOR PROVIDING STEM ON A TIBIAL COMPONENT, which is a continuation application of U.S. patent application Ser. No. 12/797,372 (now U.S. Pat. No. 8,366,783), filed Jun. 9, 2010, and entitled SYSTEMS AND METHODS FOR PROVIDING DEEPER KNEE FLEXION CAPABILITIES FOR KNEE PROSTHESIS PATIENTS, which is a continuation-in-part of U.S. patent application Ser. No. 12/482,280 (now U.S. Pat. No. 8,382,846), filed Jun. 10, 2009, and entitled SYSTEMS AND METHODS FOR PROVIDING DEEPER KNEE FLEXION CAPABILITIES FOR KNEE PROSTHESIS PATIENTS, which is a continuation-in-part of U.S. patent application Ser. No. 12/198,001 (now U.S. Pat. No. 8,273,133), filed Aug. 25, 2008, and entitled SYSTEMS AND METHODS FOR PROVIDING DEEPER KNEE FLEXION CAPABILITIES FOR KNEE PROSTHESIS PATIENTS, which claims priority to U.S. Provisional Patent Application Ser. No. 60/968,246, filed Aug. 27, 2007, and entitled SYSTEMS AND METHODS FOR PROVIDING DEEPER KNEE FLEXION CAPABILITIES FOR KNEE PROSTHESIS PATIENTS, and to U.S. Provisional Patent Application Ser. No. 60/972,191, filed Sep. 13, 2007, and entitled SYSTEMS AND METHODS FOR PROVIDING DEEPER KNEE FLEXION CAPABILITIES FOR KNEE PROSTHESIS PATIENTS, all of which are incorporated herein in their entirety by reference.

This application also claims priority to U.S. Provisional Patent Application No. 62/150,756, filed Apr. 21, 2015, entitled SYSTEMS AND METHODS FOR PROVIDING LIGHTWEIGHT PROSTHETIC IMPLANTS, which is incorporated herein in its entirety by reference.

BACKGROUND OF THE INVENTION

1. Field of the Invention

The present invention relates to prostheses, including, without limitation, knee prostheses. In particular, some implementations of the present invention relate to systems and methods for providing prosthetic implants that are relatively lightweight. While the implants can be produced in any suitable manner and have any suitable feature that allows them to be lightweight, in some instances, such implants include an internal lattice structure that supports the implants, while allowing the implants to be relatively lightweight and rigid.

2. Background and Related Art

Orthopedic surgeons are experiencing a proliferation of joint replacement surgeries. This demand appears to be driven by the fact that few procedures return as much quality of life as do joint replacements.

One common joint replacement surgery that can be especially useful in returning quality of life to an individual is that of knee replacement surgery. In this regard, the increased need for knee replacements implicates the need for durable and long lasting artificial knee devices that provide for and allow full, functional flexion. That is, there is a great need for research that provides new medical advances on the overall function and performance of knee prostheses, and improves corresponding surgical materials and technologies related to such devices.

Improvements to knee prostheses correspondingly increase with demand. Thus, currently-available knee prostheses mimic characteristics of the normal knee more than those previously used. Unfortunately, some of today's knee prostheses still have shortcomings.

Among these shortcomings is the inability of a knee prosthesis patient to achieve deep knee flexion, also known as full functional flexion. Though some currently available knee prostheses allow for knee flexion (i.e., bending) of more than 130° from full limb extension (0° being when the patient's knee is fully extended and straight); some such prostheses do not allow patients to flex from full extension to 160° and beyond (e.g., to full functional and/or deep knee flexion). Full functional or deep knee flexion is where the leg is bent to its maximum extent, which may be with the femur and tibia at an angle to each other of 140° or more, though the actual angle varies from person to person and with body habitus.

To illustrate the average range of knee motion in degrees achieved by patients having standard knee prostheses surgery, the following is provided: When a patient's knee or limb is fully extended, the femur and tibia are typically in the same plane at 0°, or up to 5-10° of hyperextension in some individuals. However, once the knee bends, and the distal tibia moves toward the buttocks, the angle increases from 0° to 90° for a person sitting in a chair. Furthermore, when the tibia is closest to the femur, and the heel is almost at, if not touching, the buttock, the angle is around 160° or more. Most conventional knee prosthesis patients are unable to consistently achieve the latter position or any position placing the knee joint at angles above 130° (e.g., at 160° and beyond).

For many people, such a limb and body position is not often achieved or desired most of the time. However, nearly everyone, at some point in time, whether or not it occurs when a person is getting on and off the ground to play with children, or merely incidental to living an active lifestyle, finds themselves in a position requiring knee flexion greater than 130°. Unfortunately, those with currently-available knee prostheses are unable to participate in any activity requiring greater knee flexion and are thus limited to watching from the sidelines.

In many populations and cultures such a limb/knee and body position is desired and necessary the majority of the time. For instance, in some Asian and Indian cultures, full functional flexion and the squatting position is common and performed for relatively long periods of time.

A need, therefore, exists for knee prostheses for those patients and especially for those in cultures where extensive squatting, sitting with knees fully flexed, and/or kneeling when praying or eating is common, to achieve knee flexion greater than presently possible among some of those who have currently-available knee prostheses.

As another example of a potential shortcoming associated with some conventional knee prostheses, some such prostheses are relatively heavy. Nevertheless, in many cases such prostheses are implanted into elderly recipients or, even if the prostheses are implanted into younger recipients, the implants are intended to remain with their recipients until such recipients age and eventually die. Accordingly, there is a need for prosthetic implants that are relatively lightweight and that do not require their recipients to carry unnecessary weight from such implants throughout their life.

As still another potential shortcoming, some conventional prostheses are relatively more rigid then the bones into which they are implanted. For instance, in some cases, a prosthetic stem extending in a medullary canal is more rigid then the cancellous bone around such a stem. As a result, in some cases, bone surrounding the rigid stem may not flex as it should. In this regard, as such a bone may experience less of the flexion forces than would typically strengthen the bone, such a bone may actually become weak and resorb. Additionally, in some cases as the bone surrounding a rigid shaft flexes, micro-abrasions may occur at the interface between the bone and the stem, resulting in the loss of bone at the interface. Moreover, in some instances in which a prosthetic implant keeps a portion of a long bone rigid, stresses that would normally be spread across a length of the bone are spread across a smaller area of the bone, often forming a stress riser in the bone at an end of the prosthetic (e.g., at an end of a rigid stem).

As still another example, some femoral prostheses place relatively large loads on the distal end of the femur, and do little to dissipate such loads. As a result, some such prostheses may do little to prevent fractures from forming and spreading in the femur (e.g., at stress risers created as a consequence of bone cuts that were made to allow the femoral prosthesis to be seated on the femur).

As yet another example, although some femoral prostheses comprise a stem to strengthen the femur's distal end, such stems often place significant limits on the physical characteristics of the femoral prosthesis that can be used therewith. Additionally, in some cases in which a femoral prosthesis includes a stem, the stem can also limit the manner in which the femoral prosthesis can be attached to a femur.

Thus, while techniques currently exist that relate to prosthetic implants (such as knee prostheses), challenges with such implants still exist, including those discussed above. Accordingly, it would be an improvement in the art to augment or even replace current techniques with other techniques.

SUMMARY OF THE INVENTION

Some aspects of the present invention relate to systems and methods for providing relatively lightweight prostheses. In some such instances, the described systems and methods include a prosthetic implant having an exterior surface that is configured to be coupled to and/or to articulate with a bone (and/or another prosthetic component), an interior space disposed within the implant, and a lattice structure disposed within the interior space. Some examples of such an implant include a femoral knee component, a tibial knee component, an intramedullary stem, and/or any other suitable implant. Additionally, in some cases, a portion of the implant is configured to have a modulus of elasticity that substantially matches that of the bone to which the implant couples. While the elasticity of the bone and the implant can be matched in any suitable manner, in some cases, the elasticity of one or more portions of the implant is modified by varying the strength provided to the implant by the lattice structure.

Additionally, some aspects of the present invention relate to systems and methods for providing deeper knee flexion capabilities for knee prosthesis patients, and more particularly by effectuating one or more of the following: (i) providing a greater articular surface area to the femoral component of a knee prosthesis, with either a modification of, or an attachment to the femoral component of a knee prosthesis, which when integrated with a patient's femur and an appropriate tibial component, results in full functional flexion; (ii) providing modifications to the internal geometry of the femoral component and the opposing femoral bone with methods of implanting; (iii) providing asymmetrical under surfaces on the tibial component of the knee prosthesis and uniquely-positioned articular surfaces to facilitate full functional flexion; (iv) providing asymmetrical femoral condylar surfaces with a lateralized patellar (trochlear) groove to more closely replicate physiologic loading of the knee and to provide better tracking of the patella; (v) resectioning essentially all of the anterior femoral articular cartilage and underlying bone, but no additional bone and replacing it with a femoral component that does not have an anterior flange as seen on contemporary prostheses; (vi) providing a femoral component having a modular stem, which allows the femoral component to be rolled onto a resected portion of a distal end of the femur, or to be slid onto the resected portion of the femur at an angle that intersects with a longitudinal axis of the femur; (vii) cutting a posterior proximal portion of a femoral condyle to allow for deep knee flexion; and (viii) providing a process for providing customized prosthetics.

In a normal knee, there is often a cessation of active flexion at approximately 120°, first, because the hamstring muscles lose their mechanical advantage, and secondly because the medial femoral condyle rolls posteriorly which does not occur up to 120°. By 120° of flexion, the medial femoral condyle often starts to roll backwards relative to the posterior horn of the medial meniscus of the tibia. At 140° of flexion, the femur moves up on to the posterior horn of the medial meniscus. Accordingly, resistance to flexion is felt at this point and beyond. By full flexion, the medial femoral condyle has moved back approximately 8 mm from its position at 120° to a position 10 mm from the posterior tibial cortex. Laterally, the femur moves back an additional 5 mm in hyperflexion so that there is little or no tibiofemoral rotation between 120° and 160°. Accordingly, the hyperflexion between 120° and 160° is a separate arc than the kinematics from 0° to 120° of flexion, and at 160°, the posterior horn of the lateral meniscus comes to lie on the posterior surface of the tibia distal to the femoral condyle. As such, the posterior horn is not compressed and the two bones are in direct contact.

The final limit to hyperflexion arises because the posterior horn of the medial meniscus impedes flexion at 140° and limits it absolutely at 160°. The posterior horn also often prevents the medial femoral condyle from moving back beyond a point 10 mm from the posterior tibial cortex. Thus, the posterior horn of the medial meniscus is a key structure in achieving deep flexion.

Implementation of the present invention takes place in association with improved knee prostheses that enable knee prosthesis patients to achieve greater deep knee flexion than previously achievable using presently-designed knee prostheses. In at least some implementations of the present invention, greater deep knee flexion is provided to the knee prosthesis by resecting portions of the femur to allow additional clearance for the posterior horn of the medial meniscus and the tibia. In other implementations in which a portion of the tibia is replaced by a prosthesis, however, the posterior horn is left intact. Additionally, at least some implementations of the present invention further provide positioning and/or installing an articular surface within resectioned portions of the femur to provide an interface between the posterior horn of the medial meniscus and the resectioned surface of the femur.

In at least some implementations of the present invention, greater deep knee flexion is provided to the knee prosthesis by providing an articular surface on the proximal, anterior surface (or portion) of the posterior condyles of the femur. At least some implementations of the present invention embrace an additional or increased articular surface on the proximal, anterior portion of either or both of the medial or lateral posterior condyles of the femoral component of the prosthesis. Embodiments of the femoral component add increased articular surface area to the proximal end of the posterior condyles of the femoral component in an anterior direction such that when the patient bends his or her knee during deep knee flexion, contact between the femoral component and the tibial component is maintained, and a greater, deeper knee flexion can be achieved.

In at least some implementations of the present invention, greater deep knee flexion can be provided or improved by modifying the tibial articulation, in which the center of the conforming medial tibial articular surface of the tibial component of the prosthesis is moved posterior relative to what is currently available. Additionally, in some such embodiments, the overall shape of the lateral tibial articular surface is modified.

In at least some implementations of the present invention, greater deep knee flexion can be achieved by providing an asymmetrical femoral component of the prosthesis. The asymmetrical femoral component permits transfer of more than one-half of the force transmitted across the joint to be transmitted to the medial side, as occurs in the normal knee. In some implementations, other modifications to the tibial and femoral components of a knee prosthesis may be made, including having asymmetric femoral condyles, having a closing radius on the femoral component, having a lateral femoral condyle with an articular surface that is substantially flat, and/or removing certain areas of the tibial and femoral components; wherein all of the foregoing may result in deeper knee flexion capabilities for knee prosthesis patients than previously achievable.

At least some implementations of the present invention include a femoral component (and associated methods for making and using such a component) that includes a femoral articular surface extending in an anterior direction from a proximal end of a posterior condyle of a femoral knee replacement component, the femoral component further having a full anterior articular extension which replaces the anterior articular cartilage of a femur. In some cases, the femoral component includes a first interior surface and a second interior surface that run substantially parallel to each other. In other cases, the first interior surface and the second interior surface of the femoral component diverge from each other less than a 45° angle. In some instances, the first interior surface and the second interior surface diverge from each other by an angle between approximately 3° and approximately 10°.

In some implementations in which the described systems and methods relate to the femoral component having a modular stem, the stem and femoral component are configured such that the femoral component can either be rolled onto a resected portion of the femur, or to be slid onto the resected portion at an angle that intersects a longitudinal axis of a distal portion of the femur, after the modular femoral stem has been inserted into the femur.

With respect to the femoral component having one or more modular femoral stems, both the femoral component and the modular stem can have any suitable characteristic. For instance, the femoral component can comprise any suitable femoral component that is configured to be fixedly attached to the stem after the stem has been inserted into the femur (e.g., within the femurs intramedullary canal). Indeed, in some implementations, the femoral component comprises a thickened posterior condyle, an extended articulation surface, one or more internal surfaces that require the femoral component to be rolled onto a resectioned portion of the femur, a modular attachment, a proximal extension, a medial femoral condylar surface, a lateral femoral condylar surface, an anterior extension that terminates at or adjacent to a proximal limit of the knee's articular cartilage, one or more internal surfaces that require the femoral component to be slid on to the femur at an angle that intersects with a longitudinal axis of a distal portion of the femur, a modular flange, a mating surface that is configured to be permanently fixed to the modular femoral stem, and/or any other suitable component or characteristic.

With respect to the modular femoral stem, the femoral stem can comprise any suitable component or characteristic that allows it to be inserted into a distal portion of the femur and then to be attached to the femoral component. In this regard, the stem can be any suitable size and shape that allows it to be inserted into the femur and then to be connected to the femoral component. In some implementations, the stem further comprises a flange at its distal end that allows the flange to be permanently fixed to the femoral component (e.g., via cement).

Additionally, in some implementations, the described systems relate to a femoral knee replacement component that includes a modular femoral stem having a proximal end and a distal end; a femoral component having an external articular surface and an internal surface, wherein the internal surface is configured to be attached to a resectioned portion of a distal end of a femur, and wherein the femoral component is configured to be applied to the femur by at least one of: sliding the femoral component onto the resectioned portion of the femur at an angle of between about 20 and about 80° with respect to a longitudinal axis of a distal one fourth to a distal one third of the femur, and rolling the femoral component onto the resectioned portion of the femur, wherein the internal surface of the femoral component comprises a mating surface that is configured to be permanently fixed to the distal end of one or more modular stems.

In other implementations, the described systems relate to a femoral knee replacement component, including: a modular intramedullary stem having a proximal end and a distal end, wherein the distal end comprises a flange; and a femoral component having an articular surface and an internal surface, wherein the femoral component is configured to be applied to a femur by sliding the femoral component onto a resectioned portion of a distal end of the femur at an angle of between about 20 and about 80° with respect to a longitudinal axis of about a distal one fourth to about a distal one third of the femur, wherein a distal cut surface of the femoral component's internal surface is configured to be permanently fixed to the flange of the modular stem.

Additionally, in some implementations, the described methods relate to a method of applying a femoral component to a femur. In some such implementations, the method includes preparing the femur to receive the femoral component by removing bone from a distal portion of the femur; providing a modular intramedullary stem having a proximal end and a distal end; inserting the modular stem into an intramedullary canal (or other suitable portion) of the femur; providing the femoral component (wherein the femoral component and the modular stem each comprise a discrete component, and wherein the femoral component comprises an articular surface and an internal surface); seating the femoral component on the distal portion of the femur (wherein the seating is accomplished by sliding the femoral component onto a resectioned surface of the femur at an angle of between about 20 and about 80° with respect to a longitudinal axis of about a distal one fourth to about a distal one third of the femur and/or rolling the femoral component onto the resectioned surface of the femur); and fixing the distal end of the modular stem to the internal surface of the femoral component.

In still other implementations, the described systems and methods relate to the use of a cutting guide block that is configured to be used to direct a cutting instrument to remove a proximal portion of a posterior condyle. In some implementations, this cutting block is configured to guide a cutting tool to cut a full flexion cut on the femur (or a cut that runs proximally and anteriorly from its distal end towards a posterior surface of the femur, such as a posterior surface of the femur's shaft).

In yet other implementations, the described systems and methods relate to processes for using a single master negative mold architecture to produce multiple prostheses having a variety of optional component or characteristics. Indeed, in some implementations, a negative master mold defining a space for a prosthetic component with at least one optional portion is provided, a positive prosthetic blank is formed in the master negative mold, at least one optional component (e.g., an anterior flange, a lateral proximal extension, a medial proximal extension, etc.) is removed from the positive blank, the modified positive blank is coated with an investment, the positive blank is removed from the investment, and a prosthetic material is placed in the investment to form a prosthetic that is missing the optional component.

While the methods, modifications and components of the present invention have proven to be particularly useful in the area of knee prostheses, those skilled in the art will appreciate that the methods, modifications and components can be used in a variety of different orthopedic and medical applications.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIGS. 2A-2C and 3A-3C depict various views of a generic knee prosthesis;

FIGS. 4A-4D depict representative perspective views of embodiments of a femoral component of a knee prosthesis in accordance with representative embodiments of the present invention;

FIGS. 5A-5D depict representative perspective views of embodiments of the femoral component of a knee prosthesis in accordance with embodiments of the present invention;

FIGS. 6A-6B depict side views of a representative prior art tibial component of a knee prosthesis;

FIGS. 6C-6D depict side views of a representative embodiment of a tibial component in accordance with embodiments of the present invention;

FIGS. 6J and 6K depict side views of a representative embodiment of a tibial component in accordance with embodiments of the present invention;

FIG. 8A illustrates a conventional femoral component while

FIGS. 15A-15E illustrate comparisons between embodiments of the femoral component;

FIG. 15F illustrates a perspective view of a representative embodiment of the femoral component comprising a lateral proximal extension and a medial proximal extension;

FIGS. 15G-15H each respectively illustrate an angled top view showing a representative embodiment in which the proximal extension (or the femoral full flexion articulation) comprises respectively comprises a rounded and a substantially flat posterior end;

FIG. 30C illustrates side view of a representative embodiment of the modular femoral stem, wherein the stem comprises a multifaceted flange;

FIG. 30D illustrates a view of a distal surface of a representative embodiment of the modular femoral stem, wherein the stem comprises a flange defining a receptacle for a turning tool;

FIG. 31A illustrates an anterior face view of a representative embodiment of the modular femoral stem, wherein the stem comprises a flange that is configured to hold the stem at an angle with respect to the femoral component;

FIG. 31B illustrates a view of a distal surface of a representative embodiment of the flange of the modular stem;

FIG. 31C illustrates a view of a distal surface of a representative embodiment of the flange of the modular stem, wherein the flange is multifaceted;

FIG. 36A illustrates a side, cross-sectional view of the modular femoral stem and a corresponding flange that is configured to couple with the femoral stem in accordance with a representative embodiment;

FIGS. 36B-36C each illustrate a top plan view of a different representative embodiment of the femoral stem coupled to the flange;

DETAILED DESCRIPTION OF THE INVENTION

Figure 1A:
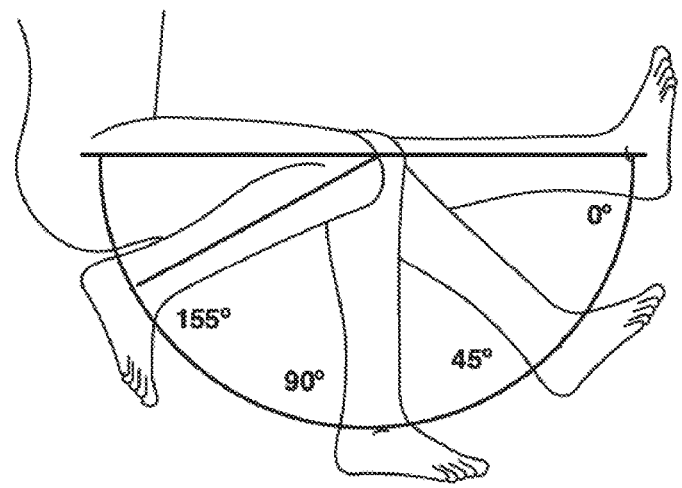
FIGS. 1A and 1B depict ranges of flexion of a knee joint.
Figure 1B:
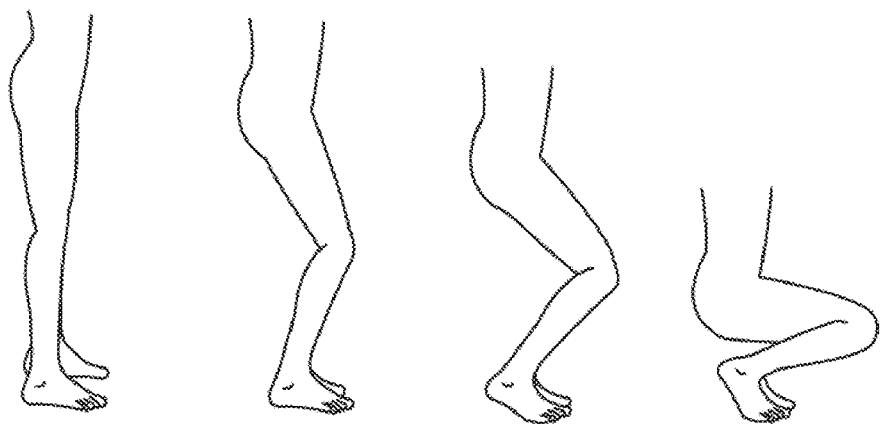

Some aspects of the present invention relates to prosthetic implants. More specifically, while some aspects of the present invention relate to prosthetic knee implants that allow for a relatively high degree of knee flexion, other aspects relate to systems and methods for providing relatively lightweight prosthetic implants.

The following disclosure of the present invention is grouped into two subheadings, namely "High Flexion Knee Components" and "Lightweight Prosthetic Implants." The utilization of subheadings is for convenience of the reader and is not, in any way, to be construed as limiting in any sense.

High Flexion Knee Components

With respect to the high flexion knee components, some aspects of the present invention relates to knee prostheses. In particular, some implementations of the present invention relate to systems and methods for providing deeper knee flexion capabilities for knee prosthesis patients, and more particularly, to systems and methods for: (i) providing a greater articular surface area to the femoral component of a knee prosthesis, with either a modification of, or an attachment to the femoral component of a knee prosthesis, which when integrated with a patient's femur and an appropriate tibial component, results in full functional flexion; (ii) providing modifications to the internal geometry of the femoral component and the opposing femoral bone with methods of implanting; (iii) providing asymmetrical under surfaces on the tibial component of the knee prosthesis and uniquely-positioned articular surfaces to facilitate full functional flexion; (iv) providing asymmetrical femoral condylar surfaces with a lateralized patellar (trochlear) groove to more closely replicate physiologic loading of the knee and to provide better tracking of the patella; (v) resectioning essentially all of the anterior femoral articular cartilage and underlying bone, but no additional bone and replacing it with a femoral component that does not have an anterior flange as seen on contemporary prostheses; (vi) providing a femoral component having a modular stem, which allows the femoral component to be rolled onto a resected portion of a distal end of the femur, or to be slid onto the resected portion of the femur at an angle that intersects with a longitudinal axis of the femur; (vii) cutting a posterior proximal portion of a femoral condyle to allow for deep knee flexion; and (viii) providing a process for providing customized prosthetics. In some implementations in which the described systems and methods relate to the femoral component having a modular stem, the stem and femoral component are configured such that the femoral component can either be rolled onto a resected portion of the femur, or to be slid onto the resected portion at angle that intersects a longitudinal axis of a distal portion of the femur, after the modular femoral stem has been inserted into the femur.

It is emphasized that the present invention, as illustrated in the FIGS. and description herein, may be embodied in other forms. Thus, neither the drawings nor the following more detailed description of the various embodiments of the system and method of the present invention limit the scope of the invention. The drawings and detailed description are merely representative of examples of embodiments of the invention; the substantive scope of the present invention is limited only by the appended claims recited to describe the many embodiments. The various embodiments of the invention will best be understood by reference to the drawings, wherein like elements are designated by like alphanumeric character throughout.

With reference now to the accompanying drawings, FIGS. 1A-3C are provided for general reference to assist in understanding the features of the embodiments of the present invention. FIGS. 1A and 1B depict a range of angles possible between the tibia and femur in a person who is extending and flexing (bending) his or her knee. Specifically, FIG. 1A depicts a range of angles possible while the person extends and bends his or her knee, realizing that some knees may flex to 160°, 165°, or beyond. FIG. 1B depicts these various angles in an alternative position. These FIGS. should be kept in mind during the discussion illustrating how with some embodiments of the present invention, knee flexion of greater than 135° is possible for knee prosthetic patients, which is not generally possible with currently-available knee prostheses.

Figure 2A:
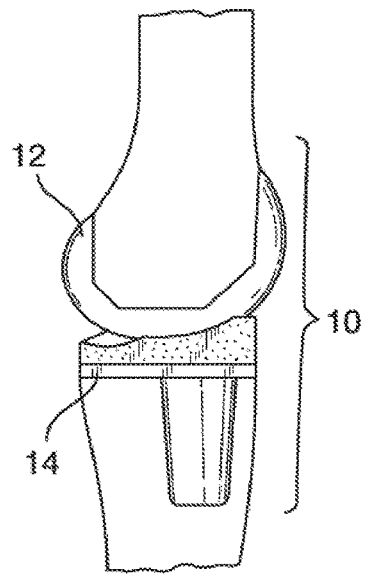
Figure 2B:
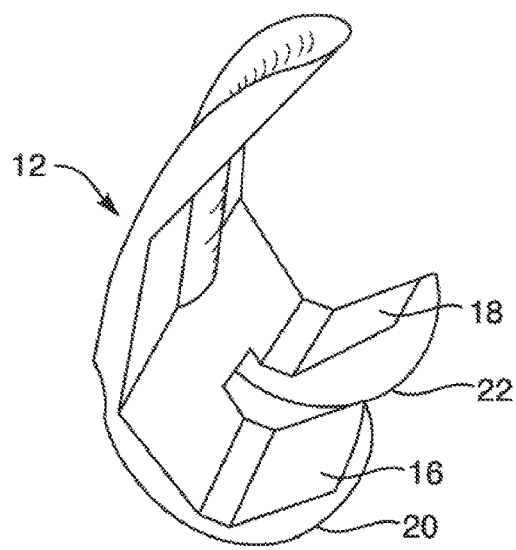
Figure 2C:
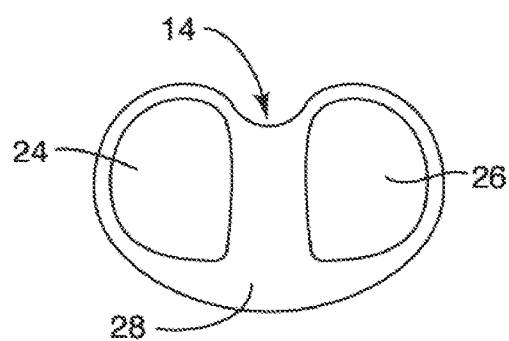

FIGS. 2A-2C depict various perspective views of a generic knee prosthesis 10. Specifically, FIG. 2A depicts a sagittal view of a left knee joint having a knee joint prosthesis 10, with the tibia and the femur of the normal knee transparent. FIG. 2B depicts an enlarged view of a femoral component 12 of the knee prosthesis 10, while FIG. 2C provides a top perspective view of a tibial component 14 of the knee prosthesis. FIG. 2B depicts certain components of the femoral component 12, such a medial receiving area 16 that may be modified in embodiments of the present invention to integrally connect with an attachment (not shown but hereinafter described) as well as a lateral receiving area 18. The internal geometry of the femoral component 12 is provided to allow a one piece femoral component 12 that is rolled into place on the resectioned femur 32, as shown in FIG. 4D. Thus, the internal geometry of the femoral component 12 includes various surfaces, including areas 16 and 18, to accommodate the patellar articulation and the anterior extensions of the proximal portions of the posterior condyles. The resectioned portions of the condyles provide flat surfaces which are loaded in compression in full knee flexion. Additionally, the resectioned surfaces are provided such that the articular surface of the femoral component is at essentially the same position as the surface being resectioned. As such, the normal relationship between the femur and the tibia is preserved with full flexion. Additionally, when the knee is fully flexed, the interface between the femoral component and the underlying femur is mainly loaded in compression rather than sheer forces. Compression forces provide a more stable interface between the femoral component and the femur thereby decreasing the chances of loosening. Therefore, in some embodiments the interface between the femoral component and the tibial component are configured to enhance a compression force between the femoral component and the underlying femur during full flexion of the knee joint.

Also visible in FIG. 2B is a medial femoral condylar surface 20 and a lateral femoral condylar surface 22. FIG. 2C depicts the tibial component 14 and its elements: a lateral tibial condylar surface 24, a medial tibial condylar surface 26, and an intercondylar surface 28. When the knee prosthesis 10 is functioning, an interface exists between the medial femoral condylar surface 20 of the femoral component 12 and the medial tibial condylar surface 26 of the tibial component 14 and between the lateral femoral condylar surface 22 of the femoral component 12 and the lateral tibial condylar surface 24 of the tibial component 14.

FIGS. 3A-3C depict additional perspective views of the generic knee prosthesis 10 with its different components. Specifically, FIG. 3A depicts a frontal view of the knee prosthesis 10 with the femoral component 12 articulating with the tibial component 14 as described above. FIG. 3B is a side view of the femoral component 12, and FIG. 3C is a side view of the tibial component 14, and specifically, of the medial side of the tibial component showing the medial tibial condylar surface 26. The medial femoral condylar surface 20 slidingly interfaces with the medial tibial condylar surface 26 so that as a person flexes or extends his or her knee, the arc of the medial femoral condylar surface 20 runs along the media tibial condylar surface 26.

In some embodiments of the present invention, greater deep knee flexion is provided to the knee prosthesis 10 by providing an articular surface on the proximal, anterior surface (or portion) of the posterior condyles of the femur. At least some embodiments of the present invention embrace an additional or increased articular surface on the proximal, anterior portion of either or both of the medial or lateral posterior condyles of the femoral component 12. Embodiments of the femoral component 12 add increased articular surface area to the proximal end of the posterior condyles of the femoral component 12 in an anterior direction such that when the patient bends his or her knee during deep knee flexion, contact between the femoral component 12 and the tibial component 14 is maintained, and a greater, deeper knee flexion can be achieved.

At least four different examples of how this may be achieved are demonstrated with reference to the figures. Any method of increasing an articular surface area to the proximal end of the posterior condyles of the femoral component 12 in an anterior direction is embraced by the embodiments of the present invention.

Figure 8A:
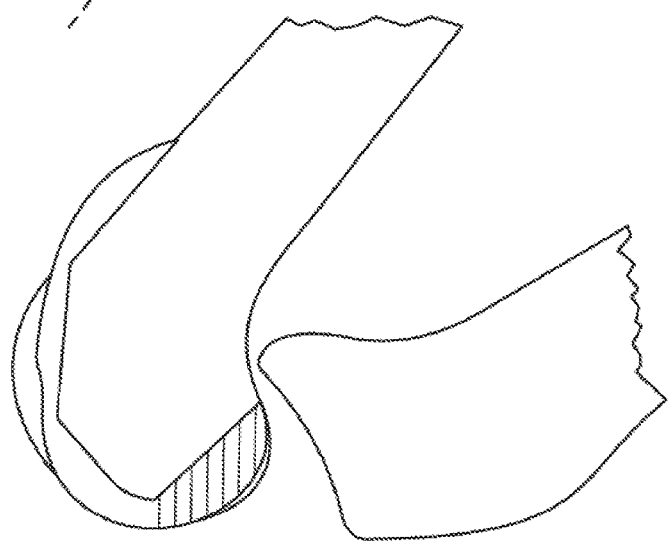
Figure 8B:
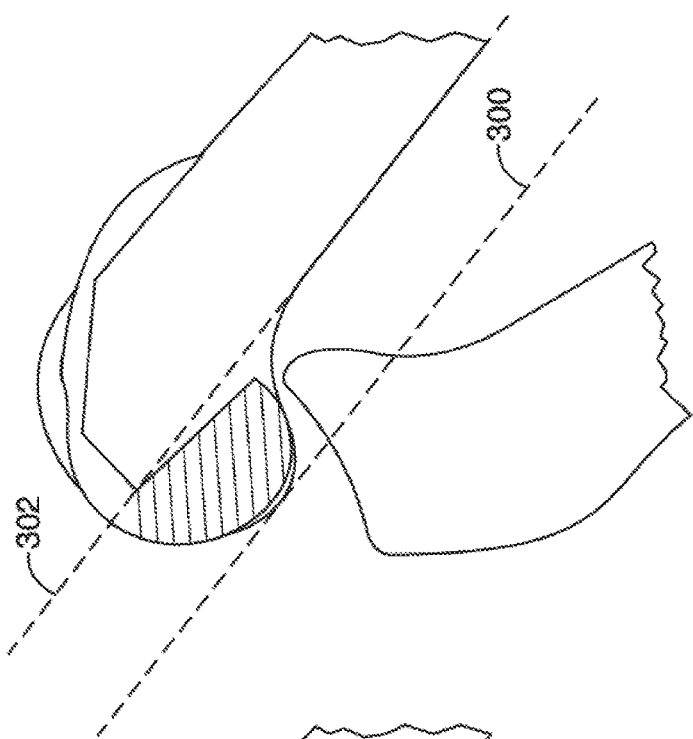
FIG. 8B illustrates an embodiment of the femoral component in accordance with the present invention.

FIGS. 8A and 8B illustrate a femoral component 12 and method of increasing an articular surface area to the proximal end of the posterior condyles of the femoral component 12. FIG. 8A illustrates a side view of a conventional femoral component 12. In the first embodiment of the inventive prosthesis, the shaded area of the femoral component 12 of FIG. 8A (i.e., the posterior condyle) is thickened in the anterior direction until the resulting surface opposing the bone is approaching the same plane as the posterior surface of the shaft of the distal femur. This thickening may be seen with reference to FIG. 8B. In particular, FIG. 8B shows that, in some embodiments, the posterior condyle is thickened from its posterior most edge (as illustrated by line 300) towards a plane 302 of a distal portion of posterior surface of the shaft of the distal femur. This results in a greater articular surface area of the posterior condyles of the femoral component 12. This requires resection of more bone but is otherwise an easy modification to current prostheses and requires little to no modification of current surgical technique.

A second type of embodiment that extends the articular surface area is illustrated by FIGS. 4A-5C. Methods of utilizing this type of embodiment are illustrated with reference to FIGS. 9-10H. This type of embodiment utilizes an extension attachment to the femoral component 12 of an embodiment of the knee prosthesis 10, which when integrated with both the femoral component 12 and a patient's femur, results in a greater surface area of the femoral component 12.

As illustrated in FIGS. 4A-5D, this type of embodiment has a modular attachment 30 that provides a modular flexion attachment surface to extend the articular surface area of the anterior portion of the proximal portion of the posterior condyles. The modular attachment 30 may be attached to the inside, or non-articular surface, of a relatively conventional total knee femoral component 12. The modular attachment 30 has a portion that may be partially received, in one embodiment, within a recessed receiving area on the flat anterior surface of one or both of the posterior condyles of the femoral component 12 and may thus be used on the medial posterior condyle, the lateral posterior condyle, or both. Alternatively, it may be implanted in a groove within either or both of the resected posterior condyles of the femur itself.

The modular attachment 30 provides an increased articular contact area as an anterior continuation of the medial femoral condylar surface 20 and/or of the lateral femoral condylar surface 22 of the femoral component 12. In some embodiments, the modular attachment 30 may be initially placed onto the femoral component 12 and then attached to the distal end of the patient's femur. In other embodiments, the modular attachment 30 may be connected first to the posterior condyles of the distal end of the femur and then integrally connected with the femoral component 12. The modular attachment 30 may be used on the medial side, on the lateral side or on both sides.

FIGS. 4A-4D depict perspective views of embodiments of the femoral component 12 and the modular attachment 30. As described, the modular attachment 30 attaches to the femoral component 12 and to the femur of a patient to enlarge the surface area of the femoral component 12 and, ultimately, to enable deep knee flexion beyond 140° in a knee prosthesis patient. FIG. 4A depicts a simplified side view of an embodiment of the femoral component 12 having the modular attachment 30 attached to the posterior condyle of the femoral component. FIG. 4D depicts a side view of the attachment integrally attached to a patient's femur and to the femoral component of the knee prosthesis. The modular attachment 30 may be modular as shown in FIGS. 4B-4D and may fit within a recess in either or both of the medial receiving area 16 and the lateral receiving area 18 (i.e., in the anterior interior surface of the posterior condyles of the femoral component 12, as shown in FIG. 2B) and/or in either or both of the medial and the lateral posterior condyles of the femur or in both the femoral component 12 and the femur. In another embodiment the modular attachment 30 may be a permanent part of the femoral component, as discussed below.

FIG. 4B depicts a side view of one embodiment the modular attachment 30 and FIG. 4C depicts a top view of the depicted embodiment of the modular attachment 30. Specific dimensions of the depicted embodiment of the modular attachment 30 are not given and one of skill in the art will recognize that the dimensions may be modified from patient to patient and will also recognize that the various portions of the modular attachment 30 may all be formed in some embodiments to be as wide as the condyle of the femoral component 12.

In some embodiments, the modular attachment 30 includes a first portion roughly perpendicular to a second portion. The first portion of the modular attachment 30 entails a flanged articular area 36 ("flanged area 36") at one end of the modular attachment 30, and an elongated stem 38 extending therefrom, which extends roughly perpendicular from the flanged area, distally from the flanged area 36. The elongated stem 38 therefore is attached to the non-articular side of the flanged area 36. Although the elongated stem is illustrated in FIG. 4C as having a medial-lateral width substantially shorter than the medial-lateral width of the flanged area 36, the elongated stem 38 of other embodiments may be of any medial-lateral width up to the medial-lateral width of the posterior condyles of the femoral component 12 itself.

The elongated stem 38 has an upper side 40 and a lower side 42. Nodules 44 may be placed on either or both of the upper side 40 and the lower side 42, to enable an integral connection with the femur 32 on the upper side 40, and the femoral component 12 on the lower side 42. Some form of a nodule-receiving groove or recess (not shown) may be made in the femur 32 and/or the femoral component 12 to receive these nodules 44 and to secure the integral connection between the femur 32, the attachment 30, and the femoral component 12; with the modular attachment 30 being disposed between the femur 32 and the femoral component 12.

In embodiments having no nodules 44 on the elongated stem 38, the attachment 30 may fit within a recess made on either or both of the medial receiving area 16 and the lateral receiving area 18 of the femoral component 12. The elongated stem 38 of the modular attachment 30 would fit within such recesses and integrally connect thereto. The modular attachment 30 may simultaneously connect with the femur 32 on the upper side 40 (generally) of the elongated stem 38. In embodiments having no nodules on the elongated stem, the stem of the modular portion may further fit into a groove prepared in the resected posterior condyles of the femur.

The modular attachment 30 increases the overall surface area of the femoral component 12 and prolongs the interface and contact that exists between the femoral component 12 and the tibial component 14. This enables greater knee flexion in prosthetic knee patients because the femoral component 12 remains interfaced with the tibial component 14 throughout the full range of flexion resulting in pain-free knee flexion.

Without this increased surface area, the medial and lateral proximal edges of the posterior femoral condyles of a prosthesis may push into the proximal surfaces of the tibial component 14 and may produce wear of the tibial component 14. In addition, the tibial component 14 may contact the bone of the distal femur 32 that is anterior and/or proximal to the proximal edges of the posterior condyles of the prosthesis and cause pain to and limit flexion of the prosthetic knee patient and may cause wear to the tibial component. Further, without this added surface area, with flexion beyond 140°, the tibial component 14 may exert a force in the distal direction on the femoral component 12, which may result in loosening of the femoral component 12. Therefore, the modular attachment 30 extends the life of the prosthetic knee, decreases pain to the patient, and ultimately, enables a prosthetic knee patient to achieve deep knee or full functional flexion.

Figure 5A:
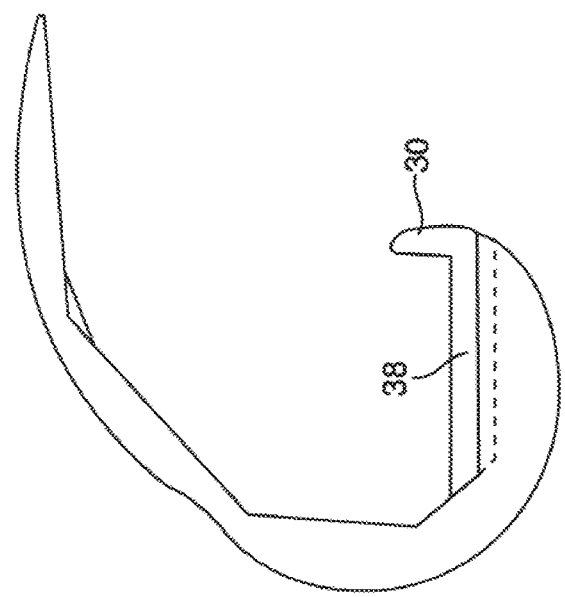
Figure 5B:
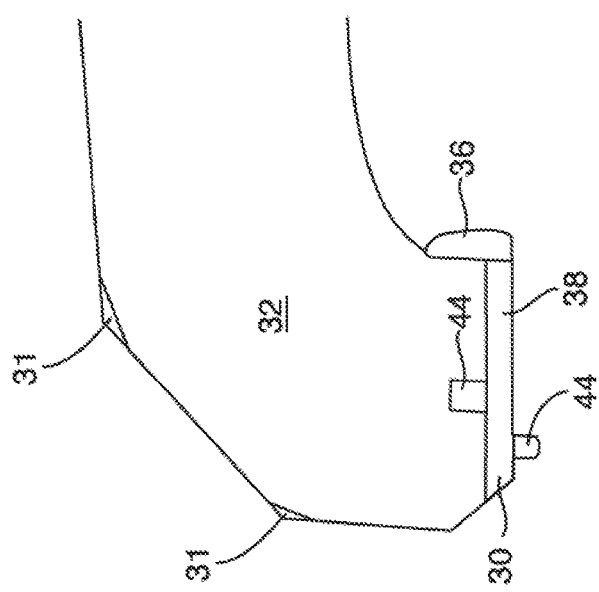

FIGS. 5A-5D depict various perspective views of the modular attachment 30 as it is attached to the femoral component 12 and to the femur 32. FIG. 5A is illustrative of the modular attachment 30 as it is attached to the femur 32 prior to attachment of the femoral component 12. FIGS. 5B-5D are illustrative of the modular attachment 30 as it is recessed within the femoral component 12 prior to attachment to the femur 32, and specifically, as the modular attachment 30 is integrally connected to either or both of the medial femoral receiving area 16 and the lateral femoral receiving areas 18.

Figure 9:
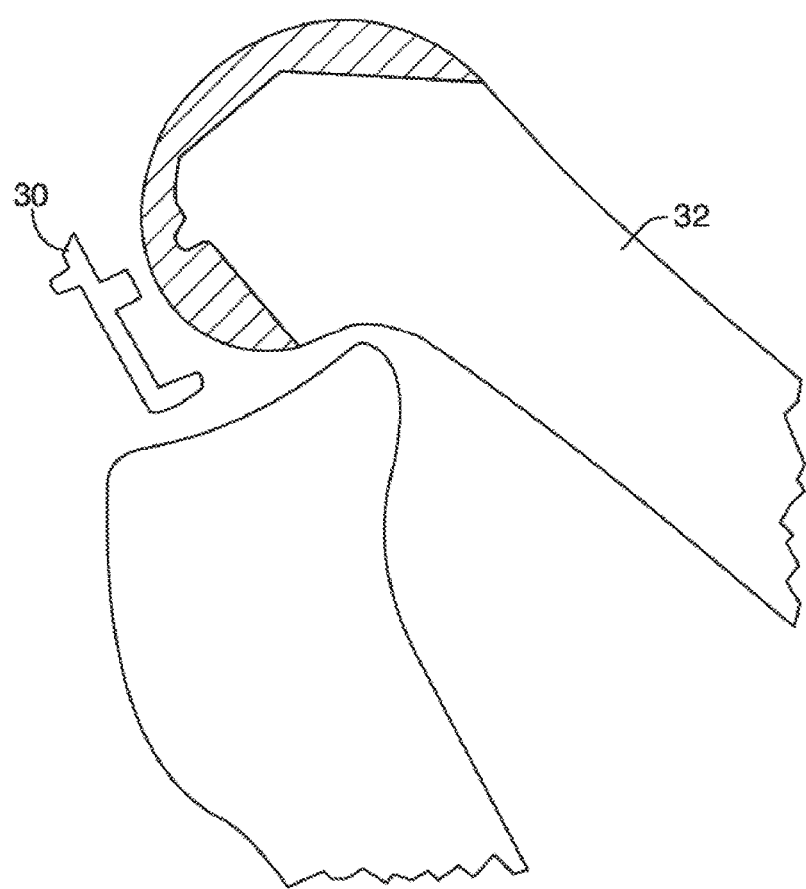
FIG. 9 illustrates a modular attachment for use with embodiments of the femoral component in accordance with embodiments of the present invention.
Figure 10A:
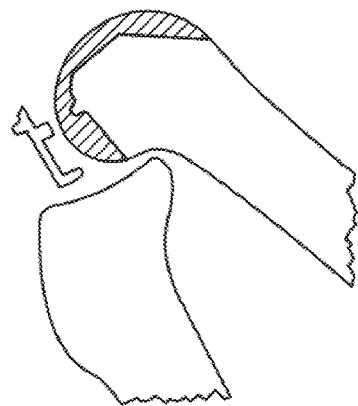
FIGS. 10A-10H illustrate representative steps for attaching an embodiment of the femoral component to a femur, the resectioned portions of the femur shown in phantom.
Figure 10B:
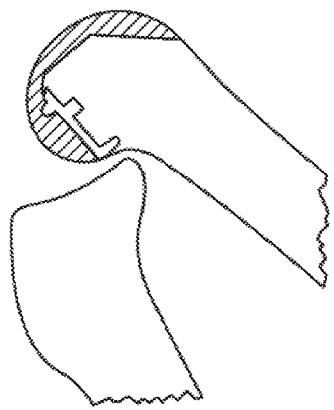
Figure 10C:
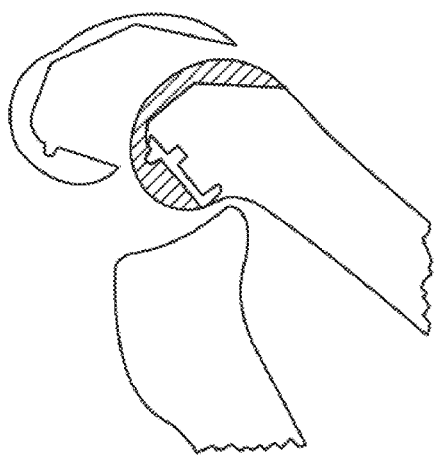
Figure 10D:
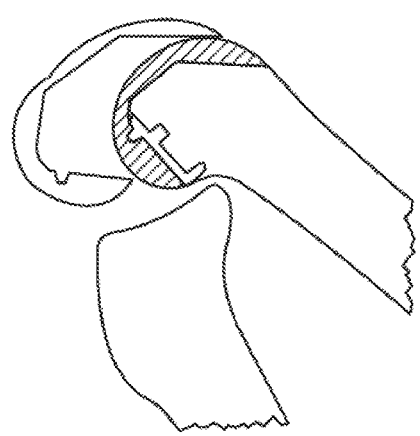
Figure 10E:
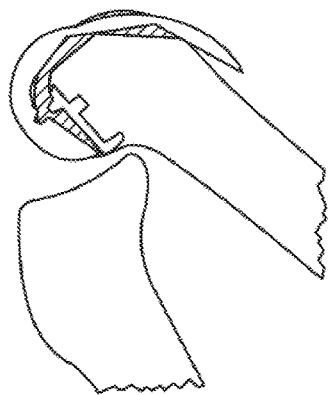
Figure 10F:
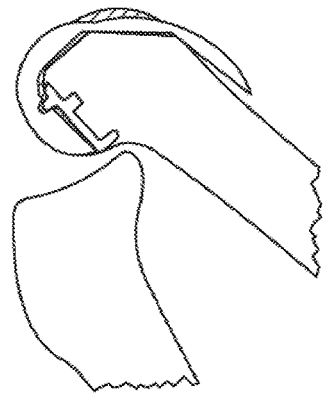
Figure 10G:
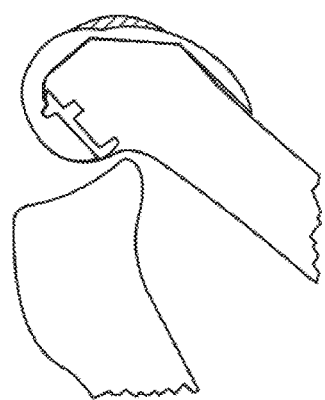
Figure 10H:
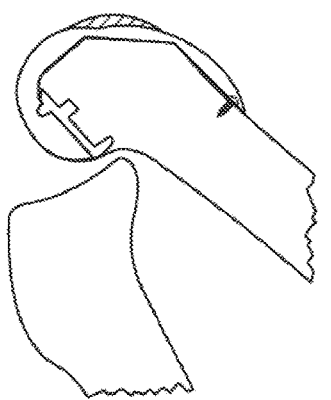

FIG. 9 and FIGS. 10A-10H illustrate methods of attaching the modular attachment 30 to the femur 32, followed by attaching the femoral component 12 to the femur 32 and modular attachment 30. FIG. 9 illustrates the resection needed on the femur 32 prior to creating the recess in the femur to allow attaching the modular attachment 30. FIG. 9 and FIGS. 10A-10H do not illustrate the specific resection needed for the modular attachment 30, but the resection needed will be appreciated by one of skill in the art. After resection is completed, as at FIG. 10A, the modular attachment 30 may be attached to the femur as at FIG. 10B. The femoral component 12 may then be attached to the femur 32 (and to the modular attachment 30, if desired) by positioning and moving the femoral component 12 as illustrated in FIGS. 10C-10H. As may be appreciated from the sequence of illustrations depicted in FIGS. 10C-10H, the femoral component 12 needs to be rotated or rolled into position, with initial contact beginning in the posterior region as illustrated in FIG. 10E and progressing to the fully-seated position illustrated in FIG. 10G. This is a new implantation technique that will require some additional practice and training over current techniques.

Figure 11A:
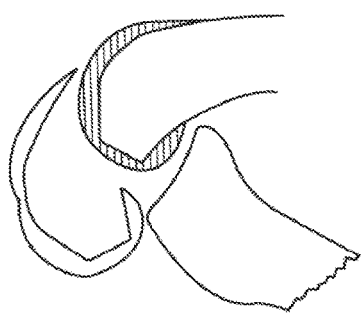
FIGS. 11A-11K illustrate representative steps for attaching an alternate embodiment of the femoral component to a femur.
Figure 11B:
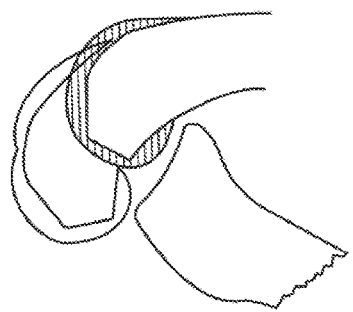
Figure 11C:
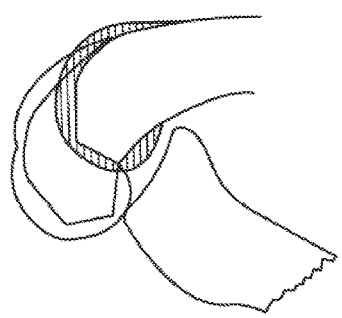
Figure 11D:
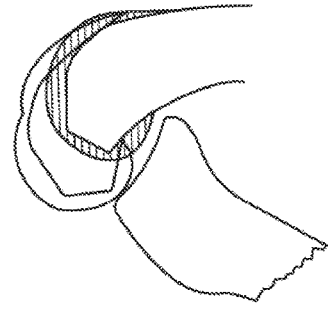
Figure 11E:
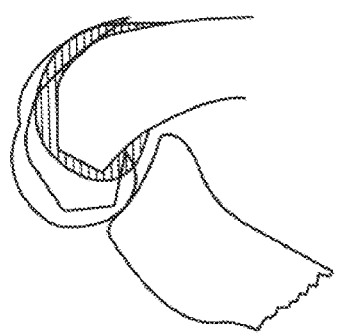
Figure 11F:
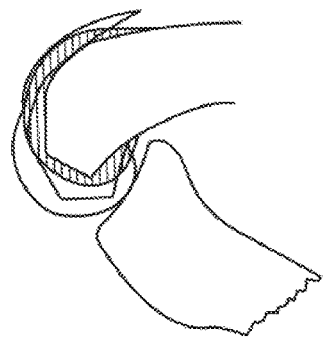
Figure 11G:
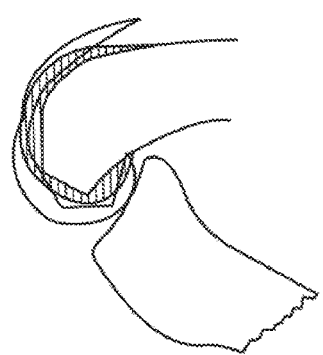
Figure 11H:
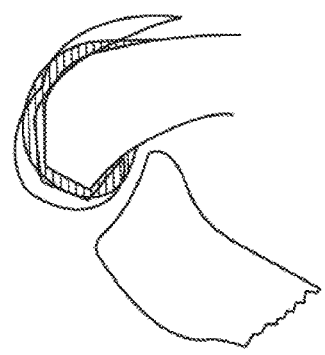
Figure 11I:
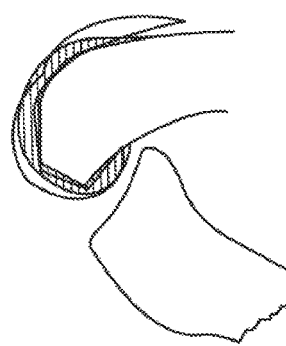
Figure 11J:
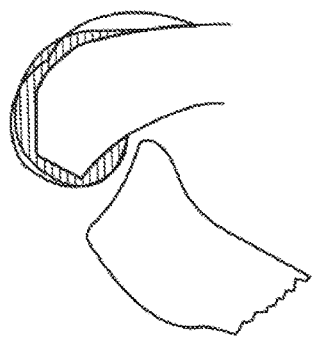
Figure 11K:
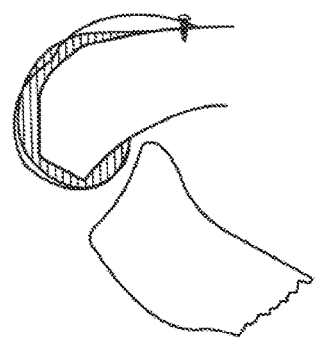

As has been set forth above in reference to FIG. 4A, a third type of embodiment having an extended articular surface is not modular and does not utilize a separate modular attachment 30. In such embodiments, an extended articular surface corresponding to the flanged area 36 of the modular attachment 30 may be integrally formed as part of one or both condyles of the femoral component 12. Placement of one such embodiment is illustrated with reference to FIGS. 11A-11K. As may be appreciated with reference to these FIGS., placement of such an embodiment also utilizes a similar rotational placement technique to that illustrated in FIGS. 10C-10H. As may be appreciated by reference to FIGS. 10H and 11K, any of the modular or non-modular embodiments may, optionally, be further secured by one or more screws placed in an anterior flange of the femoral component 12.

Figure 12B:
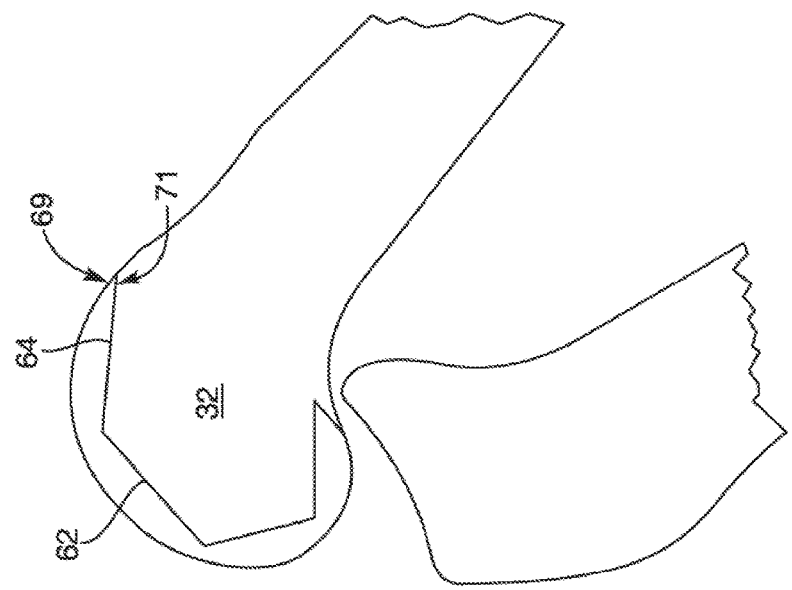
FIGS. 12A-12C and FIG. 13 illustrate comparisons between a conventional femoral component and the femoral component in accordance with embodiments of the present invention.
Figure 12A:
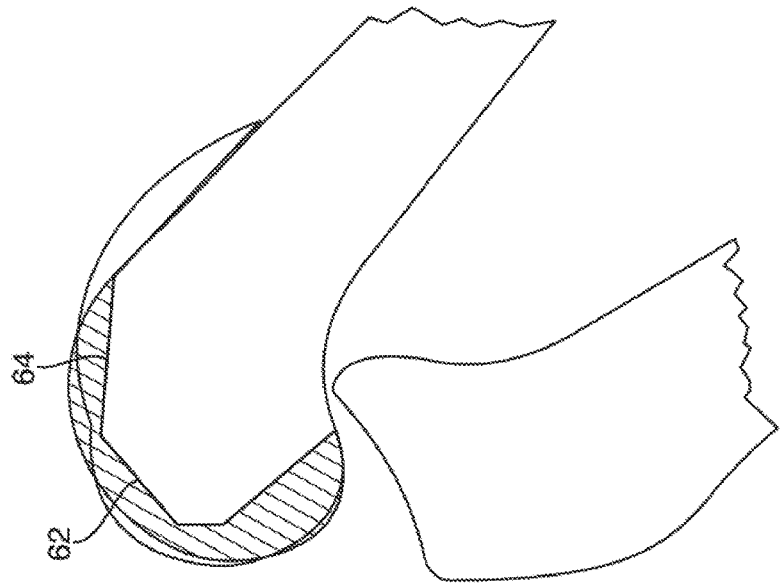
Figure 12C:
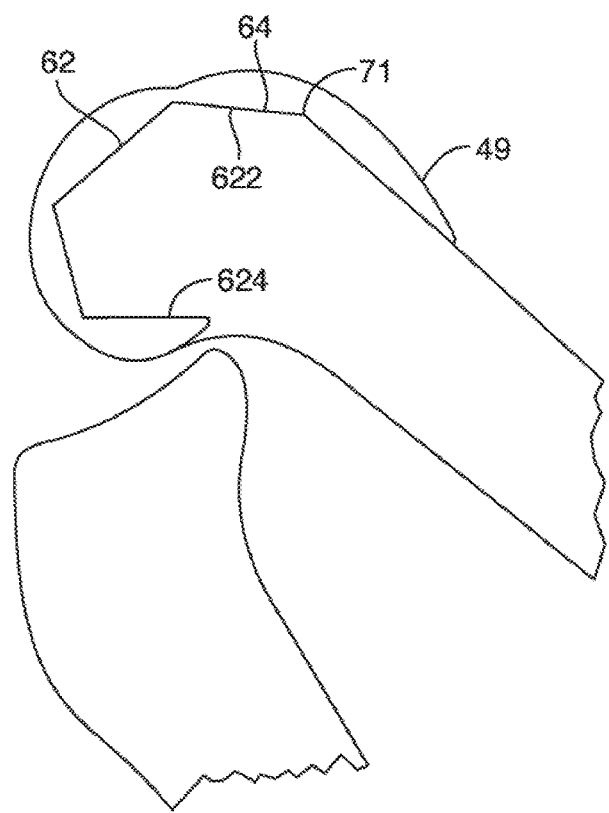
Figure 13:
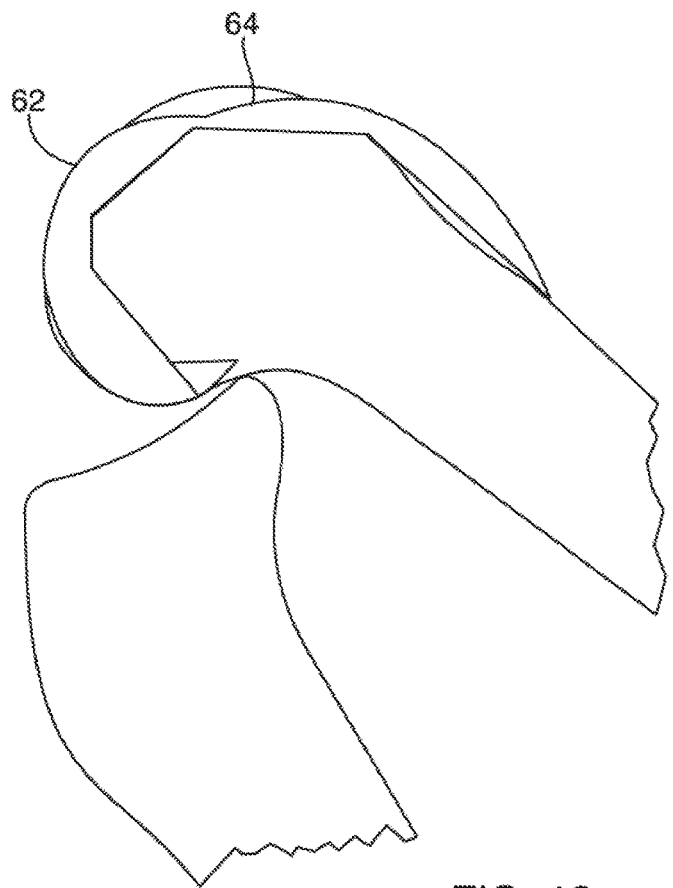

One advantage of the embodiment illustrated in FIGS. 11A-11K is that the implanting surgeon may decide whether to utilize the illustrated embodiment or a traditional femoral component 12 after the distal and anterior oblique cuts have been made. This is illustrated in FIGS. 12A through 12C. FIG. 12A shows a traditional femoral component 12. FIG. 12B shows an embodiment of the described femoral component 12 without an extended anterior flange. In other words, FIG. 12B shows that, in some embodiments, when the femoral component is seated on the femur 32, a proximal anterior end 69 of the femoral component is configured to terminate at or near a proximal end 71 of the anterior oblique cut 64 (e.g., at between about 0 and about 15 mm on either the proximal side or the distal side of the proximal limit of the knee's natural articular cartilage). FIG. 12C, on the other hand, shows an embodiment of the femoral component 12 illustrated in FIGS. 11A-11K, which include an anterior flange 49 that extends proximally past the anterior oblique cut 64. As may be appreciated by reference to the FIGS., the distal cuts 62 and anterior oblique cuts 64 are essentially identical. This may be further appreciated by reference to FIG. 13, which shows a superimposed view of FIGS. 12A and 12B, not only showing that the distal femoral cuts 62 and the anterior oblique cuts 64 are identical, but also showing that the total amount of bone resected for the illustrated embodiment is similar to or less than the amount resected using current techniques and femoral components 12.

In a non-modular embodiment of the femoral component 12 as shown in FIGS. 11A-11K and in a modular embodiment of the femoral component as shown in FIGS. 4A-5D, there are junctions where the inside flat surfaces of the prosthesis (which when implanted are in contact with the bone) meet. These flat surfaces, rather than coming together at a sharp angle, may or may not have a radius connecting the two flat surfaces. Not all of the junctions of the flat surfaces necessarily need a radius and in some embodiments none of the junctions of flat surfaces will have radii. The flat surfaces may or may not be in exactly the same planes as on conventional knees and will provide for the placement of a non-modular surface that will provide an articulation for the proximal, anterior portion of the posterior femoral condyles extending to or almost to a plane that is a continuation of the posterior cortex of the distal femoral shaft. In embodiments where one or more radii are provided to the junction(s) of the inside flat surfaces of the femoral component 12, corresponding radii 31 or curvatures may be provided to the resected bone surface of the femur, as is illustrated in FIG. 5A. As may be appreciated by one of skill in the art, the presence of the corresponding radii 31 may assist in the rotational placement of the femoral component 12 as illustrated in FIGS. 10A-10H and 11A-11K.

This internal configuration allows the femoral component 12 to be initially applied to the femur in a flexed position and then rotated into the fully extended position as it is implanted fully, as illustrated and discussed with reference to FIGS. 10A-10H and 11A-11K. Screw(s) may, optionally, be placed in the anterior flange (or other portion) of the femoral component 12 to firmly stabilize the component. This ability facilitates implanting the non-modular femoral component 12 or a modular femoral component 12 with the modular attachment 30 already implanted on the posterior condyles of the femur 32.

Figure 14:
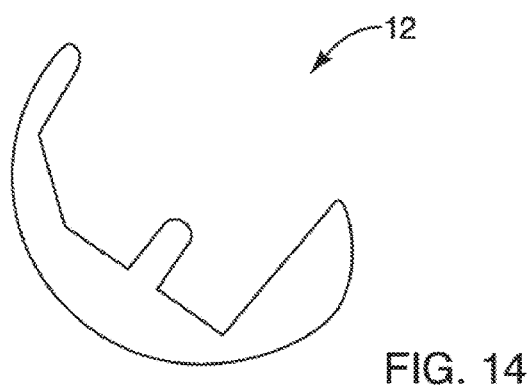
FIG. 14 illustrates an alternate embodiment of the femoral component in accordance with embodiments of the present invention.

A fourth type of embodiment of the femoral component 12 is illustrated in FIG. 14. This type of embodiment has a femoral component 12 that replaces the weight-bearing distal femoral condyles, and some or all of the anterior femoral articular surface and, in addition to some or all of the articular surface of the posterior condyles extending proximally and anteriorly to an area that is in the same plane as a continuation of the posterior cortex of the distal one fourth to one third of the femur. Such an embodiment may comprise separate medial and lateral components or they may be attached together to form one component that replaces or resurfaces the medial and lateral condyles.

Historically, many early total knee femoral components 12 did nothing regarding the patello-femoral joint. Because a certain percentage of those patients had anterior knee pain, an anterior flange was added to the femoral component 12 to resurface the trochlea (patellar groove). This weakened the patella and resulted in fractures in some patients. Recently techniques have been developed to minimize patellar pain which do not require implantation of a component. The embodiment shown in FIG. 14 does not have an anterior flange that is an integral part on the condylar portion of the prosthesis. It is anticipated that such a device 12 alone may, in some patients, be adequate to replace the femoral condyles and allow the surgeon to treat the patello-femoral joint as he/she felt was indicated. Alternatively, a separate patello-femoral articular surface or surfaces could be implanted. The patello-femoral implant(s) could be entirely separate or could be modular and attached to the device shown in FIG. 14. In some instances, the embodiment illustrated in FIG. 14 includes the ability to attach a modular anterior flange (trochlear groove) to the device shown in the Figure. In this regard, FIGS. 16T-16W (discussed below) illustrate some methods for attaching various embodiments of a modular anterior flange 57 (or modular patella-femoral component).

Implementations of the present invention embrace a femoral component 12, a tibial component 14, a modular attachment 30, stem 500 (discussed hereafter), and/or any other suitable components that each comprise a metal, metal alloy, ceramic, carbon fiber, glass, polymer (including, without limitation, bone cement, nylon, polyethylene, polyester, polytetrafluoroethylene (Teflon®), and/or any other suitable polymer), organic material, retrieved human or animal tissue, cementless material, and naturally occurring or synthetic materials used either separately or in any combination of two or more of the materials.

As may be appreciated by reference to the above discussion and the corresponding figures, currently-existing femoral components 12 provide an articular surface that only extends a short distance in the proximal anterior direction of the posterior condyle. For example, as may be seen with reference to FIGS. 2A and 8A, the articular surface at the anterior end of the posterior condyle typically extends to and replaces at most the posterior third of the posterior condyle, as measured from the most posterior portion of the patient's original posterior condyle (or from the most posterior portion of the femoral component 12) to a plane that is a continuation of the distal one fourth to one third of the posterior cortex of the femoral shaft.

In contrast, the various embodiments of the femoral component 12 illustrated in the FIGS. and discussed above provide an extended articular surface for either or both of the medial condyle and the lateral condyle that extends in a proximal anterior direction so as to extend half or more of the anteroposterior distance between the most posterior portion of the posterior condyle and the plane that is a continuation of the distal one fourth to one third of the posterior cortex of the femoral shaft. In some embodiments, the extended articular surface extends at least two-thirds of the anteroposterior distance between the most posterior portion (e.g., as shown by line 300 in FIG. 8B) of the posterior condyle and the plane (e.g., as shown by line 302 in FIG. 8B) that is a continuation of the distal one fourth to one third of the posterior cortex of the femoral shaft. In other embodiments, the extended articular surface extends nearly the entire anteroposterior distance between the most posterior portion of the posterior condyle and the plane that is a continuation of the distal one fourth to one third of the posterior cortex of the femoral shaft. In still other embodiments, the extended articular surface may extend even further, to encompass a distal portion of the posterior cortex of the femoral shaft, as illustrated in FIGS. 16A-16D.

The surface of the extension, which may or may not contact bone and is a continuation of the femoral articular surface, can be referred to as the full flex articulation. There may be a corresponding surface on the posterior edge of the medial and or lateral tibial articulation which is not part of the articular surface of the tibia when the tibia is in full extension. For example, in some implementations of the current invention there is a corresponding surface on the posterior edge of the medial tibial articulation where the center of the medial articular surface is more than 20% of the distance from the posterior edge of the component to the anterior edge.

Figure 19A:
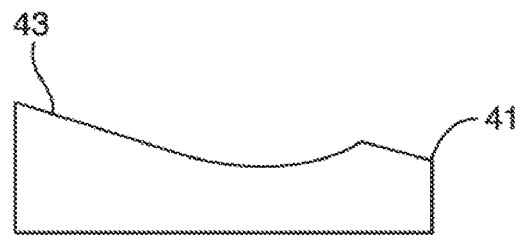
FIG. 19A illustrates a representative embodiment of a tibial component that does not have an articular surface posterior to the main articular surface.
Figure 19B:
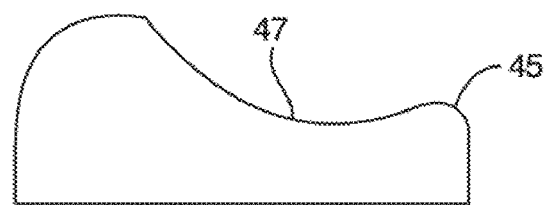
FIG. 19B illustrates a representative embodiment of the tibial full flex articulation being posterior to the main weight bearing articulation.

The embodiment illustrated in FIG. 19A shows a non-articular surface 41 posterior to the main articular surface 43. FIG. 19B illustrates a full flex articular surface 45 and an articular surface 47. The tibial full flex articulation of FIG. 19B is posterior to the main weight bearing articulation and articulates with a specific articular area on the femoral component, the femoral full flex articulation (proximal extension 50) shown in FIGS. 16A-16Q and shown in a slightly shortened embodiment in FIG. 16E.

Figure 16A:
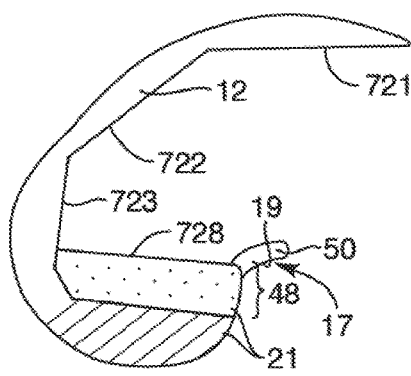
FIGS. 16A-16D illustrate a manner in which an articulating surface of the femoral components shown in FIGS. 15A-15D may be extended.
Figure 16B:
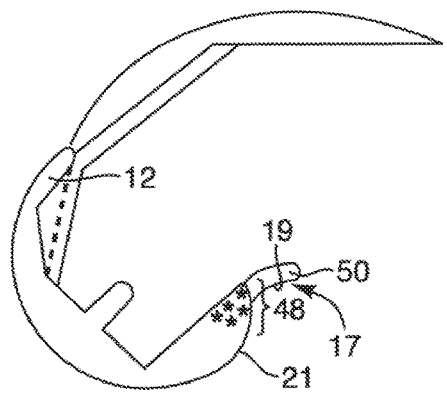
Figure 16C:
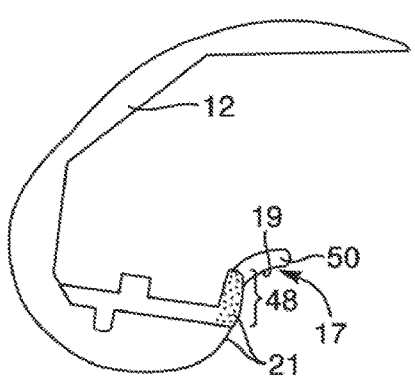
Figure 16D:
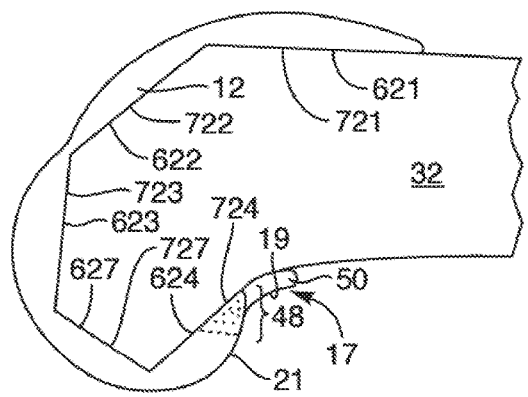
Figure 16E:
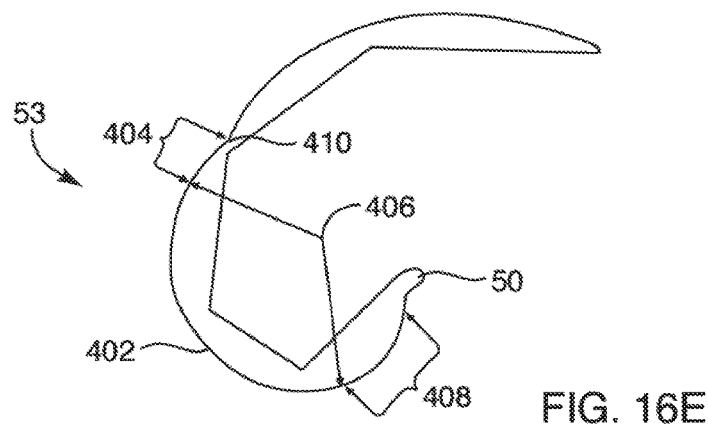
FIG. 16E illustrates a shortened embodiment in which an articulating surface of the femoral component may be extended.

With continued reference to FIG. 16E, in some embodiments of the present invention the articular surface 402 of femoral component 53 comprises sections of various surface radii 404, 406 and 408. Each section is provided as a means for controlling the relationship between the femoral component 53 and the tibial component (not shown) throughout the range of flexion for the knee. However, in some embodiments, radius 406 may be constant and replace radii 404 and 408.

Figure 16F:
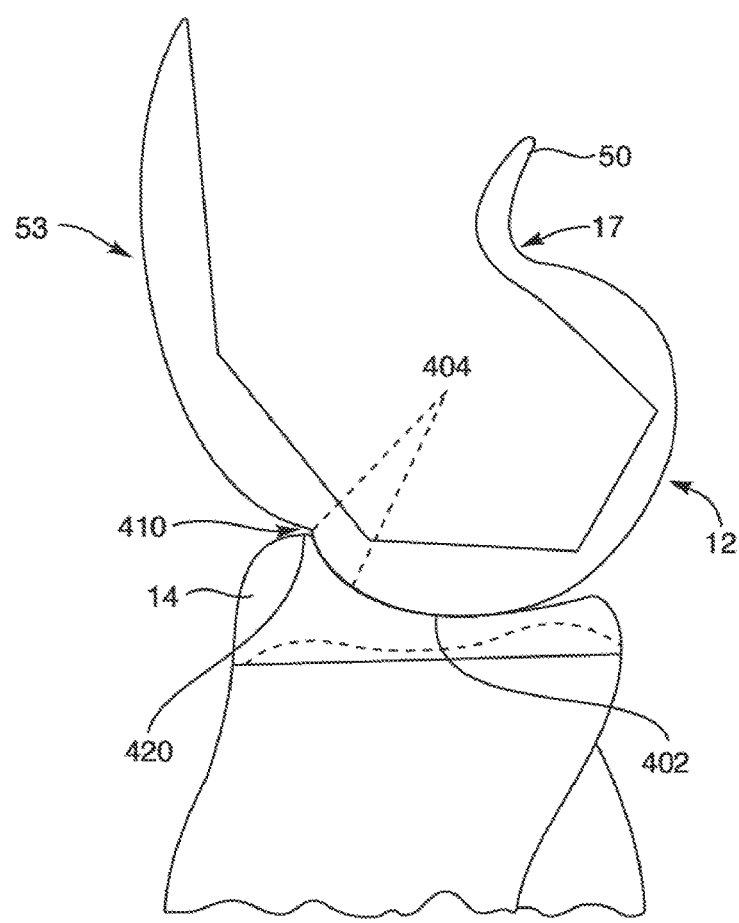
FIGS. 16F-16P illustrate flexion of a non-limiting embodiment of the femoral component having a decreasing radius, wherein the decreasing radius provides laxity over a portion of the range of flexion in accordance with a representative embodiment of the present invention.
Figure 16G:
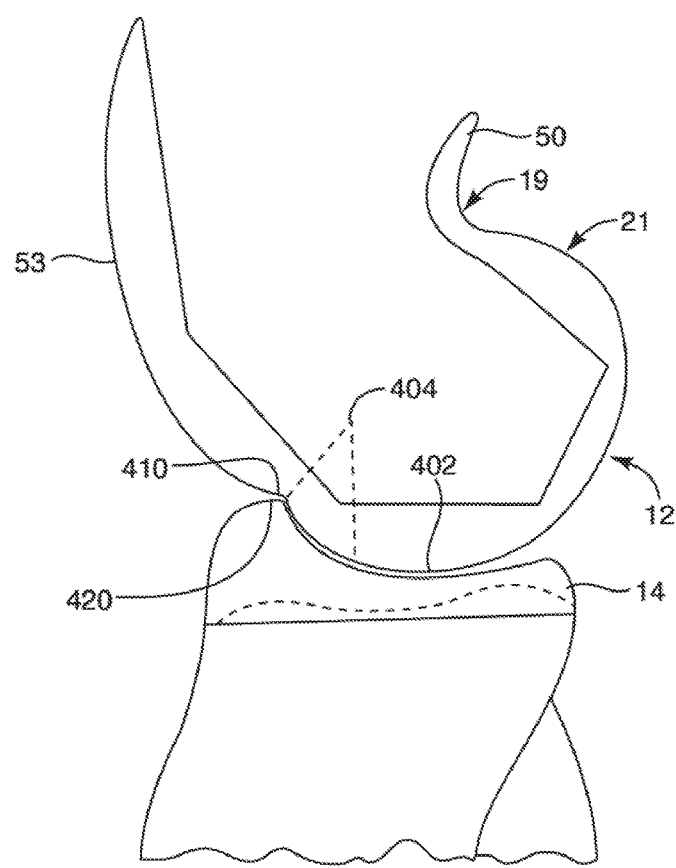

Radius 404 is characterized as having a decreasing radius such that an indentation 410 is formed on the articular surface 402. In some embodiments, indentation 410 is configured to receive anterior ridge 420 of tibial component 14 when the knee joint is hyper extended to approximately −10°, as shown in FIG. 16F. Upon further hyperextension, as shown in FIG. 16G, indentation 410 further impinges upon anterior ridge 420, such that the interface between indentation 410 and anterior ridge 420 acts as a fulcrum between femoral component 53 and tibial component 14. Therefore, as the knee joint is hyper-extended beyond approximately −10°, radius 404 of the articular surface 402 is distracted from the tibial component 14, as shown. As this distraction increases, the dense connective tissues of the knee joint are stressed thereby limiting further hyper-extension of the knee joint.

Figure 16H:
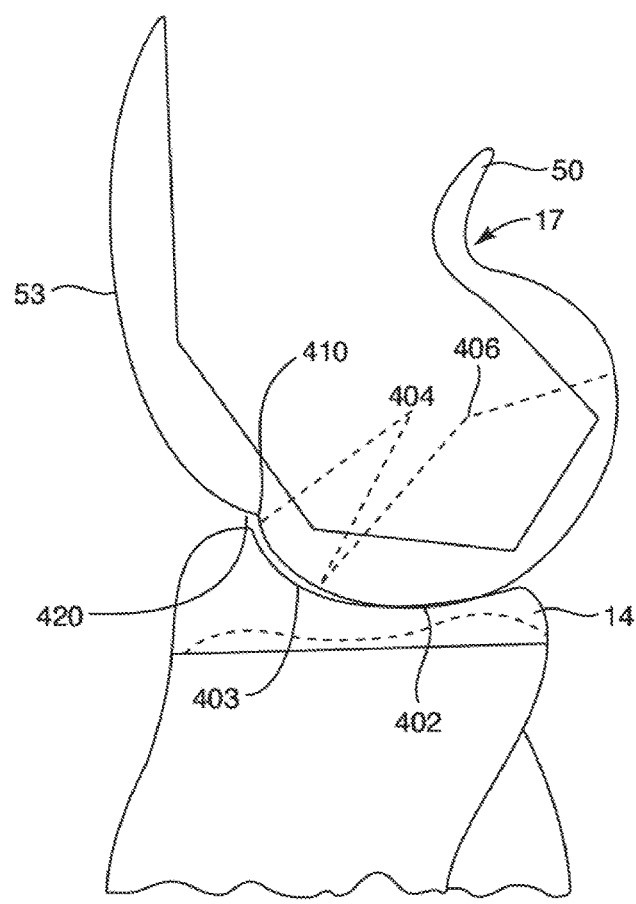

Referring now to FIG. 16H, a knee joint is shown in a neutral, extended position at approximately 0° flexion. At approximately 0° flexion, radii 404 and 406 are partially in contact with tibial articular surface 403, yet the knee joint is not fully constrained. As such, femoral component 53 is permitted to move anteriorly and posteriorly relative to the tibial component 14. In some embodiments, radii 404 and 406 provide laxity within the knee joint between approximately 0° and 20° flexion. In other embodiments, radii 404 and 406 provide laxity within the knee joint between approximately 0° and 40° flexion.

Figure 16I:
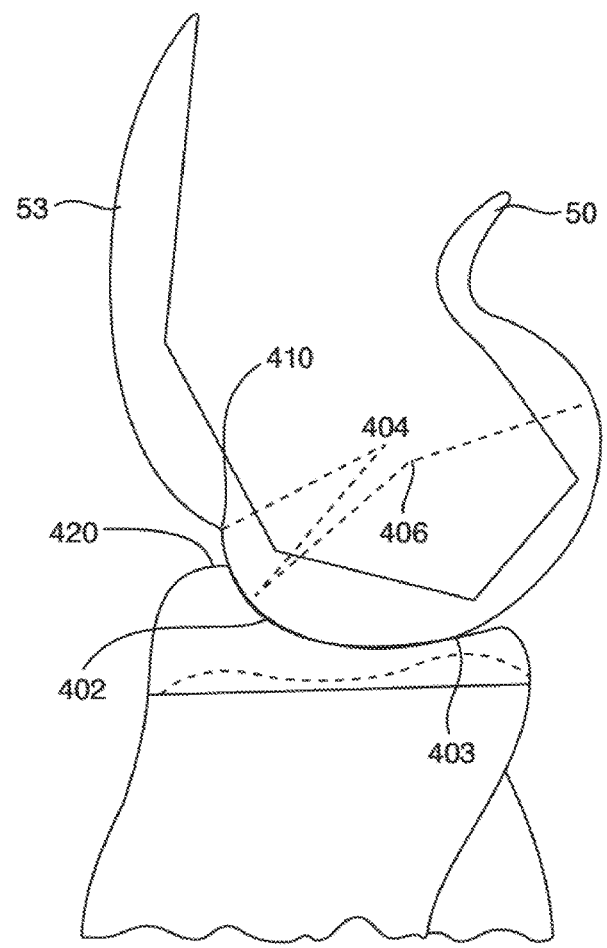
Figure 16J:
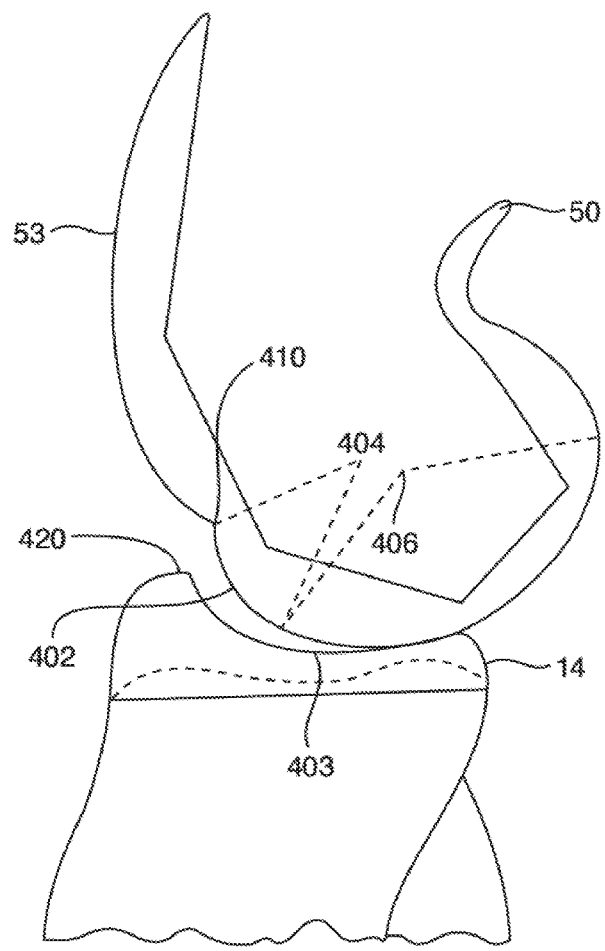

Referring now to FIG. 16I, a knee joint is shown at approximately 10° flexion with the femoral component 53 being shifted anteriorly relative to tibial component 14. FIG. 16J shows a knee joint at approximately 10° flexion wherein the femoral component 53 has been shifted posteriorly relative to tibial component 14. Anterior and posterior laxity within the knee joint, as provided by radius 404, is limited both by tension within the dense connective tissues of the knee joint, and by the curvatures of the opposing femoral and tibial articular surfaces 402 and 403. By providing laxity between approximately 0° and approximately 20° the natural mechanics of knee flexion are preserved, as sensed or experienced by the user. In some embodiments, laxity is eliminated between approximately 0° and approximately 20°, thereby modifying the natural mechanics of knee flexion as may be desired. This is achieved by having radii 404 and 408 replaced by radius 406.

Figure 16K:
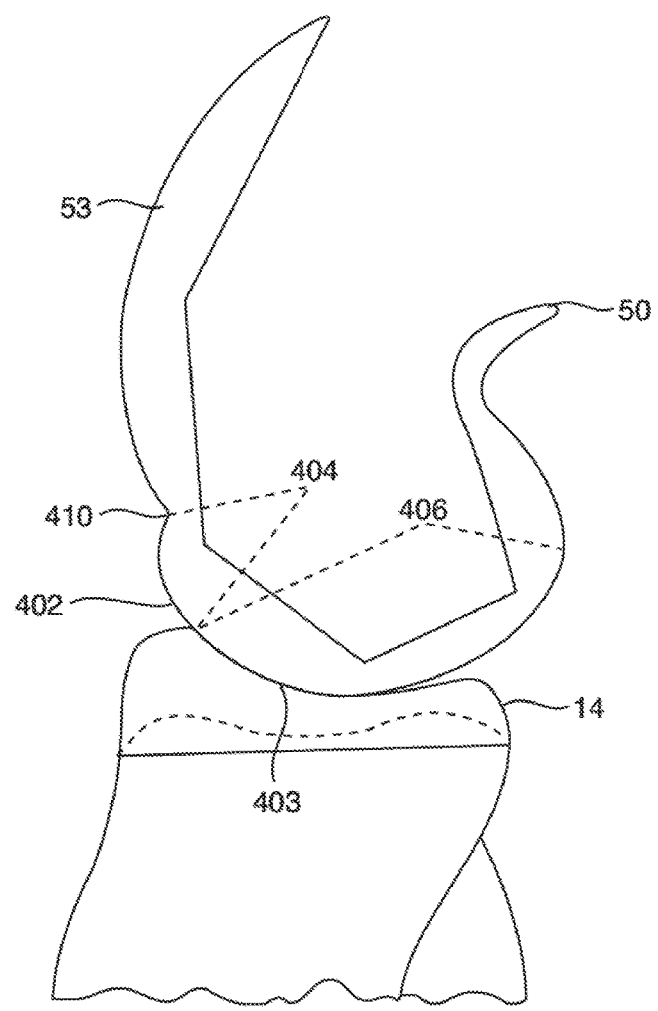
Figure 16L:
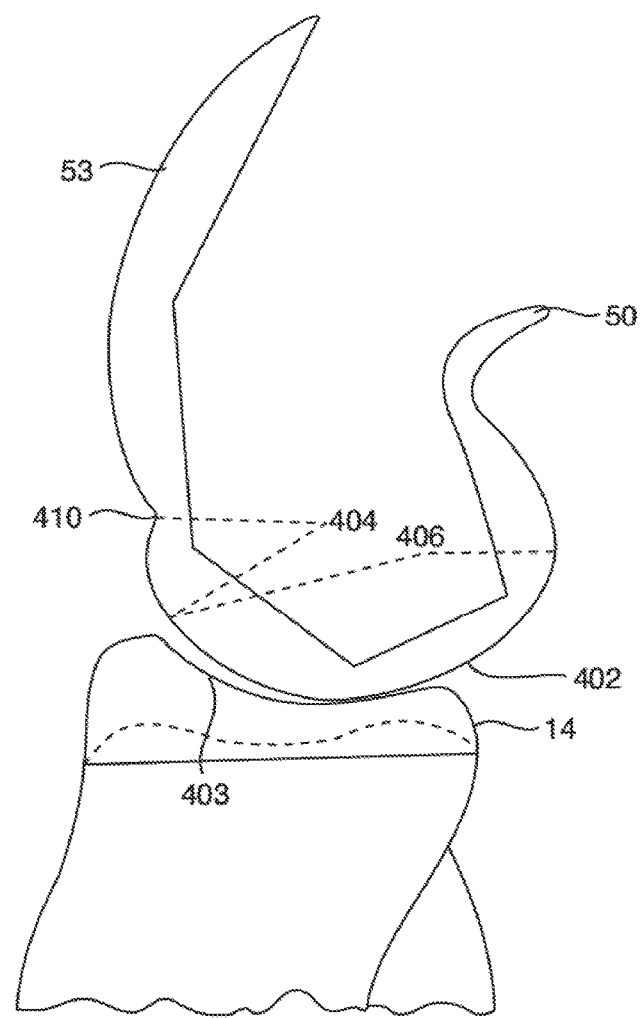
Figure 16M:
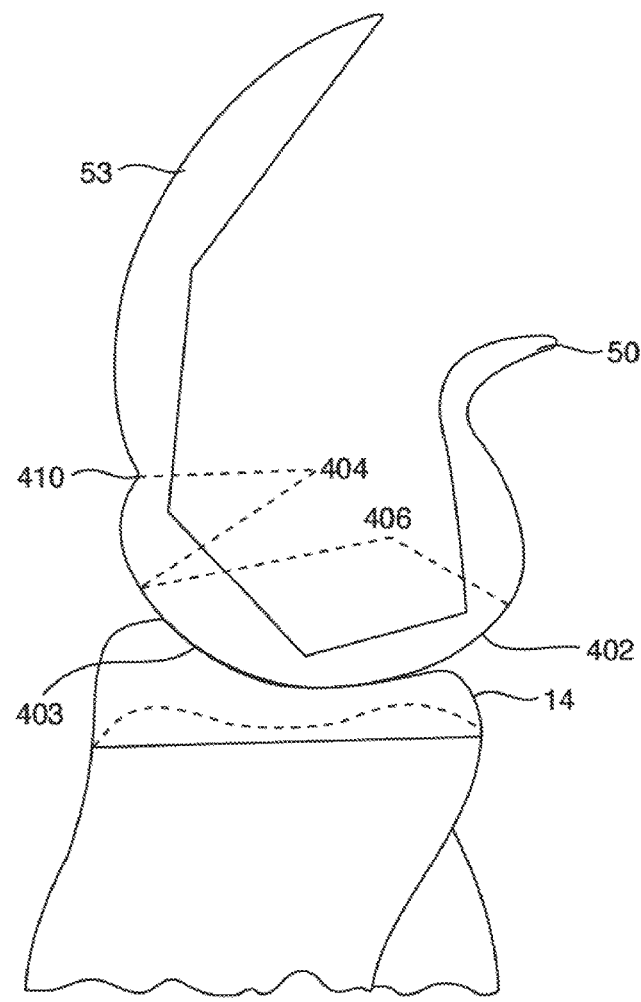
Figure 16N:
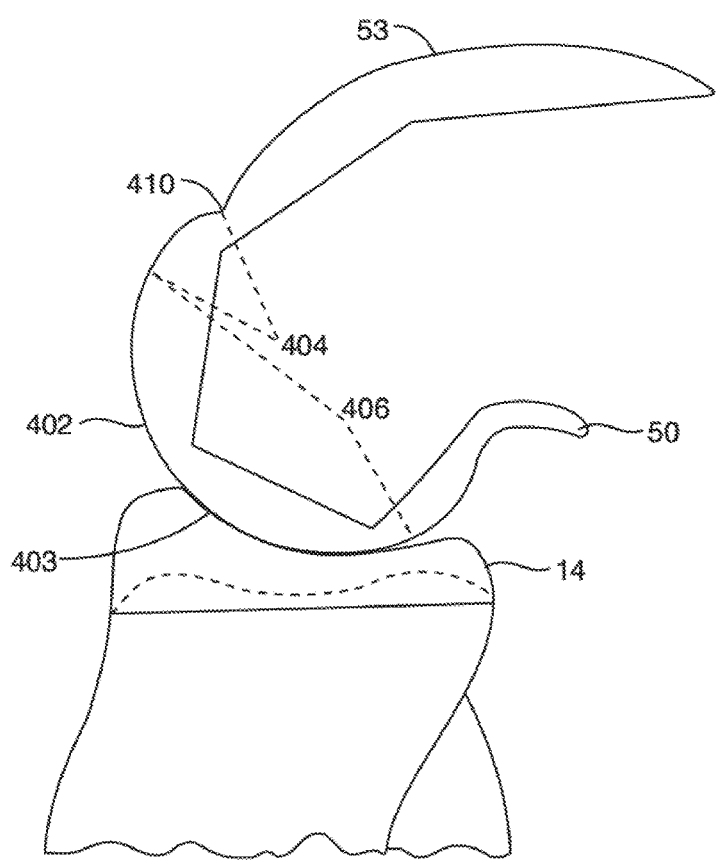
Figure 16O:
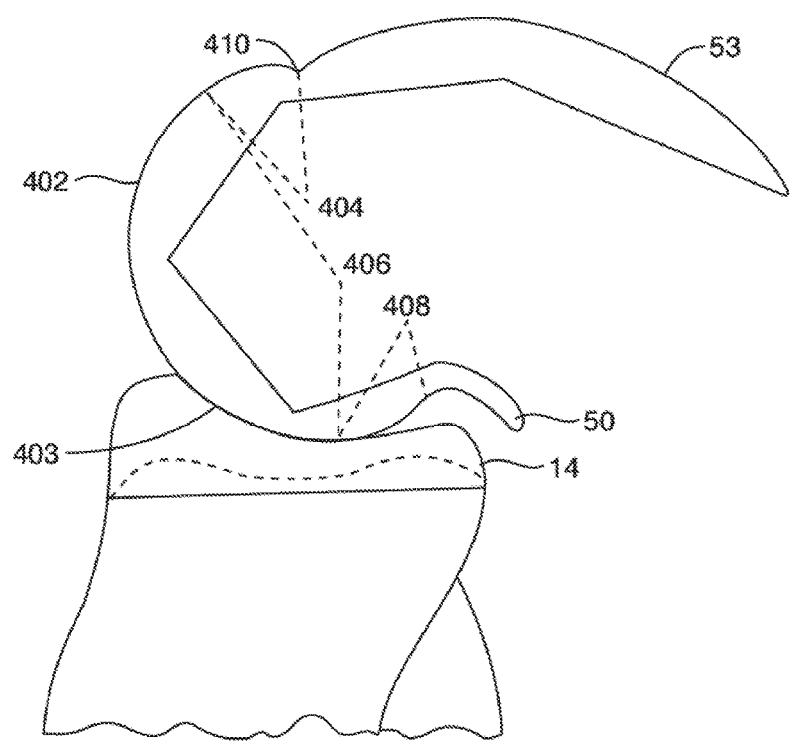
Figure 16P:
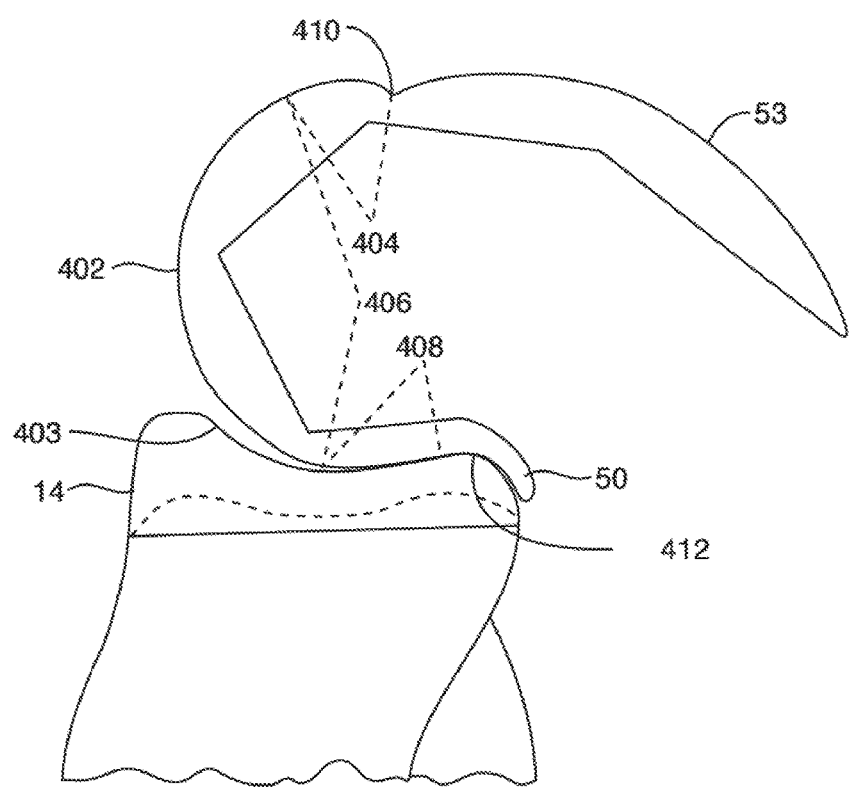

Upon further flexion of the knee joint to approximately 20°, radius 406 is largely in contact with tibial articular surface 403, as shown in FIG. 16K. However, in some embodiments laxity within the knee joint is maintained at approximately 20° flexion such that the femoral component 53 is permitted to shift anteriorly (FIG. 16K) and posteriorly (FIG. 16L) relative to the tibial component 14. As the knee joint is further flexed, radius 406 assumes full contact with the opposing tibial articular surface 403 thereby fully constraining anterior and posterior movement within the knee joint, as shown in FIG. 16M. Full contact and constraint within the knee joint is thereafter maintained through the remaining mid-flexion movement of the joint, as shown in FIGS. 16N and 16O. Beyond approximately 110° flexion, radius 408 begins to pick up contact with tibial articular surface 403 thereby causing distraction of the femoral and tibial components 53 and 14, as shown in FIG. 16P. As the knee joint is further distracted, proximal extension 50 maintains contact with posterior articular feature 412 of the tibial component 14.

Figure 16Q:
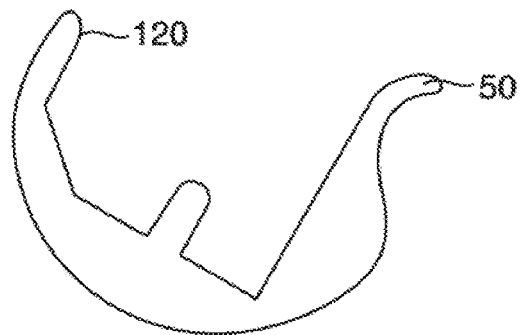
FIG. 16Q illustrates a unicompartmental femoral component including an extended articulating surface in accordance with a representative embodiment of the present invention.
Figure 16R:
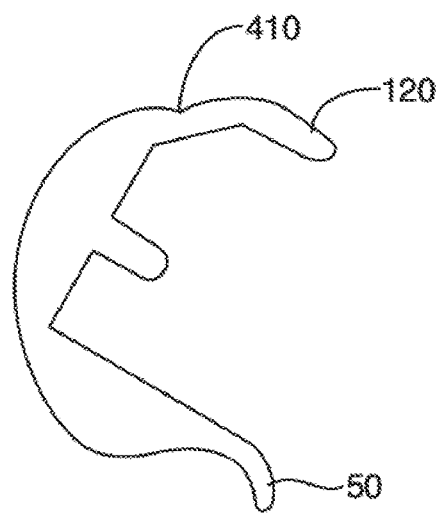
FIG. 16R illustrates a unicompartmental femoral component including a decreasing radius and an indentation in accordance with a representative embodiment of the present invention.
Figure 16S:
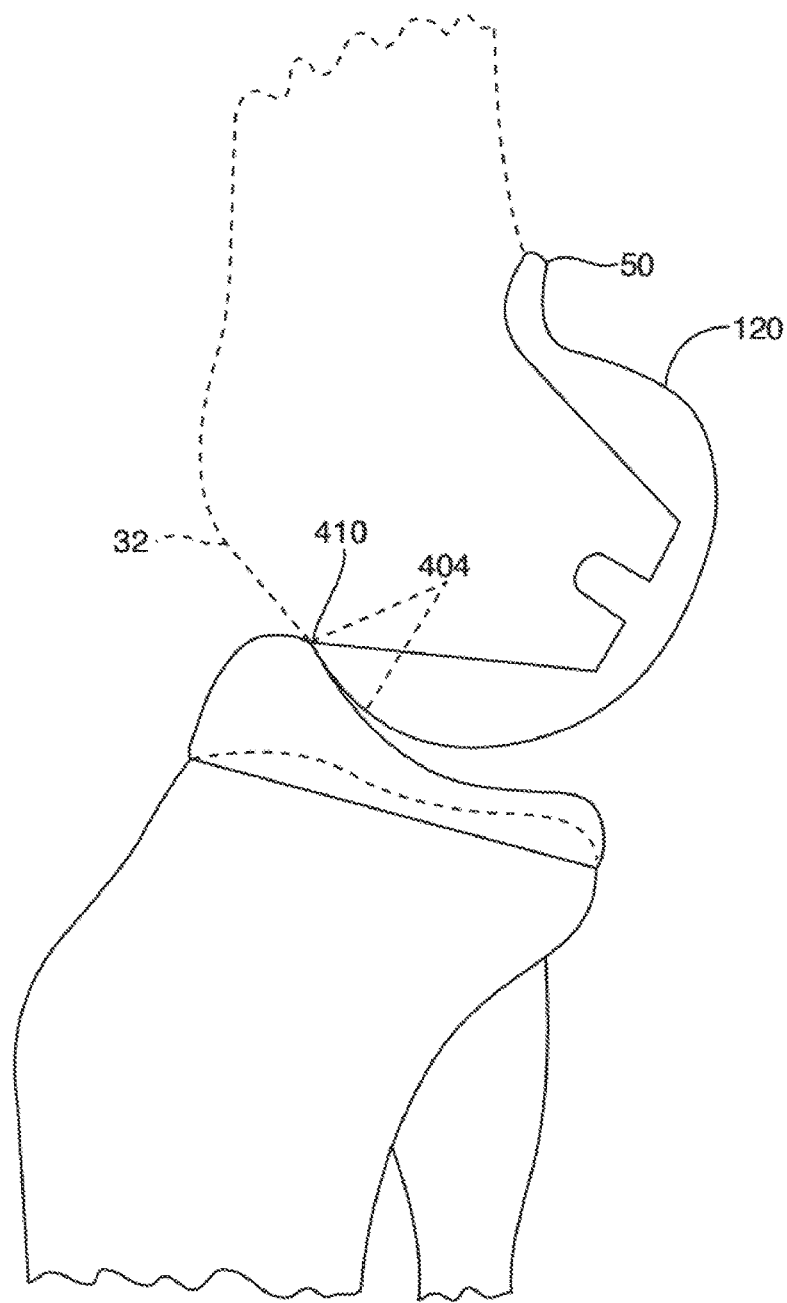
FIG. 16S illustrates a truncated femoral component including an indentation in accordance with a representative embodiment of the present invention.

With reference to FIG. 16Q, a representative embodiment of a unicompartmental femoral component 120 is shown. The various components of the present invention may be substituted with a unicompartmental component, as discussed below. In some embodiments, unicompartmental femoral component 120 further comprises a decreasing radius 404 providing indentation 410, as shown in FIG. 16R. In other embodiments, unicompartmental femoral component 120 is truncated thereby providing indentation 410 at intersection between component 120 and non-resectioned anterior condylar surface of femur 32, as shown in FIG. 16S.

The unicompartmental component is generally implanted to replace the weight bearing portion of the knee joint medially or laterally. The unicompartmental component may be used medially and/or laterally as two separate femoral and two separate tibial components on just the weight bearing portion of the joint. In some embodiments, the unicompartmental component is used with two femoral or two tibial components joined, but ignoring the patello-femoral joint. In other embodiments, the unicompartmental component is used as one femoral component replacing the medial and lateral weight bearing portions of the distal femur and also a portion of, or all of the patello-femoral joint with either a one piece tibial component or separate medial and lateral tibial components. Finally, in some embodiments the unicompartmental component is a one-piece, femoral component replacing the patello-femoral joint and either the medial or lateral weight-bearing portion of the femur.

In some embodiments, the unicompartmental component 120 includes a full flex femoral articulation surface (which may also be referred to as a proximal extension) 50. As previously discussed, the articulation surface or extension 50 is configured to provide extended contact between the unicompartmental femoral component 120 and a full flex tibial articulation surface 55 of a tibial component during deep flexion of the knee. In some embodiments, a portion of the popliteal surface 202 of the femur is removed to accept placement of the articulation surface 50. In other embodiments, a unicompartmental component (not shown) is provided for use in conjunction with a modular full flex femoral articulation surface (not shown). Thus, in some embodiments a first portion of the femur is prepared to receive the unicompartmental component 120, and a second portion of the femur is prepared to receive a modular full flex femoral articulation surface (not shown). As such, a combination of the unicompartmental component and the modular full flex femoral articulation surface provide a unicompartmental femoral component that is functionally equivalent to the unicompartmental femoral component 120.

In some embodiments, the unicompartmental femoral component 120 is used in conjunction with a unicompartmental tibial component. In other embodiments, the unicompartmental femoral component 120 is used in conjunction with a full tibial component. Finally, in some embodiments, the unicompartmental femoral component 120 is used directly in conjunction with a natural surface of the opposing tibia.

Where permitted, implementation of a unicompartmental femoral component 120 provides several advantages over total knee replacement procedures. For example, while an eight-inch incision is typically required for a total knee replacement surgery, a partial knee replacement utilizing a unicompartmental femoral component 120 requires an incision of approximately three-inches. Thus, one benefit of a unicompartmental femoral component 120 is decreased scarring following the partial knee replacement procedure.

Other benefits of a partial knee replacement include decreased recovery time, increased range of motion, and decreased overall damage to the knee. A total knee replacement procedure may require the patient to remain in the hospital for up to four days. It can also take up to three months, or longer, to recover from the surgery. However, with a partial knee replacement procedure, a patient typically requires no more than two days of hospitalization followed by one month of recovery. Additionally, a patient is typically able to walk without assistance a week or two following the partial knee replacement procedure.

Unlike some total knee replacement procedures, insertion of the unicompartmental femoral component 120 generally preserves more ligaments thereby providing a fuller range of motion. For example, in some partial knee replacement procedures, the anterior and/or posterior cruciate ligaments are preserved, as desired. A partial knee replacement also generally results in less damage to the knee because the surgery is minimally invasive thereby causing minimal tissue, muscle and tendon damage to the knee.

For some partial knee replacement procedures, various methods may be implemented to address pain and discomfort caused by patello-femoral arthritis. For example, for some partial knee replacement procedures denervation of the patella is performed. In other partial knee replacement procedures, denervation of the opposing femoral groove is performed. In some embodiments of the present invention the unicompartmental femoral component 120 is designed to reproduce the natural patello-femoral joint throughout the range of motion and to facilitate tracking of the patella in the femoral groove. In other embodiments, a combination of denervation and natural design of the unicompartmental femoral component 120 are implemented to adequately address the patello-femoral arthritis.

Figure 20A:
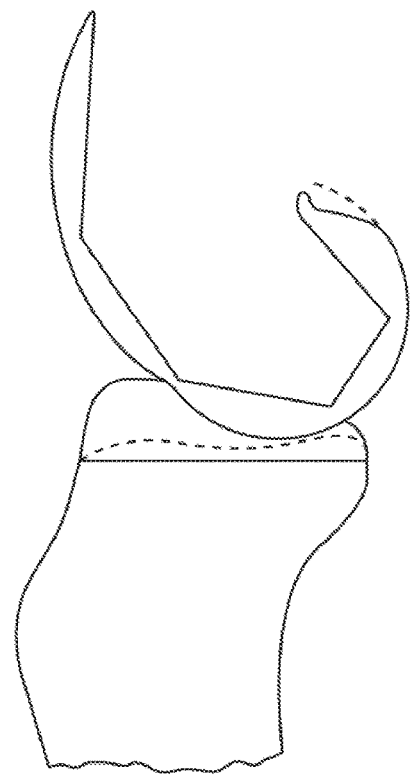
FIGS. 20A-20I illustrate a representative interaction of a femoral full flex articulation and a tibial full flex articulation.
Figure 20B:
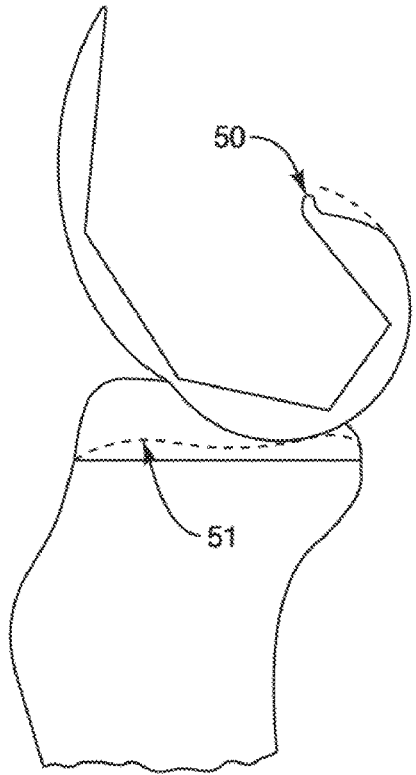
Figure 20C:
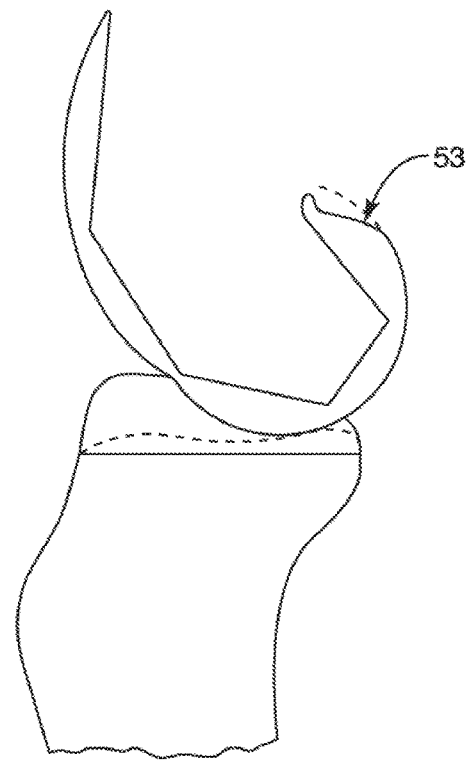
Figure 20D:
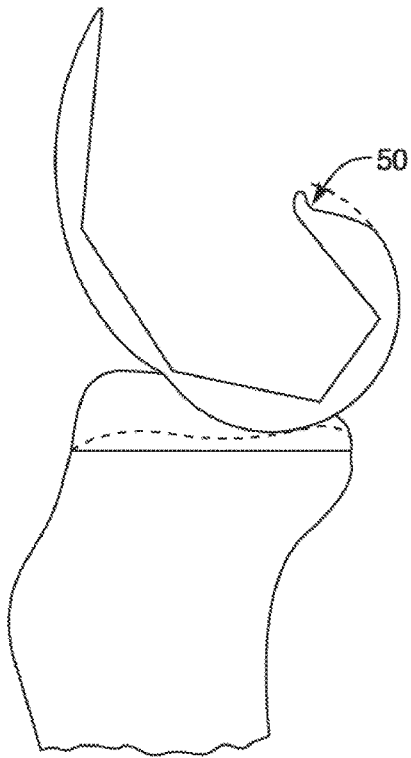
Figure 20E:
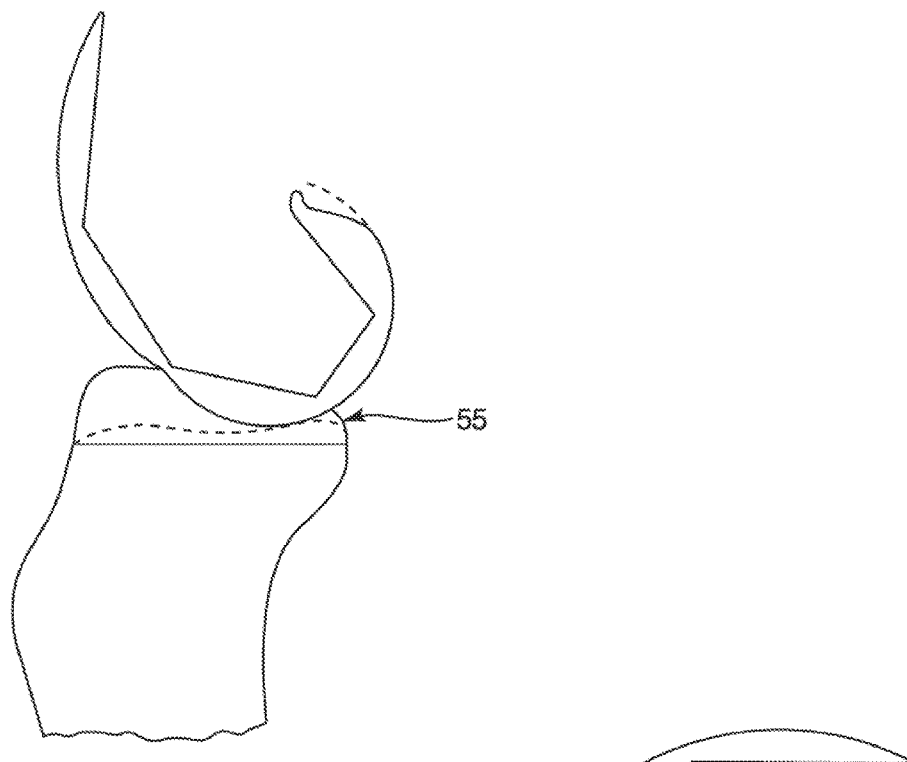
Figure 20F:
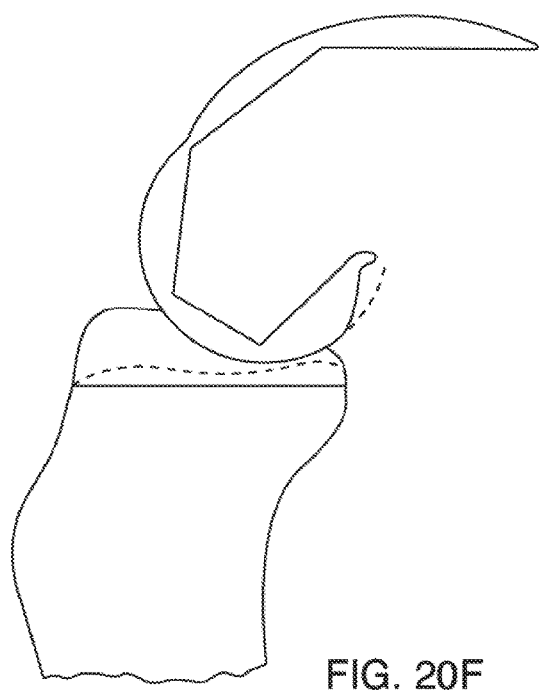
Figure 20G:
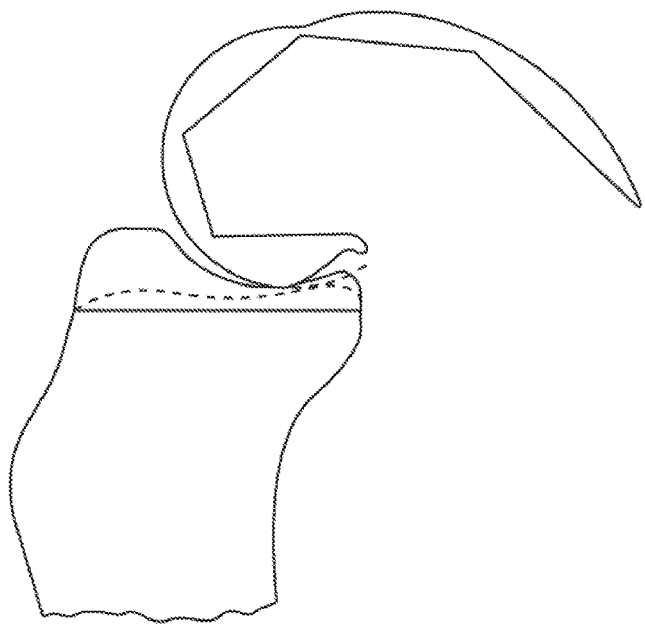
Figure 20H:
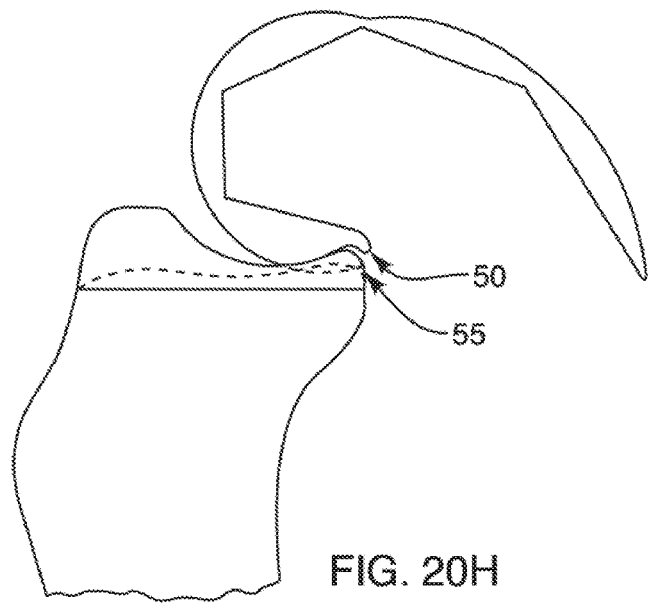
Figure 20I:
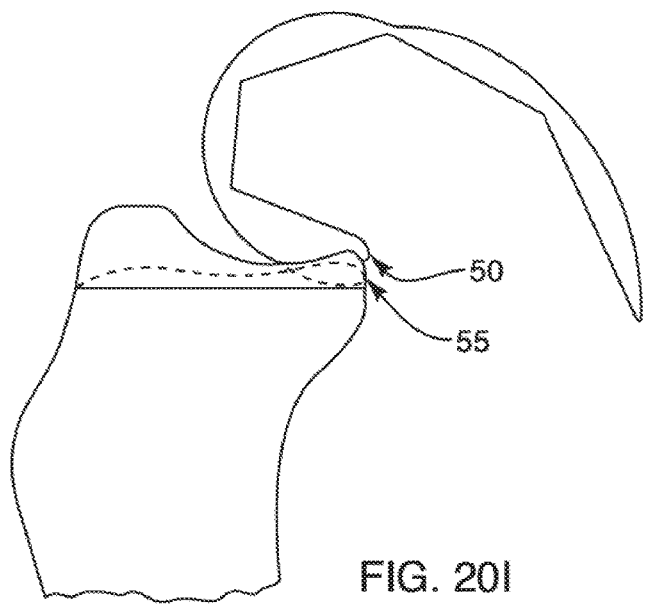

The interaction of the femoral full flex articulation 50 and the tibial full flex articulation 55 is illustrated in FIGS. 20A-20I, wherein FIGS. 20A-20E are at 0°, FIG. 20F is at 90°, FIG. 20G is at 130°, FIG. 20H is at 150°, and FIG. 20I is at 160+°. FIG. 20B identifies a representative position of unresected tibial plateau 51. FIG. 20C identifies a representative closing radius on a posterior portion of a femoral component 53. FIG. 20D identifies a representative full flex femoral articulation 50. FIG. 20E identifies a representative full flex tibial articulation 55. FIG. 20H identifies a representative approach of the full flex femoral articulation 50 to the full flex tibial articulation 55 during flexion. FIG. 20I identifies a representative contact of the full flex femoral articulation 50 to the full flex tibial articulation 55 during deep flexion.

Figure 20J:
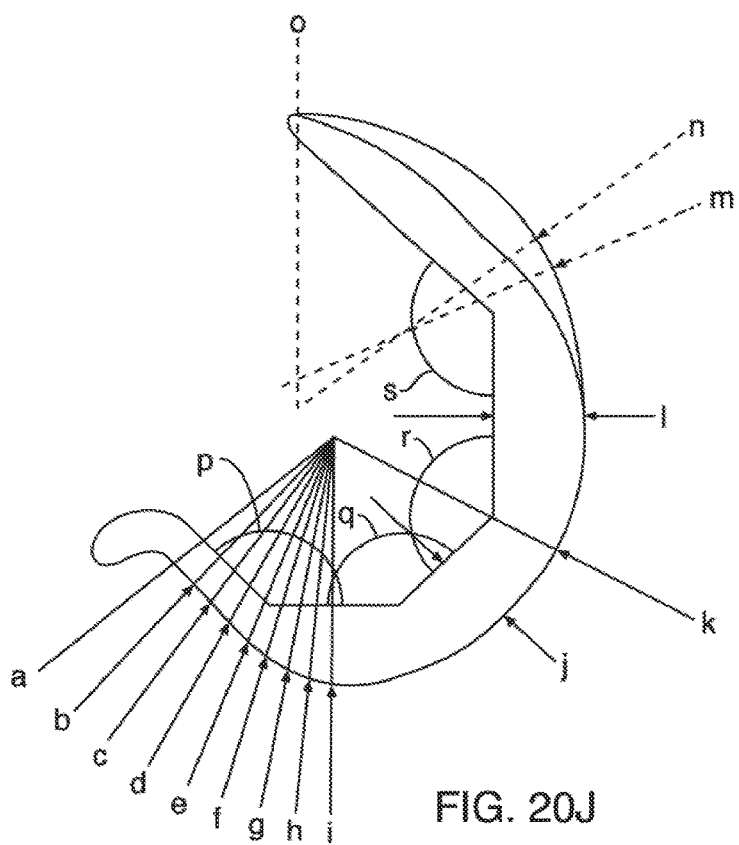
FIG. 20J illustrates a side view of a representative embodiment of the femoral component.

While with respect to the closing radius of the femoral component 12, the various portions of the femoral component can have any suitable radius, including, without limitation, a radius between about 10 and about 50 mm, or any subrange thereof (e.g., between about 18 mm and about 34 mm, or any other subrange). By way of illustration, FIG. 20J illustrates an embodiment in which the femoral component 12 comprises several radii (e.g., a-i, k, m, n, and o). While such radii can be any suitable length, in accordance with some embodiments, radius a is about 19±4 mm, radius b is about 20±4 mm, radius c is about 20.5±4 mm, radius d is about 21±4 mm, radius e is about 22±4 mm, radius f is about 23±4 mm, radius g is about 24±4 mm, radius h is about 24.5±4 mm, radius i is about 25±4 mm, radius m is about 30±4 mm, radius n is about 30±4 mm, and radius o is about 30±4 mm.

Additionally, while the angles between inner surfaces (e.g., 620) of the femoral component 12 can be any suitable angle that allow the femoral component to be fixed to a femur, in some embodiments, the angles (e.g., p, q, r, and s, as shown) between the various inner surfaces is between about 70° and about 180° (and any subrange thereof).

Indeed, in accordance with some embodiments, the angles (e.g., p, q, r, and s, as shown in FIG. 20J) between the various inner surfaces is between about 130° and about 145° (e.g., between about 133° and about 140°).

Moreover, while the various portions of the femoral component 12 can be any suitable thickness between the component's outer articular surface and inner surface, in some embodiments, the various portions of the femoral component (e.g., j and l, as shown in FIG. 20J) can be any suitable thickness, including, without limitation, between about 1 and about 20 mm thick (or any subrange thereof). Indeed, in some embodiments, the various portions (e.g., j and l, as shown in FIG. 20J) of the femoral component are between about 2 mm and about 11 mm thick (e.g., about 9 mm±1 mm).

FIGS. 15A-15D illustrate the various manners in which the four previously-discussed embodiments of the femoral component 12 provide an extended articular surface 48. The concept of adding more articular surface to the proximal portion of the posterior condyles of the femoral component may be generally accomplished by extending the proximal portion anteriorly until the articular surface approaches, or extends beyond the plane of the posterior surface of the shaft of the distal femur, if that plane were to extend distally. For example, as may be seen from FIGS. 15A-15D, the extended articular surface 48 of each embodiment extends the articular surface at the anterior end of one or both of the medial posterior condyle or the lateral posterior condyle. As illustrated in FIGS. 16A-16D, the articular surface may be further extended in a proximal direction from the end of the extended articular surface 48. This further extension may be provided by a proximal extension 50. The proximal extension 50 may be an integral part of the femoral component 12, it may be a part of the modular attachment 30 (as discussed herein), or it may be provided as a separate and additional component. In one embodiment where the proximal extension 50 is provided, the proximal extension 50 acts as a fulcrum that interacts with the tibia or with the tibial component 14 to increase separation between the femur 32 and the tibia during full functional flexion to improve the deep knee flexion. In another embodiment, the proximal extension 50 allows the normal relationships between the tibia and femur in full functional flexion to exist while maintaining contact between the two surfaces.

Where the femoral component 12 comprises a proximal extension 50 (or a femoral full flex articulation), the proximal extension can comprise any suitable shape. Indeed, in some embodiments (as illustrated by at least FIG. 16F, the proximal extension 50 extends from the femoral component 12 such that a concave articulation surface 17 (or a concave surface of any shape that is suitable for articulating against a portion of the tibia and/or tibial component 14) is disposed at or near a proximal, posterior portion of the femoral component 12. In some embodiments, FIG. 16G illustrates that the proximal extension 50 comprises a first curved articular surface 19, while the femoral component's posterior condylar surface (e.g., a lateral and/or medial condylar surface) comprises a second curved articular surface 21, wherein the first 19 and the second 21 articular surfaces form a reverse curve.

Additionally, where the femoral component 12 comprises a proximal extension 50, the proximal extension can be disposed in any suitable location on the femoral component that allows the concave articulation surface 17 to articulate against a portion of the tibia and/or the tibial component 14 when the knee is in (or is approaching) full flexion. Moreover, the proximal extension 50 can also be used in connection with any suitable femoral component (e.g., as a modular unit or as an integral part) that allows the proximal extension to function as described herein.

In some embodiments, the proximal extension 50 extends from the femoral component 12 so that the concave articulation surface 17 is disposed at or near a proximal, posterior portion of the femoral component (e.g., as shown in FIGS. 16A-16D). Indeed, in one illustration, FIG. 16D shows that in an embodiment in which the femoral component 12 has a first internal surface 721 for contacting an anterior femoral surface and/or cut 621 on the femur 32, a second internal surface 722 for contacting an anterior chamfer cut 622 on the femur, a third internal surface 723 for contacting a distal cut 623 on the femur, a fourth internal surface 727 for contacting a posterior chamfer cut 627 on the femur, a fifth internal surface 724 for contacting a full flexion cut 624 on the femur (or a cut that runs proximally and anteriorly from its distal end towards a posterior surface of the femur), the proximal extension 50 is disposed near the fifth surface 724 (e.g., so as to be disposed at or near a proximal, posterior portion of one or both of the condylar surfaces of the femoral component 24 and/or at or near a popliteal surface of the shaft of the femur).

Figure 15I:
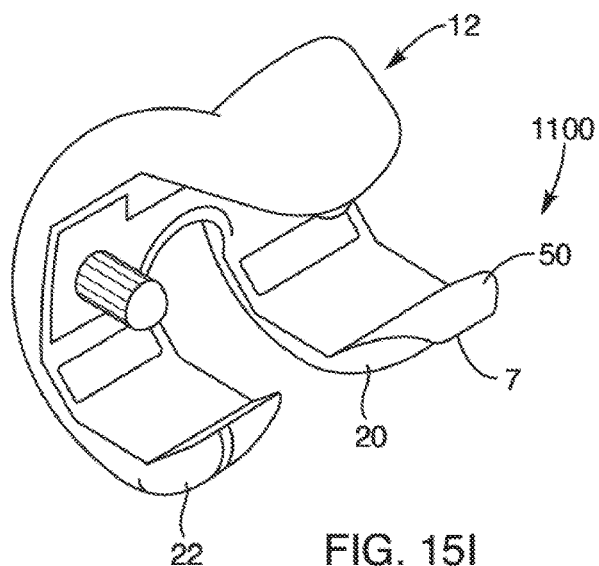
FIGS. 15I-15K each illustrate a different view of a representative embodiment in which the femoral component comprises a medial proximal extension.
Figure 15J:
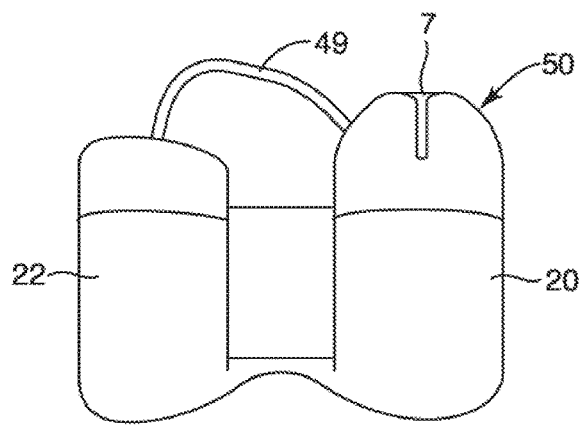
Figure 15K:
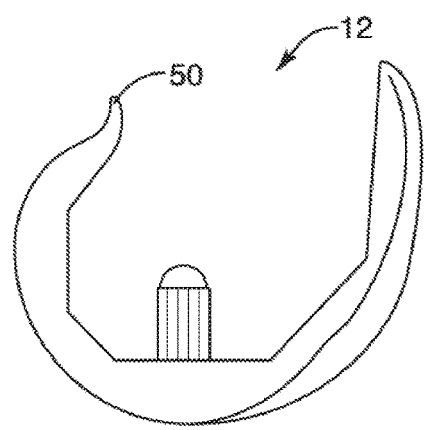

While in some embodiments, the proximal extension 50 extends from a proximal, portion of the posterior medial 20 and posterior lateral 22 condyles (e.g., as shown in FIGS. 15F-15H), in some other embodiments, only the medial or the lateral posterior condyle of the femoral component 12 comprises the proximal extension. By way of non-limiting illustration, FIGS. 15I-15K illustrate some embodiments in which the posterior medial condyle 20 comprises the proximal extension 50. In this regard, while having the proximal extension on the medial condyle and not the lateral condyle may serve several beneficial purposes, in some embodiments, it helps to maintain the fixed center of rotation for the medial condyle while allowing the lateral condyle to slide and/or otherwise move anteriorly and/or posteriorly with respect to the tibial component 14.

Figure 16T:
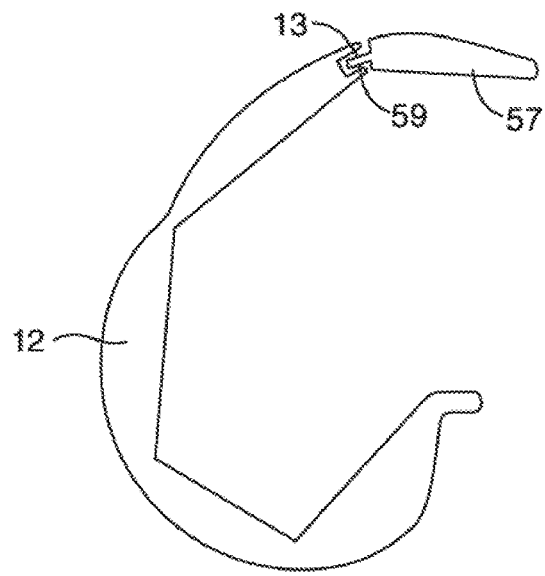
FIG. 16T illustrates a cross-section view of the femoral component coupled to a modular patella-femoral component in accordance with a representative embodiment of the present invention.
Figure 16U:
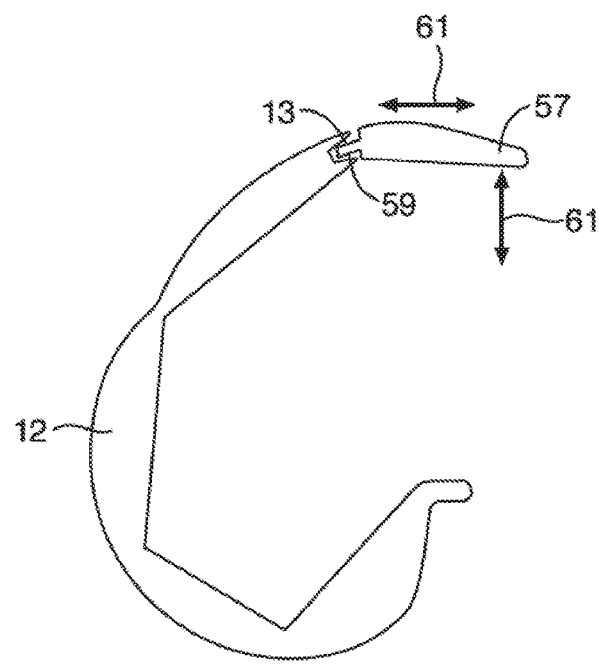
FIG. 16U illustrates a cross-section view of a femoral component slidably coupled to a modular patella-femoral component in accordance with a representative embodiment of the present invention.
Figure 16V:
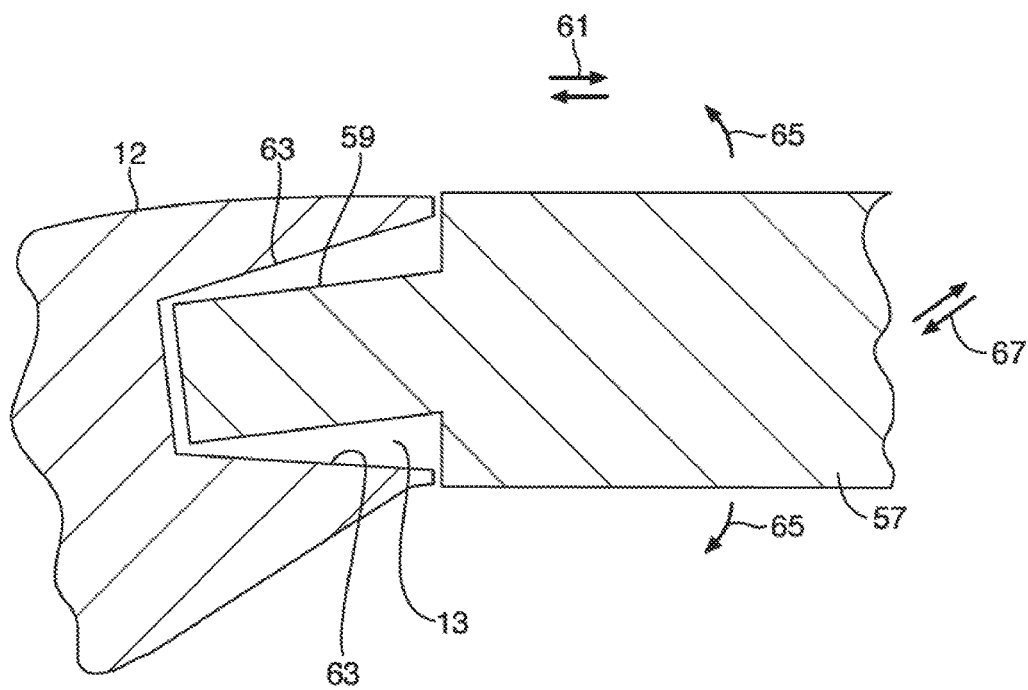
FIG. 16V illustrates a detailed cross-section view of the femoral component having a tapered opening adjustably and slidably coupled to a post of a modular patella-femoral component in accordance with a representative embodiment of the present invention.
Figure 16W:
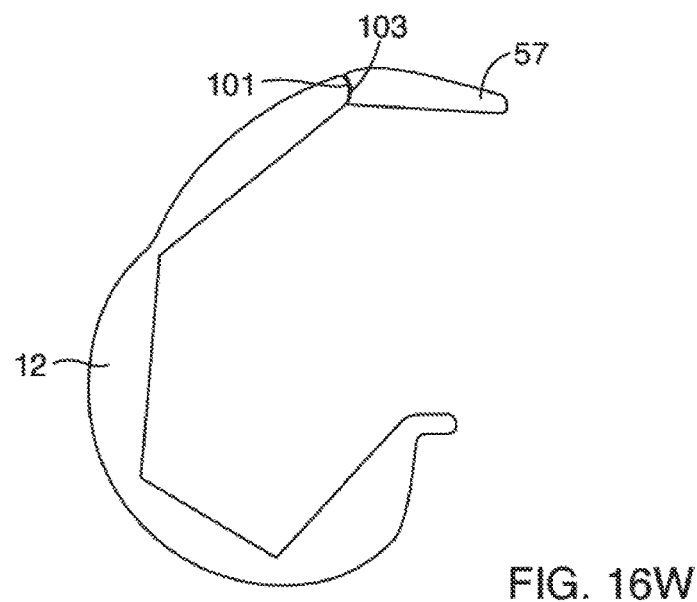
FIG. 16W illustrates a cross-sectional view of the femoral component having a convex surface abutted with a concave surface of a modular patella-femoral component in accordance with a representative embodiment of the present invention.
Figure 16X:
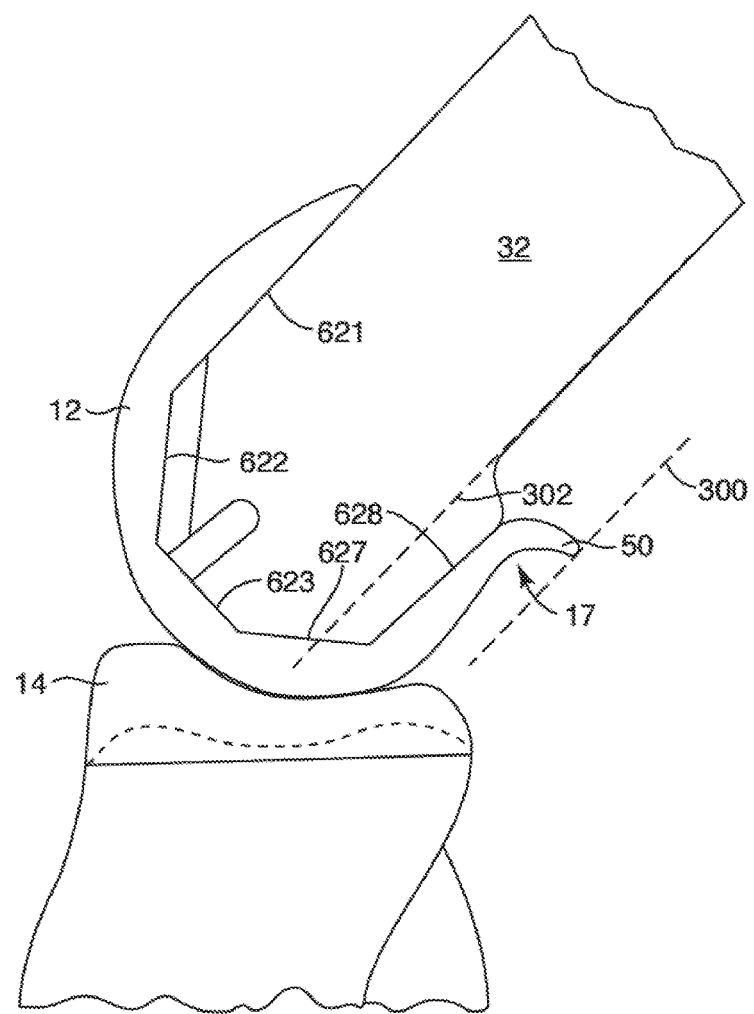
FIGS. 16X-16Z illustrate flexion of a non-limiting embodiment of the femoral component having femoral full flexion articulation (or proximal extension) in accordance with a representative embodiment of the present invention.
Figure 16Y:
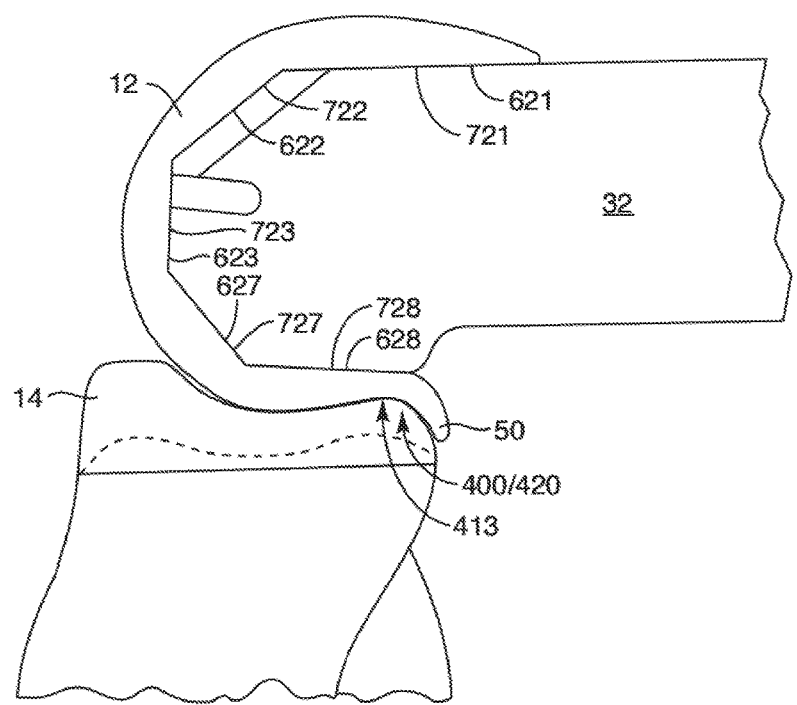
Figure 16Z:
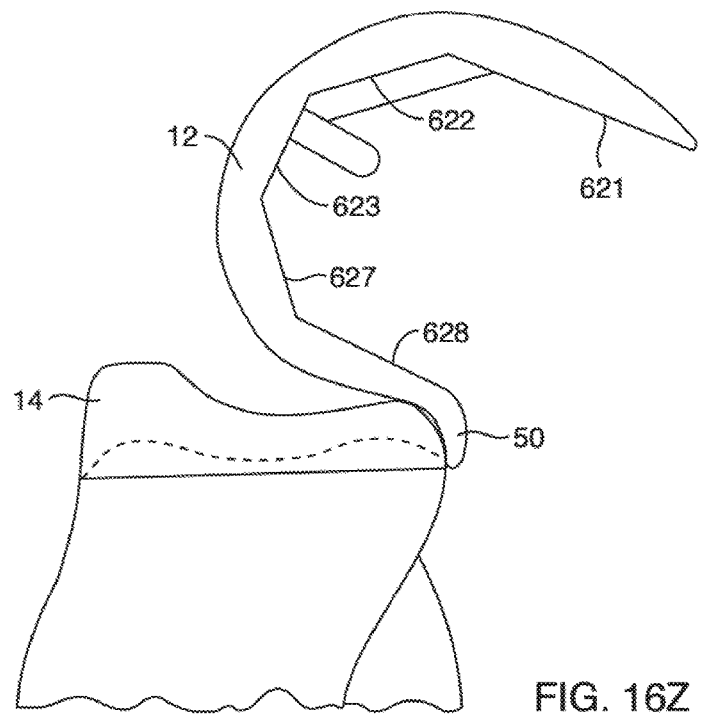

In other embodiments, FIGS. 16X-16Z show that, in some cases, the proximal extension 50 is disposed on a femoral component 12 that lacks a surface (e.g., surface 624) for contacting a full flexion cut 624 on the femur 32. In such embodiments, the proximal extension 50 can be disposed in any suitable location that allows it to perform its intended functions. Indeed, in some embodiments in which the femoral component 12 comprises a first internal surface 721 for contacting the anterior surface 621 of the femur 32, a second internal surface 722 for contacting an anterior chamfer cut 622 on the femur, a third internal surface 723 for contacting a distal cut 623 on the femur, a fourth internal surface 727 for contacting a posterior chamfer cut 627 on the femur, and an additional internal surface 728 for contacting a posterior condylar cut 628 on the femur (e.g., a cut that runs substantially parallel to, or that diverges by any suitable amount of less than about 50° (e.g., any suitable amount less than 40°) from the first interior surface 621), the proximal extension 50 is disposed proximal to surface 628.

Thus, FIGS. 16X-16Z show that conventional femoral components can easily be modified to include a femoral full flex articulation (e.g., by the addition of a modular and/or integral proximal extension 50). It should be noted that while FIGS. 16X-16Z show the femoral component 12 having a proximal extension 50 that is being used to articulate and/or act as a fulcrum against the tibial component 14 (e.g., a component comprising a tibial full flex articulation), such a femoral component can be used to articulate against an any suitable tibial articulation surface (e.g., from a unresected tibia, a partially resected tibia, and/or any suitable tibial component that can articulate with the proximal extension 50). Additionally, while FIGS. 16X-16Z show some embodiments in which the proximal extension is formed as an integral portion of the femoral components, in some embodiments (as described herein), the proximal extension comprises a modular unit that is attachable to the femoral component.

Thus, in some embodiments of the present invention, greater deep knee flexion is facilitated by providing an articular surface on the proximal posterior and/or anterior surfaces (or portions) of one or both of the posterior condyles of the femur. At least some such embodiments embrace an additional or increased articular surface on the proximal posterior and/or anterior portion (e.g., as shown in FIGS. 16A-16S and 16X-16Z) of either or both of the medial or lateral posterior condyles of the femoral component 12. Indeed, some embodiments of the femoral component 12 add increased articular surface area to the proximal end of the posterior condyles of the femoral component 12 (e.g., in an anterior direction such that when the patient bends his or her knee during deep knee or full functional flexion, contact between the femoral component 12 and the tibial component 14 is maintained, and a greater, deeper knee flexion may be achieved.

In addition to the foregoing characteristics, the described proximal extension 50 can comprise any other suitable characteristic. Indeed, while the posterior-most portion (or the posterior end 7) of the proximal extension can have any suitable shape (including, without limitation, being rounded, substantially flat, polygonal, semi-elliptical, irregular, symmetrical, and/or any other suitable shape), in some embodiments (as respectively shown in FIGS. 15G and 15H), the posterior end of the proximal extension 50 comprises a substantially rounded or a substantially flat portion. While the various shapes may provide the proximal extension with several beneficial characteristics, in some embodiments, the flat posterior end may allow the proximal extension to cover (and terminate with) resected bone at a proximal portion of a posterior condyle to prevent such resected bone from striking the tibial component and/or the tibia in deep knee flexion.

Where the posterior end 7 of the proximal extension 50 (and/or the posterior end of the posterior medial and/or lateral condyles of the femoral component 12, as shown in FIGS. 5C-5D) comprise a substantially flat edge, a width F (as shown in FIG. 15H) of the substantially flat edge can comprise any suitable portion of the width W of the maximum medial to lateral width of the articular surface of the corresponding medial and/or lateral condyle (as shown in FIG. 15H). Indeed, in some embodiments, the width of the substantially flat posterior end of the medial and/or lateral condyle is between about 5% and about 100% of the width W of the maximum medial to lateral width of the articular surface of the corresponding condyle, or any subrange thereof (e.g., between about 20% and about 98%, between about 50% and about 90%, or any other suitable subrange). Indeed, in some embodiments, the posterior end of the proximal extension comprises a substantially flat edge that is between about 50% and about 99% of the width W of the medial condyle or the lateral condyle.

In at least some embodiments of the present invention, greater deep knee flexion may be provided or improved by modifying the tibial articulation, in which the center of the conforming medial tibial articular surface of the tibial component 14 is moved posterior relative to what is currently available. Additionally, in some such embodiments, the overall shape of the lateral and/or medial tibial articular surfaces may be modified. This is illustrated with reference to FIGS. 6A-6D and 6J-6K.

In some such embodiments of the tibial component 14, the condylar or articular plateau surfaces are asymmetric. Indeed, in some embodiments, the lateral undersurface side of the tibial component 14 is shorter in the anteroposterior dimension than the medial side, and the top of the tibial component 14 may also be asymmetric.

Anatomically, the tibial plateau typically has a greater anteroposterior dimension medially than it has laterally. In order to cover as much of the cut proximal tibia as possible and avoid anterior or posterior overhang of the lateral plateau, in some instances, the tibial component is larger in the anteroposterior dimension medially than it is laterally. In one embodiment, this is accomplished by moving the center of the medial articular surface posteriorly to compensate for the dimensional differences. In some cases, in order to achieve full flexion, it can be useful to have the medial center of rotation on the tibia (which is a concave segment of a sphere) more posterior than is currently available with other designs. This allows the proximal tibia, when the knee is flexed beyond approximately 120-130°, to be positioned anteriorly enough so that there is no impingement of the posterior edge or portion of the medial tibial articular surface on the proximal portion of the posterior medial condyle of the femur. Current designs of tibial components 14, which will allow the tibia to move anterior with flexion, either have a non-spherical medial tibial articular surface or the center of rotation of the spherical articular surface is not as far posterior as is provided by the embodiments described below. However, embodiments of the current invention may be used in combination with any knee replacement design that will allow knee flexion to 120° or greater.

Currently, some available total knee tibial components 14 that have a fixed center of rotation medially, have the center of rotation located at a position that is around 35-45% of the entire anteroposterior dimension from the posterior surface of the tibial component 14. Nevertheless, in some embodiments of the tibial component 14 described herein, the center of rotation is moved posteriorly so that it is between about 18% and about 35% of the anteroposterior dimension from the posterior wall of the tibial component 14. In such embodiments, the center of rotation can be disposed in any location between about 18% and about 35% (or any subrange thereof) of the anteroposterior dimension of the tibial component 14, as measured from the component's posterior edge. Indeed, in one non-limiting example, the center of rotation of the femur with respect to the tibial component is between about 20% and about 33% of the anteroposterior dimension from the posterior edge of the tibial component 14.

In the normal knee, the medial side of the knee is constrained in that for any degree of flexion the position of the medial femoral condyle relative to the tibial articular surface is roughly fixed and does not move anteriorly or posteriorly a significant amount in the flexion range of roughly 20-130°. In contrast, on the lateral side, except for full extension and sometimes full flexion, after around 20-40° of flexion the lateral femoral condyle can move anterior and posterior on the lateral tibial plateau. In full functional flexion to 160° and beyond, the lateral femoral condyle may appear to be touching only the most posterior portion of the opposing tibial plateau or it may contact the plateau more anterior clearly on the flattened portion of the lateral tibial plateau.

Therefore, in embodiments of the tibial component 14, the lateral tibial articular surface is basically flat in the anteroposterior sense, except anteriorly where there is an anterior lip which prevents the tibial component from rotating too far externally and allowing the lateral femoral condyle to slide off the anterior edge of the tibial component. In some embodiments, the basically flat portion of the lateral tibial articular surface may comprise between about two-thirds and about seven-eighths (or any sub-range thereof) of the total anteroposterior dimension of the tibial component 14. In some embodiments, a slight lip may be present posteriorly on the lateral side; however, as long as the fixed center of rotation is positioned as described, no lip is required posteriorly on the lateral side. In other embodiments there is no anterior or posterior lip. In some embodiments, the lateral tibial articular surface is either flat or concave when viewed in the frontal plane and, if concave, may or may not be the same radius of curvature of the opposing femoral condyle or it may have a greater radius when viewed in the frontal plane. In some cases, this flat or concave groove is flat on the bottom when viewed in the sagittal plane, except for the anterior and posterior ends as noted above and is generated around a point that corresponds to the center of rotation of the medial condyle. In some embodiments, the posterolateral tibial articulation may be the same as described for the medial posterior full flex articulation. In other embodiments, the medial tibial articular surface may be the same as, or similar to the flat articular surface described for the lateral tibial plateau. However, in some embodiments, the position of the medial articular contact is mainly obligatory while the position of the lateral articular contact is non-obligatory. Thus, the position of the lateral articular contact is likely determined by the task being performed, by comfort, and/or by culture.

FIGS. 6A-6D and 6J-6K depict a comparison of a prior art tibial component 14's medial tibial condylar surface 26 and lateral tibial condylar surface 24 with some embodiments of the tibial component 14 as discussed above. Specifically, FIGS. 6A and 6B reflect side views of medial and lateral sides (respectively) of some currently available tibial components 14, while FIGS. 6C and 6J illustrate side views of medial sides, and FIGS. 6D and 6K illustrate side views of lateral sides of some embodiments of the tibial component 14, as discussed above. It will be appreciated that a number of varied configurations for the medial and lateral articular surfaces ranging from almost flat, both medially and laterally, to more conforming, as shown in FIGS. 6A and 6B, have been used in the past; however, it is currently believed that none have either a combination of a posteriorly-displaced medial articular surface and a relatively-flat lateral articular surface, or a medial femoral full flex tibial articulation. These configurations permit the lateral femoral condyle to move anteriorly and posteriorly on the lateral tibial articular surface as the knee flexes and extends. Other configurations may be provided, so that as long as the lateral tibial articular surface will allow this anteroposterior motion, the lateral tibial configuration does not need to be confined to a single configuration, as shown in FIGS. 6D and 6J.

The lateral tibial articulation may in some embodiments have no posterior lip, and in other embodiments the posterior surface may slope downward when it is accompanied by a medial tibial articulation that provides for flexion beyond 135°.

In the prior art tibial component 14, the condylar surface has a curvature centered on a fixed point 52. The distance from the fixed point 52 (or from the low point of the curvature centered on the fixed point 52) to the posterior edge 54 of the tibial component is approximately 35-45% of the anteroposterior dimension of the tibial component 14. These measurements are similar for the medial (FIG. 6A) and lateral (FIG. 6B) sides of the tibial component 14. Some currently available tibial components 14 have a lip 56.

In the embodiment of the tibial component 14 illustrated in FIGS. 6C and 6D, there is no tibial component lip 56 associated with the medial condylar surface 26. Rather, the medial tibial condylar surface 26 runs along a smooth arc. As the arc is generated, a low lip may be present in some embodiments and may extend up to and include the tibial full flex posterior articulation. The amount of the lip will be determined by the relationship of the center of rotation to the posterior edge 54 of the tibial component 14. In another embodiment, however, FIG. 6J shows an implementation in which the tibial component 14 (e.g., at the medial tibial condylar surface 26) comprises a lip 56 at the end of a smooth arc.

Though the radius from fixed point 52 to the articular surface in FIGS. 6A and 6C is essentially the same, in some embodiments of the current invention, the distance from the fixed point 52 (or from the low point of the curvature centered on the fixed point 52) to the posterior edge 54 of the tibial component 14 is shorter. Indeed, as mentioned earlier, in some embodiments, the fixed point 52 is disposed at any location between (or sub-range of) approximately 18% and less than approximately 35% of the anteroposterior dimension from the posterior end of the tibial component 14, as may be seen in FIGS. 6C and 6J. For instance, in some non-limiting embodiments of the current invention, the distance from the fixed point 52 to the posterior edge 54 of the tibial component 14 is between about 20% and about 30% (e.g., about 28%±1.5%).

With respect to the lateral side of the tibial component 14, in the embodiment illustrated in FIGS. 6D and 6K, there is both an anterior lip 58 and a small posterior lip 60. In alternate embodiments, the posterior lip 60 may be omitted as discussed above. Additionally, with respect to FIG. 6J, in some embodiments, the posterior lip 56 can raise any suitable amount above the lowest point (e.g., fixed point 52) in the tibial articulation surface (e.g., medial tibial condylar surface 26). Indeed, in some embodiments, the posterior lip rises between about 0.5 and about 8 mm (or any sub-range thereof) above the lowest point in the medial tibial condylar surface 26. Indeed, in some embodiments, the posterior lip rises between about 2 and about 6 mm (or any sub-range thereof) above the lowest point in the medial tibial condylar surface 26. Moreover, in some embodiments, the posterior lip rises between about 3 and about 5 mm (or any sub-range thereof) above the lowest point in the medial tibial condylar surface 26.

Thus, as has been illustrated with reference to FIGS. 6A-6D and 6J-6K, in at least some embodiments of the present invention, greater deep knee flexion may be provided or improved by modifying the tibial articulation, in which the center of the conforming medial tibial articular surface of the tibial component 14 is moved posterior relative to what is currently available. This change alone, with some currently-available femoral components, will increase the amount of flexion achieved when compared to a standard tibial component. Additionally, in some such embodiments, the overall shape of the lateral tibial articular surface is modified. While such modification can be used for any suitable purpose, in some embodiments, the lateral tibial articular surface is modified to allow the proximal tibia, when the knee is flexed beyond approximately 120-130°, to be positioned anteriorly enough so that there is no impingement of the posterior edge or portion of the medial tibial articular surface on the proximal portion of the medial condyle of the femur. Therefore, greater deep knee flexion may be achieved. It can thus be appreciated that the use of an embodiment of the above tibial component with a conventional femoral component will facilitate greater flexion than will the use of a conventional tibial component. Similarly, the use of any of the above-described femoral components with a conventional tibial component will facilitate more flexion than will use of a conventional tibial component with a standard femoral component.

One having skill in the art will appreciate that the knee may (as discussed above) include at least one of a lateral pivot and a medial pivot. Accordingly, the embodiments of the present invention will be understood to be compatible with either or both of the lateral and medial knee pivot configurations. In other words, while several embodiments described above discuss the lateral tibial articular surface 24 and the medial tibial articular surface 26 as having specific characteristics, in some embodiments, the placement of one or more of the aforementioned characteristics of the lateral tibial articular surface and the medial tibial articular surface are reversed. In this regard, the placement of each of the characteristics discussed above can be reversed in any suitable manner that allows the lateral tibial articular surface (or lateral tibial condylar surface) to comprise a fixed center of rotation and that allows the medial tibial articular surface (or medial tibial condylar surface) to allow the medial femoral condyle to move anteriorly and posteriorly on a medial tibial plateau of the tibial component 14. By way of non-limiting illustration, in some instances, FIGS. 6C and 6J illustrate portions of various tibial components 14 comprising a lateral tibial condylar surface (e.g., surface 26), while FIGS. 6D and 6K illustrate portions of various tibial components 14 that include the medial tibial condylar surface (e.g., surface 24).

In some embodiments of the present invention, greater deep knee flexion may be provided or improved by modifying tibial articulation, in which the articulated surface of the tibial component is modified to encourage or limit articulation of the femoral component relative to the tibial component. Examples of such modification are shown in FIGS. 6E-6I.

Figure 6E:
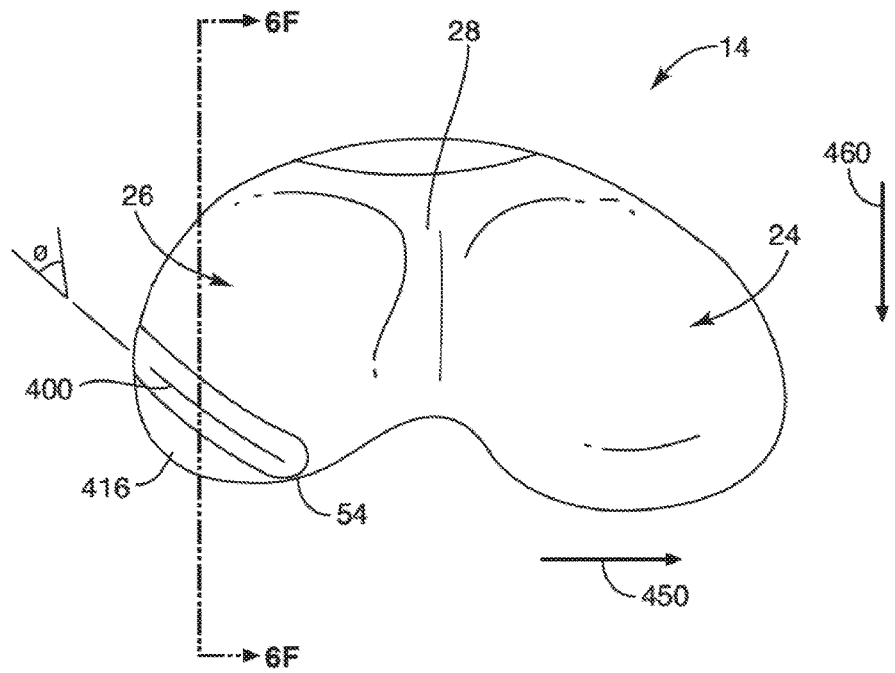
FIGS. 6E-6F depict an alternate embodiment of a representative tibial component modified to include a raised ridge articulation feature.
Figure 6F:
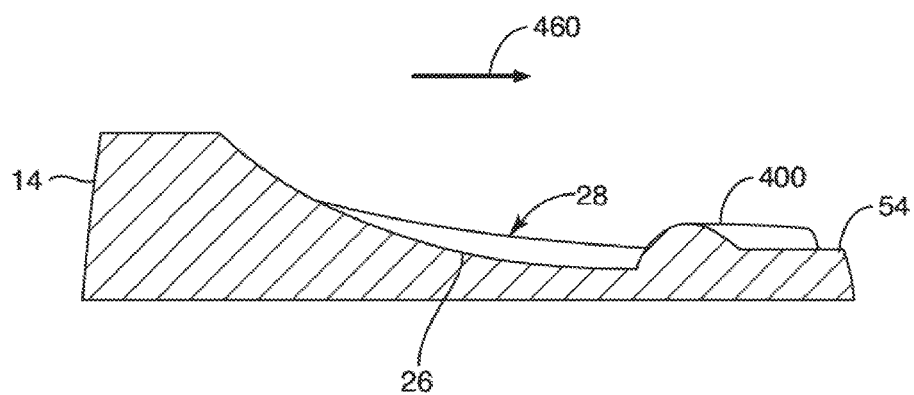
Figure 6G:
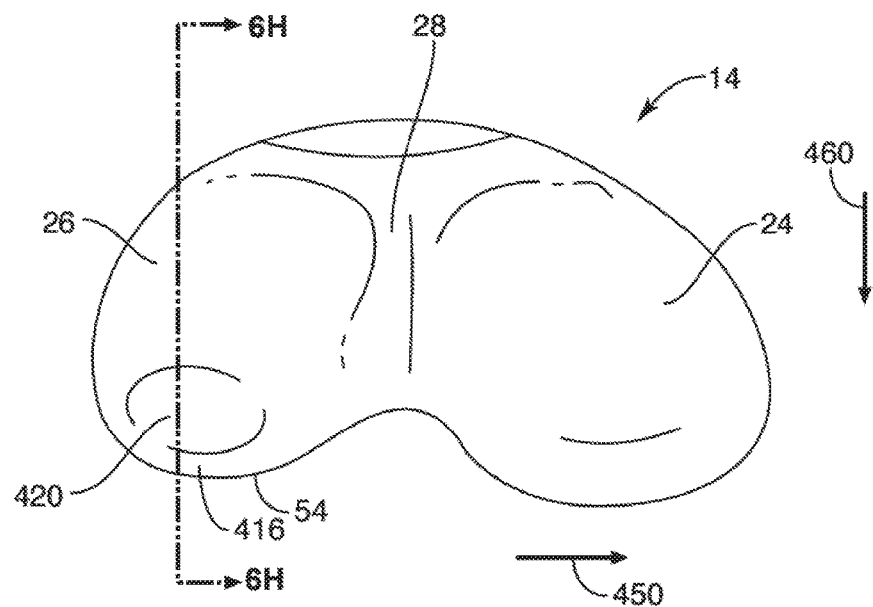
FIGS. 6G-6H depict an alternate embodiment of a representative tibial component modified to include a spherical articulation feature.
Figure 6H:
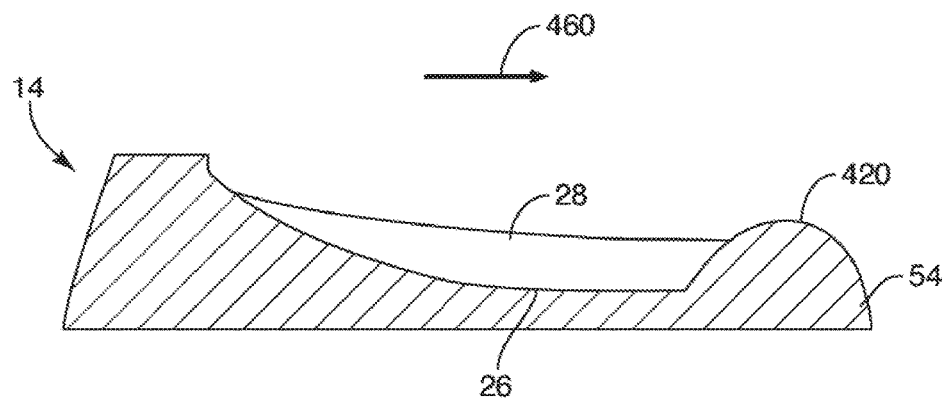
Figure 6I:
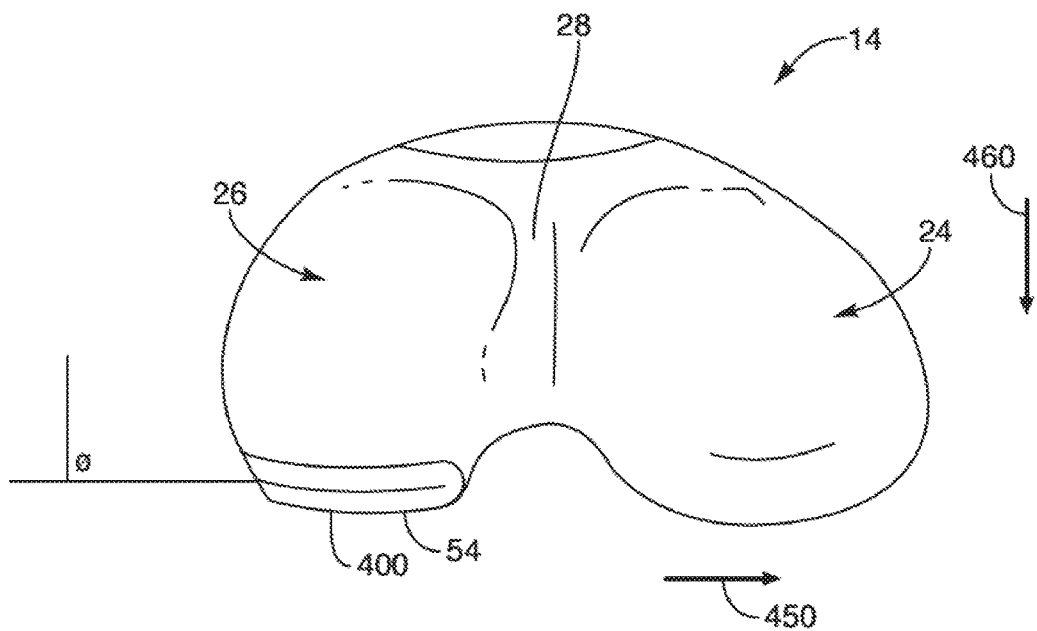
FIG. 6I illustrates an alternate embodiment of a representative tibial component modified to include the raised ridge articulation feature.

Referring now to FIGS. 6E, 6F, and 6I, a tibial component 14 is shown in accordance with a representative embodiment of the present invention. In some embodiments, the medial tibial condylar surface 26 of the tibial component 14 is modified to include an articulation feature. An articulation feature is generally provided to compatibly interact with an opposing articulation surface of the femoral component. During flexion of the knee, the articulation surface of the femoral component interacts with the articulation feature of the medial tibial condylar surface to guide or direct the articular movement of the femoral component relative to the tibial component. Thus, in some embodiments, an articulation feature is provided to control articulation of the knee during deep flexion.

Various types of articulation features may be used in accordance with the teaching of the present invention. For example, some embodiments of the articulation feature comprise an angled articular ridge 400. The articular ridge 400 is provided to compatibly interact with an opposing articular surface of the femoral component. The interaction between the articular ridge 400 and the articular surface of the femoral component affects a change in the articular movement of the femoral component during deep flexion of the knee. Indeed, in some embodiments, an interaction between the femoral component and the articular ridge 400 causes the posterior articulation of femoral component to shift when deep flexion is achieved. Additionally, in some embodiments, the articulation feature acts as the tibial full flex articulation.

The articular ridge 400 is generally disposed on the posterior surface of the tibial component 14 in a general medial-lateral direction 450. While the articular ridge can generally be disposed at any suitable angle with respect to an anteroposterior direction 460 of the intercondylar surface 28, in some embodiments, the articular ridge 400 is disposed or positioned on the posterior surface at an angle θ that is obtuse to an anteroposterior direction 460 of the intercondylar surface 28. In other embodiments, however, the articular ridge 400 is disposed or positioned on the posterior surface at an angle θ that is acute to an anteroposterior direction 460 of the intercondylar surface 28. Generally, angle θ of the articular ridge 400 is selected so as to achieve a desired articular shift of the femoral component during deep flexion. In some embodiments, an angle θ of approximately 0° to approximately 110° is selected. In some other embodiments, an angle θ of approximately 0° to approximately 90° is selected. In yet other embodiments, an angle θ of approximately 10° to approximately 45° is selected. Additionally, in some embodiments, an angle θ of approximately 20° to approximately 35° is preferred. In still other embodiments, the angle θ falls in any suitable sub-range of the aforementioned ranges. By way of illustration, FIG. 6E illustrates an embodiment in which the articular ridge 400 runs at an acute angle to the anteroposterior direction 460 of the intercondylar surface 28. Additionally, FIG. 6I illustrates an embodiment in which the articular ridge 400 runs substantially perpendicular to the anteroposterior direction 460 of the intercondylar surface 28.

The articular ridge 400 can have any suitable shape that allows the tibial component 14 to articulate against an articular surface of a femur and/or femoral component 12. Indeed, while some embodiments of the articular ridge are substantially straight along their length, in other embodiments, the articular ridge comprises an elongated ridge that is slightly bowed (as shown in FIG. 6E), that is curved along a portion of its length, that follows a contour of a posterior edge of the lateral articular surface 24, that follows a contour of a posterior edge of the medial articular surface 26 (as shown in FIG. 6I), that has a bent portion, and/or that is otherwise shaped to causes the posterior articulation of the femoral component to shift on the tibial component when deep flexion is achieved.

The articular ridge 400 may be positioned anywhere on the articular surface of the tibial component 14 so as to achieve a desired articular shift of the femoral component during deep flexion of the knee. For example, in some embodiments, the lateral tibial condylar surface 24 is modified to include the articular ridge (not shown). In this example, any suitable amount of the articular ridge (or another articulation feature) can be disposed within the lateral half (or completely within the lateral condylar surface) of the tibial component 14. Indeed, in some embodiments, the articular ridge (or other articulation feature) is disposed at the lateral half (e.g., lateral to a central axis of the intercondylar surface 28) and does not extend into the medial half of the tibial component (at least not as a single continuous articular ridge).

In other embodiments, the medial tibial condylar surface 26 includes the articulation feature. In such embodiments, any suitable amount of the articular ridge (or another articulation feature) can be disposed within the medial half (or completely within the medial condylar surface) of the tibial component 14. Indeed, in some embodiments, the articular ridge (or other articulation feature) is disposed at the medial half (e.g., medial to a central axis of the intercondylar surface 28) and does not extend into the lateral half of the tibial component (at least not as a single continuous articular ridge). By way of illustration, FIG. 6E shows a representative embodiment in which the articular ridge 400 is disposed completely within the medial condylar surface 26.

In still other embodiments, both the medial and lateral tibial condylar surfaces 26 and 24 include an articular ridge 400 (or other articulation feature). Although in some such embodiments, a single articular ridge spans between both the lateral and the medial condylar surfaces, in other embodiments, the lateral and the medial condylar surfaces each comprise a separate articular ridge (and/or other articulation feature).

In some embodiments, the articulation feature comprises a polyethylene coating or layer. In other embodiments, the polyethylene coating is strictly applied to the articular ridge 400 and precluded from extending beyond articular ridge 400 so as to impinge on the femur during flexion.

Referring now to FIGS. 6G and 6H, a tibial component 14 is shown in accordance with a representative embodiment of the present invention. In some embodiments, the medial tibial condylar surface 26 of the tibial component 14 is further modified to include an articulation feature comprising a spherical articular surface 420. The spherical articular surface 420 is provided to compatibly interact with an opposing articular surface of the femoral component. In some embodiments, the interaction between the spherical articular surface 420 and the articular surface of the femoral component enables unrestricted, natural, articular movement of the femoral component during deep flexion of the knee. In some embodiments, an interaction between the femoral component and the spherical articular surface 420 permits a natural posterior articulation of the femoral component when deep flexion is achieved. One of ordinary skill in the art will appreciate that the tibial component 14 may also be modified to permit femoral articulation on the lateral tibial condylar surface of the tibial component. Additionally, one of ordinary skill in the art will appreciate that the tibial component 14 may be modified to permit concomitant femoral articulation on both the medial and lateral tibial condylar surfaces of the tibial component, for desired applications.

The spherical articular surface 420 may comprise a true spherical shape, or may comprise any other suitable shape, including, without limitation, a parabolic shape; a protuberance; a convex shape; a rounded, raised bump; a raised, polygonal shape; a raised elliptical shape; a raised irregular shape; and/or any other suitable shape that projects from an articular surface of the tibial component (and/or tibia). One of skill in the art will appreciate that variations in the surface structure of the articular surface 420 may be required to provide an articular surface that is optimally configured for a specific application or use.

The spherical articular surface 420 may be positioned anywhere on the articular surface of the tibial component so as to achieve a desired natural movement to the femoral component during deep flexion of the knee. Indeed, in some embodiments, the lateral tibial condylar surface 24 is modified to include the spherical articular surface (not shown). In such embodiments, any suitable amount of the spherical articular surface can be disposed within the lateral half (or completely within the lateral condylar surface) of the tibial component 14. Indeed, in some embodiments, the spherical articular surface is disposed at the lateral half (e.g., lateral to a central axis of the intercondylar surface 28) and does not extend into the medial half of the tibial component (at least not as a single, continuous spherical articulation surface).

In other embodiments, the medial tibial condylar surface 26 includes the spherical articular surface (or articulation feature). In such embodiments, any suitable amount of the spherical articular surface can be disposed within the medial half (or completely within the medial condylar surface) of the tibial component 14. Indeed, in some embodiments, the spherical articular surface is disposed at the medial half (e.g., medial to a central axis of the intercondylar surface 28) and does not extend into the lateral half of the tibial component (at least not as a single continuous articular ridge). By way of illustration, FIG. 6G shows a representative embodiment in which the spherical articular surface 420 is disposed completely within the medial condylar surface 26.

In other embodiments, both the medial and lateral tibial condylar surfaces 26 and 24 include a spherical articular surface 420. Although in some such embodiments, a single spherical articular surface spans between both the lateral 24 and the medial 26 condylar surfaces, in other embodiments, the lateral and the medial condylar surfaces each comprise a separate spherical articular surface (and/or other articulation feature).

In some embodiments, the articulation feature comprises a polyethylene coating or layer. In other embodiments, the polyethylene coating is strictly applied to the spherical articular surface 420 and precluded from extending beyond spherical articular surface 420 so as to impinge on the femur during flexion.

Additionally, while the articulation feature (e.g., articular ridge 400, spherical articular surface 420, etc.) is disposed posteriorly on the tibial component 14 (and/or on a tibial articular surface), the articulation feature can be disposed in any suitable location with respect to the posterior edge of the tibial component (and/or tibial articular surface). Indeed, while in some embodiments, the articular feature is disposed at and/or extends to the posterior edge of the tibial component, in some other embodiments, the articular feature terminates (or lowers in elevation) anterior to the posterior edge. Indeed, (as shown in FIGS. 6G, 6E, and 6F) in some embodiments, a substantially flat, concave, and/or raised articulation surface 416 is disposed between a posterior portion of the articulation feature (e.g., spherical articular surface 400 and/or spherical articular surface 420) and the posterior edge of the tibial component 14. In some embodiments, no matter where the articulation feature is disposed on the tibial component, a portion of the articulation feature that is disposed posterior to a proximal-most portion 413 of the articulation feature (e.g., articular ridge 400, spherical articular surface 420, etc.) is configured to serve as an articulation surface for the femoral component 12 (e.g., as shown in FIG. 16Y).

Where the tibial component 14 comprises a unicompartmental component, the articulation feature (e.g., the articular ridge 400, spherical articular surface 420, etc.) can be disposed in any suitable location on the unicompartmental component. Indeed, while in some embodiments, the articulation feature is simply disposed within the confines of the unicompartmental component (e.g., the lateral or medial unicompartmental component), in other embodiments, the articulation feature is disposed within the articular surface (e.g., the medial tibial condylar surface 26 or the lateral tibial condylar surface 24) of the unicompartmental component.

In some embodiments, the opposing surface of the femur and/or femoral component is modified to comprise a concave surface (not shown) configured to compatibly interface with the convex, spherical articular surface 420 of the tibial component. In other embodiments, the opposing surface of the femur and/or femoral component is modified to include a concave groove (not shown) configured to compatibly interface with the convex, articular ridge 400 of the tibial component. Further, in some embodiments the tibial component comprises a concave surface (not shown) and the femoral component comprises a convex surface (not shown) to compatibly interact with the tibial concave surface. Still further, in some embodiments the polyethylene coating (not shown) or the articular surface of the tibial component is configured to compatibly interface with a desired structure, shape or feature of the opposing femoral surface, thereby achieving normal knee function and movement throughout the knee's range of motion. For example, in some embodiments a tibial component is provided without an elevated, posterior portion or articulation feature. Rather, the surgeon may elect to leave the posterior portion of the patient's tibia which in turn interfaces with the femoral component to achieve normal knee function. Thus, in some embodiments a unicompartmental tibial component is provided to achieve normal knee function.

Figure 7A:
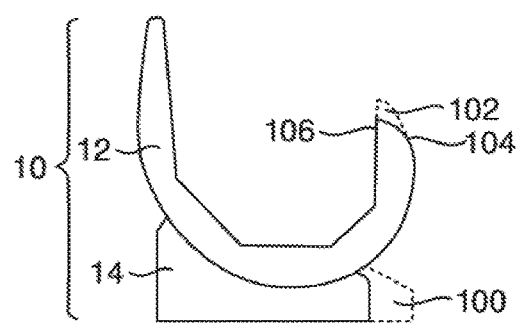
FIGS. 7A and 7B depict alternate embodiments of femoral and tibial components in accordance with embodiments of the present invention.
Figure 7B:
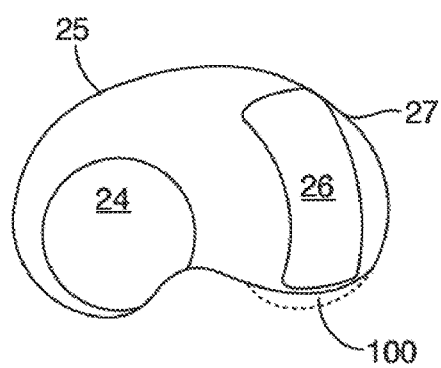

FIGS. 7A and 7B depict modifications to the femoral component 12 and the tibial component 14 to enable deeper knee flexion. Specifically, FIG. 7A depicts a sagittal sectional view of a knee prosthesis 10 with a modified femoral component 12 and tibial component 14. In FIG. 7A, an area 102 of the femoral component 12 is removed, as represented by the dashed line. This area 102 is above and between the posterior extreme 104 and the anterior side 106 of the posterior extreme 104. By removing the area 102, deeper flexion for prosthetic knee patients is partially achievable.

Similarly, with the tibial component 14 in FIG. 7B, a medial side 25 may appear to be relatively lengthened in the anteroposterior dimension anteriorly by moving the articular surface 24 posterior and thereby having more of the tibial component anterior to the posteriorly-displaced medial articulation. This may give the appearance of having removed a posterior portion of the tibial component 14 and moved it to the anterior. A lateral side 27 of the tibial component may be shortened in the anteroposterior dimension relative to the medial side 25 (i.e., area 100). FIG. 7B illustrates the foregoing in a plan view. In other words, by posteriorly shortening the lateral side 27 (i.e., by removing area 100) of the tibial component 14 and by displacing the medial articular surface 24 more posterior, deeper knee flexion is possible. And, these modifications create the opportunity for a prosthetic knee patient to achieve a deeper knee flexion than possible with currently-available prosthetic knees.

Figure 17:
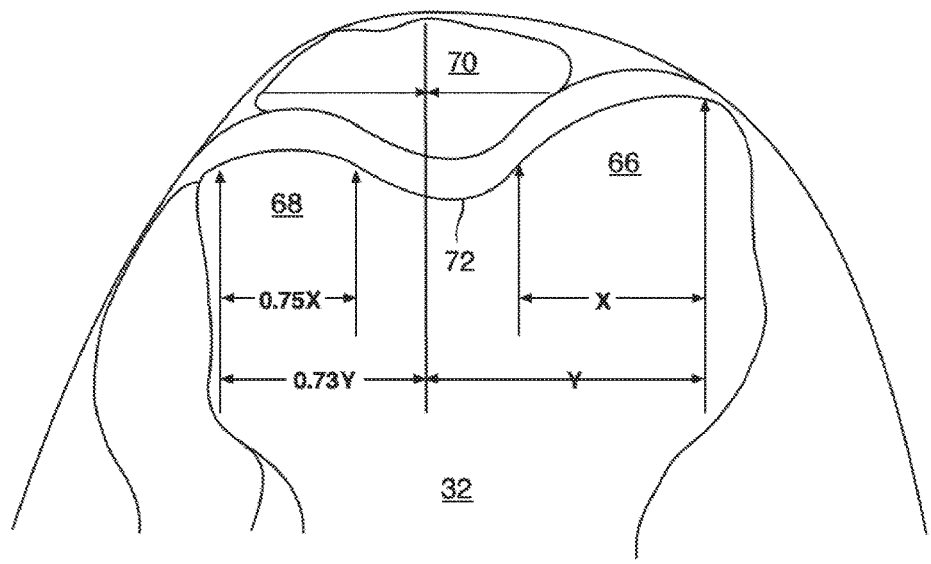
FIG. 17 illustrates drawing of a radiograph of a normal knee flexed to approximately 160°, and further illustrating the position of the patella.

In at least some embodiments of the invention, greater deep knee flexion can be achieved by providing an asymmetrical femoral component 12. The asymmetrical femoral component 12 permits transfer of more than one-half of the force transmitted across the joint to be transmitted to the medial side, as occurs in the normal knee. Some such embodiments are illustrated with reference to FIGS. 17 and 18A. FIG. 17 illustrates a drawing from a radiograph of a knee at about 160-degree flexion. In the radiograph, the femur 32 is viewed in the anteroposterior direction, and a medial condyle 66 of the femur 32, a lateral condyle 68 of the femur 32, and a patella 70 are visible. As may be appreciated by reference to the Figure, the medial-lateral width of the articulating portion of the medial condyle 66 is larger than the medial-lateral width of the lateral condyle 68. Specifically, in the Figure, the medial-lateral width of the articular portion of the medial condyle 66 is represented by X. As may be seen in the Figure, in some embodiments, the medial-lateral width of the lateral condyle 68 is approximately 75% (or any suitable amount less) of the medial-lateral width X of the medial condyle 66. Indeed, in some embodiments, the medial-lateral width of the lateral condyle 68 is any suitable amount between about 10% and about 75% of the medial-lateral width X of the medial condyle 66. In still other embodiments, the medial-lateral width of the lateral condyle 68 is any suitable amount between about 30% and about 74% of the medial-lateral width X of the medial condyle 66. In yet other embodiments, the medial-lateral width of the lateral condyle 68 is any suitable amount between about 40% and about 70% of the medial-lateral width X of the medial condyle 66.

As may also be appreciated by reference to FIG. 17, the center of the patella 70 is disposed lateral to the midline of the knee. Specifically, in the FIG. the medial-lateral distance between the most medial portion of the distal end of the femur 32 and the center of the patella 70 is represented by Y. As may be seen, the corresponding medial-lateral distance between the most lateral portion of the distal end of the femur 32 and the center of the patella 70 is approximately 75% or less (73% in the Figure) of Y. In some embodiments of the invention, the femoral component 12 may mimic the actual physical structure of the knee represented in FIG. 17.

Figure 18A:
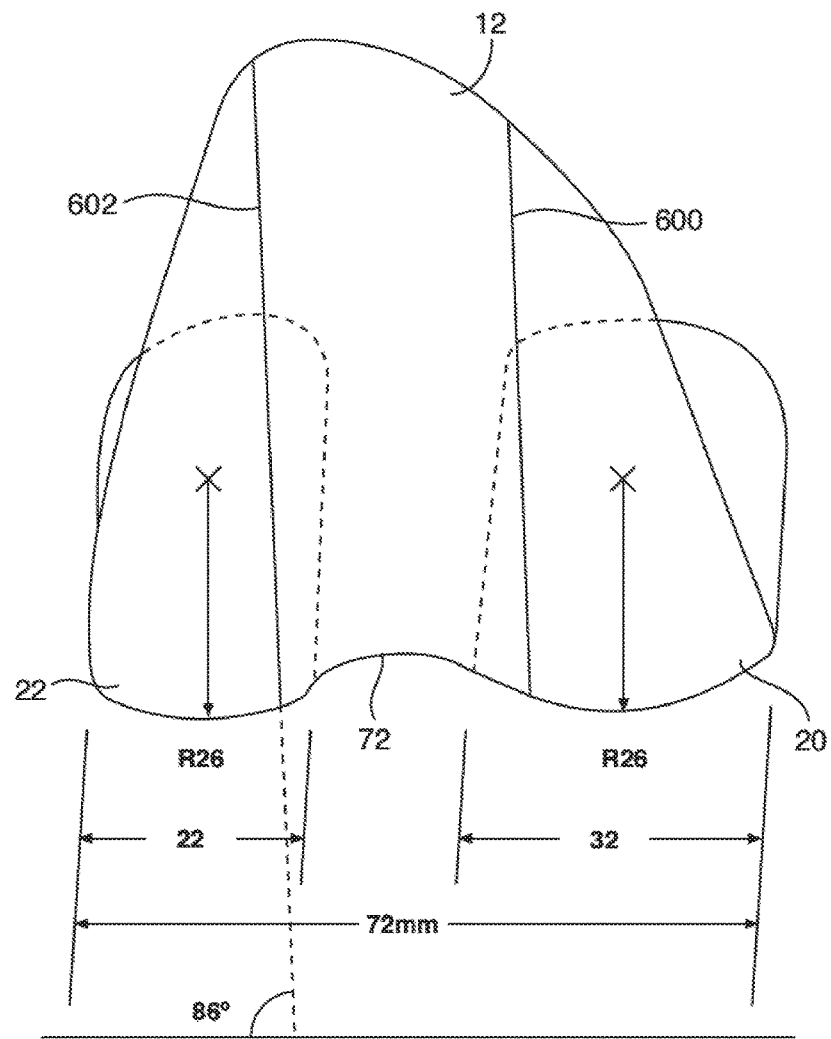
FIGS. 18A through 18C illustrate alternate embodiments of a femoral component in accordance with representative embodiments of the present invention.

In such embodiments of the femoral component as illustrated in FIG. 18A, the articular portion of the lateral condyle is, in its medial-lateral width, 75% or less than the width of the medial condyle. This allows for more than one half of the force that is transmitted across the joint to be transmitted to the medial side, which is what occurs in the normal knee. It also allows the patellar or trochlear groove to be lateralized because this groove distally is defined by its position between the medial and lateral condyles. In the normal knee the patella tends to be slightly lateralized on the femur and this lateral displacement of the groove accomplishes what many conventional total knee replacements accomplish by externally rotating the femoral component 12 in the total knee replacement. In one embodiment, the condyles in the frontal plane are seen to be circular with a constant radius. The medial and lateral condyles do not need to be the same radius, but may both be circular when viewed in that plane. When viewed in the sagittal plane the condyles will be seen to have a closing radius posteriorly and anteriorly may blend into the anterior flange in the embodiments where an anterior flange is used.

FIG. 18A illustrates a front view of one embodiment of a femoral component 12 in accordance with the described embodiments. In the Figure, illustrative measurements are illustrated to show features of the described embodiment, and are not meant to be limiting of the features of the described embodiments. As shown in FIG. 18A, the total medial-lateral width of the femoral component 12 may be approximately 72 millimeters (mm). In this embodiment, the medial-lateral width of the medial femoral condylar surface 20 in the posterior portion of the medial posterior condyle is approximately 32 mm, while the medial-lateral width of the lateral femoral condylar surface 22 is approximately 22 mm. Thus, in the illustrated embodiment, the medial-lateral width of the lateral femoral condylar surface 22 is approximately 69% of the medial-lateral width of the medial femoral condylar surface 20.

In the illustrated embodiment, a patellar groove 72 is defined by the space between the medial femoral condylar surface 20 and the lateral femoral condylar surface 22. Because the medial-lateral width of the medial femoral condylar surface 20 is larger than the medial-lateral width of the lateral femoral condylar surface 22, the patellar groove 72 is displaced laterally, which is what occurs in the normal knee. As may be appreciated by reference to FIGS. 18A through 18C, the patellar groove 72 may be provided at an angle as the patellar groove 72 moves from a most proximal anterior portion to a distal anterior portion to a distal posterior portion and to a proximal posterior portion. For example, the angle of the patellar groove 72 in FIG. 18A, as measured from a sagittal plane is approximately 86°. In other embodiments, however, the angle of the patellar groove can be any suitable angle that is less than about 90° and about greater than about 15° (or any sub-range thereof). Indeed, in some embodiments, the patellar groove extends laterally from a distal anterior portion of the femoral component to proximal-most, anterior portion of the femoral component at any suitable angle between about 40° and about 89°. In still other embodiments, the patellar groove extends at any suitable angle between about 50 and about 85°.

Thus, the illustrated embodiment shows how a femoral component 12 in accordance with embodiments of the present invention may assist in achieving deeper knee flexion and, in some embodiments, full functional flexion, by providing an asymmetric femoral component 12. The asymmetric femoral component 12 may assist in achieving deeper knee flexion by better simulating physiologic loading and patellar tracking. The asymmetric femoral component 12 allows for more normal loading of the joint with the medial side taking more of the load than the lateral side. Additionally, the asymmetrical femoral component 12 allows for more anatomically correct lateral tracking of the patella which may decrease problems of patellar pain, subluxation, and dislocation. One of skill in the art will readily recognize that in some embodiments the tibial component 14 may be modified to accommodate an asymmetric femoral component 12.

As discussed herein, at least some embodiments of the present invention embrace providing deeper knee flexion capabilities where the medial femoral side stays relatively fixed and the lateral side glides forwards and backwards. While some embodiments embrace a knee with a tibial component that keeps the femoral component relatively fixed on the medial side and able to glide on the lateral side, other embodiments embrace a knee that is relatively fixed on the lateral side and able to glide on the medial side. This, for example, would apply to the tibial component.

Additionally, while the additional articular surface on the femoral component 12 could be medial, lateral, or both, at least some embodiments of the present invention embrace its application to use the tibial and femoral full flex articulations either medially, laterally, or both.

The articular surface of the lateral condyle 22 and/or medial condyle 20 can have any suitable shape that allows the femoral component 12 to articulate against the tibial component 14 and/or a tibia in a knee joint. Indeed, in some embodiments, the articular surface of the lateral and/or medial condyles is substantially rounded, substantially flat, comprises a spline, comprises a raised articular surface, is ribbed, comprises one or more protuberances, comprises one or more recesses, comprises a segment of a sphere, comprises a portion of a cylinder, and/or has any other suitable characteristic that allows it to function as intended. Indeed, FIG. 18A shows a representative embodiment in which the articular surface of both the lateral condyle 22 and the medial condyle 20 are rounded (e.g., when viewed from a face, or anterior, view). In contrast, however, FIG. 18D shows a representative embodiment in which the articular surface of the lateral condyle comprises a substantially flat surface (e.g., at any suitable angle medially to laterally and vice versa, when viewed from a face view).

In some embodiments in which the articular surface of the lateral and/or medial condyle comprises a substantial flat surface (e.g., at any suitable angle, medially to laterally and vice versa, when viewed from the face view), any suitable portion of the width of one or both of the condyles can be substantially flat. Indeed, in some embodiments, a substantially flat portion C of the articular surface of the lateral and/or the medial condyles (as illustrated in FIG. 18D) is between about 5% and about 100%, or any subrange thereof (e.g., between about 20% and about 90%, between about 30% and about 85%, between about 60% and about 82%, etc.) of the width W (as illustrated in FIG. 18D) of the widest width W of the articular surface, medially to laterally, of the lateral and/or the medial condyles. In this regard, FIG. 18D illustrates an embodiment in which the medial condyle 20 is rounded (e.g., when viewed from a face view) and in which a portion of the lateral condyle 22 is substantially flat (e.g., when viewed from a face view).

Figure 18B:
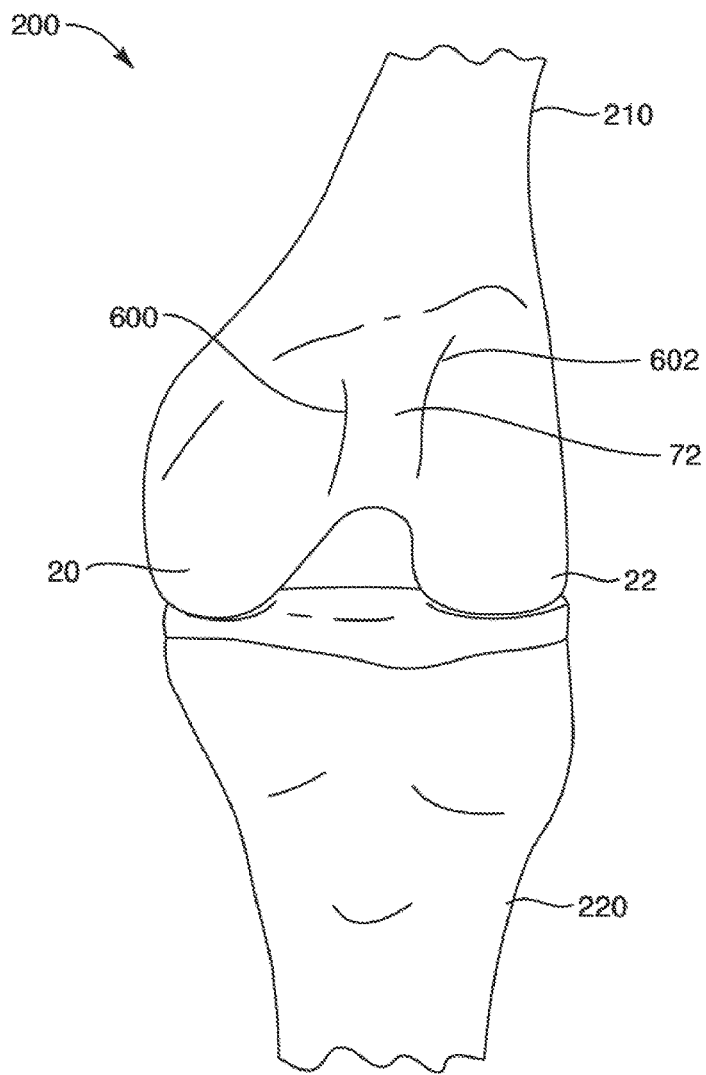
Figure 18C:
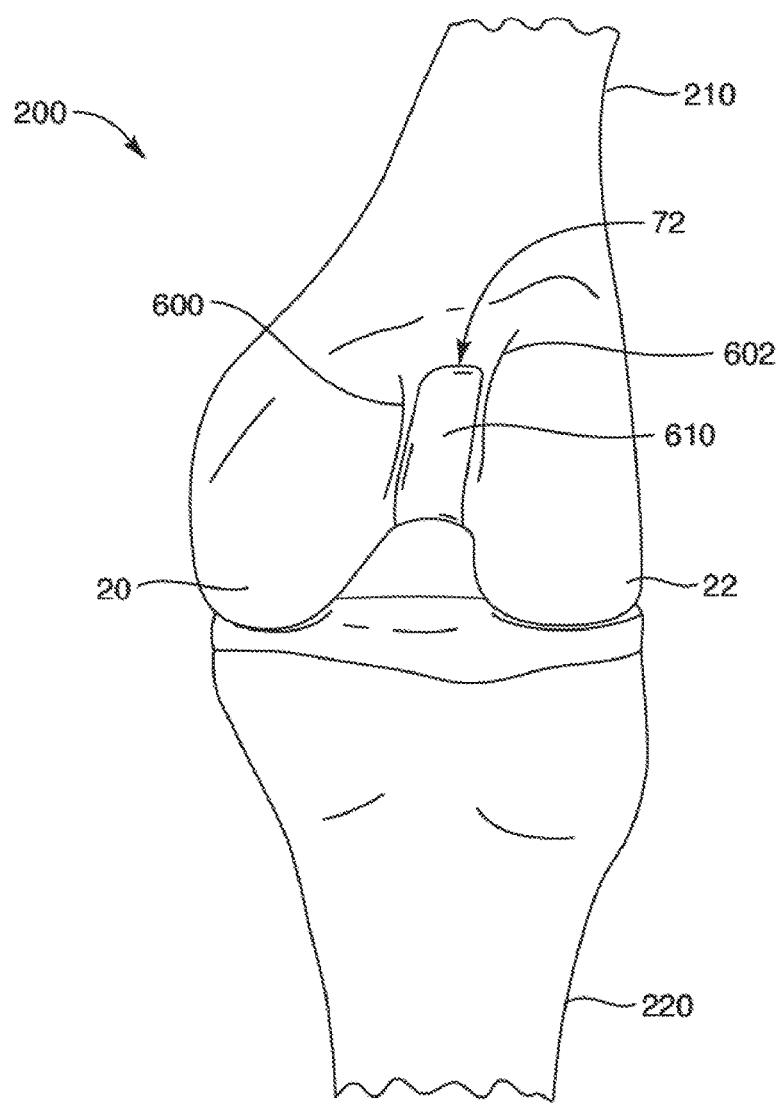
Figure 18D:
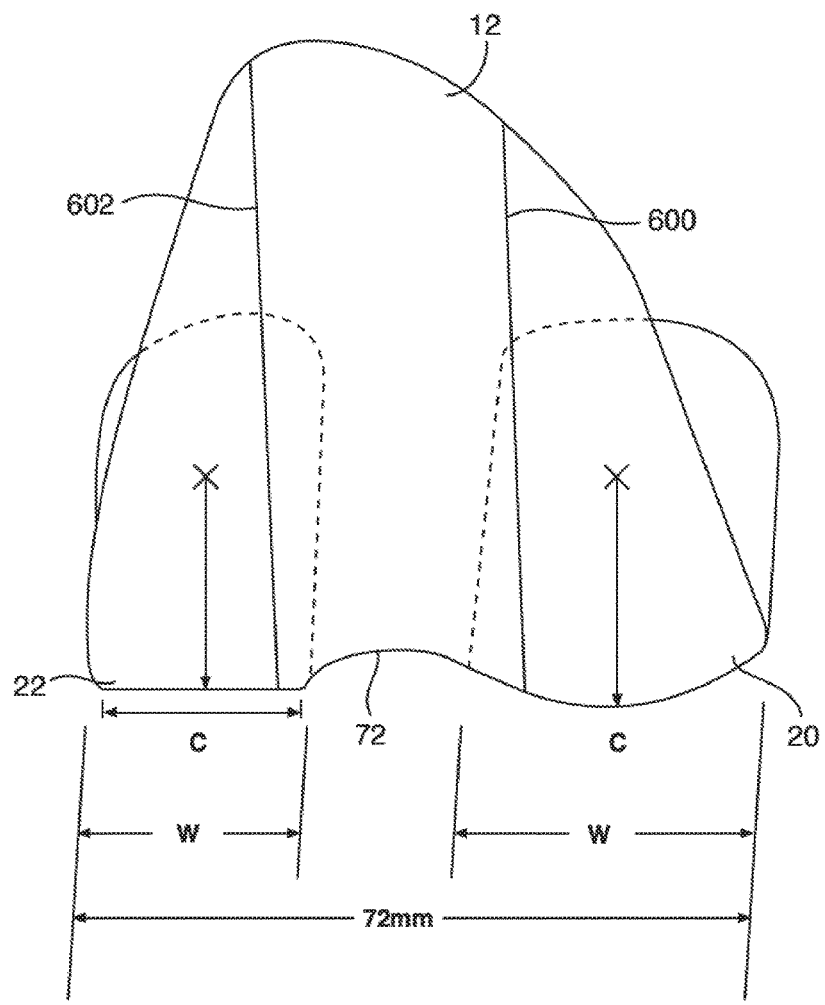
FIG. 18D illustrates a face view of a representative embodiment of the femoral component comprising a lateral condyle having a substantially flat articular surface.

In some embodiments in which the tibial component 14 comprises a substantially flat lateral tibial condylar surface 24 (e.g., as discussed above with respect to FIGS. 6D and 6K) and the medial tibial condylar surface 26 is configured to maintain a fixed center of rotation 52 for the medial femoral condyle 20 (e.g., as discussed above with respect to FIGS. 6C and 6J), a lateral condyle comprising a substantially flat articular surface and a medial condyle comprising a rounded articular surface (e.g., when viewed from a face view as shown in FIG. 18D) allow the tibia to rotate with respect to the femur such that the medial condyle has a substantially fixed center of rotation with respect to the medial tibial condylar surface of the tibial component, and while the lateral condyle of the femur is allowed slide (or otherwise move) anteriorly and/or posteriorly and with respect to the lateral tibial condylar surface.

Referring now to FIGS. 18B and 18C, in some embodiments, an abbreviated anterior flange 610 is provided to replace the trochlear surface or groove 72. In some embodiments, articular cartilage and underlying bone is optionally removed, which is typically removed with the antero-distal chamfer cut. In some embodiments, anterior flange 610 is provided to compensate for individual patient anatomy where the lateral portion of the anterior condyle on a conventional prosthesis extends or sits more proud than the bony condyle of the knee 200. For these anatomies, the proud position of the conventional prosthesis tents or otherwise separates the lateral soft tissues which may result in decreased flexion and discomfort or pain. In some embodiments, anterior flange 610 is provided without replacing anterior condyles 20 and 22 of the distal femur 210, such as for use with a patient having severe patello-femoral arthritis that would not be adequately treated with the prosthesis shown in FIGS. 12A, 12B, 14 and 16Q through 16S. Providing only anterior flange 610 may also provide relief with reduced cost and/or reduced evasiveness. In other embodiments, anterior flange 610 is provided in addition to replacing the anterior condyles 20 and 22.

In some embodiments, the length of the abbreviated anterior flange 610 is very short so as to only replace a portion of the trochlear surface 72. In other embodiments, the length of anterior flange 610 is extended to entirely replace trochlear surface 72. Further, in some embodiments anterior flange 610 is extended distally between the distal condyles 20 and 22 to a length approximately equal to flanges of currently-available, non-abbreviated prostheses.

Figure 21:
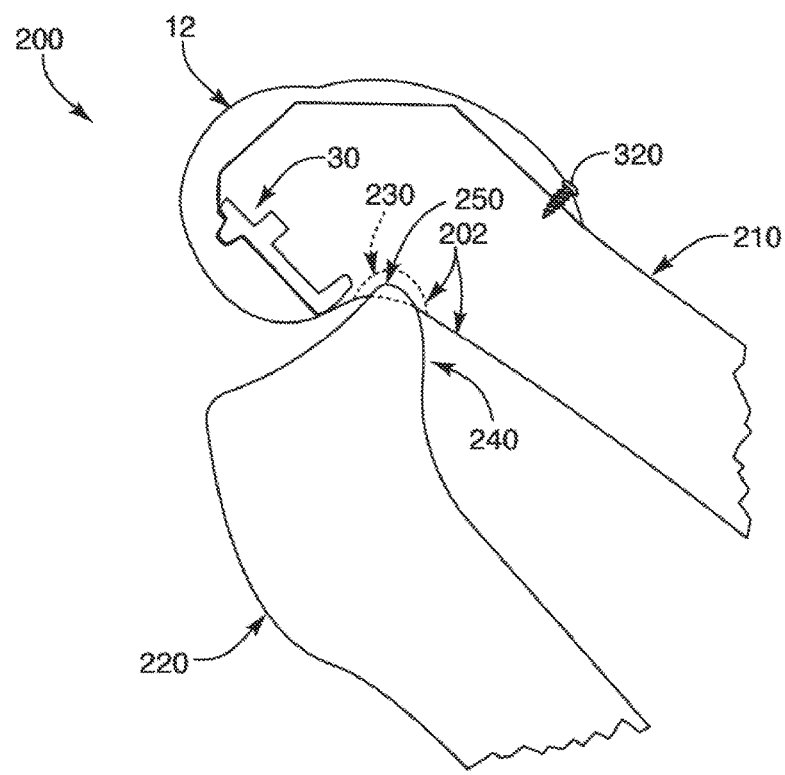
FIG. 21 illustrates a representative interaction of the posterior articulate surface of the medial plateau of the tibia and the popliteal surface during deep flexion of the knee.

Referring now to FIG. 21 a perspective side view of a knee 200 is shown. In at least some of the embodiments of the present invention, greater deep knee flexion may be further provided, improved, or enhanced by removing a portion of the popliteal surface 202 of the femur 210. The popliteal surface 202 may include bone proximal to the posterior articular surfaces of the medial condyle, the lateral condyle, or both the medial and lateral condyles. Resection of the popliteal surface 202 may be accomplished by any appropriate method known in the art. For example, in one embodiment a portion of the tibia is first resectioned thereby providing sufficient clearance to resect the necessary portion of the popliteal surface 230.

The amount of bone resected from the tibia, the femur or both will vary from individual to individual depending upon the specific anatomy of the tibia and the femur. The resectioned popliteal surface 230 provides additional clearance between opposing surfaces of the tibia 220 and the femur 210. Specifically, the resectioned popliteal surface 230 prevents an impingement of the posterior articulate surface 250 of the medial condyle 240 of the tibia 220 on the femur 210 during deep flexion of the knee 200. As such, the knee 200 may flex freely without the tibia 220 adversely binding on, or contacting any portion of the femur 210. Additionally, the resectioned popliteal surface 230 may provide flexion exceeding 140°. In one embodiment, the resectioned popliteal surface 230 provides flexion exceeding 160°.

Figure 22:
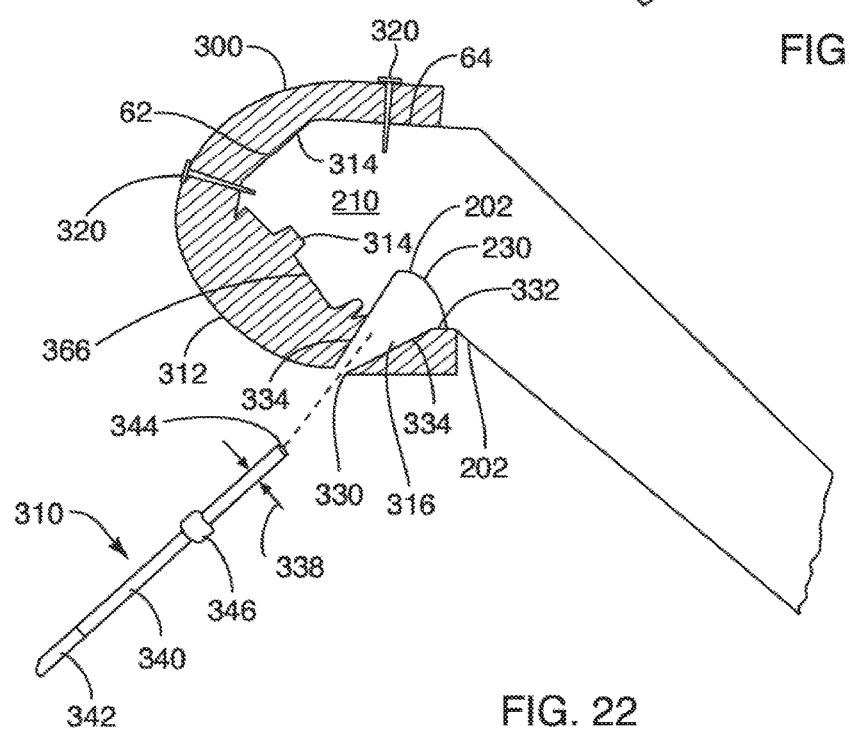
FIG. 22 illustrates a representative implementation of a resection block and the femur following resection of the popliteal surface.

Referring now to FIG. 22, a perspective side view of a knee 200 is shown following resection of the popliteal surface 202 to provide the resectioned surface 230. As previously discussed, resection of the popliteal surface 230 may be accomplished by any appropriate method known in the art. However, in one embodiment a resection block 300 is utilized to guide a cutting device 310 in making the resection 230. The resection block 300 is comprised of a metallic material, similar to the metallic materials previously discussed, and includes an outer surface 312, an inner surface 314, and a slot 316. The outer surface 312 is contoured and adapted to substantially overlap the lateral and medial condyles of the femur 210, however, in some embodiments, the guide would cover only the medial or lateral condyle. The inner surface 314 includes a plurality of angled surfaces that mirror the resectioned and shaped surfaces of the lateral and medial condyles of the femur 210. Thus, the inner surface 314 of the resection block 300 is adapted to compatibly engage the resectioned surfaces 62, 64, and 366 of the femur 210. The engaged resection block 300 and femur 210 are further secured via a plurality of fasteners 320, such as screws. This may not be necessary in all cases. The fasteners 320 are required only to firmly attach the guide to the femur. In some embodiments, the interaction between the guide and the femur is such that the guide is held firmly in place without fasteners. In another embodiment, the guide is held in place by any means to facilitate an accurate resection of the above mentioned area of the femur.

The interaction between the resection block 300 inner surface 314 and the resectioned surfaces 62, 64, and 366 of the femur 210 accurately aligns the slot 316 with the popliteal surface 202 of the femur 210. The slot 316 generally comprises an external opening 330 and an internal opening 332. The external opening 330 comprises a first width that is slightly greater than the width 338 of the cutting device 310. As such, the external opening 330 is adapted to compatibly receive the cutting device 310. The internal opening 332 is positioned exactly adjacent to the popliteal surface 202 and comprises a second width that is greater than the first width and approximately equal to the desired width of the popliteal resection 230. Thus, the walls 334 of the slot taper inwardly from the second opening to the first opening thereby providing a wedged slot 316.

The cutting device 310 may include any device compatible with the slot 316. In one embodiment an oscillating blade 340 is provided. The oscillating blade 340 includes a shank 342, a cutting head 344 and a stop 346. The shank 342 generally comprises a surface that is adapted to compatibly and securely engage a tool (not shown) capable of moving the blade 340 relative to the resection block 300 and femur 210. The cutting head 344 generally comprises a plurality of teeth suitable for removing the desired portions of the popliteal surface 202 to form the resection 230. The stop 346 generally comprises a ferule, a crimp, or some other feature that provides a point on the blade 340 that is wider than the first opening 330 of the slot 316. As such, the stop 346 is unable to enter the slot 316 thereby limiting the depth into which the blade 340 is permitted to enter the slot 316. Thus, the stop 346 acts as a depth gauge to control or limit the final depth of the popliteal resection 230. In one embodiment, the stop 346 further comprises a set screw whereby the stop 346 is loosened and repositioned on the blade 340 to change the depth into which the blade 340 is permitted to enter the slot 316. In another embodiment, the cutting device 310 is a burr bit having a stop 346 to limit the cutting depth of the burr.

Figure 22A:
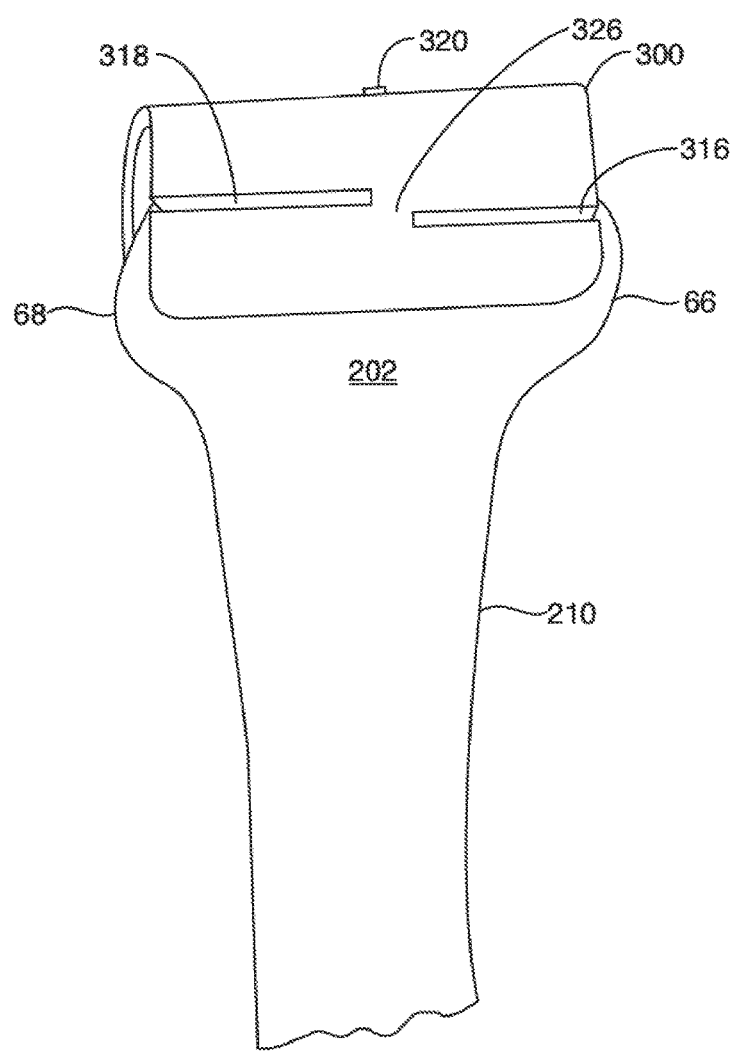
FIG. 22A illustrates a representative implementation of a resection block and the femur prior to resection of the popliteal surface.

Referring now to FIG. 22A, an underside, perspective view of the femur 210 and resection block 300 are shown. In one embodiment, the resection block 300 includes a first slot 316 and a second slot 318 separated by a connecting portion 326 of the resection block 300. The first slot 316 is positioned adjacent to the medial condyle 66 of the femur 210 and the second slot 318 is positioned adjacent to the lateral condyle 68. Each slot is positioned at a different height relative to the asymmetric, natural positions of the medial and lateral condyles 66 and 68. Thus, the first and second slots 316 and 318 of the resection block 300 are adapted to optimally resect the popliteal surface 202 of the femur 210 with respect to the asymmetric positions of the condyles 66 and 68. In another embodiment, the first and second slots 316 and 318 are positioned at equal heights so as to provide a resectioned popliteal surface 230 that is symmetrical without respect to the asymmetrical condyles 66 and 68. In yet another embodiment, the positioning of the external opening 330 relative to the internal opening 332 of the first slot 316 is different than the positioning of the external opening 330 relative to the internal opening 332 of the second slot 318. As such, the radius of each wedge opening 316 and 318 is different and the resultant contours or shapes of the resectioned popliteal surface 230 for the first and second slots 316 and 318 will be asymmetrical. In another embodiment, connecting portion 326 is eliminated thereby providing a single guide slot. In this embodiment, upper and lower portions of the guide are held in place relative to one another via lateral and medial bridges. The lateral and medial bridges maintain the position of the upper and lower portions of the guide, as well as define the outer edges of the slot. In another embodiment, lateral and medial bridges are used to provide multiple slots within the guide.

Referring now to FIGS. 22 and 22A, the popliteal resection 230 is made by inserting the cutting device 310 into the slot 316 and removing the popliteal surface 202 to the desired depth, as limited by the stop feature 346 and the radial limitations of the wedged slot 316. The wedged shape of the slot 316 permits the cutting device 310 to be pivoted along the radius of the wedge, wherein the contact between the stop 346 and the external opening 330 acts as a fulcrum for the radius of the wedge. The resultant resection 230 therefore comprises a radial surface configured and shaped to receive the femoral component 12 of the knee prosthesis. Following formation of the popliteal resection 230, the screws 320, or other stabilizing methods, and the resection block 300 are removed from the femur 210.

Figure 23:
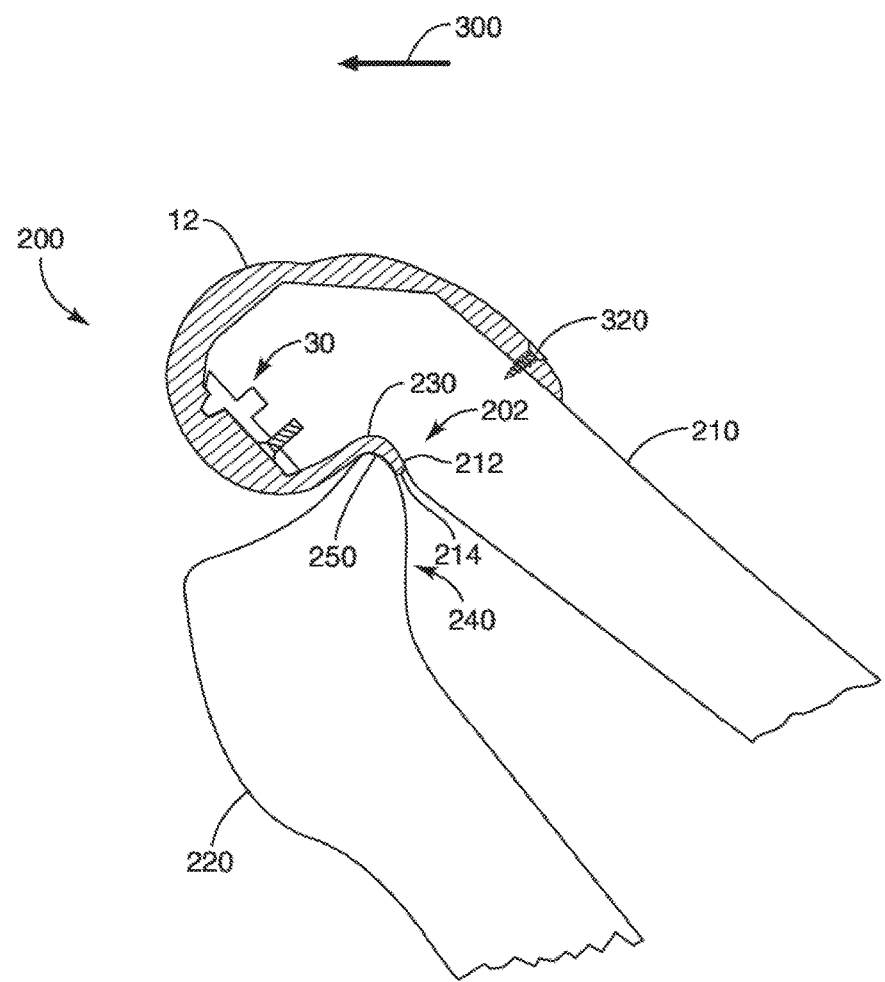
FIG. 23 illustrates a representative interaction of the posterior articular surface of the medial plateau of the tibia and an extended portion of the femoral component of the knee prosthesis during deep flexion.
Figure 23A:
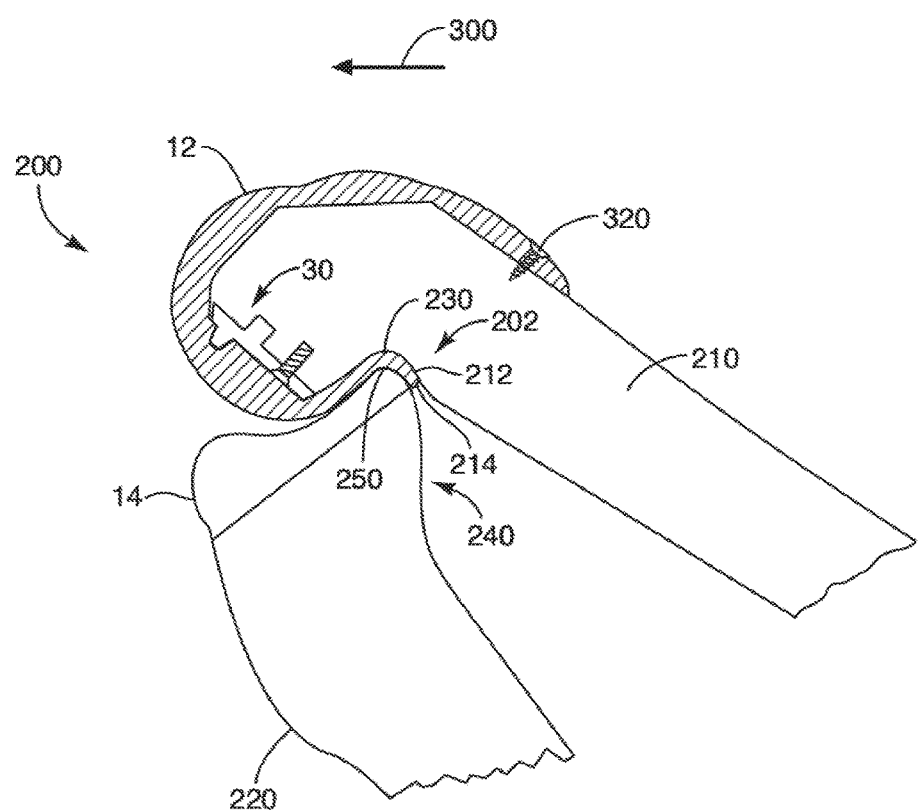
FIG. 23A illustrates a representative interaction of the posterior full flex articular surface of the medial tibial plateau of a tibial component and an extended portion of the femoral component of the knee prosthesis during deep flexion.

Referring now to FIGS. 23 and 23A, a cross-sectional side view of a knee 200 is shown following resection of the popliteal surface 230. The femoral component 12 of the knee prosthesis may be modified to correspond to the resectioned portion 230 of the popliteal surface 202. For example, in one embodiment a portion 212 of the femoral component 12 of the knee prosthesis is extended and contoured to seat within the resected portion 230 of the popliteal surface 202. As such, the posterior articular surface 250 of the medial plateau 240 of the tibia 220 compatibly and smoothly interacts with the extended portion 212 thereby further enabling the knee 200 to achieve deep flexion. Furthermore, the interaction between the posterior articulate surface 250 and extended portion 212 prevents the posterior articulate surface 250 from binding on a terminal surface 214 of the femoral component and displacing the femoral component 12 in an anterior direction during deep flexion. In some embodiments of the present invention, the extended portion 212 is used in conjunction with a tibial implant having a partial spherical or convex medial side. In another embodiment, the extended portion 212 is used in conjunction with any knee replacement that will allow knee flexion to 120° or greater. For example, in one embodiment a femoral component of a knee prosthesis system is modified to include a piece of metal up the back of the posterior portion of the component to provide an extended portion 212 compatible with the tibial component of the knee prosthesis system.

In some embodiments of the present invention including the extended portion 212, the femoral component 12 does not include an anterior flange or any provision for patella-femoral articulation anteriorly, as shown in FIGS. 15B and 16B (and 12B) above. As such, the lack of an anterior flange allows the component 12 to be impacted onto the femur in a relatively conventional manner, except that, in some embodiments, the component 12 is implanted after being rotated posteriorly relative to a conventional prosthesis. Additionally, the femoral component 12 can be used without a separate patella-femoral articular implant. In some embodiments, the component 12 is used with a modular flange attached to the proximal end of the anterior oblique condyle of the condylar implant to provide an anterior femoral articulation for the patella to prevent patellar subluxation and to be used in cases of patella alta. In another embodiment, the femoral component 12 is used with separate, unattached anterior patella-femoral implant articulations. In still other embodiments, a separate femoral flange is used for a patella that does not have an implanted component. In yet other embodiments (as shown in FIG. 15E), the femoral component 12 comprises a truncated anterior flange 213.

Where the femoral component 12 comprises a truncated anterior flange 213, the truncated anterior flange can extend any suitable distance (e.g., to any suitable distance between about 0 and about 15 mm) on either the proximal side or the distal side a proximal limit of the articular cartilage, which is a physiological marker that would be recognized by one of skill in the art). Similarly, in some embodiments in which the femoral component 12 comprises a truncated anterior flange 213, the truncated anterior flange can extend proximally any suitable amount past an anterior proximal end 71 of the anterior oblique cut 64 (and/or of the proximal limit of the articular cartilage) on a prepared femur 32 (e.g., between about 0 mm and about 15 mm, between about 1 mm and about 10 mm, as little as between about 2 mm and about 5 mm, or any suitable sub-range of the aforementioned distances).

In some embodiments, femoral component 12 further comprises a modular patella-femoral component 57 (or a modular anterior flange), as shown in FIG. 16T. Modular patella-femoral component 57 is generally configured to compatibly couple to femoral component 12 in an adjustable manner. For example, in some embodiments, modular patella-femoral component 57 comprises a post 59 which is sized and configured to slidably insert within a groove or socket 13 of femoral component 12. The slidable interaction between post 59 and socket 13 allows for infinite adjustment of modular patella-femoral component 57 with respect to femoral component 12, as shown in FIG. 16U.

The modular nature of femoral component 12 and patella-femoral component 57 provides customized fitting of the prosthesis to the patient. For example, in some embodiments, a patella-femoral component 57 is selected based upon an anatomical need or feature of the patient. In other embodiments, a femoral component 12 and a patella-femoral component 57 are selected based upon a mechanical need for this feature for the patient. Further, in some embodiments, a patella-femoral component 57 is selected to most accurately match a resectioned surface of the patient's femur. Accordingly, some embodiments of the present invention comprise a plurality of modular patella-femoral components 57 which are interchangeably coupled with femoral component 12 as may be required or desired to meet the needs of a patient.

The modular nature of femoral component 12 and patella-femoral component 57 further facilitates the fitting process of the knee prosthesis. For example, in some embodiments a structural configuration of a unitary femoral component may preclude installation or may require that additional bone be resectioned from the patient's femur to permit installation. Accordingly, some embodiments of the present invention provide a method for fitting a patient with the knee prosthesis, wherein the femoral component 12 of the knee prosthesis is initially fitted and secured to a resectioned surface of a patient's femur. The modular patella-femoral component 57 is then coupled or otherwise attached to the femoral component 12 and adjusted 61 to accommodate the specific anatomy of the patient. Once the position of modular patella-femoral component 57 is optimized, component 57 is secured to the patient's femur.

Referring now to FIG. 16V, a detailed view of an embodiment of socket 13 of femoral component 12 and post 59 of modular patella-femoral component 57 is shown. In some embodiments, socket 13 further comprises a tapered opening. In accordance with some embodiments, the tapered opening 63 permits upward and downward adjustments 65 of modular patella-femoral component 57 relative to a fixed position of femoral component 12. In some embodiments, the tapered opening 63 further permits lateral adjustments 67 of the modular patella-femoral component 57 relative to a fixed position of femoral component 12. Thus, in some embodiments, the tapered opening 63 provides infinite adjustment of modular patella-femoral component 57 with respect to a fixed position of modular component 12. Further, in some embodiments, post 59 is tapered (not shown) thereby providing additional adjustment of modular patella-femoral component 57 with respect to femoral component 12, as may be desired.

In addition to the illustrated embodiments discussed above, the patella-femoral component 57 and the femoral component 12 can be modified in any suitable manner that allows the two components to be affixed to a femur 32. Indeed, in some embodiments, instead of including a post and socket coupling, the two components are coupled to each other through any other suitable manner, including, without limitation, through the use of a butt joint, a lap joint, a butt-lap joint, a rebated joint, a mortise and tenon, a dove-tail joint, a hinge, a flexible member, and any other suitable type of joint or combination of joints that allow the modular patella-femoral component 57 to be coupled to the femoral component 12.

In some embodiments, the patella-femoral component 57 and the femoral component 12 are coupled by a butt joint. While such a butt joint can have any suitable characteristic, in some embodiments, one of the components (e.g., the patella-femoral component 57 or the femoral component 12) comprises a convex surface, while the other (e.g., the femoral component 12 or the patella-femoral component 57) respectively comprises a concave surface. By way of illustration, FIG. 16W shows a representative embodiment in which the femoral component 12 comprises a convex surface 101 that couples with (i.e., abuts) a concave surface 103 of the patella-femoral component 57. In such embodiments, the rotatable interaction between the convex surface 101 and the concave surface 103 allows for virtually infinite adjustment of the modular patella-femoral component 57 with respect to the femoral component 12.

Where the patella-femoral component 57 and the femoral component 12 are coupled by a butt joint (or any other suitable joint), the surfaces between the patella-femoral component 57 and the femoral component 12 (e.g., the convex surface 101 and the concave surface 103) can have any suitable characteristic that allows the two components to be connected to each other. Indeed, while in some embodiments, the surfaces between the two components are smooth, in other embodiments, such surfaces are texturized to allow cement (or another adhesive) to bind tightly to the two components. While the surfaces between the components can be texturized in any suitable manner, in some embodiments, such surfaces are porous, roughened, knurled, comprise scaffolding, comprise ridges, comprise recesses, comprise protuberances, and/or are otherwise texturized to hold cement (i.e., any other suitable adhesive) and/or bone growth.

Referring now to FIG. 23A, a cross-sectional side view of a knee 200 is shown following resection of the popliteal surface 230, wherein the femoral component 12 is used in conjunction with a tibial component 14. In some embodiments of the present invention, the above described femoral component 12 is used in conjunction with a conventional tibial component 14 that does not have the tibial full flex articulation. For example, in one embodiment the above described femoral component 12 is used in conjunction with a tibial component 14 that has the center of the medial tibial articulation displaced posteriorly. In another embodiment, the femoral component 12 is used in conjunction with a tibial component 14 that has the center of the medial tibial articulation in a position that corresponds with currently available designs. In addition to occupying or lining the resected popliteal surface 230, the extended portion 212 may include additional features to modify the position of the tibia and the femur during full flexion.

For example, in one embodiment the extended portion 212 is modified to rotate the tibia relative to the femur with the knee in full flexion. In another embodiment, the extended portion 212 is modified to prevent rotation of the tibia relative to the femur with the knee in full flexion. In yet another embodiment, the extended portion 212 is modified to include a spherical surface on its upper or most proximal portion. As such, this spherical surface allows the tibia to rotate relative to the femur in full flexion. In some implementations of the present invention it may be desirable to have the spherical surface articulate with a corresponding concave surface in the femoral full flex articulation. Such a concavity would offer medial-lateral stability, provide area contact between the femoral and tibial components, and decrease polyethylene wear of the prosthesis. Referring again to FIG. 23, in some implementations of the present invention, the femoral component 12 is used in conjunction with a non-resected posterior portion of the patient's own tibial plateau to articulate with extended portion 212.

Figure 24:
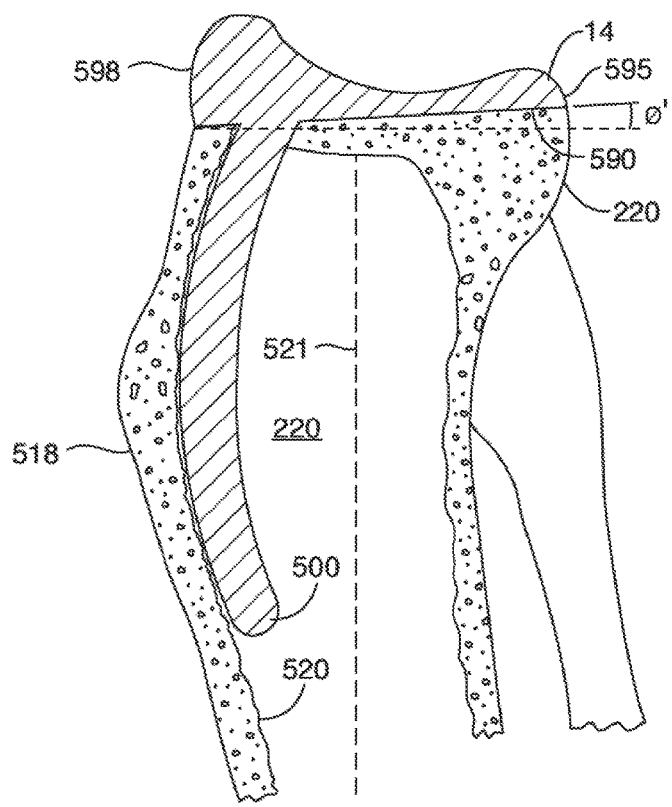
FIG. 24 illustrates a cross-section view of a tibial component and stem inserted within a tibia in accordance with a representative embodiment of the present invention.

Referring now to FIGS. 24 through 28, some embodiments of tibial component 14 are further modified to include a tibial stem 500 generally attached to the anterior undersurface of tibial component 14. As shown in FIG. 24, anterior placement of the tibial stem 500 is calculated to compensate for and decrease the compressive load applied to the posterior tibia during flexion of the knee joint. In some embodiments, as a compressive load is applied to the posterior tibia, the tibial stem 500 forms an interface with the inner surface 520 of the tibial anterior cortex 518, thereby preventing at least one of rotation, sinking, and/or subsidence of tibial component 14 relative to the tibia 220. Thus, the shape, size, angle, and placement of tibial stem 500 are selected to achieve a desired interface between tibial stem 500 and the inner surface 520.

Figure 25:
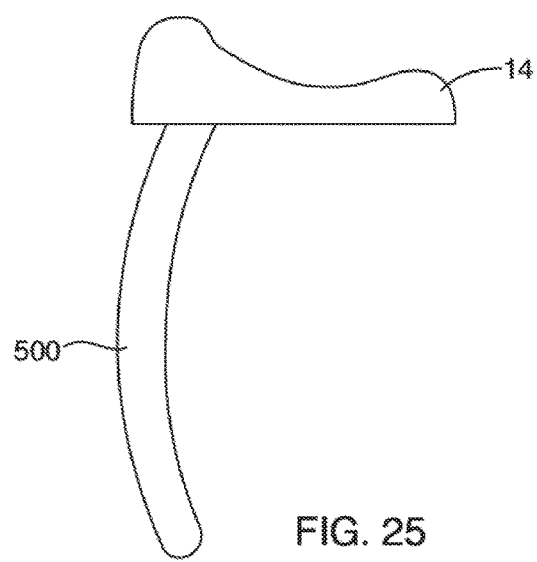
FIGS. 25-27 illustrate various embodiments of stems in accordance with representative embodiments of the present invention.
Figure 28A:
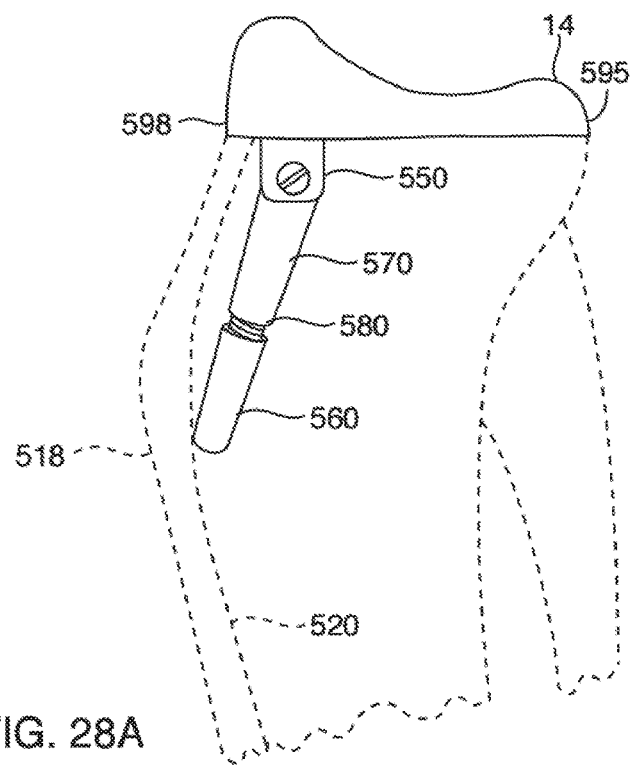
FIG. 28A illustrates an adjustable stem in accordance with a representative embodiment of the present invention.

In some embodiments, tibial stem 500 is curved or otherwise shaped to closely approximate the contours of a portion of inner surface 520, as shown in FIGS. 24 and 25. In other embodiments, tibial stem 500 is tapered such that one or more portions of the stem's exterior surface contact various portions or areas of the tibia's inner surface 520, as shown in FIG. 26. Still, in other embodiments, the tibial stem 500 is extended such that a tip portion 530 of the stem 500 contacts the inner surface 520. In some instances, the tibial stem 500 further includes one or more tapered fins 540 to increase the stability of the tibial stem 500 while under compressive loads. In still other embodiments, the tibial stem 500 comprises an adjustable linkage 550 whereby the angle of stem 500 is adjusted to accommodate the individual anatomy of the patient, as shown in FIG. 28A. In yet other embodiments, the tibial stem 500 further includes an adjustable tip 560 whereby the length of the stem 500 is adjusted to accommodate the individual anatomy of the patient. Indeed, FIG. 28A shows some embodiments in which the stem's tip 560 is adjustably coupled to a shaft 570 via a set of threads 580. In other embodiments, however, the tip 560 is slidably coupled to the shaft 570, wherein the position of the tip 560 relative to the shaft 570 is maintained via a set screw, a mechanical impingement, an adhesive (not shown), and/or any other suitable mechanism.

Thus, the tibial stem 500 may generally comprise any suitable shape, size, length, and/or angle that allows the stem to accommodate the needs of the patient. Additionally, the tibial stem 500 can comprise any suitable material. Indeed, in some embodiments, the stem comprises metal. In other embodiments, however, the stem 500 comprises a plastic, polymer, and/or other material that can be trimmed at the time of surgery to allow an optimal fit.

Figure 28B:
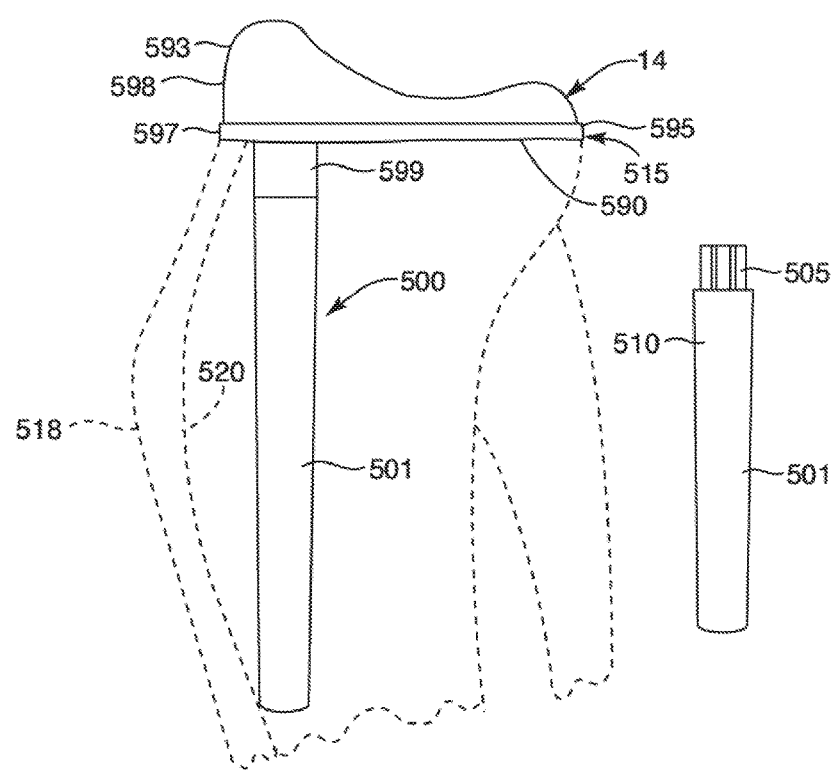
FIG. 28B illustrates a tibial component comprising a modular stem in accordance with a representative embodiment of the present invention.

In some embodiments, the tibial stem 500 comprises a modular tibial stem that is interchangeable with one or more other stems of a varying size (e.g., length, circumference, diameter, volume, etc.) and/or shape (e.g., angle, curvature, taper, etc.). In this manner, a single tibial component 14 can be modified such that its stem 500 is able to contact the inner surface 520 of the tibial anterior cortex 518 of a variety of tibias having a different size and/or shape. For instance, in some embodiments in which the tibial component 14 is being placed on a relatively short tibia, a relatively short modular stem is attached to the tibial component such that a portion (e.g., a tip) of the stem is able to contact an inner surface of the bone's anterior cortex. In contrast, in some embodiments in which the tibial component is being attached to a relatively long tibia, a relatively long modular stem is attached to the tibial component.

Where the tibial stem 500 comprises a modular tibial stem, the modular stem can connect to the tibial component 14 in any suitable manner, including, without limitation, through the use of one or more threaded connectors, frictional engagements, catches, stirrups, adhesives, cements, fasteners (e.g., screws, bolts, pins, rivets, pawls, etc.), mechanical connectors, and/or other mechanisms that allow one of a variety of stems to be connected to the tibial component. By way of illustration, FIG. 28B shows a representative embodiment in which the undersurface 590 of the tibial component 14 (e.g., a tibial component comprising a polymer articulation surface 593 and metal base 597) comprises a connector 599 (e.g., a socket) that is configured to frictionally engage with a modular tibial stem 501 (e.g., via a splined member 505 that is sized and shaped to be inserted into connector 599, as seen on a replacement stem 510).

Where the tibial stem 500 comprises a modular tibial stem (e.g., stem 501), the modular stem can be used in any suitable manner. Indeed, in some embodiments, one or more modular stems (or even trial stems, such as stems made from a disposable material, stems having a smaller diameter to reduce unnecessary damage to the medullary cavity, autoclavable stems, etc.) are coupled to and/or removed from the tibial component's undersurface 590 (e.g., connector 599) until the proper sized and/or shaped stem is found. At that point, the desired stem is permanently connected to the tibial component 14 (e.g., via cement, one or more fasteners, mechanical engagements, etc.). Although, in some embodiments, the modular tibial stem is configured to be coupled with the tibial component 14 before the tibial component is attached to the proximal end of the resectioned tibia, in some other embodiments, the modular stem is configured to be inserted into the tibia before the tibial stem and the tibial component are coupled together (e.g., via a cement, a frictional engagement, a mechanical engagement, and/or in any other suitable manner).

Where the tibial stem 500 comprises the modular tibial stem (e.g., stem 501), the modular stems of various sizes and shapes can be sold in any suitable manner, including, without limitation, separately and/or in sets.

Additionally, where the tibial stem 500 comprises the modular tibial stem (e.g., stem 501), the various modular stems can be configured to extend any suitable distance from the undersurface 590 of the tibial component 14. In some embodiments, the modular tibial stems (and/or some embodiments of the non-modular stems) are configured to extend (when attached to the undersurface 590 of the tibial component 14) to any suitable distance between about 1 cm and about 20 cm from the undersurface 590. In other embodiments, the modular tibial stems are configured to extend between about 3 and about 15 cm from the undersurface of the tibial component 14. In still other embodiments, the modular stems are configured to extend between about 5 and about 10 cm from the undersurface of the tibial component. In yet other embodiments, the modular tibial stems are configured to extend to within any suitable subrange of the aforementioned extension lengths.

Where the tibial component 14 includes the tibial stem 500 (e.g., the modular stem or the permanent stem that is configured to contact the inner surface 520 of the tibia, or the tibial anterior cortex 518), the undersurface 590 of the tibial component can contact the tibia in any suitable manner. Indeed, while the undersurface of the tibial component can be contoured in any suitable manner, in some embodiments, the undersurface of the tibial component 14 is substantially flat (e.g., as shown in FIG. 24).

Additionally, where the undersurface 590 of the tibial component 14 comprises a substantially flat portion, the proximal end of the tibia can be cut at any suitable angle, and the undersurface 590 of the tibial component can have any suitable angle with respect to a longitudinal axis of the tibia (and/or any other suitable portion of the tibia) that allows the tibial component to attach to the tibia. In one example, the undersurface of the tibial component 14 is angled and/or the proximal end of the tibia is cut such that the undersurface of the tibial component slopes (with respect to a longitudinal axis 521 of the tibia) distally from the tibial component's posterior edge 595 towards the component's anterior edge 598 (see e.g., FIG. 24). In this example, the undersurface of the tibial component may run at any suitable angle, including, without limitation, at an angle θ' that is between about 0 and about 15° (e.g., above), or any subrange thereof (e.g., between 4-12°, 6-10°, 7-9°, etc.) from being perpendicular with the tibia's longitudinal axis.

Figure 26A:
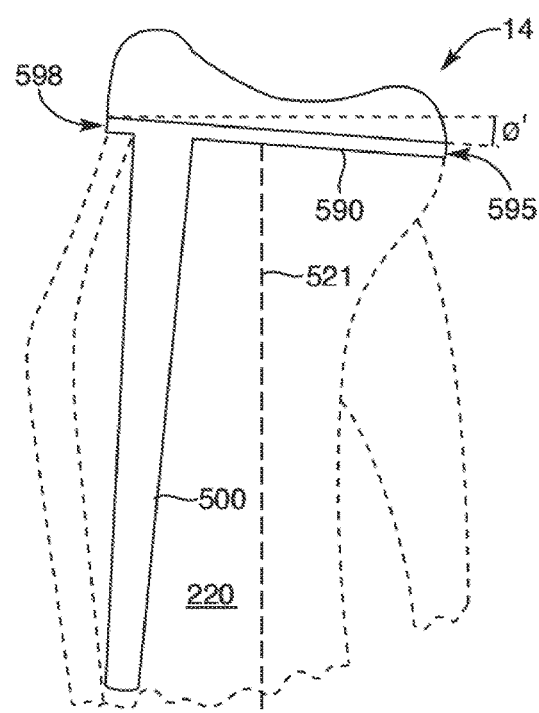
Figure 26B:
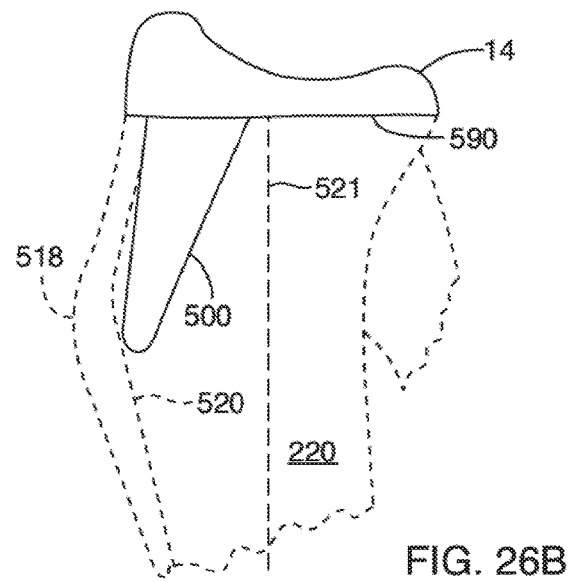
Figure 26C:
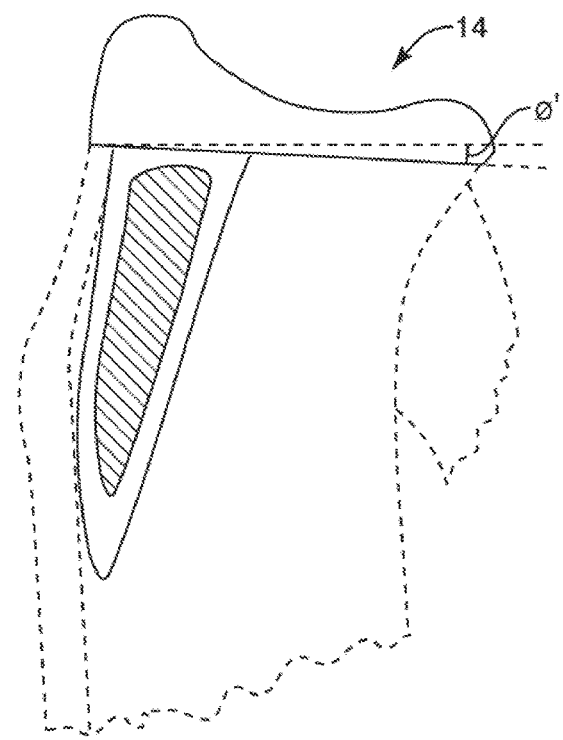
Figure 27:
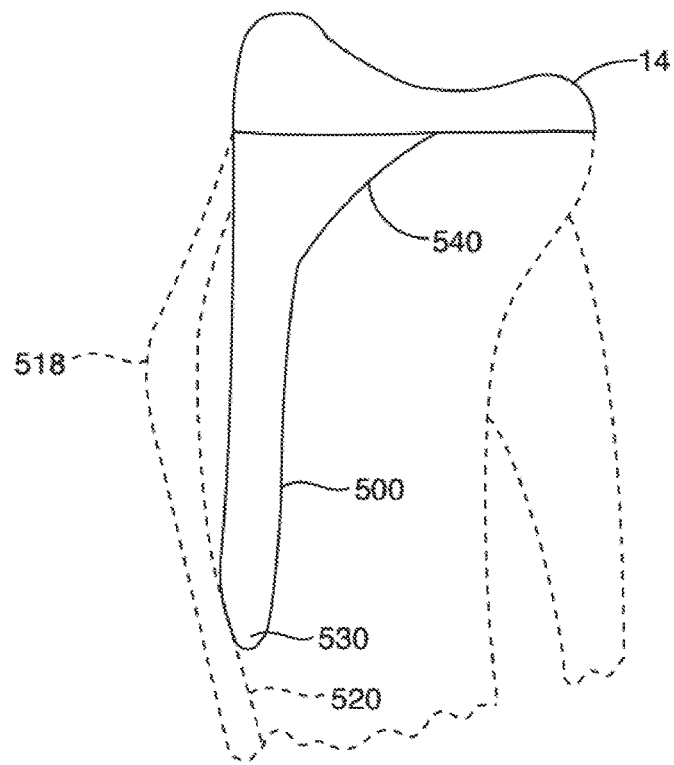

In another example, a portion of the tibial component's undersurface 590 is angled and/or and the proximal end of the tibia is cut, such that when the tibial component 14 is seated on the tibia, the undersurface of the tibial component slopes (with respect to the longitudinal axis 521 of the tibia) distally from the tibial component's anterior edge 598 to the component's posterior edge 595 (e.g., as shown in FIGS. 26A and 26C). In this example, the under surface of the tibial component may run at any suitable angle including, without limitation, at an angle θ' that is between about 0 and about 15° (e.g., below), or any subrange thereof (e.g., between 4-12°, 6-10°, 7-9°, etc.) from being perpendicular with the tibia's longitudinal axis. In this regard, it should be noted that while the tension in a knee joint comprising some embodiments of the tibial component may increase as the joint flexes such that the tension prevents deep knee flexion (at least without undesirable pain), in some embodiments in which the tibial component is angled distally from its anterior edge to its posterior edge such tension can be avoided or reduced—thus allowing the knee to be deeply flexed with little to no pain. It should also be noted that, in accordance with some embodiments, the described tibial stem 500 that is configured to contact a tibial anterior cortex of the tibia allows the tibial component to be sloped on the tibia more than some conventional tibial components could be.

In still another example, the undersurface of the tibial component 14 is configured such that the undersurface runs substantially perpendicular to a longitudinal axis 521 of the tibia 220 (e.g., as shown in FIG. 26B).

In still other embodiments (not shown), the tibial component 14 lacks a stem 500 altogether. In such embodiments (as well as in embodiments in which the tibial component 14 comprises the modular tibial stem 501 or a non-modular tibial stem), the tibial component can be attached to a tibia in any suitable manner, including, without limitation through the use of cement (and/or another adhesive); one or more screws, bolts, pins, or other fasteners; any other suitable connection mechanism; and/or any suitable combination thereof. In this regard, in some embodiments in which the tibial component lacks a stem, the undersurface 590 of the tibial component comprises one or more types of scaffolding, recesses, knurling, features (e.g., protuberances, holes, dovetailed grooves, etc.), and/or any other structures or surface characteristics that allows cement (and/or bone) to attach securely to the undersurface of the tibial component.

Figure 29A:
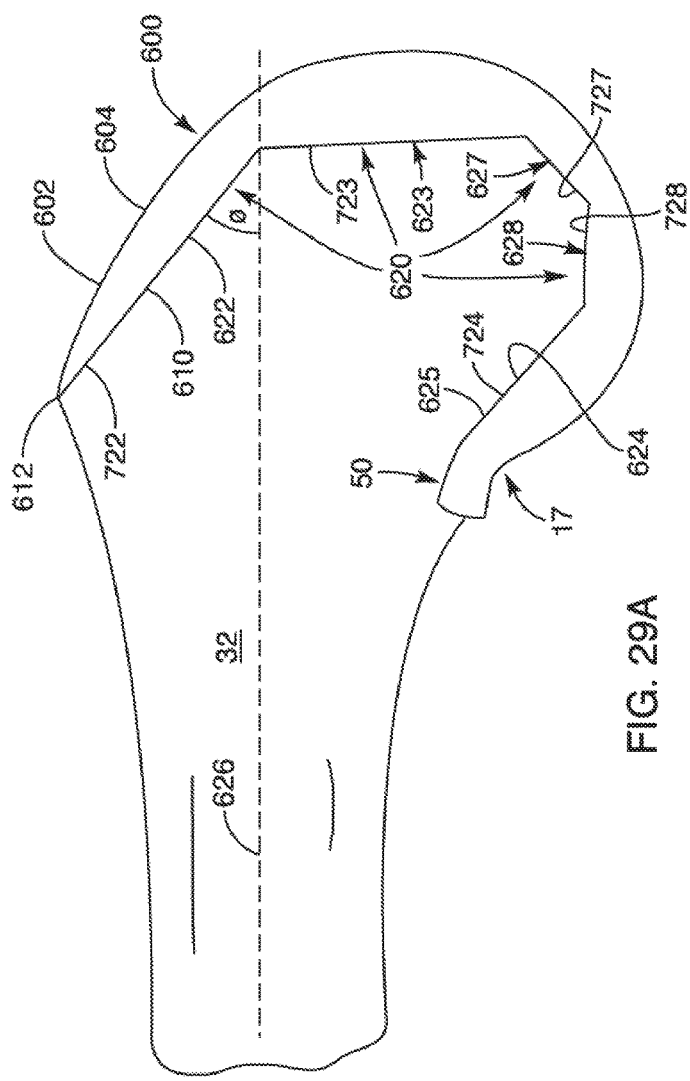
FIGS. 29A-29C each illustrate a different representative embodiment of an implanted femoral component having two opposing internal surfaces that run substantially parallel to each other.

In some embodiments, a femoral component 600 (which may also be referred to as femoral component 12) is provided having an anterior extension 602 that generally replaces a resectioned antero-proximal portion of the anterior condyles 610, as shown in FIG. 29A. In some embodiments, the antero-proximal portion of the anterior condyles 610 is prepared by resecting the anterior condyle surface to (or near) the proximal limit 612 of the articular cartilage. As such, essentially all of the anterior articular cartilage is removed from the resected femur 32. In other embodiments, however, the anterior condyle surface of the femur is resected to any suitable distance within (or any sub-range of) about 0 mm and about 15 mm on either the distal or the proximal side of the proximal limit 612 of the articular cartilage. In one non-limiting example, the anterior condyle surface of the femur is resected to between about 1 mm and about 6 mm on either the distal or the proximal side of the proximal limit 612 on the articular cartilage. In another non-limiting embodiment, the anterior surface of the femur is resected proximally to any suitable amount less than about 15 mm of the proximal limit 612 of the articular cartilage.

In some embodiments, the anterior articular cartilage is removed while removing little or no other bone, anteriorly. In other words, in some embodiments, the femoral component 600 replaces essentially all anterior articular cartilage, but little or no other bone anteriorly. Accordingly, in some embodiments, the only bone removed is sub-chondral bone next to the cartilage and any bone necessary to allow a femoral component 600 to fit the distal end of the femur. Thus, in some embodiments, the femoral component 600 is able to terminate at or adjacent to (e.g., within about 0 and about 15 mm (or any suitable sub-range thereof) on either the distal or the proximal side of) the proximal limit 612. Moreover, in some embodiments, a resected distal end of the femur 32 is fitted with the femoral component 600, wherein patellar force against the femur (in extension) is substantially, if not completely, eliminated due to having replaced the anterior articular cartilage with which the patella normally articulates. Accordingly, in some embodiments, the resectioned antero-proximal portion of the anterior condyles 610 is replaced with an anterior condylar extension 602 thereby providing a new surface 604 against which the patient's patella may articulate.

As shown in FIG. 29A, in some embodiments, the femoral component 600 lacks an anterior flange (as discussed above) such that the femoral component substantially ends at or distally (e.g., within about 0 mm and about 15 mm, or any sub-range thereof) the proximal limit 612.

In some embodiments, the new articular surface 604 provides a substantially smooth transition between the femoral component 600 and the femur 32 at (or near) the proximal limit 612. Further, by removing only the articular cartilage and the underlying sub-chondral and cancellous bone from femur 32, a smaller, less expensive femoral component 600 may be provided, which can also result in a less invasive implantation for the patient. Moreover, by allowing more bone to be preserved anteriorly on the femur, the femoral component 600 may allow for faster, less complicated preparation of the femur than may be accomplished with some competing femoral prosthesis.

In some embodiments, femoral preparation and implantation of femoral component 600 is performed using surgical instruments common to standard knee systems and procedures. In other embodiments, standard surgical instruments are used to make all of the desired cuts to the distal femur. That said, in some embodiments, the standard anterior femoral cut is not made. The standard antero-distal femoral cutting guide with most systems is typically adequate to remove essentially all anterior cartilage to the proximal limit 612. Accordingly, there is no significant increase in instrument costs to implant femoral component 600 as opposed to a standard femoral component.

Further, since the antero-distal condylar cuts to the femur 32 may comprise standard cuts for fitting a standard femoral component, in some embodiments, a surgeon does not need to predetermine use of the femoral component 600 or a standard femoral component until the surgeon has completed all femoral cuts excepting the antero-distal cut, as this cut lies in roughly the same plane as the anterior femoral cortex. If the surgeon desires to implant the femoral component 600, the surgeon cuts the antero-proximal portion of the posterior condyles 625 using a non-standard cutting guide. The standard antero-distal cut removes essentially all anterior cartilage to the proximal limit 612. Conversely, if the surgeon desires to implant a standard femoral component, the surgeon makes the standard anterior cut necessary to accommodate implantation of a standard femoral implant.

In one non-limiting example of a resected femur 32 suitable for use with the femoral component 600, FIG. 29A shows some embodiments in which the femur 32 is resected to include an anterior chamfer cut 622 (or anterior oblique cut, see FIG. 12C), a distal cut 623, a posterior chamfer cut 627, a posterior condylar cut 628, and a full flexion cut 624 (e.g., a cut extending proximally and anteriorly from the posterior condylar cut 628 and/or towards a popliteal surface and/or posterior surface on the shaft of the femur).

The interior profile surfaces 620 of the femoral component 600 can be designed to match the interior profile of any conventional, standard femoral component. In some embodiments, however, the interior profile surfaces of opposing surfaces (e.g., internal surface 722, which interfaces with the anterior chamfer cut 622 and the internal surface 724, which interfaces with the full flexion cut 624) of the femoral component are exactly parallel or (in some cases) substantially parallel to allow a press-fit (including, without limitation, a cementless) or cemented application of the femoral component 600 to resected surfaces (e.g., 622, 623, 624, 627, and 628). In other embodiments, the interior profile surfaces of the opposing surfaces (e.g., 722 and 724) diverge from each other (or from being parallel with each other) by more than about 45°. In still other embodiments, however, the opposing surfaces (e.g., 722 and 724) diverge by less than about 45°. Indeed, in some embodiments, the opposing surfaces diverge from each other by between about 0° and about 45°. In still other embodiments, the opposing surfaces diverge from each other by between about 3° and about 25°. In even other embodiments, the opposing surfaces diverge from each other by between about 5° and about 10°. In yet other embodiments, the opposing surfaces diverge from each other by any suitable sub-range of any of the aforementioned ranges (e.g., between about 4° and about 8°). Additionally, while the opposing surfaces (e.g., 722 and 724) may diverge in any suitable direction, in some embodiments, when the femoral component 600 is attached to the femur 32, the opposing surfaces (or at least a portion of opposing surfaces) diverge from each other as the surfaces run proximally.

The femoral component 600 can be attached to a resected portion of the femur 32 in any suitable manner. Indeed, while, in some embodiments, the femoral component is configured to be rolled onto the femur, in other embodiments, the femoral component is slid onto the femur without rolling. In the latter embodiments, the femoral component can be slid onto the femur in any suitable manner. In one non-limiting example, where the opposing surfaces (e.g., 722 and 724) diverge as they run distally on the femur 32, the opposing surfaces are forced slightly further apart to allow the component to be slid onto and press-fitted to the femur. In this example, once the femoral component is in place, the opposing surfaces are allowed to return to their original position, which can help maintain the femoral component in place on the femur. In another example, where the opposing surfaces (e.g., 722 and 724) diverge as they run proximally on a femur 32 (e.g., giving the femur a slightly wedge-like characteristic), the femoral component 600 is slid on and press-fitted to the femur.

Where the femoral component 600 is slid onto the femur 32, the femoral component can be slid on at any suitable angle relative to a longitudinal axis of the femur's shaft (e.g., the distal one fourth to one third of the femur) that allows the femoral component to replace a desired portion of the femur's articulating surfaces. In some embodiments, where the femoral component is slid onto the femur, it is slid at an angle θ (with respect to a longitudinal axis 626 of femur 32, as shown in FIG. 29A) of between about 20° and about 80°. In other embodiments, the femoral component is slid on the femur at an angle between about 30° and about 55°. In other embodiments, the femoral component is slid onto the femur at an angle between about 30° and about 45°. In yet other embodiments, the femoral component 600 is slid on the femur any angle that falls in any suitable combination or sub-range of the aforementioned ranges of angles.

The femoral component 600 can be attached to the femur 32 in any suitable manner, including through the use of cement (i.e., any suitable adhesive); one or more screws, pins, or other mechanical fasteners; a pressure fitting (e.g., a friction fitting with or without cement); stems, and/or any other known or novel method for attaching a prostheses to a femur. In some embodiments, however, the femoral component is simply cemented (as mentioned earlier) to the femur. In still other embodiments, one or more internal surfaces of the femoral component 600 that attach to the femur 32 comprise a roughened texture (e.g., a porous texture, scaffolding, recesses, and/or other features) that allows bone to grow into the texturized surface.

The femoral component 600 can be modified in any suitable manner. Indeed, while in some embodiments, the femoral component is configured to replace all of the articulating surfaces of a femur (e.g., in a full femoral knee replacement), in other embodiments, the femoral component is configured to be used in a unicompartmental femoral knee replacement. Where the femoral component is used in a unicompartmental knee replacement, the component can be used in any suitable location (e.g., medially and/or laterally on the femur).

Figure 29B:
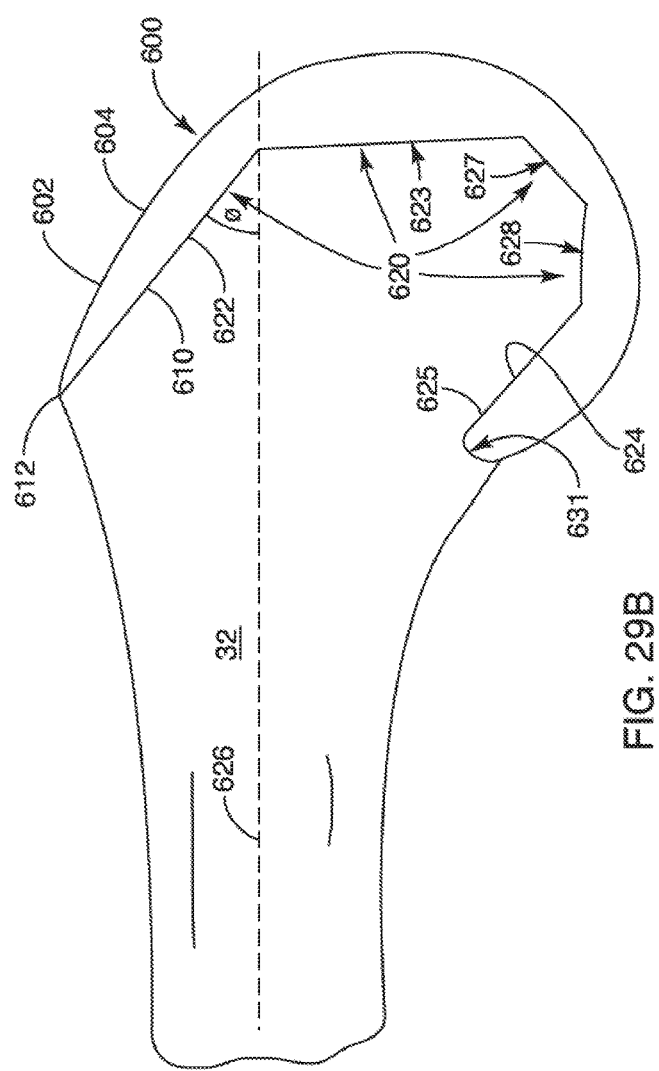
Figure 29C:
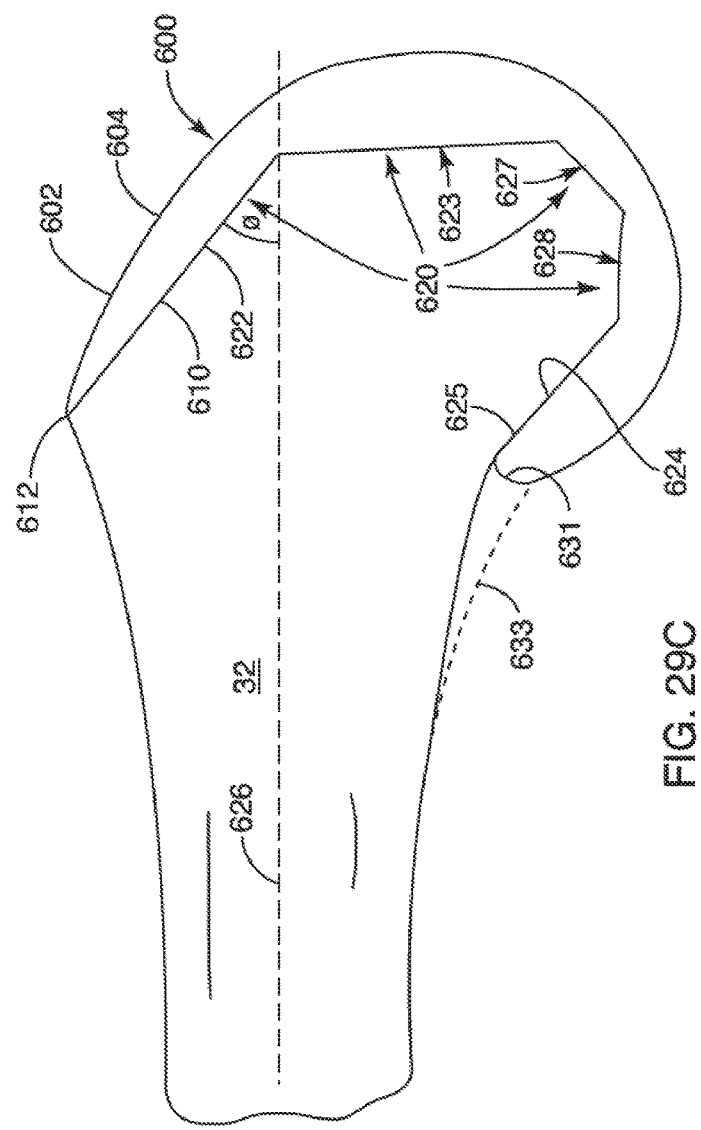

In another example of how the femoral component 600 can be modified, in some embodiments, the femoral component comprises a full flex articulation 50 (as discussed above, and as shown in FIG. 29A). In another example, however, FIGS. 29B and 29C show that some embodiments of the femoral component 600 optionally lack the full flex articulation. Indeed, FIG. 29B shows that, in some such embodiments, a posterior portion of the femur 32 can be removed so that the bone abuts and substantially corresponds with the shape of the proximal end 631 of femoral component 600. In contrast, FIG. 29C shows that, in some embodiments, either because of the natural shape of a patient's femur 32 or because a surgeon removes a posterior portion of the femur 32 (as illustrated by the dashed line 634), the posterior portion of the femur 32 does not abut with the proximal end 631 of the posterior portion of the femoral component 600.

In still another example, the full flexion articulation 50 is added to the femoral component 600 as a modular unit (as discussed above). In yet another example, the femoral component 600 replaces a popliteal surface of femur 32. In still another example, the femoral component is configured to receive a modular anterior flange 57 (as discussed above).

In still another example of how the femoral component 600 (or 12) can be modified, in some embodiments, the femoral component is configured to be fixed to (and/or otherwise used with) one or more modular femoral stems that are configured to extend into a femur's intramedullary canal, into compact bone of the femur 32, into cancellous bone of the femur, and/or any other suitable part of the distal portion of the femur. Indeed, in some embodiments, the femoral component is configured to be used with a stem that is configured to extend into the intramedullary canal 35 of the femur.

Figure 30A:
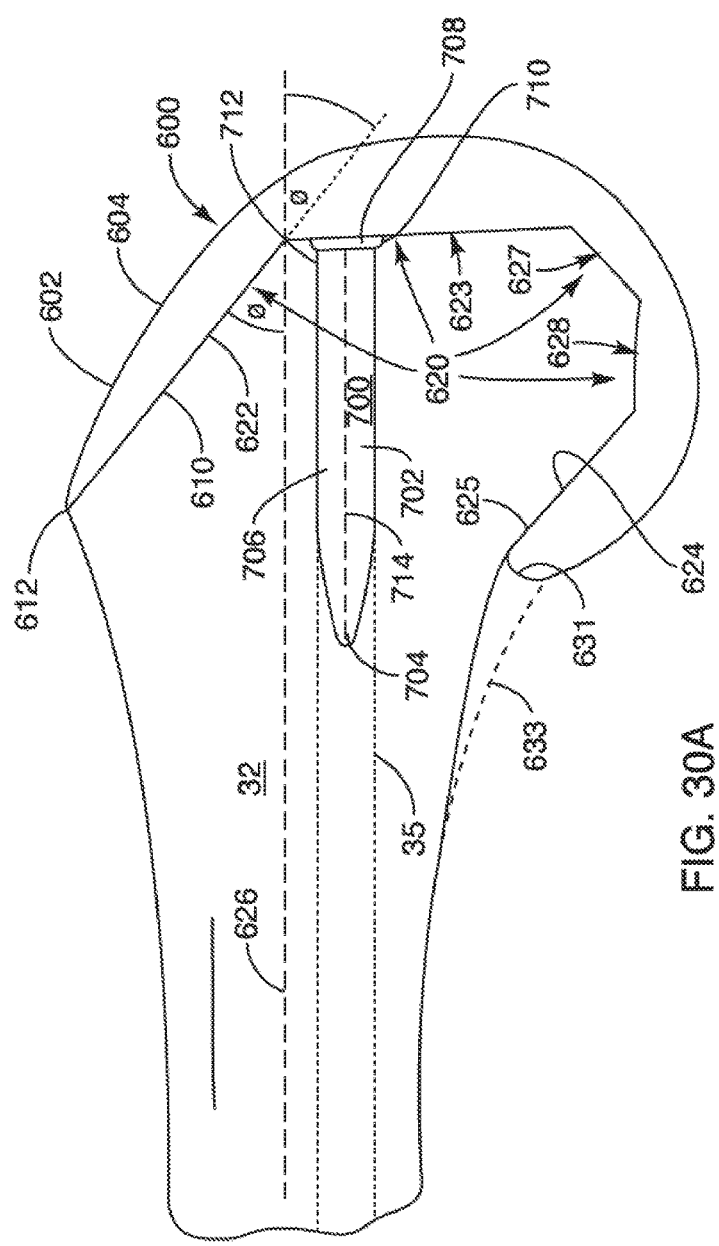
FIGS. 30A-30B each illustrate a representative embodiment of the femoral component comprising a representative embodiment of a modular femoral stem.

Although, in some embodiments, the stem is fixed to the femoral component 600 prior to the femoral component being seated at the distal end of the femur 32, in some other embodiments, a modular femoral stem and the femoral component are configured in such a manner that the modular stem is first inserted into the femur with the femoral component then being placed on a resectioned portion of the distal end of the femur 32 (and/or the femoral component then being connected to the stem). In some of such latter embodiments, once the modular stem is inserted into the femur, the femoral component is seated on the femur by having the femoral component be: rolled on to the femur, slid on to the femur at an angle that intersects with the longitudinal axis of at least a portion of the femur (e.g., a distal one third to one fourth of the femur), placed on the femur in a manner other than sliding the femoral component onto the femur in a direction that runs substantially parallel to the longitudinal axis 626 of the femur's distal portion, placed on the femur by moving the femoral component onto the femur in a direction that runs substantially parallel to a longitudinal axis of the femur's distal portion, slid laterally or medially onto a resectioned portion of the femur, and/or by otherwise being placed on the femur.

Where the femoral component 600 comprises a modular femoral stem (or a stem that can be coupled to the femur 32 separate from the femoral component), the femoral component can comprise any suitable characteristic that allows it to be attached (directly or indirectly) to the stem after the stem has been inserted into a distal portion of the femur 32. Some non-limiting examples of such characteristics include, but are not limited to, a recess in the femoral component that is configured to receive a portion of the stem and/or a plate or flange that is coupled to the stem; one or more projections and/or recesses configured to engage or otherwise help couple the stem to the femoral component; scaffolding, molding, recesses, knurling, texturizing, processes, and/or another suitable characteristic that allows cement and/or an adhesive to couple the modular femoral stem to the femoral component; one or more frictional or mechanical engagements configured to couple the modular femoral stem to the femoral component; a thickened posterior condyle (e.g., as discussed above with respect to at least FIG. 8B); an extended articulation surface 48 (e.g., as discussed above with respect to at least FIGS. 4A, 15A-15E, etc.); one or more internal surfaces that require the femoral component 12 to be rolled onto the resectioned portion of the femur 32 (e.g., as discussed above with respect to FIG. 4D); the modular attachment 30 (e.g., as discussed above with respect to FIGS. 4B-5D, 9, 10A-10H, 15C, 16C, 21, etc.); the proximal extension 50 (e.g., as discussed above with respect to FIGS. 16A-16Z, 20A-20I, 23, 23A, etc.); the medial femoral condylar surface 20; the lateral femoral condylar surface 22 (e.g., for a unilateral or full knee replacement; and as discussed with respect to FIG. 18A); the anterior extension 602 that terminates at or adjacent to the proximal limit 612 of the knee's articular cartilage (e.g., as discussed above with respect to FIGS. 29A-29C); one or more internal surfaces (e.g., surfaces 622 and 624) that require the femoral component to be slid on to the femur at an angle that intersects with the longitudinal axis 626 of a distal portion of the femur (e.g., as discussed above with respect to FIGS. 29A-29C); a modular flange 57 (e.g., as discussed above with respect to FIGS. 16T-16W); and/or any other suitable component or characteristic. In some embodiments, however, FIG. 30A shows the femoral component 600 comprises one or more interior profile surfaces 620 that require the femoral component to be slid on to the femur 32 at an angle θ (e.g., any suitable angle θ between about 20 and about 80°, as discussed above with respect to FIG. 29A) that intersects with the longitudinal axis 626 of a distal portion of the femur.

With respect to the modular femoral stem, the femoral stem can comprise any suitable component or characteristic that allows it to be inserted into a distal portion of the femur 32 and then to be attached to the femoral component 12. In this regard, the stem can be configured to be inserted into any suitable location at the distal portion of the femur, including, without limitation, to be inserted into the femur's intramedullary canal, the cancellous bone of either of the condyles, compact bone of the femur, and/or in any other suitable location at the distal portion of the femur. By way of non-limiting illustration, FIG. 30A shows some embodiments in which the modular femoral stem 700 comprise an intramedullary stem that is configured to be inserted into the intramedullary canal 35 of the femur 32. In some other embodiments in which the femoral component 600 comprises a unicompartmental component, the stem 700 is configured to extend into cancellous and/or compact bone at a distal end of the femur 32.

The modular femoral stem 700 can have any suitable shape that allows it to be inserted into the femur 32 and that further allows the femoral component 600 (or 12) to be fixed to it (directly or indirectly). In some embodiments, the femoral stem comprises an elongated shaft (e.g., a cylinder, an elongated polygonal shaft, an elongated elliptical shaft, an elongated star shaped shaft, a curved shaft, an angled shaft, a straight shaft, a non-tapered shaft, a shaft that is configured to contact an interior surface of an anterior cortex of a femur, a fluted shaft, a stem having any of the characteristics of the tibial stem 500 (discussed above), and/or any other suitable shaft), one or more fins (e.g., projections that are relatively thin and wide), a tapered shaft (e.g., a cone-shaped object, a cylindrical object having a tapered proximal end, a shaft having a rounded proximal end, etc.), a curved projection, a relatively straight projection, and/or any other suitable shape. By way of illustration, FIG. 30A shows that, in some embodiments, the modular stem 700 comprises a relatively straight cylindrical shaft 702 having a tapered proximal end 704.

The outer surface of the modular stem 700 can have any suitable surface characteristic that allows the stem to accommodate the needs of the patient, and that allows the stem to be used with the femoral component. Indeed, although some embodiments of the modular femoral stem comprise a relatively smooth outer surface, some other embodiments comprise a roughened outer surface, fluting (e.g., one or more grooves and/or furrows) extending along a portion of the stem's length, scaffolding or another lattice (as discussed below), one or more openings (as discussed below), one or more splines or ridges extending down a portion of the length of the stem, one or more fins that extend from the stem (e.g., tapered fins that extend at a distal end of the shaft to lock the stem in place with respect to the femur), one or more flat surfaces extending along a portion of the stem's length, and/or any other suitable texture or feature. In some embodiments, however, FIG. 30A shows that the modular stem 700 comprises a relatively smooth outer surface 706.

The modular femoral stem 700 can be any suitable length that allows it to strengthen the femur 32 and/or to disperse the load from the femoral component 600 (or 12) across a distal portion of the femur 32. In some embodiments, the femoral stem has a length that is longer than a length selected from about 1 cm, about 3 cm, about 5 cm, and about 7 cm. In some embodiments, the femoral stem has a length that is shorter than a length selected from about 20 cm, about 15 cm, about 12 cm, and about 32 cm. In still other embodiments, the femoral stem has a length that falls within any suitable combination or sub-range of the aforementioned lengths. For instance, some embodiments of the femoral stem are between about 4 cm and about 30 cm.

Although, in some embodiments, each modular femoral stem 700 is sized and shaped to be used with a femoral component 600 of a particular corresponding size, in some other embodiments, the femoral stem 700 is interchangeable with one or more other femoral stems of a varying characteristics (e.g., size, length, circumference, diameter, shape, angle, curvature, taper, texture, and/or any other suitable characteristic). In this manner, a single femoral component 600 (or 12) can be modified such that its stem 700 is able to be used with a variety of femurs having a different size, shape, and/or other characteristic. Indeed, as femoral components and modular stems each come in a variety of sizes and shapes to fit particular patients, in accordance with some embodiments, a variety of femoral components and stems can be mixed and matched with each other, thus allowing a medical provider to have a smaller inventory of femoral components than would otherwise be needed if each size femoral component could only have a single size stem coupled thereto. For instance, in some embodiments in which the femoral component is being placed on a relatively short femur, a relatively short modular femoral stem is attached to the femoral component, after the femoral stem has been inserted into the femur. In contrast, in some embodiments in which the same sized femoral component is being attached to a relatively long femur, a relatively long modular femoral stem is attached to the femoral component.

Although some embodiments of the femoral stem 700 lack a plate, base, or other broadened contact surface (sometimes referred to herein as a flange) at the stem's distal end, some other embodiments comprise a stem flange that has a larger width, length, contact surface, and/or diameter than does the stem. In such embodiments, the flange can serve any suitable purpose, including, without limitation, providing a surface that can be fixedly connected to the femoral component 600 (or 12), providing a support for the stem, providing a surface for receiving cement (and/or any other suitable adhesive), providing a surface to be coupled with the femur, and/or providing an interface between the stem and the femoral component. In this regard, the flange can have any suitable characteristic that allows it to be fixedly attached to the stem. For instance, from a view of the distal face of the flange, the flange can be any suitable shape, including, but not limited to, being circular, oval-shaped, elliptical, trapezoidal, square, rectangular, polygonal, irregular, symmetrical, non-symmetrical, and/or any other suitable shape that allows it to be fixed to the femoral component. By way of non-limiting illustration, FIGS. 30A, 31B, and 31C show some embodiments in which the flange 708 (from its face view) is substantially circular in shape. In another example, FIGS. 34-37C illustrate that the flange 708 can be any other suitable shape (e.g., substantially rectangular).

Where the femoral stem 700 comprises the flange 708 at the stem's distal end, the flange can be any suitable width or thickness. Indeed, in some embodiments, an outer perimeter 710 of the flange extends any suitable distance between about 0.1 mm and about 50 mm past an outer perimeter 712 of the femoral stem (e.g., anteriorly, posteriorly, medially, laterally, and/or on any other direction). In other embodiments, the outer perimeter of the flange extends between about 1 mm and about 45 mm past the outer perimeter of the femoral stem. In still other embodiments, the outer perimeter of the flange extends between about 2 and about 5 mm past the outer perimeter of the femoral stem. In yet other embodiments, the outer perimeter of the flange extends past the outer perimeter of the femoral stem by an amount that falls in any sub-range of the aforementioned ranges. Indeed, by way of non-limiting example, in some embodiments, the flange extends laterally and medially from the stem between about 5 mm and about 35 mm, and extends anteriorly and posteriorly from the stem by between about 0.1 mm and about 20 mm.

Where the femoral stem 700 comprises the flange 708, the flange can also be any suitable thickness between its distal face and proximal face that allows it to be used with the femoral component 600. In some embodiments, the flange has a thickness between about 0.1 mm and about 25 mm. In other embodiments, the flange has a thickness between about 1 mm and about 10 mm. In still other embodiments, the flange has a thickness between about 2 mm and about 5 mm. In still other embodiments, the flange has a thickness that falls in any sub-range of the aforementioned ranges.

Where the femoral stem 700 comprises the flange 708, the flange can also have any other suitable characteristic. Indeed, in some embodiments, the flange is permanently fixed to the stem. In other embodiments, however, the flange comprises one or more threaded engagements, frictional engagements, male engagements, female engagements, coupling mechanisms, holes to allow one or more screws and/or other fasteners to anchor the flange to the stem by extending through the flange and into the stem, and/or any other mechanisms that are configured to allow the stem 700 to be selectively coupled to and/or decoupled from the flange. By way of non-limiting illustration, FIG. 36A shows an embodiment in which the stem 700 is configured to be threadingly coupled to the flange 708.

Figure 36D:
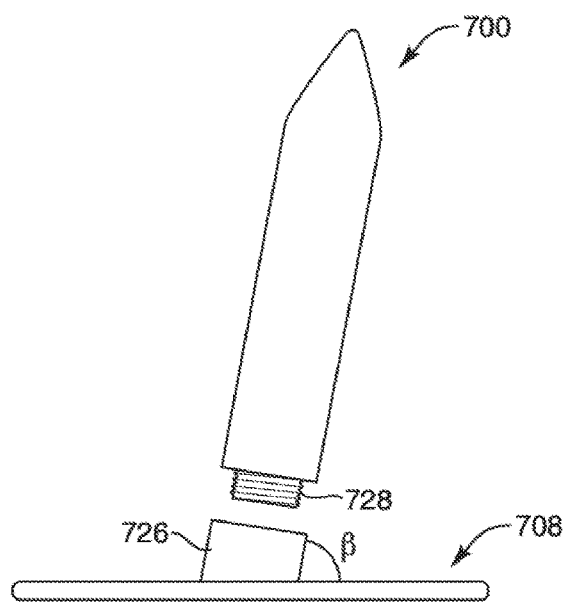
FIG. 36D illustrates a face view of the femoral stem and the flange in accordance with a representative embodiment.

In another non-limiting illustration, FIG. 36D shows that, in some embodiments, the flange 708 comprises a first coupler 726 (e.g., a machine taper, a Morse taper, a female socket, a male shaft, male threading, female threading, and/or any other suitable coupler) that is configured to mate with a second coupler 728 (e.g., a machine taper, a Morse taper, a female socket, a male shaft, male threading, female threading, and/or any other suitable coupler) of the stem 700. Thus, in at least some embodiments, the first coupler sets the angle $\beta$ of the stem (e.g., medial to lateral, lateral to medial, posterior to anterior, and/or anterior to posterior) and allows a stem of any suitable size and shape to be rapidly coupled to and/or decoupled from the flange. Accordingly, in some such embodiments, a single flange for a right leg or a single flange for a left leg can readily be used with a wide variety of modular stems.

As another example of a suitable characteristic of the flange 708, in some embodiments, the flange defines one or more recesses, holes, protuberances, textures, catches, and/or other components that couple with one or more corresponding components (e.g., protuberances, holes, textures, etc.) from the femoral component 600 and/or that allow cement (and/or any other suitable adhesive) to pass into and/or through the flange (e.g., to help couple the flange the femur and the femoral component to both the flange and the femur). By way of non-limiting illustration, FIGS. 36B and 37B illustrate some embodiments in which the flange 708 defines a plurality of holes 711 that allow cement to pass through and solidify in the flange. In this regard, while the holes can be any suitable shape (e.g., dovetailed, flared, tapered, square, circular, rectangular, triangular, symmetrical, asymmetrical, polygonal, regular, irregular, and/or any other suitable shape), FIGS. 36B and 37B illustrate some embodiments in which the holes 711 are substantially circular. Additionally, while the holes can have any suitable width (or diameter), in some embodiments, the holes have a width between about 0.1 mm and about 15 mm, or any subrange thereof, including, without limitation, 3 mm±2 mm.

Figure 33:
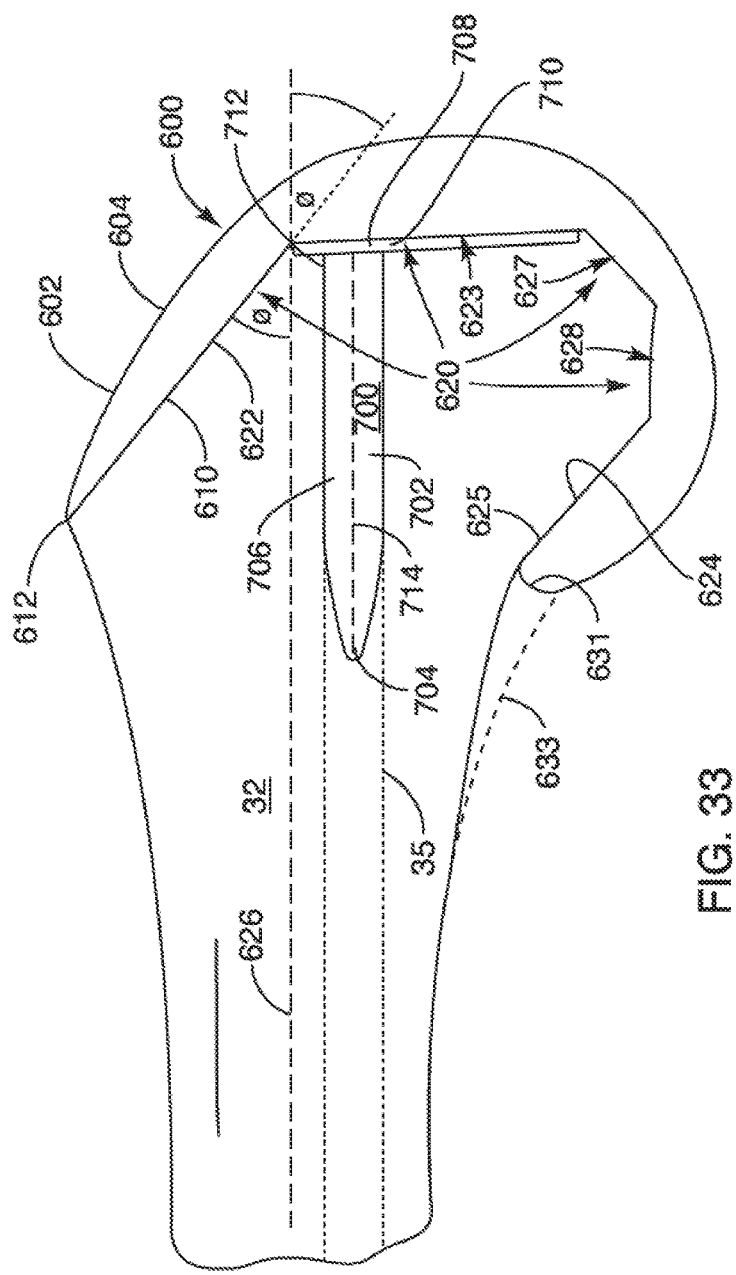
FIGS. 33-34 each illustrate a different representative embodiment of the femoral component comprising a different representative embodiment of the modular femoral stem.

In accordance with some embodiments, the distal end of the femoral stem 700 and/or the flange 708 can be configured to contact any suitable portion of the femoral component 600 (or 12) (e.g., the second internal surface 722, which is configured to contact the anterior chamfer cut surface 622 on the femur; the third internal surface 723, which is configured to contact the distal cut surface 623 on the femur; and/or any other suitable internal surface 620 of the femoral component (or any conventional or novel femoral component)). Indeed, in some embodiments, as illustrated in FIGS. 30A, 33, and 35B, the distal end of the femoral stem 700 (e.g., flange 708) is configured to contact (e.g., via cement or otherwise) and be fixed to the internal surface of the femoral component (e.g., the third internal surface 723, or any other suitable surface) that is configured to contact the distal cut surface 623 on the femur 32 (or any other suitable cut surface of the femur).

Figure 30B:
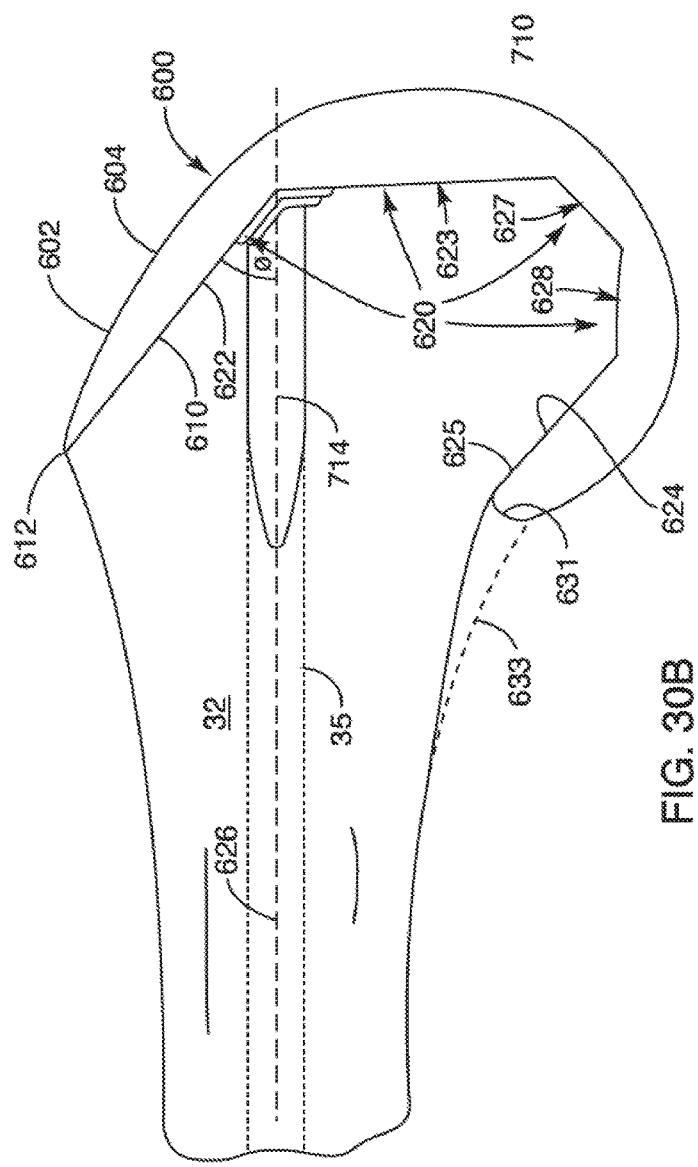
Figure 34:
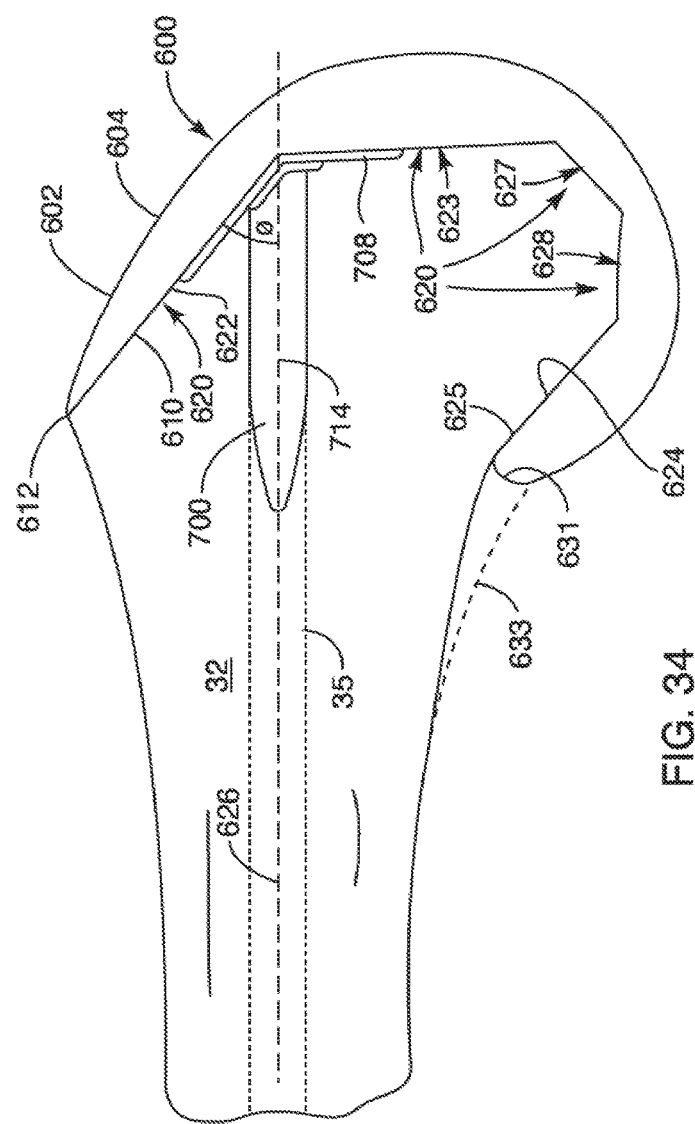

In accordance with some other embodiments, FIGS. 30B and 34 show that the stem's distal end (e.g., the flange 708) is multifaceted (or has multiple surfaces that run at an angle to each other) so as to allow the femoral stem 700 (e.g., the flange 708) to contact (e.g., via cement, one or more couplings, and/or in any other suitable manner) at least two internal surfaces of the femoral component (e.g., the second internal surface 722, which is configured to contact the femur's anterior chamfer cut surface 622, and the third internal surface 723, which is configured to contact the femur's distal cut surface 623).

Figure 35A:
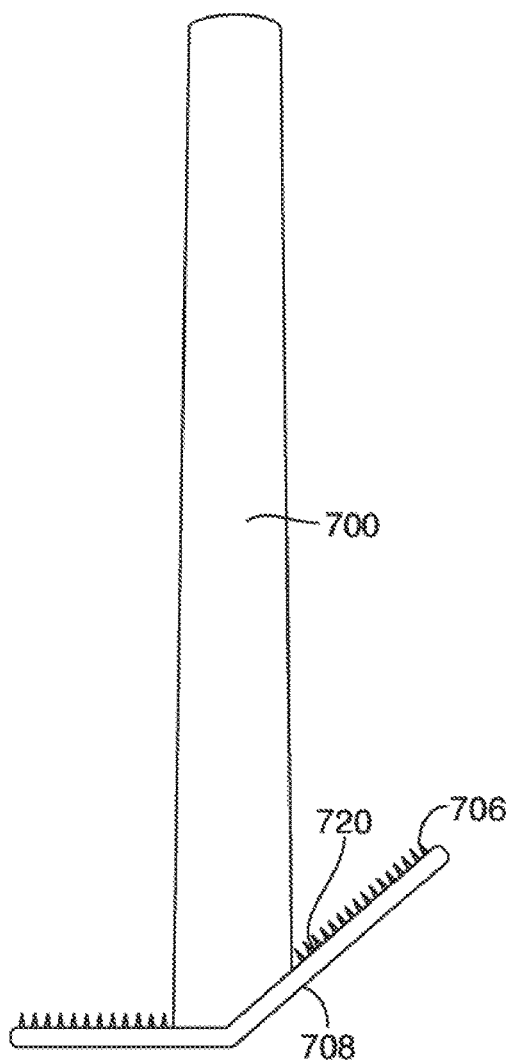
FIGS. 35A-35C each illustrate a side view of a different representative embodiment of the modular femoral stem, wherein the stem comprises a multifaceted flange.
Figure 35B:
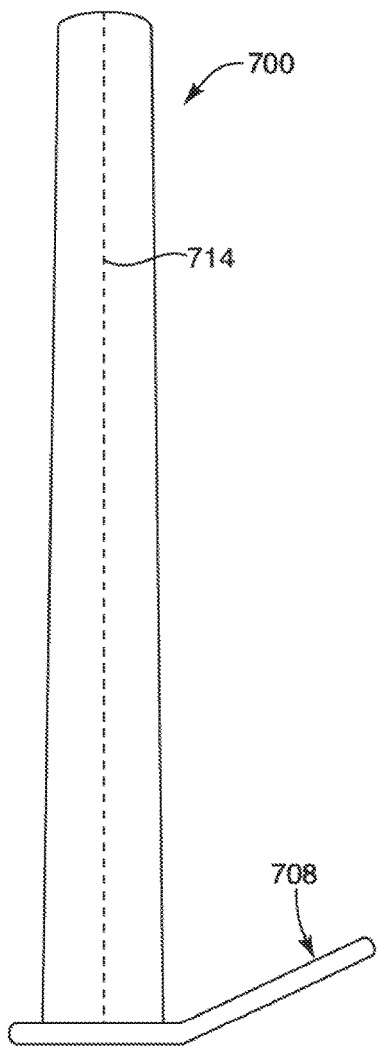
Figure 35C:
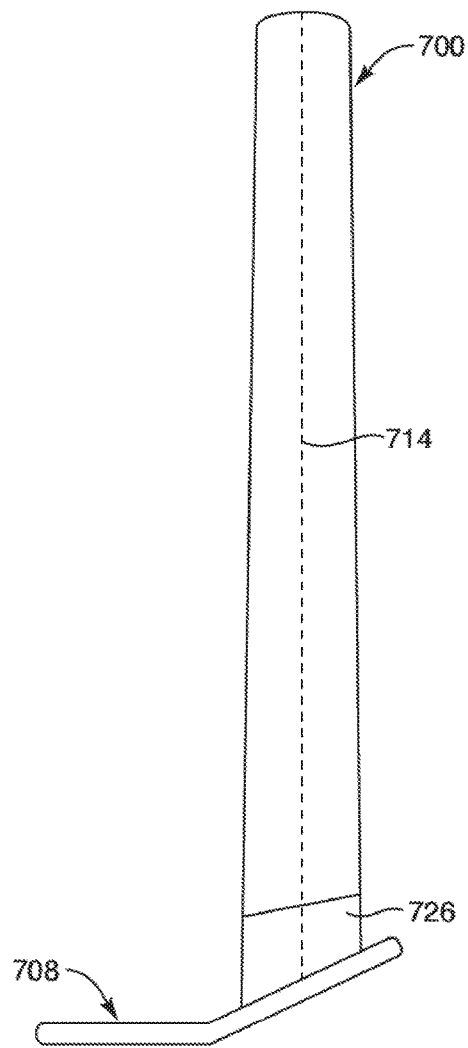

Additionally, FIG. 35C shows that, in accordance with some other embodiments, the stem's distal end (and/or a portion of the flange 708) is configured to indirectly or directly contact the second internal surface 722 of the femur 32, which is configured to contact the femur's anterior chamfer cut surface 622.

Additionally, instead of comprising multiple facets that are angled with respect to each other, some embodiments (not shown) of the distal end of the stem 700 (e.g., the flange 708) are curved to contact and be fixed (e.g., via cement or otherwise) to a curved portion of the femoral component's internal surface 620 (e.g., a curved portion between the second 722 and third 723 internal surfaces). In this regard, it should be noted that where the stem's distal end (e.g., the flange 708) contacts multiple walls of the internal surface 620 of the femoral component 600, the flange can greatly strengthen the joint between the modular femoral stem 700 and the femoral component to which it connects.

In some embodiments, the distal end (e.g., flange 708) of the femoral stem 700 is shaped such that a longitudinal axis 714 of the stem is configured to run at an angle (medially to laterally (or vice versa) and/or posteriorly to anteriorly (or vice versa) with respect to an internal surface of the femoral component (e.g., the third internal surface 723, which is configured to contact the femur's distal cut surface 623, and/or any other suitable surface) when the femoral stem is connected to such a component. In this regard, the femoral stem can run at any suitable angle with respect to the femoral component 600 that allows the stem to be inserted into the femur (e.g., the intramedullary canal) and then to have the femoral component be connected to it (e.g., by being slid into place at an angle that intersects with the longitudinal axis 626 of the femur). In some non-limiting embodiments, however, the stem's longitudinal axis 714 is configured to run parallel (or substantially parallel) with the angle of the femoral component's patellar groove 72 (e.g., as discussed above with respect to FIG. 18A). Accordingly, in some embodiments, a distal face of the femoral stem (or flange) runs at an angle that is not perpendicular to the longitudinal axis of the femoral stem.

In some embodiments, the femoral stem 700 is configured to attach to the femoral component 600 (or 12), such that the stem's longitudinal axis 714, as measured from a sagittal plane, is between about 40 and about 95° (e.g., where the angle opens laterally for both right and left leg prostheses). In other embodiments, the femoral stem is configured to attach to the femoral component such that the stem's longitudinal axis, as measured from a sagittal plane, is between about 75 and about 90°. In still other embodiments, the femoral stem is configured to attach to the femoral component such that the stem's longitudinal axis, as measured from a sagittal plane, is between about 80 and about 88°. In yet other embodiments, the stem is configured such that its longitudinal axis runs within any sub-range of the aforementioned ranges.

Figure 37A:
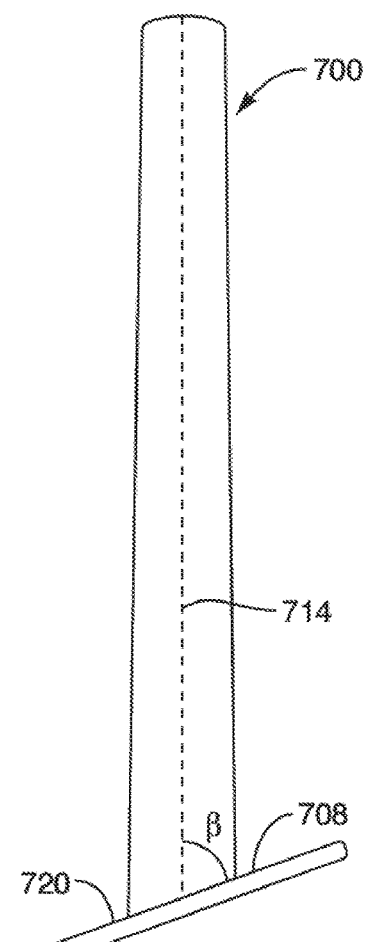
FIG. 37A illustrates an anterior and/or posterior view of a representative embodiment of the femoral stem.
Figure 37B:
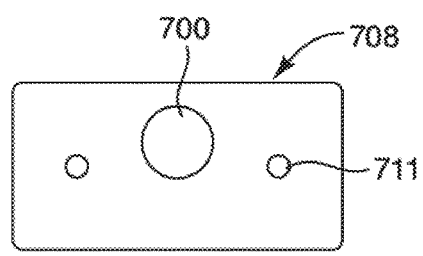
FIGS. 37B-37C each illustrate a top plan view of a different representative embodiment of the femoral stem coupled to the flange.
Figure 37C:
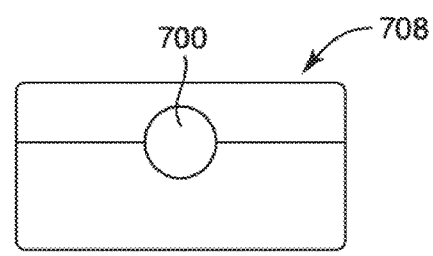

By way of illustration, FIGS. 31A and 37A show some embodiments in which the flange 708 runs at an angle θ with respect to the longitudinal axis 714 of the femoral stem 700 that allows the stem to connect to the internal surface 620 (e.g., the third internal surface 723, which is configured to contact the femur's distal cut surface 623) of the femoral component (not shown in FIG. 31A) such that the longitudinal axis of the stem runs at any suitable angle between about 75° and about 90° (e.g., between about 80° and about 88° medial to lateral) with respect to the internal surface of the femoral component to which the stem is connected.

In addition to the aforementioned characteristics, the femoral stem 700 and femoral component 600 (or 12) can comprise any other suitable component or characteristic that allows the femoral component to be used as intended. In one example, the femoral stem's distal end (and/or flange 708) is configured to be fixed to a corresponding mating surface (see e.g., mating surface 709 in FIGS. 5C and 5D) on the internal surface 620 of the femoral component. In this example, the femoral stem's distal end (e.g., the flange 708) and the mating surface of the femoral component can comprise any suitable characteristic that allows them to be connected to each other. In some embodiments, the femoral stem's distal end (e.g., the flange) and/or the femoral component's mating surface comprises a roughened texture (e.g., a knurled, a porous surface, one or more processes, one or more recesses, dovetail grooves, recesses, processes, etc.), scaffolding, and/or any other suitable feature that is configured to receive cement and/or any other suitable biocompatible adhesive. Indeed, in some embodiments, both the flange and the femoral component's mating surface comprise a roughened surface that is configured to provide for cement interdigitation. By way of non-limiting illustration, FIGS. 31B and 31C shows some embodiments in which the femoral stem's distal face 716 comprises a roughened surface 718.

In another example of a suitable characteristic, some embodiments of the flange 708 comprise a roughened surface on a proximal surface 720 (and/or a distal surface) of the flange 708 (with FIGS. 30C and 35 showing protuberances 706 on the proximal surface 720) that allows the flange to better bind with cement (or another suitable adhesive) disposed between the flange and the resected portion of the femur. In this regard, the proximal and/or distal surface of the flange can comprise any suitable roughened texture (e.g., a knurled, a porous surface, one or more processes, one or more recesses, dovetail grooves, recesses, processes, spines, etc.), scaffolding, and/or any other suitable feature that is configured to receive cement and/or any other suitable biocompatible adhesive.

In another example, the femoral stem 700 and/or flange 708 can comprise any suitable material or materials. Indeed, in some embodiments, the femoral stem comprises one or more metals. In other embodiments, however, the femoral stem 700 comprises one or more plastics, polymers, and/or other materials that can be trimmed at the time of surgery to allow an optimal fit.

In addition to the aforementioned characteristics, the described femoral stem 700 and femoral component 600 can be modified in any suitable manner. In one example, the distal end of the femoral stem and/or the flange 708 are optionally configured to couple with a turning tool (e.g., drill, wrench, screw driver, lever, and/or other turning tool) that is adapted to rotate the femoral stem when it is disposed within the femur (e.g., the intramedullary canal or otherwise). In this regard, the femoral stem can comprise any suitable characteristic that allows it to receive a turning tool. In some embodiments, the distal face 716 of the femoral stem's distal end (e.g., the flange's distal face) defines a turning tool receptacle (e.g., a receptacle for a Phillips, flathead, hex, star, torx, wrench, Alan wrench, and/or other screw driver or other suitable tool). Indeed, FIG. 30D shows some embodiments in which the distal face 716 of the flange 708 comprises a receptacle 722 for a Phillips screwdriver. In still another example (which is not illustrated), the stem and/or the flange comprise one or more flat surfaces, openings, and/or other contact surfaces that allow a turning tool to capture and apply a turning force to the stem to ensure that the stem is properly aligned with the femoral component.

In some embodiments, instead of (or in addition to) attaching the femoral stem 700 to the femoral component 600 through the use of cement (e.g., by inserting cement between the proximal face of the flange and the bone, by inserting cement between the distal face of the flange and an internal surface 620 of the femoral component, and/or between the stem's distal end or flange 708 and a corresponding mating surface 709 on the femoral component), the femoral stem and femoral component are configured to be connected in any other suitable manner that allows the femoral component to be attached to the femoral stem after the stem has been inserted into (e.g., fully seated in) the femur. Indeed, in some embodiments, the flange 708 and/or the distal end of the femoral stem comprises a first feature (e.g., a tongue or other suitable component) that can be captured by (or can capture) a second feature (e.g., a groove or other suitable component in the femoral component) as the femoral component is slid onto the femur (e.g., at an angle that intersects with the femur's longitudinal axis 626). In other embodiments, a portion of the flange and/or femoral stem is configured to be received (e.g., frictionally, mechanically, with cement (e.g., poly-methyl methacrylate and/or any other suitable adhesive), etc.) within a recess in the femoral component (or vice versa).

The described femoral stem 700 and femoral component 600 can be used in any suitable manner. Indeed, while the methods described herein can be modified in any suitable manner (including, without limitation, by rearranging, adding to, removing, substituting, and otherwise modifying various portions of the methods), FIG. 32 shows that, in some embodiments, the described method 800 begins at 802 with obtaining a femoral component 600 (or 12) and modular femoral stem 700 (which may include a flange 708) that have desired characteristics.

Figure 32:
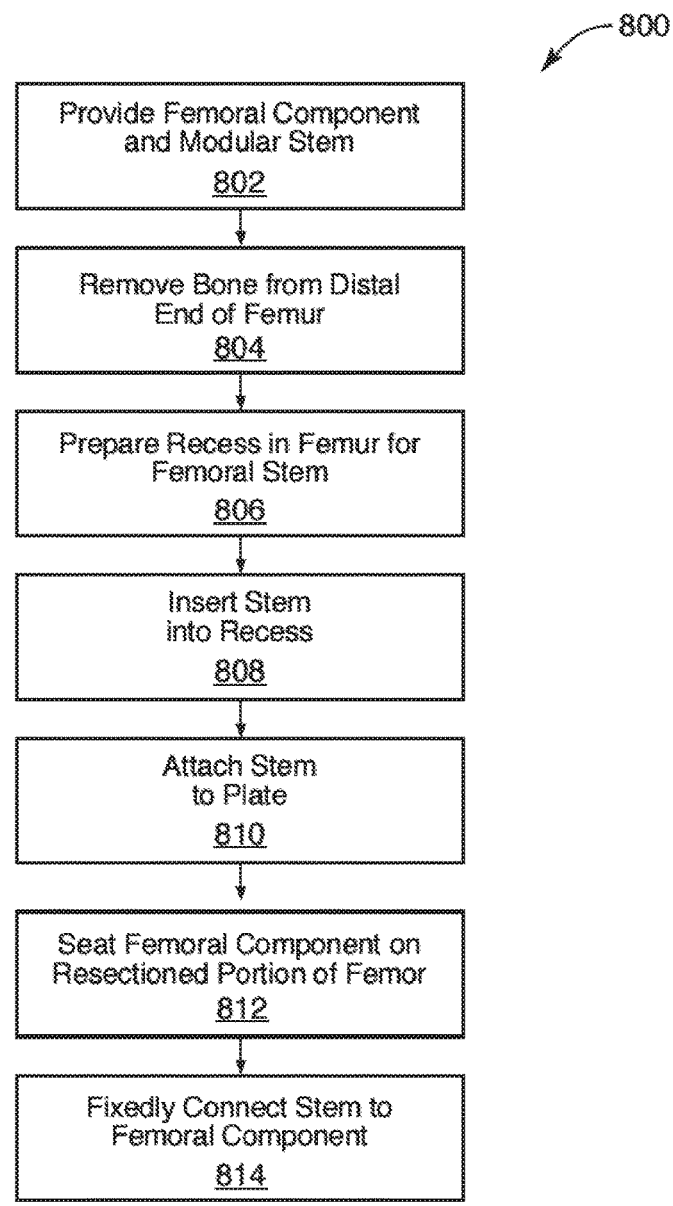
FIG. 32 illustrates a flow chart, depicting a method for applying the femoral component and the modular femoral stem to a femur in accordance with a representative embodiment.

At 804, FIG. 32 further shows that some embodiments of the method 800 include removing bone from a distal end of the femur 32. In this regard, the bone can be removed in any suitable manner (e.g., with any suitable number and type of cuts) and through any suitable method that allows the femoral component to be seated on the femur's distal end.

At 806, FIG. 32 shows some embodiments of the method 800 further include preparing a recess in the femur 32 (e.g., the intramedullary canal 35 and/or another suitable location) to receive the femoral stem 700 (e.g., an intramedullary stem). While this recess can be prepared in any suitable manner, including, without limitation, through the use of a reamer, a chisel, a milling tool, a file, etc., in some embodiments, the recess is prepared through the use of a drill that is used to hollow out a portion of the intramedullary canal.

At 808, FIG. 32 shows some embodiments of the method 800 continue as the femoral stem 700 is inserted into the recess. While the stem can be inserted into the recess in any suitable manner, in some embodiments, the stem is pounded into the recess (e.g., through the use of a hammer or mallet). Additionally, in some embodiments, to ensure that the stem is inserted into the femur in a desired orientation, the stem is inserted into the femur through the use of a guide that maintains the stem in a desired orientation as the stem is inserted into the femur. In still other embodiments, the orientation of the stem is adjusted through the use of a turning tool as (or after) the stem is inserted into the femur. In still other embodiments, the opening of the recess is optionally countersunk, filed, or otherwise modified to allow the flange 708 to be seated within such opening.

At 810, FIG. 32 shows that, in some embodiments, the stem 700 is attached to the flange 708 (or plate). While the stem and plate can be attached to each other in any suitable manner (e.g., via a friction engagement, a mechanical engagement, an adhesive, and/or in any other suitable manner), in some embodiments, the stem and flange are threadingly coupled together.

The femoral stem 700 can be fixed to the femur 32 in any suitable manner, including, without limitation, via friction between the stem and femur. In some embodiments, however, the stem is cemented to the femur. Indeed, in some embodiments, cement (and/or another adhesive) is disposed between the proximal face of the flange and a resected surface of the femur.

After the stem has been inserted into the recess in the femur, FIG. 32, at 812, shows that some embodiments of the method 800 continue as the femoral component 600 is seated on the resectioned portion of the femur. In this regard, the femoral component can be seated on the femur in any suitable manner. Although, in some embodiments, the femoral component is applied to the distal femur along a plane that is substantially parallel to the longitudinal axis 626 of the femur 32, in other embodiments, the femoral component is applied by rolling the component onto the femur (as discussed above) and/or by sliding the component onto the femur at an angle that intersects with the femur's longitudinal axis.

At 814, FIG. 32 shows that some embodiments of the method 800 continue as the femoral component 600 is fixedly connected to the seated femoral stem 700. The two components can be fixedly connected to each other in any suitable manner, including, without limitation, through the use of cement (or another biocompatible adhesive), microlaser welding, a frictional engagement, a mechanical engagement, a pin that is inserted through a portion of the femoral component and the femoral stem (e.g., through a hole cut or drilled in the femur), and/or in any other suitable manner. In some embodiments, however, the femoral component and the femoral stem are fixedly connected to each other through the application of cement between the distal surface of the stem's flange 708 and the femoral component's mating surface 709.

In addition to the aforementioned features, the described femoral stem 700 may provide the femoral component 600 with several beneficial features. In one example, some embodiments of the described femoral stem allow a femoral component that normally could not be used with a relatively long femoral stem to be used with such a stem. Indeed, as discussed above, some embodiments of the described systems and methods allow a femoral component that is rolled onto the femur and/or slid onto the femur at an angle that intersects the femur's longitudinal axis 626 to be used with the femoral stem. In contrast, if some conventional femoral components comprising a relatively long stem were rolled on or slid on to the femur at such an angle, the stem on such components would have to penetrate the femur's cortex during installation.

In another example, some embodiments of the described femoral component 600 and femoral stem 700 are fixedly connected to each other without the need for twisting (or screwing) one component into the other.

In still another example, unlike some conventional femoral prostheses that have a stem connected to a process extending from an internal surface of the prosthesis, some embodiments of the described femoral stem 700 are able to connect directly (e.g., via cement) to an internal surface of the femoral component (e.g., the second internal surface 722, which is configured to contact the anterior chamfer cut surface 622 on the femur; the third internal surface 723, which is configured to contact the distal cut surface 623 on the femur; and/or any other suitable internal surface 620 of the femoral component). As a result, such embodiments of the described stem and femoral component can allow the components to be applied to a femur 32, while requiring a relatively small amount of bone to be removed from the femur.

In another example, some embodiments of the described femoral stem 700 and femoral component 600 are configured to strengthen a distal portion of the femur 32. Indeed, by having the stem extend from the femoral component into the femur, the femoral stem can disperse and distribute some of the load that is placed on the distal portion of the femur by the femoral component, which can prevent stress risers that were created as a consequence of bone cuts from spreading.

In addition to the aforementioned systems and methods, in some embodiments, the described systems and methods further comprise a cutting guide block that is configured to guide a cut of a proximal portion of the femur's medial and/or lateral posterior condyles. While the guide block can be used to make any suitable cut to one or both of the posterior condyles, in some embodiments, the guide block is configured to guide a posterior condyle cut (or a cut at a proximal portion of a posterior condyle that is configured to remove bone from the posterior condyle to prevent the posterior condyle from striking a tibia and/or tibial component during deep knee flexion) and/or a full flexion cut 624 on the femur (or a cut that runs proximally and anteriorly from its distal end in a posterior condyle towards a posterior surface of the femur so as to allow a femoral component 600 having an extended posterior articulation surface (as shown in FIGS. 29A and 33) to be seated on the femur 32.

The guide block can comprise any suitable component or characteristic that allows it to guide resection of a proximal portion of one or both posterior condyles of the femur 32. In one example, the guide block comprises a component that is configured to be seated on one or more resected and/or unresected portions of the distal end of the femur such that a cutting tool guide slot is disposed adjacent to a proximal portion of a posterior condyle. Indeed, as shown in FIG. 38, in some embodiments, the cutting guide block 900 is configured to be seated on one or more resected portions 620 at the distal end of the femur 32.

Figure 38:
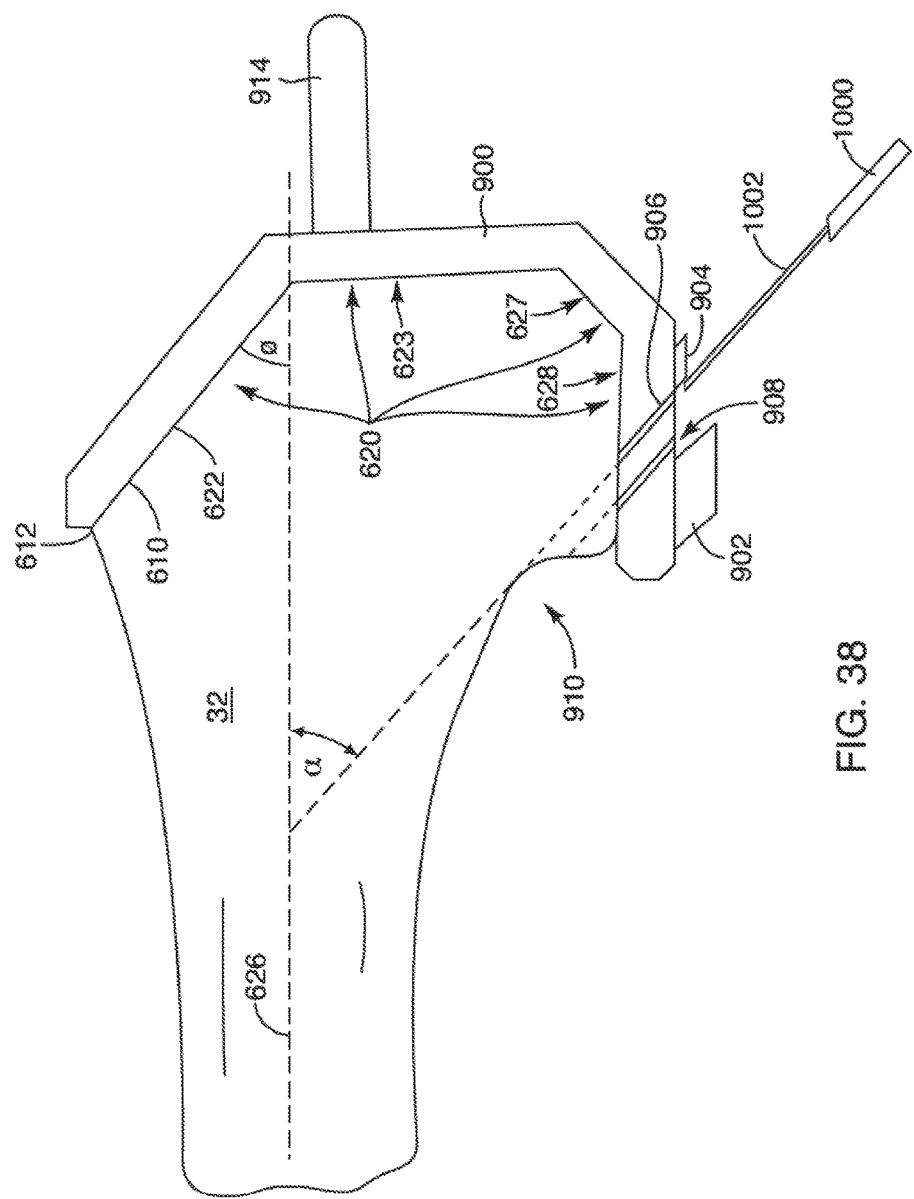
FIG. 38 illustrates a side view of a representative embodiment of a cutting guide block that is configured to guide resection of a proximal portion of a lateral and/or medial posterior condyle.

While the cutting guide block 900 can be configured to contact any suitable number of resected surfaces of a femur (e.g., 1, 2, 3, 4, 5, 6, 7, 8 or more), FIG. 38 illustrates an embodiment in which the block 900 is configured to abut four or more resected surfaces. In this regard, while FIG. 38 illustrates a representative embodiment in which the cutting block 900 abuts an anterior chamfer cut 622, a distal cut 623, a posterior chamfer cut 627, and a posterior condylar cut 628, the described cutting guide block can have any other suitable configuration and can be configured to abut any suitable resectioned surface that is at the distal end of the femur. Thus, in accordance with some embodiments, a distal end of a femur can be resectioned (e.g., as described herein and/or in accordance with any known or novel method) so as to receive any suitable femoral component. Moreover, in accordance with some embodiments, if it is decided that a proximal portion of one or more posterior condyles needs to be removed (e.g., to prevent the one or more posterior condyles from striking the tibia and/or a tibial component and/or to allow for one of the described femoral components 600 having an extended posterior condyle to be used on the femur), then a surgeon can place the cutting guide block on the femur and remove a desired amount of the proximal portion of the lateral and/or medial condyles.

Figure 39A:
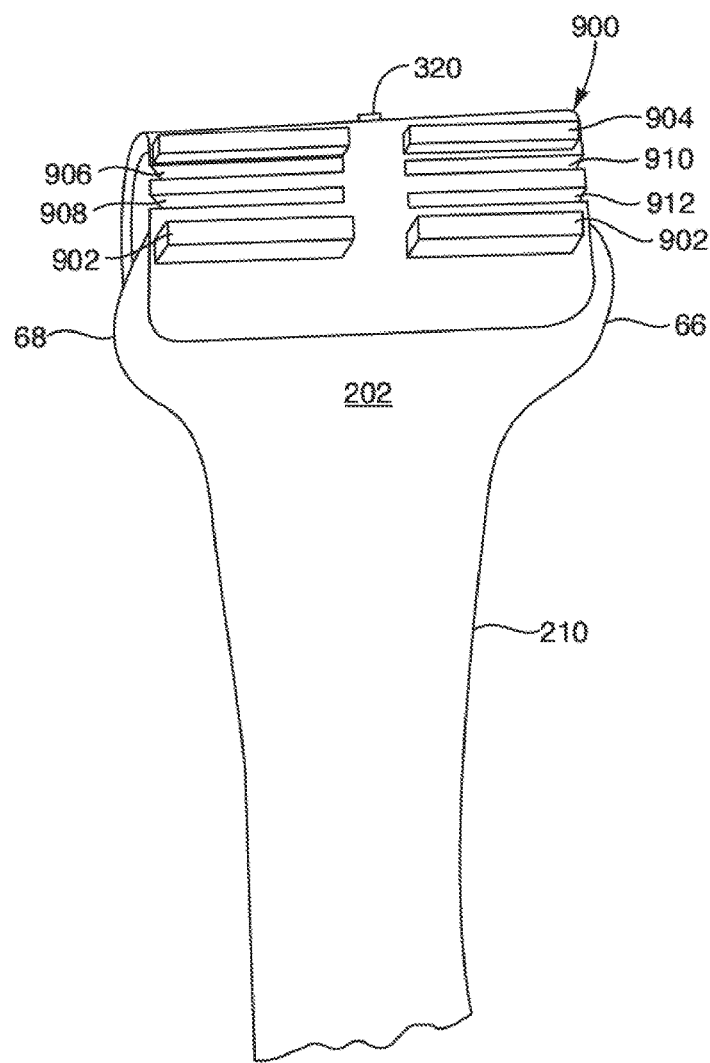
FIGS. 39A-39B each illustrates a perspective view of a different representative embodiment of the cutting guide block.

In some embodiments, the cutting guide block comprises 1, 2, 3, 4, 5, 6, or more cutting tool guide slots that are configured to receive and direct a cutting tool (e.g., a chisel, knife, file, reciprocating blade, blade, and/or other suitable tool that is capable of cutting the femur) to remove a proximal portion of a posterior condyle of the femur. By way of non-limiting illustration, FIG. 39A shows a representative embodiment in which the cutting guide block 900 defines four guide slots (e.g., slots 906, 908, 910, and 912). Additionally, while the guide block can define the one or more slots in any suitable location (including, without limitation, adjacent to a posterior medial and/or lateral condyle), FIG. 39A illustrates an embodiment in which two slots 906 and 908 are defined adjacent to a medial posterior condyle, and two additional slots 910 and 912 are defined adjacent to a lateral posterior condyle. Moreover, while the slots are illustrated in FIG. 39A as being disposed at equal heights in the lateral and medial sides of the guide block with respect to either a proximal-most and/or a distal-most portion of the guide block 900, in some other embodiments, the slots on the lateral side may be higher than the slots on the medial side (or vice versa) with respect to either a proximal-most and/or a distal-most portion of the guide block.

The guide slots (e.g., slots 906, 908, 910, and 912) can be configured to guide the cutting tool (e.g., a chisel and/or other suitable cutting) at any suitable angle that allows the cutting tool to remove a proximal portion of a posterior condyle. Indeed, in some embodiments, the cutting guide block 900 is configured to guide the cutting tool at an angle (shown as a in FIG. 38) of between about 20° and about 65° (or any sub-range thereof) with respect to the longitudinal axis 626 of a distal portion of the femur 32. Indeed, in some embodiments, the guide block 900 is configured to guide the cutting tool (e.g., the blade 1002 of the chisel 1000) at an angle α of between about 35° and about 55° (e.g., between about 40° and about 50° or between about 43° and about 47°) with respect to the longitudinal axis 626 of the distal portion of the femur 32. In some embodiments, the guide block 900 is configured to guide the cutting tool (e.g., the blade 1002 of the chisel 1000) at an angle α that is substantially parallel with the angle of the anterior chamfer cut 622 of the femur 32.

In some embodiments, all of the guide slots (e.g., slots 906, 908, 910, and 912) in the guide block 900 are configured to hold (e.g., surround a portion of, pinch, channel, and/or otherwise direct) the cutting tool (e.g., chisel 1000) in such a manner that the cutting tool is guided at the same angle in each of the slots. In some other embodiments, however, one or more of the guide slots are configured to guide the cutting tool at a different angle with respect to the longitudinal axis 626 of the distal portion of the femur. Accordingly, in some such embodiments, the cutting block is configured to be used with femurs having a variety of anatomical features and/or to tailor the distal end of the femur for a variety of femoral components.

In accordance with some embodiments, the cutting guide block 900 and/or the cutting tool (e.g., chisel 1000 and/or any other suitable cutting tool) is configured to limit the depth to which the cutting tool is able to extend through the guide block and into the femur. In this manner, the guide block and/or cutting tool can be configured to prevent an undesired amount of bone from being removed from the proximal portion of the medial and/or lateral posterior condyles.

In some embodiments, in order to prevent the cutting tool (e.g., chisel 1000) from extending too far into the femur 32, the cutting tool itself comprises one or more features (e.g., protuberances, stops, handles, etc.) that are configured to contact the a portion of the guide block to prevent the blade (e.g., chisel blade 1002) from extending too far into the femur. Additionally, in some embodiments, the guide block comprises a relatively narrow opening in its guide slots, a process, a stop, and/or any other suitable component that is configured to contact a portion of the cutting tool to limit the tool's cutting depth. Accordingly, in some embodiments, the cutting block is configured to prevent a surgeon from accidentally (or otherwise) cutting into the popliteal surface 202 of the femur, the femoral shaft, muscle, flesh, ligaments, and/or blood vessels at a posterior portion of a patient's leg while the surgeon is using the cutting guide to remove a proximal portion of the patient's posterior condyle.

Figure 39B:
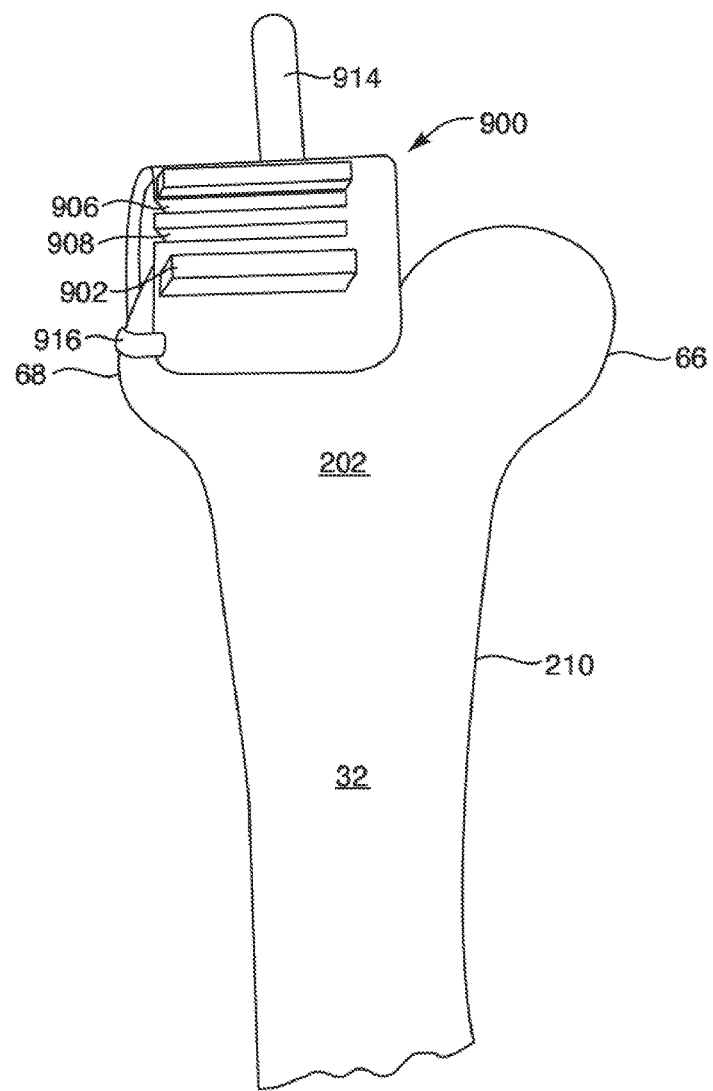

With reference to the mechanism for preventing the cutting tool (e.g., chisel 1000) from extending too deep into the femur 32, FIGS. 38, 39A, and 39B show some embodiments in which the cutting guide block 900 comprises one or more stops 902 and 904 that are configured to contact a portion of the cutting tool (e.g., chisel 1000) to limit the cutting tool's depth in the femur. Moreover, while the stops 902 and 904 can have any suitable characteristic that allows them to limit the amount of cutting that can be performed by the cutting tool, in some embodiments, one stop is configured to let the cutting tool extend further into the femur than does another stop. For instance, FIGS. 38 and 39A-39B show some embodiments in which a proximal-most stop 902 is configured to prevent the chisel 1000 from extending as far into the femur as is possible when the chisel blade 1002 is inserted into the distal-most slot 906.

Where the cutting tool comprises a chisel 1000, the chisel can comprise any suitable characteristic that allows it to be used with the cutting guide block 900 to remove a desired portion of the femur. In some embodiments, however, the chisel is thick enough (e.g., between about 0.5 and about 5 mm thick or any subrange thereof) and/or comprises a material that is sufficiently strong to prevent the chisel's blade 1002 from deflecting as it is forced into the femur.

In light of the foregoing, the described cutting guide block 900 can provide a quick and accurate way to remove a proximal portion of the medial and/or lateral posterior condyle to prevent the posterior condyle from gouging into a tibial component (or tibia) and/or to allow a modified femoral component 600 (as discussed herein) to be seated onto the femur. In this regard, during the surgery, the surgeon may decide to make a cut (e.g., via slot 908) that allows a conventional femoral component that lacks a proximal extension 50 to be seated on the femur. In contrast, during the surgery, the surgeon may instead choose to make a cut (e.g., a full flexion cut 624 via slot 906) to allow the femoral component 12 with the proximal extension 50 (e.g., medial and/or a lateral) to be seated on the femur.

In addition to the foregoing components and characteristics, the cutting block 900 can comprise any other suitable component or characteristic that allows it to function as intended. In one example, some embodiments of the block comprise one or more handles, grips, finger holes, nail holes, and/or other features that allow it to be held in place during use. By way of non-limiting illustration, FIGS. 38 and 39B show some embodiments in which the cutting block 900 comprises a handle 914. Additionally, FIG. 39A shows an embodiment in which the guide 900 is configured is configured to be held in place during its use with one or more fasteners 320.

As another example of a suitable modification of the cutting block 900, in some embodiments, the block comprises one or more placement guides that are permanently fixed in place on the cutting block and/or that are selectively adjustable (e.g., via one or more fastening mechanisms, fasteners, ratchet mechanisms, clamps, and/or other adjustment mechanism) so as to hold the guide in a desired location with respect to the femur 32 during use. While such placement guides can have any suitable characteristic, FIG. 39B shows that, in some embodiments, the guides 916 are configured to contact a portion (e.g., side and/or other portion) of the femur 32 to properly align the cutting block with the femur during use of the block.

As still another example of a suitable modification, while some embodiments of the cutting block 900 are configured to be used for full knee replacements (e.g., as shown in FIG. 39A), some other embodiments (e.g., as shown in 39B) are configured to be used in unicompartmental knee surgeries. In still another modification, the cutting block comprises two discrete pieces that are configured to be selectively coupled together (e.g., via one or more catches, slots and grooves, clamps, fasteners, and/or other coupling mechanisms) for use in total knee replacement surgery and to be selectively decoupled from each other to be used separately in unicompartmental knee surgeries (and/or any other suitable application).

Thus, as discussed herein, the embodiments of the present invention embrace knee prostheses. In particular, some implementations of the present invention relate to systems and methods for providing deeper knee flexion capabilities for knee prosthesis patients, and more particularly, to systems and methods for: (i) providing a greater articular surface area to the femoral component of a knee prosthesis, with either a modification of, or an attachment to the femoral component of a knee prosthesis, which when integrated with a patient's femur and an appropriate tibial component, results in full functional flexion; (ii) providing modifications to the internal geometry of the femoral component and the opposing femoral bone with methods of implanting; (iii) providing asymmetrical under surfaces on the tibial component of the knee prosthesis and uniquely-positioned articular surfaces to facilitate full functional flexion; (iv) providing asymmetrical femoral condylar surfaces with a lateralized patellar (trochlear) groove to more closely replicate physiologic loading of the knee and to provide better tracking of the patella; (v) resectioning essentially all of the anterior femoral articular cartilage and underlying bone, but no additional bone and replacing it with a femoral component that does not have an anterior flange as seen on contemporary prostheses; (vi) providing a femoral component having a modular stem, which allows the femoral component to be rolled onto a resected portion of a distal end of the femur, or to be slid onto the resected portion of the femur at an angle that intersects with a longitudinal axis of the femur; (vii) cutting a posterior proximal portion of a femoral condyle to allow for deep knee flexion; and (viii) providing a process for providing customized prosthetics. In some implementations in which the described systems and methods relate to the femoral component having a modular stem, the stem and femoral component are configured such that the femoral component can either be rolled onto a resected portion of the femur, or to be slid onto the resected portion at angle that intersects a longitudinal axis of a distal portion of the femur, after the modular femoral stem has been inserted into the femur.

Lightweight Prosthetic Implants

Some aspects of the present invention relate to systems and methods for providing relatively lightweight prostheses. In some such instances, the described systems and methods include a prosthetic implant having an exterior surface that is configured to contact a bone (and/or another prosthetic component), an interior space disposed within the prosthetic, and a lattice structure disposed within the interior space. Additionally, in some cases, a portion of the prosthetic is configured to have a modulus of elasticity that substantially matches that of the bone to which the prosthetic couples. While the elasticity of the bone and the prosthetic can be approximately matched in any suitable manner, in some cases, the elasticity of one or more portions of the prosthetic is modified by varying the strength provided to the prosthetic by the lattice structure.

While the described systems and methods can be used to create any suitable prosthetic that can be implanted in a patient, in some embodiments, the described systems and methods are used to create any suitable: femoral knee component (including, without limitation, any of the components discussed herein, a patellar component, and/or any other suitable femoral knee component), tibial knee component (including, without limitation, any of the components discussed herein and/or any other suitable tibial knee component), intramedullary rod, prosthetic stem (including, without limitation, a femoral stem, a tibial stem, and/or any other suitable prosthetic stem), femoral hip component (e.g., femoral head, stem for a femoral head, and/or any other suitable femoral hip component), acetabular cup component, glenoid component, humeral head component, ulnar component, humeral component, cranial component, femoral component, vertebral component, tibial component, rib component, mandibular component, and/or any other suitable prosthetic that can be implanted in a patient. By way of non-limiting illustration, FIGS. 40A-40B show that, in some embodiments the implantable prosthetic 1100 respectively comprises a femoral component 12, a tibial component 14, and stem 500.

Figure 40A:
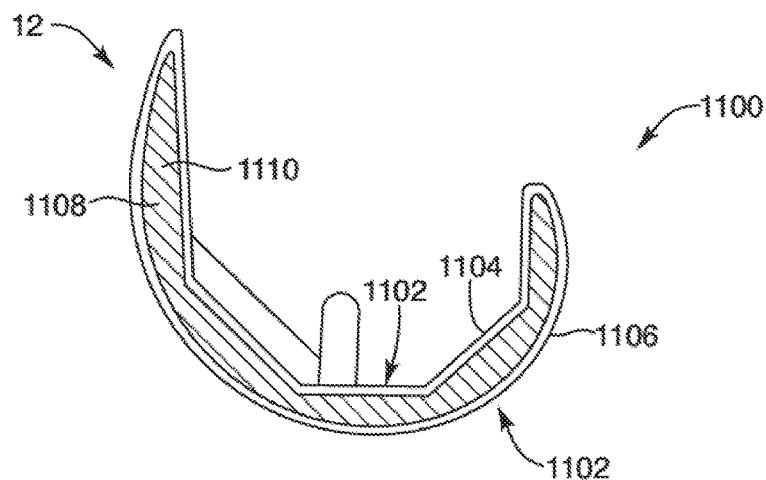
FIG. 40A illustrates a side, cross-sectional view of the femoral component comprising an internal lattice structure in accordance with a representative embodiment.
Figure 40B:
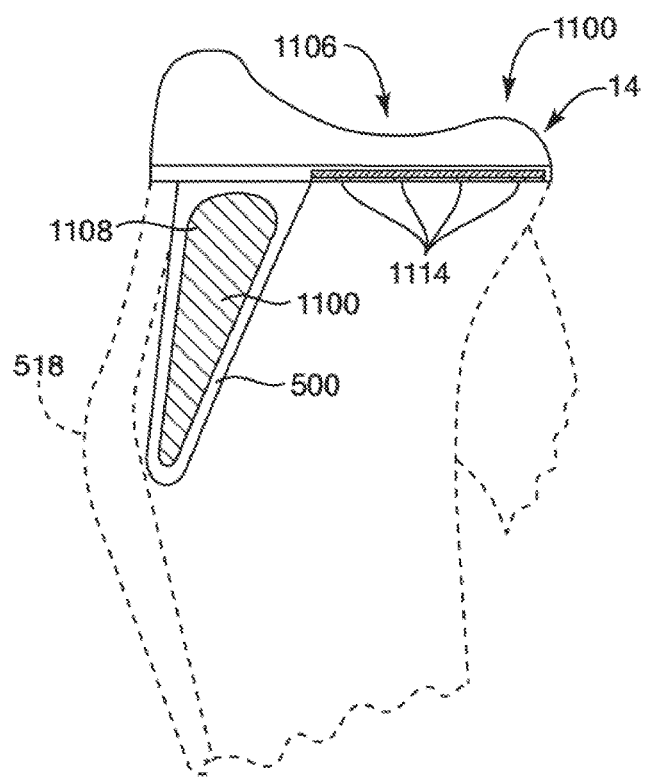
FIG. 40B illustrates a side, cross-sectional view of the tibial component comprising the internal lattice structure in accordance with a respective embodiment.

Although the described implantable prosthetic 1100 can have any suitable component or characteristic, FIG. 40A shows that, in some embodiments, the prosthetic 1100 comprises an external surface 1102. While the external surface can serve any suitable characteristics, FIG. 40A shows that, in some embodiments, the external surface 1102 comprises a first surface 1104 that is configured to contact the bone and/or another prosthetic device to which the prosthetic 1100 attaches (e.g., the femur in the case of FIG. 30A). FIG. 40A further shows that, in some embodiments, the prosthetic 1100 optionally comprises an articular surface 1106 that is configured to articulate against another surface (e.g., in the case of the femoral component 12 illustrated in FIG. 40A, a tibia, a tibial implant 14, a patella, etc.). Moreover, FIG. 40A shows that, in some embodiments, the prosthetic 1100 defines one or more interior spaces 1108, which are hollow and/or which comprise one or more lattice structures 1110 that are configured to strengthen and/or otherwise support a portion of the prosthetic.

Figure 40C:
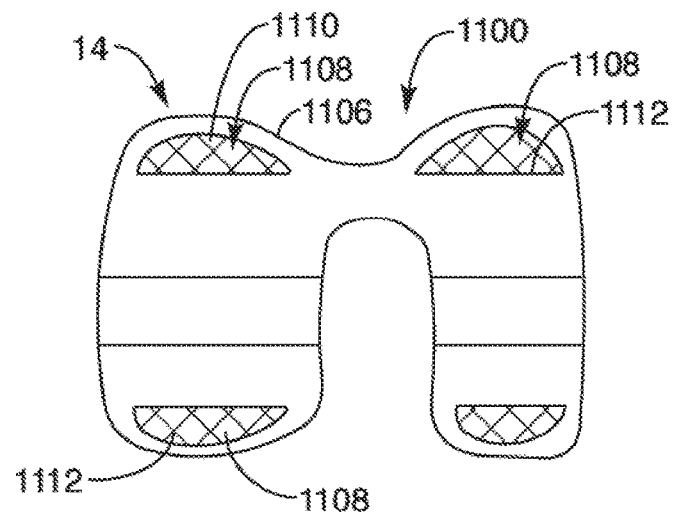
FIG. 40C illustrates a top, cross-sectional view of the femoral component, which comprises the lattice structure in accordance with a representative embodiment.
Figure 40D:
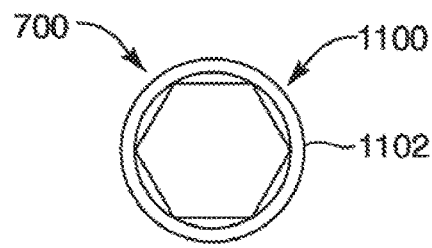
FIG. 40D illustrates a top, cross-sectional view through the stem comprising the lattice structure in accordance with representative embodiment.

With respect to the lattice structure 1110, the lattice structure can comprise any suitable component or characteristic that allows it to strengthen and/or otherwise support a portion of the prosthetic 1100. Indeed, in some embodiments, the lattice comprises one or more struts, trusses, fins, honeycomb-shaped supports, buttresses, columns, braces, triangular supports, triangular cells, diamond-shaped supports, diamond-shaped cells, cellular-shaped supports, meshes, micro-trusses, K trusses, triangular trusses, cuboidal trusses, graphite-shaped lattices, honeycomb-shaped lattices, diamond lattices, scaffolding, carbon-nanotube-shaped lattices, cuboidal lattices, pyramidal-shaped lattices, lattices, tubes, spicules, frameworks, grids, grid topologies, X-topologies, X-twist topologies, webs, spokes, stalactites, stalagmites, cancellous cells, helical supports, expanded closed cells, expanded open cells, foams (e.g., metal foams, polymer foams, and/or other suitable foams), closed-cell foams, open-cell foams, rails, solid blocks of material, and/or any other suitable support, supports, filler, and/or fillers. By way of non-limiting illustration, FIG. 40C illustrates an embodiment in which the lattice structure 1110 comprises a cross-hatched structure 1112. Additionally, FIG. 40D illustrates an embodiment in which the lattice structure 710 in the stem comprises a honeycomb shape.

Where the prosthetic 1100 comprises the lattice structure 1110, the lattice structure can be disposed in any suitable location that allows the prosthetic to function as intended. Indeed, in some embodiments (as shown in FIGS. 40A and 40B), the lattice structure 1110 is disposed in an interior space 1108, on an external surface of the prosthetic, between an articular surface 1106 of the prosthetic 10000 (e.g., the femoral 12 and/or tibial 14 component) and another surface 1104 of the prosthetic that is configured to contact a bone (and/or another prosthetic) upon implantation. In some such embodiments, the lattice structure allows for an overall weight of the prosthetic to be reduced without substantially reducing the prosthetic's strength.

While the lattice can reduce the overall weight of the prosthetic 1100 by any suitable amount, in some instances, by using the lattice and not just having the prosthetic comprise a solid piece of material, the prosthetics weight can be reduced by between about 5% and about 95%, or any subrange thereof (e.g., by between about 10% and about 45%, by between about 15% and about 35%, by between about 18% and about 25%, or any other suitable amount). Indeed, in some embodiments, the by providing the prosthetic with one or more internal spaces and/or lattices, the overall weight of the prosthetic is reduced by about 20%.

FIGS. 40B and 40C illustrate that in some embodiments the lattice structure 1110 is disposed in a portion of the prosthetic 1100 that is configured to be inserted into a bone (e.g., the stem). In some such embodiments, the placement of the lattice structure and the other characteristics of the lattice structure (e.g., size, shape, pattern, type, strut thickness, material composition, etc.) are able to provide one or more portions of the prosthetic with a desired modulus of flexibility, rigidity, strength, and/or other characteristic.

While FIGS. 40A and 40B illustrate some embodiments in which the lattice structure 1110 extends throughout the majority of the prosthetic 1100, the lattice structure can fill any suitable amount of the prosthetic, including, without limitation, between about 1% and about 99% of the total volume of the prosthetic, or any suitable subrange thereof (e.g., between about 5% and about 85%, between about 10% and about 60%, between about 15 and about 25%, etc.).

Additionally, while FIGS. 40A and 40B show some embodiments in which the prosthetic 700 comprises a single, contiguous interior space 1108, the prosthetic can comprise any suitable number of interior spaces 1108, and any number of contiguous and/or non-contiguous lattice structures 1110. By way of non-limiting illustration, FIGS.

40E-40F show some embodiments in which the prosthetic 1100 comprises multiple interior spaces 708 that each comprise a discrete lattice structure 1110. In such embodiments, the placement of the lattice structure can serve any suitable purpose, including, without limitation, allowing portions of the prosthetic: to be substantially solid (e.g., to allow portions of the prosthetic that may be subject to high forces be filled with the material used to create the prosthetic (and/or any other suitable material) while being void of the lattice structure), to have a stronger, thicker, denser, thinner, weaker, or otherwise different type of lattice than is found in another portion of the prosthetic, to have a more or less flexible lattice than is found another portion of the prosthetic, to have a more or less rigid lattice than is found in another portion of the prosthetic, to have a smaller or larger interior space than is found in other portions of the prosthetic, to have a smaller or larger interior space than would be possible without the lattice, and/or to otherwise allow the prosthetic to be biocompatible, comfortable, long-lasting, and/or to withstand the forces to which the prosthetic may be subjected. Similarly, the placement of the lattice structure can allow for a relatively lightweight lattice to be disposed in any suitable portion of the prosthetic (e.g., in places in which a solid portion of the material used to create the prosthetic can suitably be replaced with the lattice structure). Moreover, the placement of the lattice structure can further provide a specific characteristic (e.g., flexibility, rigidity, reduced density, etc.) to one or more specific portions of the prosthetic.

Although some embodiments of the prosthetic 1100 comprise a single type of lattice structure 1110 (or a lattice structure having substantially similar characteristics in all places in which the lattice is present throughout the prosthetic), in some other embodiments, the characteristics of the lattice structure or structures vary throughout the prosthetic. In this regard, the characteristics of the lattice structure can vary in any suitable manner throughout the prosthetic. By way of non-limiting example, the size of one or more components of the lattice structure (e.g., struts, trusses, spokes, cells, fillers, and/or other support structures), the density of the lattice structure in the prosthetic, the type of the lattice structure in the prosthetic, the size of the interior spaces in the prosthetic, the proximity of various support structures in the lattice, the material used to form the lattice structure in the prosthetic, the rigidity of the lattice, the flexibility, the weight, and/or any other suitable characteristic of the lattice structure may vary from one portion of the prosthetic to another. Accordingly, in some embodiments, the lattice structure is used to provide portions of the prosthetic with a desired characteristic (e.g., modulus of flexibility, rigidity, weight, balance, etc.).

Figure 40E:
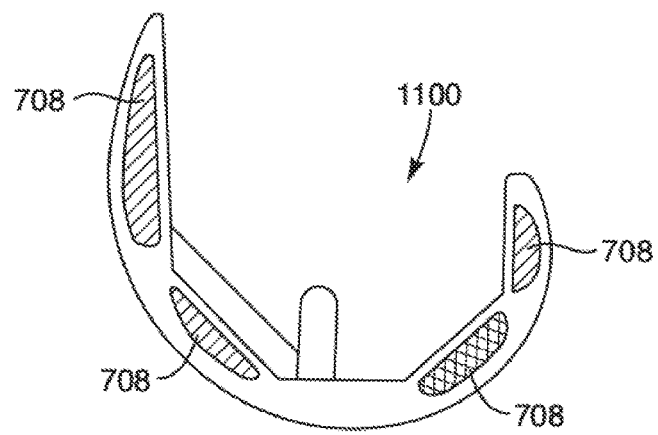
FIG. 40E illustrates a side, cross-sectional view of the femoral component defining multiple interior spaces comprising the lattice structure in accordance with a representative embodiment.
Figure 40F:
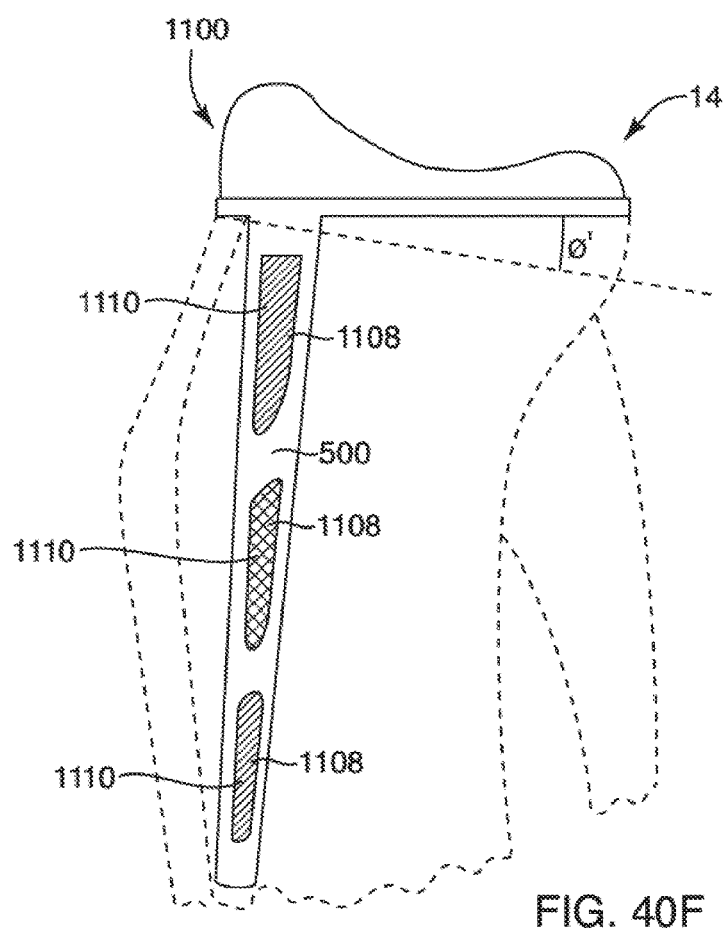
FIG. 40F illustrates a side, cross-sectional view of the tibial component comprising a stem that comprises multiple interior spaces defining the lattice structure in accordance with a representative embodiment.
Figure 40G:
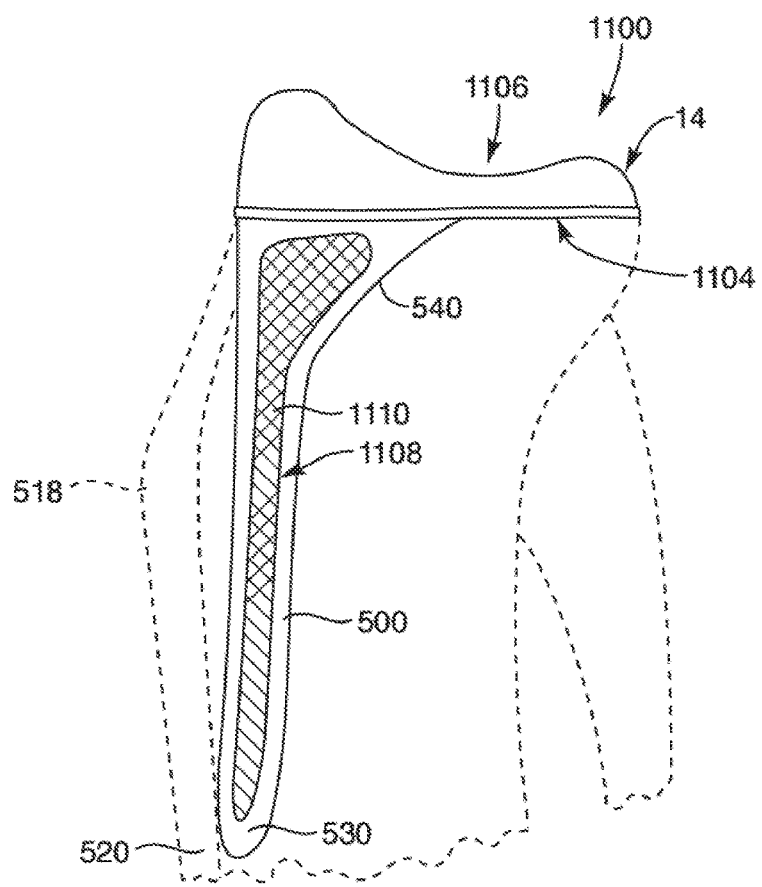
FIG. 40G illustrates a side, cross-sectional view of the tibial component defining an interior space comprising a modified version of the lattice structure in accordance with a representative embodiment.
Figure 40H:
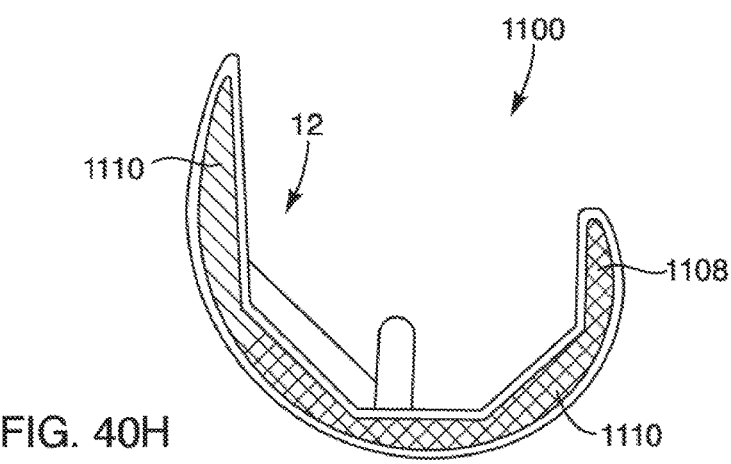
FIG. 40H illustrates a side, cross-sectional view of the femoral component comprising multiple types of the lattice structure in accordance with a representative embodiment.

In one non-limiting illustration showing how the lattice structure can vary within the prosthetic 1100, FIGS. 40G and 40H shows that, in some embodiments, as the lattice structure 1110 extends within a portion of the prosthetic (e.g., the stem 500 or the femoral component), the density, structure, material, architecture, and/or other characteristic of the lattice structure can vary within a single interior space 1108 to provide portions of the prosthetic with desired characteristics. Similarly, FIGS. 40E and 40F show that, in some embodiments, the architecture of the lattice structure 1110 varies from one portion of the prosthetic 1100 to another. Thus, in some embodiments, the prosthetic can be tailored to have specific portions with a desired strength, weight, rigidity, flexibility, balance, and/or other desirable characteristic.

The various components of the lattice 1110 can comprise any suitable material or materials that allows the prosthetic to function as intended. Some examples of suitable materials include, but are not limited to, one or more suitable types of: metal (e.g., titanium, titanium alloy, cobalt, cobalt-chromium, cobalt-chromium alloy, tantalum, trabecular metal, zirconium, zirconium alloy, stainless steel, tungsten, tungsten alloys, and/or any other biocompatible metal or metals), plastic (e.g., polyethylene, polypropylene, ultra-high cross linked polyethylene, ultra-high molecular weight polyethylene, high density polyethylene, nylon, polyoxybenzylmethylenglycolanhydride (e.g., Bakelite™), styrene-butadiene, polytetrafluoroethylene, polysulfone, polyethylene terephthalate, and/or any other biocompatible plastic or plastics), ceramic (e.g., alumina, oxinium oxidized zirconium, zirconia, and/or any other suitable biocompatible ceramic or ceramics), and/or any other biocompatible material or materials. In some non-limiting embodiments, however, the described lattice comprises cobalt chromium.

The prosthetic 1100 and/or lattice 1110 can be formed in any suitable manner, including, without limitation, via any suitable known or novel method involving additive manufacturing (e.g., 3D printing, sintering, laser sintering, selective laser sintering, direct metal laser sintering, selective laser melting, heat sintering, selective heat sintering, fused deposition molding, stereo-lithography, directed energy deposition, laminated object manufacturing, fused filament fabrication, robocasting, electron beam freeform, electron beam melting, digital light processing, a powder bed process, a powder bed and inkjet head 3D printing process, computer numerical control electrical discharge machining, and/or other additive manufacturing techniques), vapor deposition, molding, extrusion, sintering, welding, grinding, etching, polishing, drilling, smoothing, coupling with one or more mechanical, chemical, frictional, other suitable fasteners, laser polishing, laser radiation, heat glossing, heating, re-melting, and/or any other suitable process.

In some embodiments, the prosthetic 1110 is "printed" via additive manufacturing, such as selective laser melting electron-beam freeform fabrication, laser sintering, sintering, direct metal laser sintering, and/or in any other suitable manner. Indeed, in some embodiments, a portion of the prosthetic is made through a sintering process (e.g., laser sintering). In some such embodiments, one or more portions of the prosthetic define an opening to allow excess material (e.g., un-sintered material) to be released from the prosthetic. In this regard, the excess material can be removed from the prosthetic in any suitable manner, including, without limitation, by shaking, rinsing, washing, blowing, etching, and/or otherwise removing unwanted material from the prosthetic.

Figure 40I:
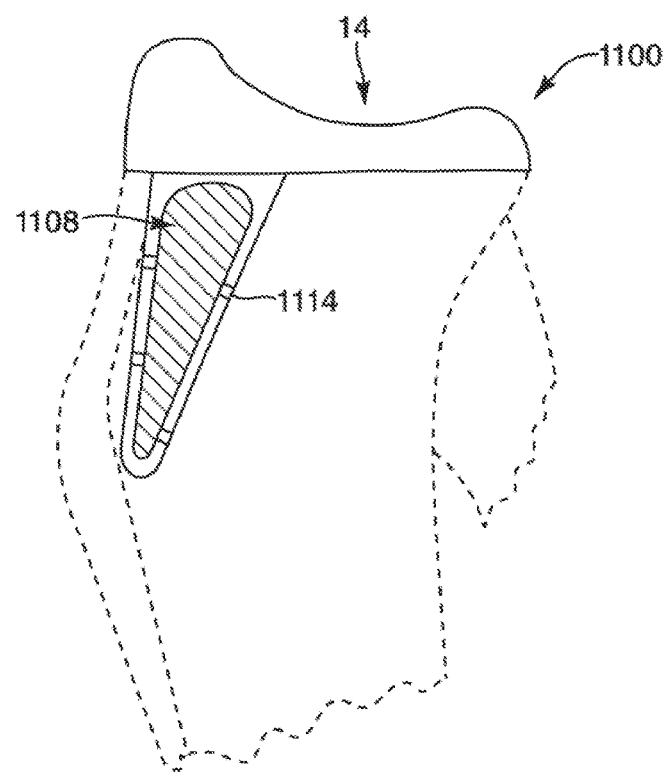
FIG. 40I illustrates a side, cross-sectional view of the tibial component defining an interior space comprising the lattice structure in accordance with a representative embodiment.
Figure 40J:
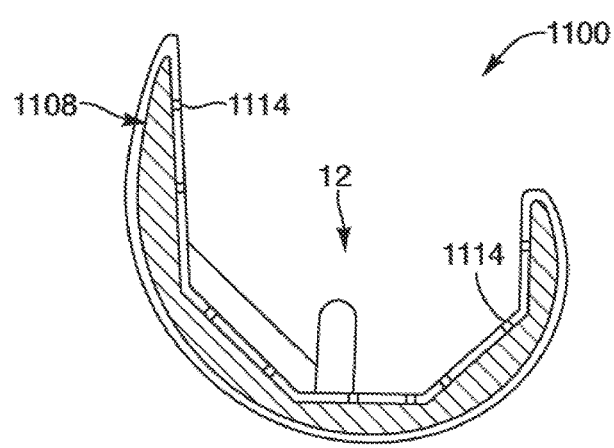
FIG. 40J illustrates a side, cross-sectional view of the femoral component in accordance with a representative embodiment.

By way of non-limiting illustration, FIGS. 40B, 40I, and 40J show that, in accordance with at least some embodiments, one or more interior spaces 1108 in the prosthetic 1000 define one or more openings 1114 that allow unwanted materials (e.g., un-sintered powder) to be removed from the prosthetic, that allow cement to extend into the prosthetic, and/or that allow bone to grow into the prosthetic. In this regard, the openings can have any suitable characteristic (e.g., be any suitable size, shape, architecture, proximity to another opening, in portion of the prosthetic, and/or other suitable characteristic) that allow cement to enter and/or bone to grow into the prosthetic as or once the prosthetic has been implanted, and/or that allow unwanted materials (e.g., un-sintered metal powder) to exit the prosthetic prior to implantation. By way of non-limiting illustration, FIG. 40B shows an embodiment in which a distal side of the tibial component 14 defines openings 1114 that are configured to allow bone to grow into the lattice structure 1110 of the tibial component 14 to help anchor the tibial component to the tibia.

While, in some embodiments, the openings 1114 into the interior spaces 1108 are disposed in one or more articular surfaces 1106 of the prosthetic 1100, in some other embodiments, the openings are disposed in non-articular surfaces (and may even not be disposed in any articular surfaces) or are disposed in surfaces 1104 that interface with the bone to which the prosthetic is coupled. In some such embodiments, cement, marrow, and/or bone growth can extend into the openings (e.g., the scaffolding) in the prosthetic that is attached to a bone to further secure the prosthetic to the bone. In some embodiments in which the prosthetic defines openings that extend into an interior space and/or a lattice structure 1110, bone grows into the bone such that a relatively small amount, or no cement, need be used to couple the prosthetic to the bone.

Figure 41:
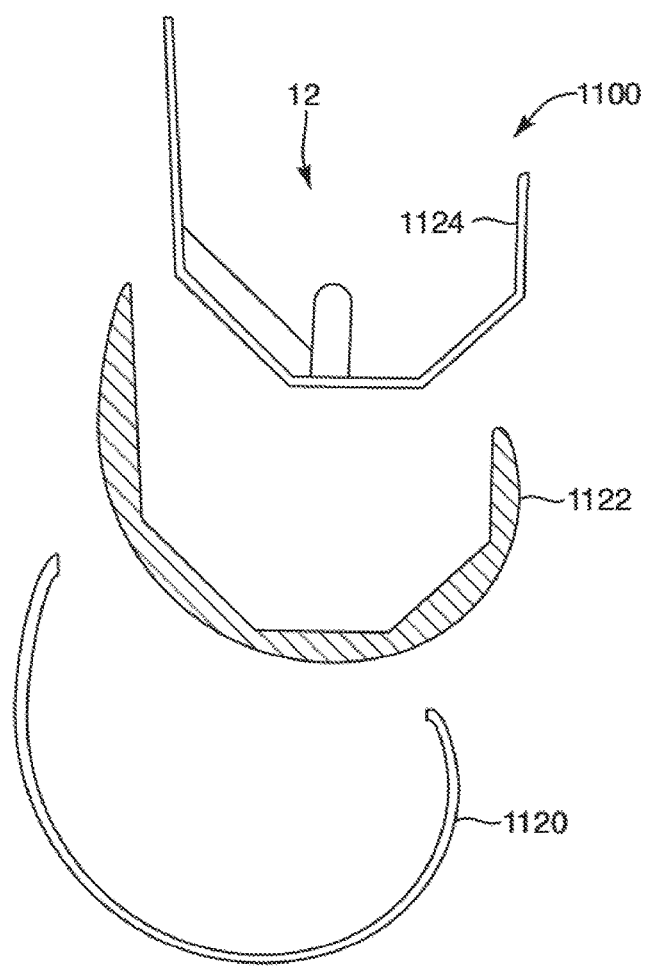
FIG. 41 illustrates a side, cross-sectional, exploded view of the femoral component comprising the lattice structure in accordance with a representative embodiment.

In accordance some other embodiments, instead of having all of the pieces of the prosthetic 1100 be integrally formed together (e.g., via additive manufacturing, molding, sintering, and/or any other suitable process), one or more portions of the prosthetic are formed separately and then coupled to other portions of the prosthetic. By way of non-limiting illustration, FIG. 41 shows that, in some embodiments, various portions of the prosthetic 700 (e.g., a first exterior portion 1120, a second exterior portion 1124, and an internal support structure 1122) are formed separately (e.g., via molding, milling, additive manufacturing, foaming, extrusion, etching, forging, and/or in any other suitable manner) and are then joined together (e.g., via welding and/or one or more friction fittings, mechanical fasteners, adhesives, cements, glues, couplers, seals, and/or other suitable mechanisms). In this regard, while FIG. 41 shows that the first exterior portion 1120, the second exterior portion 1124, and the internal support structure 1122 are initially made separate, in some other embodiments, any of the components of the prosthetic can be made together with any other suitable component being fixed to the other components to form the prosthetic. By way of non-limiting example, in some embodiments the first exterior portion and the internal support structure (e.g., metal foam, trusses, support struts, and/or any other suitable lattice) are integrally formed and/or otherwise coupled with each other before the second exterior portion is joined to (e.g., welded, glued, and/or otherwise coupled with) the first exterior portion and the internal support structure.

In addition to the aforementioned components and characteristics, the described systems and methods can be modified in any suitable manner. In one example, in addition to, or in place of, the lattice structure 1110, the interior space 1108 of the described prosthetic 1100 comprises one or more additional materials that provide the prosthetic with a desired characteristic. In this regard, the interior space 1108 and/or lattice can comprise bone growth stimulators, cements, coating materials, and/or any other material that is suitable for use in the prosthetic. In some embodiments, however, the lattice structure within in at least one interior space in the prosthetic comprises a solid material (e.g., polyethylene, rubber, vulcanized rubber, etc.) a foam, a metal foam, and/or any other suitable lattice material) that is configured to provide support to a portion of the prosthetic and that is less dense than the material used to make other portions of the prosthetic. In some embodiments, such a material comprises a solid piece of ultra-high cross linked polyethylene.

Where the prosthetic 1100 comprises a lattice 1110 in the interior space 1108 which varies from the material surrounding the interior space, such material can be placed in the internal space in any suitable manner. Some examples of such methods include, but are not limited to, injection, additive manufacturing, sintering, extrusion, foaming, and/or any other suitable method or methods. Indeed, in some embodiments, the material used to create the lattice structure is placed in the prosthetic through additive manufacturing (e.g., via laser sintering, laser polishing, and/or any other suitable process).

Figure 40K:
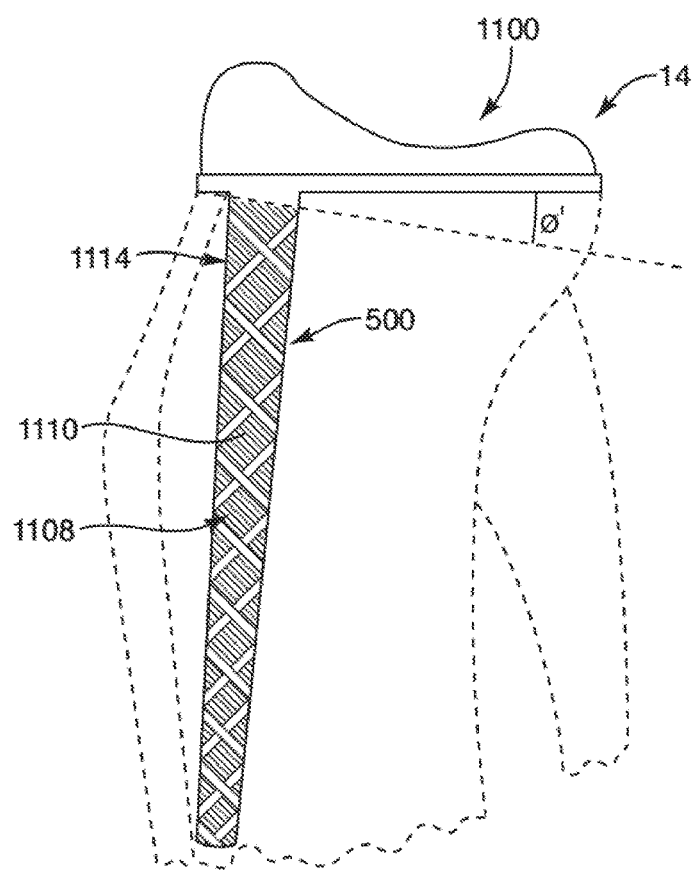
FIG. 40K illustrates a side view of the tibial component in accordance with a representative embodiment.

In another example of a suitable modification, some embodiments of the described prosthetic 1100 have a portion of the lattice structure 1110 disposed on the external surface 1102 of the prosthetic so as to contact a bone when the prosthetic is implanted. In such embodiments, the bone may grow into the lattice structure to further anchor the prosthetic to its corresponding bone. For instance, FIG. 40K shows that, in some embodiments, the openings 1114 in the external surface 1102 of the prosthetic 1100 are defined by a scaffolding 1116 (or a lattice or other surface having plurality of holes). In this regard, while FIG. 40K illustrates the tibial component 14, the described openings 1114 and/or the scaffolding 1116 can be used with any other suitable prosthetic, including, without limitation, the femoral component 12 (as illustrated in FIG. 40J).

In still another example of a suitable modification, some embodiments of the described systems and methods include specifically tailoring a prosthetic 1100 for use with a specific bone in a specific patient. In this regard, one or more characteristics (actual and/or desired) of a person's bone, including, without limitation, size, shape, thickness, strength, flexibility, rigidity, contour, density, and/or any other suitable characteristic, can be measured and the prosthetic can be specifically made (e.g., via additive manufacturing or otherwise) to match, substantially match, and/or otherwise complement such characteristics. Indeed, in some embodiments, a portion of the prosthetic is sized to specifically fit a particular bone. In some other embodiments, the prosthetic is modified to have a modulus of flexibility that substantially matches that of the bone to which the prosthetic is to be attached. Indeed, in some embodiments, the prosthetic can be modified to include several portions with one or more different moduli of flexibility (e.g., as illustrated in FIGS. 40E, 40G, and 40H). In some other embodiments, when a portion of a bone is relatively weak, a corresponding portion of the prosthetic 1100 is strengthened to provide the bone with a desired strength.

In order to tailor the prosthetic 1100 to a particular bone, the density, flexibility, rigidity, size, shape, thickness, and/or any other desired characteristic of such bone can be measured in any suitable manner. In this regard, some examples of suitable methods for measuring bone density, flexibility, rigidity, and/or any other desired characteristic include, but are not limited to, X-ray, dual energy X-ray Absorptiometry, quantitative computed tomography, peripheral quantitative computed tomography, qualitative ultrasound, ultrasound, infrasound, single photon absorptiometry, digital X-ray radiogrammetry, bone mineral density scan, single energy X-ray absorptiometry, and/or any other suitable method. Indeed, in some embodiments, characteristics of specific portions of a bone (e.g., femur, tibia, etc.) are measured and the prosthetic is made (e.g., via additive manufacturing) to complement the bone with its specific characteristics.

In another example of a suitable modification to the described systems and methods, instead of forming a prosthetic implant 1100, some embodiments of the described systems and methods include providing one or more surgical tools that define an internal space 1106 comprising a lattice structure 1110. In this regard, the described systems and methods can be used to form any suitable surgical instrument, including, without limitation, one or more impactors, osteotomes, retractors, elevators (e.g., key, freer, cobb, etc.), clamps, scalpels, rongeurs, scissors, cutters, mallets, forceps, bone curettes, chisels, drills, pin pullers, and/or any other suitable instrument that can comprise an internal space with a lattice structure. In this regard, where an instrument comprises an internal space with a lattice structure, the overall weight of the instrument may be reduced, thus simplifying surgical procedures, especially those involving many instruments that, when taken together, could otherwise be relatively heavy.

The described systems and methods for providing a prosthetic 1100 and/or a surgical tool with an interior space 1108 and/or lattice structure 1110 can provide several benefits. In this regard, some embodiments of the described systems and methods allow the weight of prosthetic 1100 (and/or surgical tool) to be reduced (e.g., to weigh 1%-90% less (or any sub-range thereof) than the component would otherwise weigh). Additionally, in some embodiments, the described systems and methods allow a prosthetic to complement one or more characteristics of a corresponding bone, and to thereby improve the life of the prosthetic and the strength and function of the bone.

In another example of a suitable modification to the described systems, in some embodiments, the described prosthesis 1100 (e.g., the femoral component 12, the tibial component, and/or any other suitable prosthetic and/or implantable prosthetic—with an implantable prosthetic being one that is configured to completely contained within a patient's body after it is coupled to a bone) and/or surgical tool is formed through a molding method that allows the prosthesis to readily be tailored to meet a specific need. In this regard, some conventional molding methods for forming the described prosthetics comprise forming a relatively expensive master negative mold for each variation of a prosthetic (e.g., a mold for a femoral component: comprising an anterior flange 49, missing the anterior flange, comprising the proximal extension 50 on a medial posterior condyle, comprising the proximal extension on a lateral posterior condyle, comprising and/or missing any other desired characteristic, and/or any suitable combination of the foregoing). Unlike some such methods, some embodiments of the described systems and methods comprise forming several variations of a desired prosthetic from a single master negative mold (or from a single master negative mold architecture). An example of such a method 1200 is shown in FIG. 42.

Figure 42:
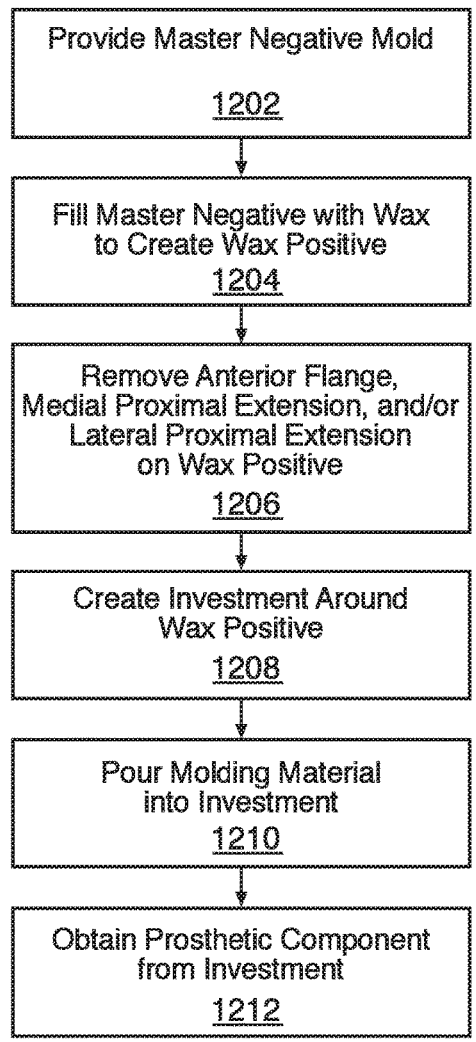
FIG. 42 illustrates a representative embodiment of method for forming a prosthetic implant.

While the method 1200 shown in FIG. 42 can be modified in any suitable manner (including, without limitation, by rearranging, adding to, removing, substituting, and/or otherwise modifying various portions of the method), FIG. 42 shows at 1202 that, in some embodiments, the method 1200 begins by providing a master negative mold defining a mold for a prosthetic (e.g., a femoral component 12, a tibial component 14, and/or any other suitable prosthetic) having one or more optional components (e.g., an anterior flange 45, a femoral full flex articulation or proximal extension 50 on a posterior medial condyle, a femoral full flex articulation or proximal extension 50 on a posterior lateral condyle, an articulation feature 400 and/or 420, an anterior lip, etc.). In this regard, the master negative mold can be made of any suitable material, including, without limitation, one or more metals, ceramics, types of silicon, types of latex, types of polyurethane, plastics, plasters, rubbers, clays, and/or other suitable materials.

Continuing at 1204, FIG. 42 shows that, in some embodiments, the method 1200 further comprises filling the master negative mold with a material that can be used to make a positive blank of the prosthetic. In this regard, any suitable material or materials can be used to make the positive blanks, including, without limitation, one or more waxes, plastics, polymers, metals, ceramics, synthetic materials, plasters, clays, and/or any other suitable material. In some embodiments, however, wax is poured into the master negative mold to make a positive wax blank.

Figure 43:
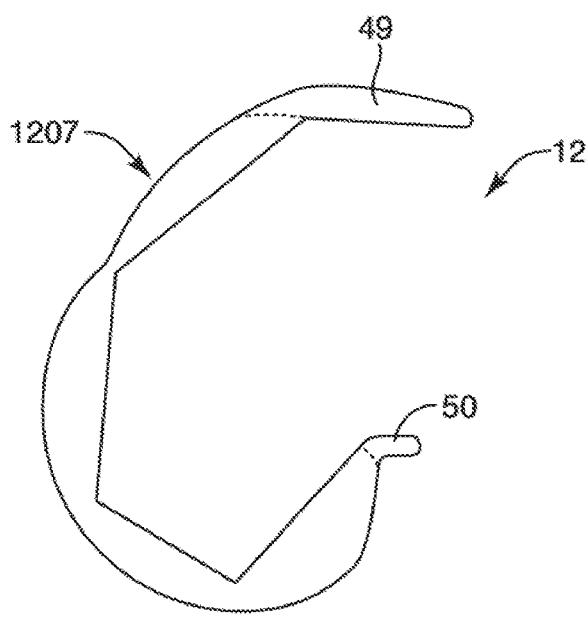
FIG. 43 illustrates a side view of a positive prosthetic blank in accordance with a representative embodiment.

At 1206, FIG. 42 shows that, in some embodiments, the method 1200 continues as one or more optional portions of the positive blank (and any corresponding prosthetic formed therefrom) are removed. Indeed, in some embodiments, where the blank 1207 is in the shape of the femoral component 12 (as shown in FIG. 43), a portion (or all) of the anterior flange 49, the proximal extension 50 on the posterior medial condyle, the proximal extension 50 on the posterior lateral condyle, and/or any other suitable portion of the positive blank is removed (e.g., along the dotted lines and/or in any other suitable location). Similarly, where the blank 1207 is in the shape of a tibial component, a portion (or all) of a medial articular ridge, a lateral articular ridge, a medial spherical articular surface, lateral spherical articular surface, lateral anterior lip, medial anterior lip, and/or other suitable component or characteristic of the blank is removed to create a customized positive blank. Similarly, whether the prosthetic comprises any other optional component or characteristic, one or more such components and/or characteristics are removed.

In this regard, unwanted portions of the positive blank can be removed in any suitable manner, including, without limitation, by being shaved off, cut off, ground off, sanded off, filed off, etched of, polished off, melted off, sandblasted off, and/or otherwise removed. In some embodiments, the blank is further prepared by being polished, buffed, reshaped, gated, sprued, and/or otherwise prepared for investment.

In contrast, instead of removing one or more unwanted portions of the blank, in some embodiments, one or more desired components or characteristics are added to the blank. In this regard, any suitable component or characteristic can be added to the positive blank (including, without limitation, one or more anterior flanges, proximal extensions, anterior lips, posterior lips, articulation features, textures, objects, and/or other suitable features). Such features can be added to the blank in any suitable manner, including, without limitation, by being melted together with the blank, being welded to the blank, being attached with a coupler, being glued together, being forced together, being sprayed or otherwise deposited on the blank, and/or in any other suitable manner.

Once a positive blank 1207 with one or more desired characteristics is prepared (e.g., missing and/or with the addition of one or more optional components or characteristics), FIG. 42 at 1208 shows that, in accordance with at least some embodiments, the method 1200 continues as an investment (or hard shell) is formed around the positive blank. Such an investment can be formed on the positive blank in any suitable manner, including, without limitation, by being sprayed on the blank, by having the blank be dipped in a bath of investment material, and/or in any other similar manner. Additionally, the investment can comprise any suitable material, including, without limitation, one or more ceramics, plasters, silicons, latexes, polyurethanes, polymers, synthetic materials, clays, rubbers, metals, sands, silicas, and/or other suitable materials. Indeed, in some embodiments, the investment comprises a ceramic material that is dried, heated, cured, and/or otherwise hardened around the positive blank, and the positive blank is melted out of, washed from, de-waxed from, and/or otherwise removed from the investment.

At 1210, FIG. 42 shows that (in accordance with some embodiments) once the investment is made and the positive blank is removed from the investment, a molding material (e.g., titanium, titanium alloy, cobalt, cobalt-chromium, a cobalt-chromium alloy, tantalum, trabecular metal, zirconium, zirconium alloy, stainless steel, tungsten, tungsten alloy, plastic, polyethylene, polypropylene, ultra-high cross linked polyethylene, ultra-high molecular weight polyethylene, high density polyethylene, nylon, polyoxybenzylmethylenglycolanhydride, styrene-butadiene, polytetrafluoroethylene, polysulfone, polyethylene terephthalate, a ceramic, alumina, oxinium oxidized zirconium, zirconia, and/or any other suitable biocompatible material or materials) is poured (or otherwise introduced) into the investment. Indeed, in some embodiments, cobalt chromium is poured into the investment.

Once the molding material in the investment is allowed to cool and/or to otherwise harden, FIG. 42 shows that (in some embodiments) the method 1200 continues at 1212 as a prosthetic component 1100 with desired characteristics is removed from the investment or devested. This devestment can be done in any suitable manner, including, without limitation, by parting the investment at one or more seams to allow the investment to be reused, breaking the investment away from the prosthetic, dissolving the investment, cutting the investment way from the prosthetic, and/or in any other suitable manner. In some embodiments, however, the investment is parted at a seam, such that the investment can be reused to form additional prostheses.

Once the prosthetic 1100 is removed from the investment, the prosthetic can further be polished, shaped, buffed, chased, finished, heat glossed, sterilized, coated with a desired material (e.g., a patina, a porous coating that helps increase friction between the prosthetic and a bone to which the prosthetic is coupled, and/or other suitable coating), and/or otherwise be prepared for implantation into a patient.

As a modification to the method 1200 set forth in FIG. 42, in some embodiments, the prosthetic 1100 itself is formed in the master negative mold, and then one or more unwanted components of the prosthetic are removed from the prosthetic (e.g., via a plasma cutter, grinding, polishing, etching, and/or in any other suitable manner).

Thus, instead of needing a specific master negative mold for every possible permutation of the prosthetic 1100 (e.g., a femoral component, a tibial component, and/or any other suitable prosthetic component), in every available size (e.g., small, medium, large, etc.), and for use in the right side or the left side of the body, in at least some embodiments, the described systems and methods can produce several prosthetics, with different components (e.g., with or without the anterior flange 49, the medial proximal extension 50, the lateral proximal extension, and/or any other suitable component) from the same master negative mold (or from the same architecture of the master negative mold).

Thus, some aspects of the present invention relate to systems and methods for providing relatively lightweight prostheses. Moreover, in some such instances, the described systems and methods include a prosthetic implant having an exterior surface that is configured to be coupled to a bone, an interior space disposed within the prosthetic, and a lattice structure disposed within the interior space. Some examples of such a prosthetic include a femoral knee component, a tibial knee component, an intramedullary stem, and/or any other suitable prosthetic. Additionally, in some cases, a portion of the prosthetic is configured to have a modulus of elasticity that substantially matches that of the bone to which the prosthetic couples. While the elasticity of the bone and the prosthetic can be matched in any suitable manner, in some cases, the elasticity of one or more portions of the prosthetic is modified by varying the strength provided to the prosthetic by the lattice structure.

The present invention may be embodied in other specific forms without departing from its spirit or essential characteristics. For example, one of skill in the art will appreciate that the methods and systems of the present invention may be modified for use in unicompartmental knee arthroplasty procedures and prostheses. The methods and systems of the present invention may further be used on the lateral side of the knee instead of, or in combination with the medial side. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A cutting guide block comprising:
a first portion configured to contact an anterior portion of a distal end of a femur;
a second portion configured to contact a posterior resected surface of a posterior condyle at the distal end of the femur; and
a first guide slot that is defined in the second portion, the first guide slot extending along a first axis that intersects a longitudinal axis of a distal portion of the femur at an acute angle, inside the distal portion of the femur when the second portion contacts the posterior resected surface of the posterior condyle, wherein the first guide slot is configured to guide a cutting tool in a proximal-anterior direction into a proximal portion of the posterior condyle of the femur when the cutting guide block is seated at the distal end of the femur such that the first portion contacts the anterior portion of the femur's distal end and the second portion contacts the posterior resected surface of the posterior condyle.

2. The cutting guide block of claim 1, wherein the first guide slot is configured to direct the cutting tool to cut proximally and anteriorly into the proximal portion of the posterior condyle at an angle between about 20° and about 65° with respect to the longitudinal axis of the distal portion of the femur when the cutting guide block is seated at the distal end of the femur.

3. The cutting guide block of claim 1, wherein the first guide slot is configured to direct the cutting tool to cut proximally and anteriorly into the proximal portion of the posterior condyle at an angle between about 35° and about 55° with respect to the longitudinal axis of the distal portion of the femur when the cutting guide block is seated at the distal end of the femur.

4. The cutting guide block of claim 1, wherein the cutting guide block comprises a stop that extends from the second portion and that is configured to prevent the cutting tool from cutting a popliteal portion of the femur while the cutting tool is disposed in the first guide slot.

5. The cutting guide block of claim 1, wherein the second portion further defines a second guide slot that is configured to align the cutting tool with the proximal portion of the posterior condyle of the femur, wherein the first guide slot is disposed proximally to the second guide slot when the cutting guide block is seated on the distal end of the femur, and wherein the second guide slot extends along a second axis that intersects the longitudinal axis of the distal portion of the femur when the cutting guide block is seated at the distal end of the femur such that the second portion contacts the posterior resected surface of the posterior condyle.

6. A cutting guide block for resection of a proximal portion of a posterior condyle of a femur, the cutting guide block comprising:
- a first portion configured to contact an anterior, resected surface at a distal end of the femur;
- a second portion that couples the first portion with a third portion of the cutting guide block;
- the third portion, which is configured to contact a posterior resected surface of the posterior condyle at the distal end of the femur, and
- a first cutting tool guide slot that is defined in the third portion and that is configured to direct a cutting tool to cut in a proximal-anterior direction into the proximal portion of the posterior condyle of the femur, adjacent to a popliteal surface of the femur,
- wherein the first cutting tool guide slot extends along an axis that intersects a longitudinal axis of a distal portion of the femur at an acute angle, inside the distal portion of the femur when the third portion contacts the posterior resected surface of the posterior condyle at the distal end of the femur and when the cutting guide block is seated on the distal end of the femur.

7. The cutting guide block of claim 6, wherein the cutting guide block comprises a placement guide that is configured to contact a side of the distal end of the femur when the cutting guide block is seated on the distal end of the femur to align the first cutting tool guide slot with the posterior condyle.

8. The cutting guide block of claim 6, wherein the first portion of the guide block is configured to contact an anterior chamfer cut surface and the second portion is configured to contact a distal cut surface of the distal end of the femur when the guide block is seated on the distal end of the femur.

9. The cutting guide block of claim 6, wherein, when the cutting guide block is seated at the distal end of the femur, the first portion of the cutting guide block is configured to contact at least one of an anterior chamfer cut surface and an anterior cut surface, the second portion is configured to contact a distal cut surface of the femur, and the third portion is configured to contact at least one of a posterior condylar cut surface and a posterior chamfer cut surface of the distal end of the femur.

10. The cutting guide block of claim 6, further comprising a handle that extends from an exterior surface of the cutting guide block.

11. A cutting guide block for resection of a proximal portion of a posterior condyle of a femur, the guide block comprising:
- a first portion configured to contact an anterior resected surface of a distal end of the femur;
- a second portion configured to contact a distal resected surface at the distal end of the femur;
- a third portion configured to contact a posterior resected surface of the posterior condyle;
- a first cutting tool guide slot defined in the third portion and configured to direct a cutting tool to cut in a proximal-anterior direction into a first proximal portion of the posterior condyle of the femur when the guide block is seated on the distal end of the femur; and
- a second cutting tool guide slot configured to direct the cutting tool to cut proximally and anteriorly into a second posterior portion of the posterior condyle when the cutting guide block is seated on the distal end of the femur,
- wherein the first cutting tool guide slot extends along a first axis that intersects a longitudinal axis of a distal portion of the femur at an first acute angle, inside the distal portion of the femur when the cutting guide block is seated on the distal end of the femur such that the third portion contacts the posterior resected surface of the posterior condyle, and wherein the second cutting tool guide slot extends along a second axis that intersects the longitudinal axis of the distal portion of the femur at a second acute angle, inside the distal portion of the femur when the cutting guide block is seated on the distal end of the femur such that the third portion contacts the posterior resected surface of the posterior condyle.

12. The cutting guide block of claim 11, wherein the first portion of the cutting guide block is configured to contact an anterior chamfer cut surface and the second portion is configured to contact a distal cut surface of the distal end of the femur when the cutting guide block is seated on the distal end of the femur.

13. The cutting guide block of claim 12, wherein the first cutting tool guide slot is disposed distally in the cutting guide block with respect to the second cutting tool guide slot, wherein the cutting guide block is configured to allow the cutting tool to extend further through the first cutting tool guide slot than through the second cutting tool guide slot, and wherein the first cutting tool guide slot is configured to direct the cutting tool into the proximal portion of the posterior condyle at an angle between about 35° and about 55° with respect to the longitudinal axis of the distal portion of the femur.

14. The cutting guide block of claim 11, wherein the first portion of the guide block is configured to contact at least one of an anterior chamfer cut surface and an anterior cut surface, the second portion is configured to contact a distal cut surface, and the third portion is configured to contact at least one of a posterior condylar cut surface and a posterior cut surface of the distal end of the femur when the cutting guide block is seated on the distal end of the femur.

15. The cutting guide block of claim 11, wherein the first and second guide tool slots are configured to guide the cutting tool to remove bone from a lateral posterior condyle of the distal end of the femur, and wherein the guide block further comprises a third and a fourth guide tool slot that are each configured to guide the cutting tool to remove bone from a medial posterior condyle of the distal end of the femur.

16. The cutting guide block of claim 11, wherein the first cutting tool guide slot is disposed distally in the cutting guide block with respect to the second cutting tool guide slot when the cutting guide block is seated at the distal end of the femur, and wherein the cutting guide block is configured to allow the cutting tool to extend further through the first cutting tool guide slot than through the second cutting tool guide slot.

17. The cutting guide block of claim 11, wherein the first cutting tool guide slot is configured to direct the cutting tool into the posterior condyle in the proximal-anterior direction at an angle that is between about 20° and about 65° degrees with respect to the longitudinal axis of the distal portion of the femur when the guide block is seated at the distal end of the femur.

18. The cutting guide block of claim 11, wherein the first cutting tool guide slot and the second cutting tool guide slot are each configured to direct the cutting tool into the posterior condyle at a different angle with respect to the longitudinal axis of the distal portion of the femur.

19. The cutting guide block of claim 11, wherein the cutting guide block comprises a placement guide that is configured to contact a side of the distal end of the femur when the guide block is seated on the distal end of the femur to align the first cutting tool guide slot with the posterior condyle.

20. The cutting guide block of claim 11, wherein the first axis and the second axis are substantially parallel with each other.

21. A resection block for resecting a proximal portion of a posterior condyle, the resection block comprising:

a resection block having a posterior portion that defines a first slot that is sized and shaped to receive a cutting device, wherein the resection block comprises an inner surface that is configured to be seated on and to receive a distal end of a femur that has been resected such that the first slot is configured to substantially align with the proximal portion of the posterior condyle of the femur, adjacent to a popliteal surface of the femur, when the resection block is seated on the distal portion of the femur, and wherein the first slot extends in a proximal-anterior direction along a first axis that intersects a longitudinal axis of a distal portion of the femur at an acute angle, inside the distal portion of the femur when the cutting guide block is seated at the distal end of the femur.

\* \* \* \* \*